United States Patent
Graham et al.

(10) Patent No.: US 11,591,607 B2
(45) Date of Patent: Feb. 28, 2023

(54) OPTIMIZED CRISPR-CAS NUCLEASES AND BASE EDITORS AND METHODS OF USE THEREOF

(71) Applicant: Pairwise Plants Services, Inc., Durham, NC (US)

(72) Inventors: Nathaniel Graham, Durham, NC (US); Aaron Hummel, Hillsborough, NC (US); Yongjoo Kim, Durham, NC (US); Joseph Matthew Watts, Cary, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 0 days.

(21) Appl. No.: 17/078,576

(22) Filed: Oct. 23, 2020

(65) Prior Publication Data

US 2021/0147861 A1 May 20, 2021

Related U.S. Application Data

(60) Provisional application No. 62/925,422, filed on Oct. 24, 2019.

(51) Int. Cl.
| | |
|---|---|
| *C12N 15/82* | (2006.01) |
| *C12N 9/22* | (2006.01) |
| *C12N 15/113* | (2010.01) |

(52) U.S. Cl.
CPC ........... *C12N 15/8218* (2013.01); *C12N 9/22* (2013.01); *C12N 15/113* (2013.01); *C12N 2310/20* (2017.05)

(58) Field of Classification Search
CPC ................................................ C12N 15/8216
See application file for complete search history.

(56) References Cited

U.S. PATENT DOCUMENTS

| | | | |
|---|---|---|---|
| 2014/0283200 A1 | 9/2014 | Chittoor et al. | |
| 2015/0191721 A1* | 7/2015 | Kelker ................ | C12N 15/63 435/252.34 |
| 2016/0068864 A1* | 3/2016 | Doudna ............... | C12N 15/111 435/188 |
| 2017/0218384 A1 | 8/2017 | Abbitt et al. | |
| 2018/0073012 A1* | 3/2018 | Liu .................. | C12Y 305/04004 |
| 2018/0327784 A1* | 11/2018 | Jin .................... | C12N 15/11 |
| 2019/0292553 A1* | 9/2019 | Gao .................... | C12N 15/90 |

FOREIGN PATENT DOCUMENTS

WO 2019067910 A1 4/2019

OTHER PUBLICATIONS

GenBank AWD73737.1 (published online May 1, 2018; see alignment appended to office action) (Year: 2018).*
Christensen et al (Transgenic Research, 1996, 5: 213-218) (Year: 1996).*
Endo, Masaki, et al., "Genome editing in plants by engineered CRISPR-Cas9 recognizing NG PAM", Nature Plants 5, 2019, 14-17.
Hua, Kai, et al., "Expanding the base editing scope in rice by using Cas9 variants", Plant Biotechnology Journal 17 (2), 2019, 499-504.
Jin, Shuai , et al., "Cytosine, but not adenine, base editors induce genome-wide off-target mutations in rice", Science 364(6437), 2019, 292-295.
Li, Jingying , et al., "Generation of Targeted Point Mutations in Rice by a Modified CRISPR/Cas9 System", Molecular Plant: Letter to the Editor 10(3), 2016, 526-529.
Lu, Yuming , et al., "Precise Editing of a Target Base in the Rice Genome Using a Modified CRISPR/Cas9 System", Molecular Plant: Letter to the Editor 10 (3), 2017, 523-525.
Xue, Chenxiao , et al., "Manipulating mRNA splicing by base editing in plants", Science China Life Sciences 61(11), 2018, 1293-1300.
Zong, Yuan , et al., "Precise base editing in rice, wheat and maize with a Cas9-cytidine deaminase fusion", Nature Biotechnology 35(5), 2017, 438-440.
International Search Report and the Written Opinion of the International Searching Authority corresponding to International Patent Application No. PCT/US20/56963 (13 pages) (dated Mar. 3, 2021).
Komor, A. C. et al. "Programmable editing of a target base in genomic DNA without double-stranded DNA cleavage" Nature, 533(7603):420-424 (2016).
Zong, Y. et al. "Precise base editing in rice, wheat and maize with a Cas9-cytidine deaminase fusion" Nature Biotechnology, 35(5):438-440 (2017).
Mauro and Chappell "A critical analysis of codon optimization in human therapeutics" Trends Mol Med., 20 (11):604 613 2014.

\* cited by examiner

*Primary Examiner* — Weihua Fan
(74) *Attorney, Agent, or Firm* — Myers Bigel, P.A.

(57) ABSTRACT

This invention relates to CRISPR-Cas nucleases codon optimized for expression in plants and nucleic acid constructs encoding base editors comprising a CRISPR-Cas nuclease and a deaminase domain, wherein the nucleic acid constructs are optimized for expression in a plant. The invention further relates to methods of modifying nucleic acids using the nucleic acid constructs.

20 Claims, 3 Drawing Sheets

Specification includes a Sequence Listing.

SEQUENCE LISTING

```
<160> NUMBER OF SEQ ID NOS: 76

<210> SEQ ID NO 1
<211> LENGTH: 4101
<212> TYPE: DNA
<213> ORGANISM: Artificial
<220> FEATURE:
<223> OTHER INFORMATION: Cas9 polynucleotide

<400> SEQUENCE: 1
gacaagaagt acagcatcgg gctggcgatc gggaccaact ccgtcggctg ggctgtgatt      60
accgacgagt acaaggtgcc atccaagaag ttcaaggtcc tcggcaacac tgaccggcac     120
agcattaaga agaacctgat tggggcgctg ctgttcgatt cggggagac tgcggaggcg     180 accaggctga agcggactgc gcgccggagg tacaccagga ggaagaatcg gatctgctac     240
ctccaggaga tttttctcgaa tgagatggcc aaggtggacg attccttctt ccatcgcctg     300
gaggagtcgt tcctcgttga ggaggacaag aagcatgaga ggcatcccat tttcgggaat     360
atcgttgacg aggtggctta ccatgagaag tacccgacca tctaccatct gcggaagaag     420
ctcgtcgatt cgaccgataa ggccgacctg cggctgatct acctggccct cgcgcacatg     480
attaagttcc ggggccattt cctcatcgag ggcgacctca acccggacaa ctcggacgtg     540
gataagctct tcattcagct cgtgcagaca taaccagc tcttcgagga gaatcccatt     600
aacgcctcgg gggtcgacgc taaggctatt ctctcggctc ggctgtcgaa gtcgcgccgg     660
ctggagaatc tcattgccca gctcccaggc gagaagaaga acgccctctt cggcaacctg     720
attgccctgt cgctggggct cacaccgaat ttcaagtcga acttcgacct cgccgaggac     780
gctaagctcc agctcagcaa ggatacttac gatgatgacc tcgataacct gctcgcccag     840
attggggatc agtacgcgga tctgttcctc gcggccaaga atctcagcga tgctattctc     900
ctgtcggaca tttcccgcgt caacacagag attactaagg ccccactgtc ggcgagcatg     960
attaagaggt acgatgagca tcatcaggac ctgacactgc tcaaggcgct ggtccggcag    1020
cagctccccg agaagtacaa ggagatttc ttcgatcagt caaagaatgg gtacgcgggc    1080
tacattgatg gcggcgcgtc ccaggaggag ttctacaagt tcattaagcc catcctggag    1140
aagatggacg gaccgagga gctgctggtg aagctcaatc gggaggacct gctccggaag    1200
cagcgcacat tcgacaatgg ctcgattcct caccagattc acctgggcga gctgcacgcc    1260
attctccgca ggcaggagga cttctacccg ttcctcaagg acaaccgcga gaagatcgag    1320
aagatcctga ccttccgga tccatactac gtggggccgc tcgcgcgggg gaactcccgg    1380
```

```
ttcgcgtgga tgactcgcaa gtccgaagaa acgattacac cgtggaattt cgaggaggtc    1440
gtcgacaagg gcgctagtgc gcagtcattc attgagagga tgaccaattt cgataagaac    1500
ctgcctaacg agaaggtgct gccgaagcat tcgctgctct acgagtactt caccgtttac    1560
aatgagctga ccaaggtgaa gtatgtgact gagggcatga ggaagccagc gttcctgagc    1620
ggcgagcaga agaaggctat cgtggacctg ctcttcaaga ctaaccggaa ggtgactgtg    1680
aagcagctca aggaggacta cttcaagaag attgagtgct tcgattccgt tgagattagc    1740
ggggtggagg atcggttcaa tgcttcgctc gggacatacc acgatctcct gaagatcatt    1800
aaggataagg acttcctcga caacgaggag aacgaggaca ttctcgaaga tattgtcctg    1860
accctcaccc tcttcgagga tcgggagatg atcgaggaga ggctcaagac atacgctcat    1920
ctgttcgatg ataaggtcat gaagcagctg aagcgcaggc ggtacacagg gtggggcgg    1980
ctgagccgga agctgatcaa cgggattcgg ataagcagt ccgggaagac aattctcgac    2040
ttcctcaagt ccgacgggtt cgctaaccgg aacttcatgc agctcattca tgatgactcg    2100
ctgacattca aggaggatat tcagaaggcg caggtttcgg ggcagggcga ctcgctccac    2160
gagcatattg cgaatctggc gggctccccc gcgattaaga agggcattct gcaaaccgtc    2220
aaggtggttg atgagctggt caaggtcatg gggcggcata agccagagaa tattgtcatc    2280
gagatggcgc gggagaatca gaccacacag aaggggcaga agaactcacg ggagcggatg    2340
aagcgcatcg aggagggcat caaggagctg gggtcgcaga tcctgaagga gcatcccgtg    2400
gagaacactc agctgcaaaa tgagaagctg tacctctact acctccagaa cgggagggac    2460
atgtatgtgg atcaggagct ggatattaat aggctgagcg attacgatgt cgaccacatt    2520
gtcccacagt cgttcctgaa ggacgacagc attgacaaca aggtgctgac ccgctcggat    2580
aagaacaggg gcaagagcga taatgttcca agcgaggagg ttgtgaagaa gatgaagaac    2640
tactggcggc agctcctgaa cgcgaagctc atcacacagc ggaagttcga caacctcacc    2700
aaggctgagc gcgggggcct gagcgagctg acaaggcgg ggttcattaa gaggcagctg    2760
gtcgagacac ggcagattac aaagcatgtt gcgcagattc tcgattcccg gatgaacacc    2820
aagtacgatg agaacgataa gctgattcgg gaggtcaagg taattaccct gaagtccaag    2880
ctggtgtccg acttcaggaa ggacttccag ttctacaagg ttcgggagat caacaactac    2940
caccacgcgc atgatgccta cctcaacgcg gtcgtgggga ccgctctcat caagaagtac    3000
ccaaagctgg agtcagagtt cgtctacggg gattacaagg tttacgacgt gcggaagatg    3060
atcgctaaga gcgagcagga gattggcaag gctaccgcta agtacttctt ctactccaac    3120
atcatgaact tcttcaagac agagattacc ctcgcgaatg gcgagatccg gaagaggccc    3180
ctcatcgaga caaatgggga gacaggggag attgtctggg ataaggggcg ggatttcgcg    3240
accgtccgga aggtcctgtc gatgccccag gttaatattg tcaagaagac tgaggtccag    3300
actggcggct tctcaaagga gtcgattctc ccaaagagga actccgataa gctcattgct    3360
cggaagaagg attgggaccc caagaagtac ggggattcg actcccccac tgttgcttac    3420
tctgttctgg ttgttgctaa ggtggagaag gggaagtcga agaagctgaa gagcgtgaag    3480
gagctgctcg ggattacaat tatggagagg tcatccttcg agaagaatcc catcgacttc    3540
ctggaggcca agggctacaa ggaggtgaag aaggacctga ttattaagct gcccaagtac    3600
tcgctcttcg agctggagaa tgggcggaag cggatgctgg cgtccgcggg ggagctgcaa    3660
aaggggaacg agctggcgct ccctccaag tatgtgaact tcctctacct ggcgtcgcac    3720
tacgagaagc tgaaggggtc cccagaggat aatgagcaga agcagctctt cgtcgagcag    3780
```

| | | |
|---|---|---|
| cataagcact acctggacga gattatcgag cagattagcg agttctcgaa gcgggtcatc | 3840 | |
| ctcgcggatg cgaacctgga taaggtgctc agcgcctaca ataagcaccg ggacaagccg | 3900 | |
| attcgggagc aggcggagaa tattattcac ctcttcacac tcaccaacct cggggcacca | 3960 | |
| gctgcgttca agtacttcga cactactatc gaccggaagc ggtacacctc gacgaaggag | 4020 | |
| gtgctcgacg ccaccctcat tcaccagtcg atcacaggcc tgtacgagac acggattgac | 4080 | |
| ctgtcccagc tcgggggcga c | 4101 | |

<210> SEQ ID NO 2
<211> LENGTH: 4101
<212> TYPE: DNA
<213> ORGANISM: Artificial
<220> FEATURE:
<223> OTHER INFORMATION: Cas9 polynucleotide

<400> SEQUENCE: 2

| | | |
|---|---|---|
| gacaagaagt actccattgg cctggcgatt gggacaaact cggtgggtg ggccgtgatt | 60 | |
| acggatgagt acaaggttcc aagcaagaag ttcaaggtcc tcgggaacac agatcggcat | 120 | |
| tcgattaaga gaatctcat tggggcgctc ctcttcgact cggggagac agcggaggct | 180 | |
| accaggctca gcggacagc caggcggcgg tacacaaggc ggaagaatcg catctgctac | 240 | |
| ctccaggaga ttttctcgaa tgagatggcg aaggtggacg acagcttctt ccatcggctg | 300 | |
| gaggagtcct tcctggtgga ggaggataag aagcacgaga ggcatccaat tttcgggaac | 360 | |
| atcgtggacg aggttgcgta ccatgagaag tacccctacaa tctaccatct gcggaagaag | 420 | |
| ctggttgact ccacagacaa ggcggacctg aggctgatct acctcgctct ggcccacatg | 480 | |
| attaagttcc gcgggcatt cctgatcgag ggggacctga tcccgacaa ttcggatgtg | 540 | |
| gacaagctct tcatccagct ggtgcagacc tacaaccagc tgttcgagga gaatcccatc | 600 | |
| aatgcgtcgg gcgttgacgc taaggccatt ctgtccgcta ggctgtcgaa gagcaggagg | 660 | |
| ctggagaacc tgatcgccca gctgccaggc gagaagaaga tgggctcttt cgggaatctg | 720 | |
| attgcgctct ccctggggct gacaccgaac ttcaagagca atttcgatct ggctgaggac | 780 | |
| gcgaagctcc agctctcgaa ggacacttac gacgatgacc tcgataacct cctcgcgcag | 840 | |
| atcggggacc agtacgctga tctcttcctc gccgctaaga acctctcgga tgctatcctg | 900 | |
| ctctccgaca ttctccgggt taataccgag attacaaagg ccccactgtc ggcgtccatg | 960 | |
| atcaagcggt acgatgagca tcatcaggat ctcaccctgc tcaaggccct cgtgcggcag | 1020 | |
| cagctgcccg agaagtacaa ggagattttc ttcgaccaga gcaagaatgg gtacgctggc | 1080 | |
| tacattgacg gcggggcctc acaggaggag ttctacaagt tcatcaagcc aatcctggag | 1140 | |
| aagatggatg gcacagagga gctgctggtg aagctcaacc gggaggatct gctcaggaag | 1200 | |
| cagcggacgt tcgacaacgg gtcgattccc catcagatcc acctggggga gctgcacgcg | 1260 | |
| atcctgcgcc ggcaggagga tttctaccct ttcctgaagg ataatcggga gaagatcgag | 1320 | |
| aagattctca ccttccggga tccctactac gtcgggccac tcgcgcgggg caatagcagg | 1380 | |
| ttcgcctgga tgacacggaa gagcgaggag acaatcaccc cctggaactt cgaggaggtt | 1440 | |
| gtcgacaagg gggcgtccgc ccagtcattc attgagcgga tgaccaattt cgacaagaat | 1500 | |
| ctgccaaatg agaaggttct cccaaagcat agcctcctct acgagtactt cactgtttac | 1560 | |
| aacgagctga ccaaggtgaa gtatgtgacc gagggcatgc ggaagcccgc gttcctgtcc | 1620 | |
| ggcgagcaga agaaggccat tgtggacctc ctgttcaaga ccaatcgcaa ggtcacagtc | 1680 | |

```
aagcagctca aggaggatta cttcaagaag atcgagtgct tcgactcggt tgagattagc    1740
ggggtggagg atcggttcaa cgcgagcctc ggcacttacc acgacctcct gaagatcatc    1800
aaggataagg acttcctcga caacgaggag aacgaggata ttctggagga catcgtgctc    1860
accctgacgc tgttcgagga tcgggagatg atcgaggagc gcctgaagac ctacgctcat    1920
ctcttcgatg ataaggtcat gaagcagctg aagaggaggc ggtacaccgg gtggggccgc    1980
ctgagcagga agctcattaa cgggatcagg gacaagcaga gcggcaagac catcctggac    2040
ttcctcaaga gcgatggctt cgccaaccgg aatttcatgc agctcatcca cgacgactcc    2100
ctcaccttca aggaggacat tcagaaggct caggtcagcg ccagggcga ctcgctgcat     2160 gagcacatcg ctaacctggc gggcagccca gccatcaaga agggcatcct ccagacagtg    2220
aaggtcgtgg atgagctggt gaaggtcatg ggccggcata agcccgagaa tattgtgatt    2280
gagatggcgc gggagaatca gaccactcag aagggccaga agaactcgcg ggagcgcatg    2340
aagaggatcg aggaggggat taaggagctg ggcagccaga ttctcaagga gcaccccgtg    2400
gagaataccc agctccagaa cgagaagctg tacctctact acctccagaa tgggcgggac    2460
atgtatgttg atcaggagct ggacatcaat cgcctctcgg attacgacgt ggaccacatc    2520
gtgccccaga gcttcctgaa ggatgatagc atcgacaata aggtcctgac ccgctccgac    2580
aagaatcgcg gcaagagcga caacgtgccg agcgaggagg tcgtgaagaa gatgaagaac    2640
tactggcggc agctgctgaa cgcgaagctc attacacagc ggaagttcga taacctgacg    2700
aaggcggaga ggggcggcct ctccgagctg gacaaggcgg gcttcattaa gaggcagctc    2760
gtggagactc gccagatcac caagcacgtg gctcagatcc tcgatagccg gatgaatacg    2820
aagtacgatg agaatgacaa gctcatccgg gaggtgaagg taatcaccct gaagtcaaag    2880
ctcgttagcg atttccggaa ggacttccag ttctacaagg tgcgggagat taacaactac    2940
catcatgcgc acgatgcgta cctcaatgcg gtggtgggca cagccctgat taagaagtac    3000
cccaagctgg agagcgagtt cgtctacggg gactacaagg tgtacgatgt tcggaagatg    3060
atcgccaaga gcgagcagga gattgggaag gccaccgcta agtacttctt ctactcgaat    3120
attatgaatt tcttcaagac cgagatcaca ctcgctaatg gggagattcg gaagcggccc    3180
ctcatcgaga ctaacgggga gactggcgag attgtgtggg acaaggggcg cgacttcgct    3240
accgtgcgca aggtcctctc gatgccccag gttaatattg ttaagaagac agaggtgcag    3300
acgggcgggt tctccaagga gtctatcctg ccgaagcgga actcggacaa gctgatcgcc    3360
cgcaagaagg attgggaccc caagaagtac gggggattcg atagcccaac cgtggcttac    3420
agcgtcctgg tggtcgccaa ggttgagaag gggaagtcga agaagctcaa gagcgttaag    3480
gagctgctgg gcatcaccat catggagcgg tccagcttcg agaagaatcc tatcgacttc    3540
ctggaggcta aggggtacaa ggaggtcaag aaggacctga tcattaagct gcccaagtac    3600
tctctgttcg agctggagaa cgggaggaag cggatgctgg cgtctgctgg cgagctacag    3660
aagggcaatg agctggcgct ccctccgaag tatgtcaact tcctctacct ggcttcccat    3720
tacgagaagc tgaagggctc gcccgaggat aatgagcaga agcagctctt cgtggagcag    3780
cacaagcact acctcgacga gatcattgag cagatttcgg agttctcgaa gcgggtcatt    3840
ctcgcggacg cgaacctcga caaggtcctc tcggcgtaca acaagcaccg ggacaagccc    3900
atccgggagc aggccgagaa cattatccac ctcttcacac tgaccaacct cggcgctccc    3960
gccgcgttca gtacttcga caccaccatt gaccgcaaga gatacacatc caccaaggag    4020
```

```
gtgctggacg cgaccctcat ccaccagagc atcacaggcc tctacgagac acggatcgac    4080
ctctcgcagc tcgggggcga t                                              4101

<210> SEQ ID NO 3
<211> LENGTH: 4092
<212> TYPE: DNA
<213> ORGANISM: Artificial
<220> FEATURE:
<223> OTHER INFORMATION: Cas9 polynucleotide

<400> SEQUENCE: 3
gacaagaagt actcgatcgg cctggcgatt ggcacaaaca gcgtgggtg ggctgtgatc      60 actgatgagt acaaggtgcc atcgaagaag ttcaaggtgc tgggaatac agaccggcat     120 tcgatcaaga gaatctcat tggcgctctc ctcttcgatt ccggcgagac tgctgaggcg     180
acccgcctga agcgcaccgc ccggcggcgc tacactcggc ggaagaatag gatttgctac    240
ctccaggaga ttttctcgaa tgagatggcc aaggtggatg acagcttctt ccaccgcctg    300
gaggagtcgt tcctggtcga ggaggacaag aagcatgagc ggcaccctat cttcgggaat    360
atcgttgatg aggtcgccta ccacgagaag taccccacta tctaccatct ccgcaagaag    420
ctcgtggaca gcacagataa ggccgacctc cgcctgatct acctcgccct cgcgcacatg    480
attaagttcc gggggcactt cctcattgag ggggatctga tcccgataa ctccgacgtg     540 gacaagctgt tcatccagct ggtgcagaca tacaaccagc tgttcgagga gaatcccatc    600
aacgcgagcg cgtggacgc taaggccatt ctgtcggcta ggctctcgaa gtcgaggcgg     660
ctggagaacc tgattgcgca gctccccggc gagaagaaga cgggctgtt cgggaatctc     720 atcgccctct ccctcggcct cacaccaaac ttcaagagca atttcgacct ggctgaggac    780
gctaagctgc aactctcaaa ggatacatac gatgacgacc tggacaatct cctggctcag    840
atcggcgacc agtacgctga cctgttcctc gcggccaaga atctgtcgga cgcgattctc    900
ctcagcgaca tcctgcgcgt caataccgag attacgaagg ctccactgtc tgcgtcaatg    960
attaagcggt acgatgagca tcaccaggat ctgaccctcc tgaaggcgct cgtgcggcag   1020
cagctgcccg agaagtacaa ggagattttc ttcgatcaga gcaagaatgg ctacgccggc   1080
tacatcgacg ggggcgcgag ccaggaggag ttctacaagt tcatcaagcc catcctggag   1140
aagatggacg gcaccgagga gctactcgtg aagctcaatc gggaggatct cctccggaag   1200
cagcggacat cgataacgg gtctatccca caccagatcc acctcggcga gctgcatgcg   1260
attctgcggc ggcaggagga tttctaccct ttcctgaagg acaaccggga gaagatcgag   1320
aagatcctca cattccggat tccatactac gtcggccccc tggcgagggg caatagccgg   1380
ttcgcgtgga tgacaaggaa gtccgaggag actattaccc cgtggaattt cgaggaggtg   1440
gttgacaagg gcgcttccgc gcagagcttc attgagcgga tgacaaactt cgacaagaat   1500
ctccccaacg agaaggtcct gccgaagcat agcctcctgt acgagtactt caccgtctac   1560
aatgagctaa ctaaggtcaa gtatgtgaca gagggcatga ggaagccagc cttcctctca   1620
ggcgagcaga gaaggccat tgtggacctc ctgttcaaga caaaccgcaa ggtgacagtg    1680
aagcagctga aggaggatta cttcaagaag attgagtgct tcgactcagt ggagatttca   1740
ggcgtggagg atcggttcaa cgcgagcctg gggacttacc acgacctgct gaagattatt   1800
aaggacaagg acttcctgga taacgaggag aatgaggaca tcctggagga tattgtgctc   1860
accctcaccc tgttcgagga cagggagatg attgaggaga ggctcaagac ctacgcgcac   1920
```

```
ctgttcgatg acaaggtcat gaagcagctg aagaggcggc gctacactgg gtggggccgc    1980
ctgtcgcgga agctgatcaa cggcattcgg gataagcagt ccgggaagac cattctggat    2040
ttcctgaagt cggacggctt cgccaacagg aatttcatgc agctgatcca cgacgactcc    2100
ctcaccttca aggaggacat tcagaaggcc caggttagcg gccaggggga ctcactccac    2160
gagcatattg ccaatctggc cggctctcca gctatcaaga agggcatcct gcaaacagtt    2220
aaggttgttg acgagctggt taaggtcatg gggcggcata gcccgagaa cattgtcatc     2280
gagatggctc gggagaacca gacaactcag aagggccaga agaactccag ggagcgcatg    2340
aagcggattg aggagggcat taaggagctg ggtcccagat cctcaaggaga gcaccctgtc   2400
gagaacactc agctgcaaaa cgagaagctc tacctgtact acctccagaa cgggcgggat    2460
atgtatgtgg atcaggagct ggacatcaac aggctctccg actacgacgt ggatcacatt    2520
gtcccacagt ctttcctcaa ggatgattcc atcgacaaca aggtgctgac gcgcagcgac    2580
aagaataggg ggaagtcgga caacgttccg agcgaggagg tcgtgaagaa gatgaagaat    2640
tactggaggc agctcctgaa tgcgaagctg atcactcaga ggaagttcga caatctgaca    2700
aaggcggaga ggggcgggct ctcggagctg gataaggcgg gcttcatcaa gcggcagctc    2760
gttgaaaccc ggcagatcac caagcatgtc gcccagatcc tcgatagccg catgaacacc    2820
aagtacgatg agaacgacaa gctcattcgg gaggttaagg tcattacgct gaagtccaag    2880
ctcgtcagcg acttcaggaa ggatttccag ttctacaagg ttcgggagat taacaactac    2940
caccacgcgc atgatgcgta cctgaacgct gttgtcggca ctgctctcat caagaagtac    3000
ccaaagctgg agtccgagtt cgtctacggg gactacaagg tctacgatgt ccggaagatg    3060
atcgccaagt cggagcagga gatcgggaag gctactgcga agtacttctt ctacagcaac    3120
attatgaatt tcttcaagac ggagattacg ctggcgaacg gggagattag gaagaggccc    3180
ctcattgaga ctaatgggga gacaggcgag attgtttggg acaagggccg cgacttcgcg    3240
actgtgcgga aggtcctgtc catgccacag gtgaatattg ttaagaagac agaggtgcag    3300
actgggggct tctcgaagga gagcattctc ccaaagcgga acagcgataa gctcatcgcg    3360
cgcaagaagg attgggaccc taagaagtac ggcggcttcg attctcccac tgtggcctac    3420
tccgttctcg tggttgccaa ggttgagaag gggaagtcga agaagctgaa gtcggtcaag    3480
gagctgctcg ggattacaat catggagcgg agcagcttcg agaagaaccc tattgatttc    3540
ctggaggcca agggctacaa ggaggttaag aaggatctca ttatcaagct ccctaagtac    3600
tctctgttcg agctggagaa tggccggaag aggatgctgg cctcggctgg cgagctacag    3660
aagggggaatg agctggccct cccgtcgaag tatgtgaatt tcctgtacct cgcgtcgcac    3720
tacgagaagc tcaagggcag cccggaggat aatgagcaga agcagctctt cgtggagcag    3780
cataagcact acctggacga gatcattgag cagatcagcg agttctcgaa gcgggttatt    3840
ctggctgatg ctaacctgga caaggttctg agcgcctaca ataagcatcg cgacaagccg    3900
attcgcgagc aggcggagaa tattatccac ctgttcaccc tcactaacct cggggctccc    3960
gcggccttca agtacttcga taccacaata gataggaagc ggtacacctc gacgaaggag    4020
gtcctcgacg ccacactcat ccatcagtcg attacaggcc tgtacgagac acggattgac    4080
ctctcgcagc tg                                                        4092
```

<210> SEQ ID NO 4
<211> LENGTH: 4101
<212> TYPE: DNA
<213> ORGANISM: Artificial

<220> FEATURE:
<223> OTHER INFORMATION: Cas9 polynucleotide

<400> SEQUENCE: 4

```
gacaagaagt attccatagg cctggctatc ggcaccaaca gcgtgggctg ggccgtcatc      60
accgacgagt acaaagtgcc gagtaaaaag ttcaaagtgc tcggcaacac cgaccgccac     120
tccataaaga aaaacctgat cggggcgctc ctgttcgaca gcggcgagac ggcggaggcc     180
acccgcttga acgcacggc ccgacggcgc tacacgcggc gcaagaaccg gatctgttac      240
ctacaggaga ttttctctaa cgagatggcg aaggtggacg actcgttctt tcaccgcctc     300
gaagagtcct tcctcgtgga ggaggacaag aaacacgagc gccacccgat cttcggcaac     360
atcgtggacg aggtggccta ccacgagaag tacccgacca tctaccacct ccggaagaaa     420
ctcgtggaca gcacggacaa ggccgacctg aggctcatct acctcgccct ggcgcacatg     480
attaagttcc ggggccactt cctgatcgag ggcgacctga acccggacaa cagcgacgtg     540
gacaagctgt tcatccagct agtccagacc tacaaccagc ttttcgagga aaaccccatc     600
aacgccagcg gggtggacgc gaaggcgatc ctgtccgccc ggctgagcaa gtcccggcgg     660
ctggagaacc tcatcgcgca gttgcccggc gagaagaaga cgggctgtt cgggaacctg      720
atcgccctct ccctggggct caccccgaac ttcaagtcca acttcgacct cgccgaggac     780
gccaaactac agctgagcaa ggacacctac gacgacgacc tcgacaacct gctggcccag     840
atcgggggacc agtacgcaga cctgttcctc gccgccaaga acctctccga cgccatcctg     900
ctgtcggaca cctgcgggt gaacacggag atcacgaagg ccccgctctc ggcctcgatg      960
attaaacgct acgacgagca ccaccaggac ttgaccctcc tcaaggcgct ggtccgccag    1020
cagcttcccg agaagtacaa ggaaatcttt ttcgatcaga gcaagaacgg gtacgccggg    1080
tacatcgacg gcggggcgtc ccaggaggag ttctacaagt tcatcaagcc catcctggag    1140
aaaatggacg gaccgaggagg gctgctcgtg aagctcaacc gcgaagattt gctccgcaag    1200
cagcgcacgt tcgacaacgg gtcgatcccg caccagatcc acctgggcga gctgcacgcg    1260
atcctcaggc gtcaggaaga cttctacccc ttcctcaagg acaaccgcga agatagag      1320
aagattctga ccttcagaat tccttattac gtgggcccgc tggctcgggg caactcgcgc    1380
ttcgcctgga tgacgcgcaa gtccgaggag accatcaccc cgtggaactt cgaggaggtg    1440
gtggataagg gtgcctcggc ccagtccttc atcgagcgga tgaccaactt cgacaagaac    1500
ctgccgaacg agaaggtgct cccccaagcac agcctgctct acgaatattt cacggtgtac    1560
aacgagctga cgaaggtcaa gtacgtgacc gagggaatgg ggaaacctgc attcctctcc    1620
ggggagcaga agaaagccat agtcgacctc ctgttcaaga ccaaccggaa ggtcaccgtc    1680
aagcagctca aggaggacta cttcaagaag atcgagtgct tcgattcagt ggagatcagc    1740
ggcgtcgagg accggttcaa cgccagcctg ggcacctacc acgacctgct caagatcatc    1800
aaggacaagg acttcctcga caacgaggag aacgaggaca cctggagga catcgtgctg    1860
acccctgacgc tcttcgagga ccgcgagatg atcgaggagc gcctcaagac ctacgcccac    1920
ctgttcgacg acaaggtgat gaagcagctc aagcggcgga gatatactgg gtggggccgc    1980
ctctcccgga agctcattaa cggtatcagg gataagcagt ccgggaagac gatcctcgac    2040
ttcctcaagt cggacgggtt cgccaaccgc aacttcatgc agctcatcca cgacgactcc    2100
ctgacgttca aggaggacat ccagaaggcc caagtgtctg gtcaaggtga ctcgctccac    2160
gagcacatcg ccaacctcgc gggcagcccg gccatcaaga agggaatact ccagaccgtc    2220
```

| | |
|---|---|
| aaggtggtgg acgagctggt gaaggtcatg ggccgccaca agccggagaa catcgtcatc | 2280 |
| gagatggcgc gggagaacca gaccacgcag aagggggaga aaaatagccg tgagcgcatg | 2340 |
| aagcgcatcg aggaggggat taaggagttg ggcagccaga tcctcaagga gcaccctgtg | 2400 |
| gagaacacgc agttgcaaaa cgagaagctc tacctgtact acctccagaa cgggagggat | 2460 |
| atgtacgtgg accaagaact ggacatcaac cgcctgtccg actacgacgt ggaccacatc | 2520 |
| gtgccgcaga gcttcctcaa ggacgacagc atcgacaaca aggtgctcac ccggtccgac | 2580 |
| aagaatcggg gcaagtccga caacgtgccc agcgaggagg tcgtcaaaaa gatgaaaaac | 2640 |
| tactggcgac aactactgaa cgccaagctc atcacccagc gcaagttcga caacctcaca | 2700 |
| aaagccgagc gcggcgggtt gagcgagctg acaaggccg ggttcatcaa cgccagctc | 2760 |
| gtcgagacgc gccagatcac gaagcacgtc gcgcagatac tcgacagccg gatgaacacc | 2820 |
| aagtacgacg agaacgacaa gctcatccgg gaggtgaagg tcatcaccct caagtcgaag | 2880 |
| ctcgtgagcg acttccgcaa ggacttccag ttctacaagg tccgggagat caacaactac | 2940 |
| caccacgccc acgatgctta tcttaacgcc gtggtgggga cggccctcat taagaaatac | 3000 |
| ccgaagctgg agtcggagtt cgtgtacggc gactacaagg tgtacgacgt caggaagatg | 3060 |
| atcgccaagt ccgaacagga gatcgggaag gccacgcgca atacttctt ctacagcaac | 3120 |
| atcatgaact tcttcaagac cgagatcacc ctcgccaacg gcgagatccg caagcgcccg | 3180 |
| ctcatcgaga cgaacgggga gaccggcgag atcgtctggg acaaggggcg cgacttcgcc | 3240 |
| actgtgcgga aggtgctgtc gatgccccag gtcaacatcg tcaagaagac ggaggtccag | 3300 |
| acgggcgggt tcagcaagga gagcatcctg ccgaagcgca acagcgacaa gctgatcgcc | 3360 |
| cgcaaaaagg actgggatcc aaaaaagtac ggcggcttcg acagccccac cgtcgcctac | 3420 |
| agcgtcctcg tcgtcgctaa agtcgagaag ggcaagtcca aaaagctcaa gagcgtcaag | 3480 |
| gagctgctcg ggatcaccat catggagcgg tccagcttcg agaagaaccc aattgatttc | 3540 |
| ctggaggcga agggctacaa ggaggtcaag aaagacctca tcataaagct gccgaagtac | 3600 |
| tcactcttcg agctggagaa cgggcgcaag cggatgctgg cgtcggccgg agagctccaa | 3660 |
| aagggcaacg agctggcgct gccgagcaag tacgtgaact tcctctacct ggcgtcccac | 3720 |
| tacgagaagc tcaagggcag tccagaggat aacgagcaga agcagctatt cgtggagcag | 3780 |
| cacaagcact acctggacga gatcatcgag cagatcagcg agttctccaa gcgcgtcatc | 3840 |
| ctggcggacg ccaacctgga caaggtgctg tccgcgtaca acaagcaccg cgacaagccg | 3900 |
| atccgcgagc aagccgagaa catcatccac ctgttcaccc tcacgaacct cggggcaccc | 3960 |
| gccgccttca atatttcga cacgaccatc gaccgcaagc gctacaccag cacgaaggag | 4020 |
| gtgctcgacg ccaccctgat ccaccagagc atcaccgggc tgtacgagac ccgcatcgac | 4080 |
| ctctcgcagc tcggcgggga c | 4101 |

<210> SEQ ID NO 5
<211> LENGTH: 4101
<212> TYPE: DNA
<213> ORGANISM: Artificial
<220> FEATURE:
<223> OTHER INFORMATION: Cas9 polynucleotide

<400> SEQUENCE: 5

| | |
|---|---|
| gacaagaagt acagtattgg attggccatc gggacgaaca gcgtgggctg ggccgtcatc | 60 |
| accgacgagt acaaggtgcc atccaagaag tttaaggttc tggggaatac cgaccgccac | 120 |
| tcgatcaaga aaaatctcat cggggcgctg cttttcgaca cggcgagac ggcggaagcg | 180 |

```
acgcggctca agcggacggc tcgtcgccgt tacacccggc gtaagaaccg catctgttac    240
ctccaggaga tattcagcaa cgagatggcg aaggtggacg actcctttt ccaccgtctt    300 gaggagtcct tcctggtcga ggaggacaag aagcacgagc gccacccgat cttcgggaac    360
atcgtggacg aggtggccta ccacgagaag taccccacga tctaccacct ccgcaaaaaa    420
ctcgtggact caactgacaa ggccgatttg aggcttatct acctcgccct cgcccacatg    480
attaagttcc gtgggcactt cctaatcgag ggtgacctca accccgacaa ctctgacgtg    540
gacaagctgt tcatccagct tgtgcagacc tacaatcagc tctttgagga gaatccgatc    600
aacgcatctg gtgtggacgc aaaggccatc ctcagcgcgc ggctgagcaa gtctaggcgg    660
ttggagaacc tgatcgccca actgcccggc gagaagaaaa atggcctctt cggcaacctg    720
atcgccctgt cgctgggct cacgccgaac ttcaagagta actttgacct ggcggaggac    780
gctaagctcc agctatctaa ggacacatac gacgacgacc tggacaacct gctggcccag    840 atcgcgacc agtacgccga cctcttccta gccgccaaga acctgtccga cgccatcctc    900
ctcagcgaca tcctgcgcgt gaacacggag atcacgaagg ctccgctcag cgcctccatg    960
attaagcggt acgacgagca ccaccaagac ctaactttac tcaaagccct cgtgcggcag    1020
cagcttcccg agaagtacaa agagatattt tttgatcagt ccaagaacgg ttatgcgggc    1080
tacatcgacg gcgcgcgag ccaggaggag ttctacaagt tcatcaagcc catcctggag    1140
aagatggacg gcacggagga gctgctcgtg aagctcaacc gtgaagacct cctgcgaaag    1200
cagcgaacct tcgacaacgg ttcgatcccg caccagatcc acctcgggga gctgcacgcc    1260
atcctgaggc gacaggagga cttctaccct ttcctaaagg acaaccgcga gaagattgaa    1320
aaaatcctga cgtttcgcat accctactac gtcggcccgc tggcgcgcgg caactcccgg    1380
ttcgcctgga tgacccgtaa gagcgaggag acgatcaccc cgtggaactt cgaggaggtc    1440
gtggacaagg cgcgagcgc gcagagcttc atcgagcgca tgaccaactt cgacaagaac    1500
ctcccgaacg agaaggtgct cccaaagcac tccctcctgt acgagtattt caccgtgtac    1560
aacgagttga caaaggtgaa gtacgtgacg gagggaatgc ggaagcctgc gttcctctcg    1620
ggcgagcaga agaaggcaat cgtggacctg ctcttcaaga ccaaccggaa ggtgacggtg    1680
aagcagctca aggaggacta cttcaaaaaa atcgagtgct tcgactccgt ggagataagc    1740
ggcgtggagg accgattcaa cgcctccctc ggcacctacc acgacctcct taagatcatc    1800
aaggacaagg acttcctgga caacgaggag aacgaggaca tcctggagga catcgtgctc    1860
accctgaccc tcttcgagga ccgggagatg atcgaggagc cctcaagac gtacgcccac    1920 ttgttcgacg acaaggtgat gaagcagctc aagcggcggc gatacaccgg gtggggccgc    1980
ctatcccgca aacttatcaa cggcatccgc gacaagcagt ccggcaagac gatcctggat    2040
ttcctcaagt cggacgggtt cgccaaccgg aacttcatgc agctcatcca cgacgacagc    2100
ctcacgttca aggaggacat ccagaaggcc caagtgagcg tcaagggga cagcctccac    2160 gagcacattg cgaaccttgc tgggagccct gcgatcaaga aggggatatt gcaaaccgtg    2220
aaggtcgtgg acgagttggt gaaggtcatg gggcgacaca gcccgagaa catcgtgatc    2280 gagatggcca gggaaaatca gaccacgcag aagggccaaa aaacagccg cgagcggatg    2340 aagcggatcg aggagggcat caaggagctg gggtcgcaga tcctcaagga gcacccggtg    2400
gagaacacgc agctccagaa cgagaagctg tacctctatt acctacagaa cgggcgggat    2460
atgtacgtgg accaggagct agacatcaac cgcctgtccg actacgacgt ggaccatatc    2520
```

-continued

```
gtcccgcagt cgttcttgaa ggacgacagc atcgacaaca aggtgctcac aagatcggat    2580
aagaatcgag gcaagtccga caacgtgccc tcggaggagg tggtcaagaa atgaaaaac     2640
tactggcggc agttgctgaa cgccaagctc attacgcagc ggaagttcga caacctgacg    2700
aaggctgaac gtggtgggct cagcgagcta gacaaggcgg ggttcatcaa gcggcagctc    2760
gtcgagaccc ggcagatcac caagcacgtg gcgcagatcc tggactcgcg catgaacacc    2820
aagtacgacg agaacgacaa gctcatccgt gaggtgaagg tcatcaccct taagtctaag    2880
ctggtcagtg acttccgcaa ggacttccag ttctacaagg tccgggagat caacaactac    2940
caccacgcgc acgacgccta cctcaacgcg gtggtgggga cggcgcttat taagaaatat    3000
cccaagctgg aaagcgagtt cgtttacggc gactacaagg tgtacgacgt ccgcaagatg    3060
atcgcaaagt cggaacagga aatcggaaag gcgacggcca atatttctt ttactccaac     3120
atcatgaatt ttttttaagac ggagatcacc ctggcgaacg ggagatccg caagcggccc    3180
ctcatcgaga ccaacgggga gacgggcgag atcgtctggg acaagggccg ggacttcgcc    3240
accgtgcgga aggtgctttc tatgcctcaa gtcaatatcg tcaaaaagac agaggtgcag    3300
accggcgggt tcagcaagga gtctatcctg ccgaagcgca actcggacaa gctcatcgcg    3360
cgcaagaaag actgggaccc caaaaaatat ggcgggttcg actcgccgac cgtcgcctac    3420
agcgtcctcg tggtggctaa ggtcgagaag ggcaagagca aaaagctaaa gtcggtgaag    3480
gagctgctgg gcatcaccat catggagcgc tcgtctttcg agaagaatcc aatcgacttc    3540
ctagaggcga agggtacaa ggaggtcaaa aaggatctta tcatcaaact gccgaagtac    3600
agtctgttcg agctggagaa cgggcggaag cggatgctgg ctagtgcggg cgagttgcag    3660
aagggcaacg agttggcact gccctccaag tacgtgaact tcctgtacct ggcctcccac    3720
tacgagaagc tcaaggggag ccccgaggac aacgagcaga gcagctatt cgtcgagcag    3780
cacaagcact acctggacga gatcatcgag cagatcagtg agttctccaa gcgggtcatc    3840
ctcgcggacg ccaacctgga caaggtgctg agcgcgtaca acaagcacag ggacaagcca    3900
atcagggaac aggccgagaa catcatccac ctgttcaccc tgaccaacct gggtgcaccg    3960
gctgccttca gtactttga cacgaccatc gaccggaagc gctacacctc cacgaaggag    4020
gtgctggacg ccacgctgat ccaccagagc atcaccgggc tctacgagac acggatcgac    4080
ctgagccagc ttggcgggga c                                             4101
```

<210> SEQ ID NO 6
<211> LENGTH: 4092
<212> TYPE: DNA
<213> ORGANISM: Artificial
<220> FEATURE:
<223> OTHER INFORMATION: Cas9 polynucleotide

<400> SEQUENCE: 6

```
gacaaaaagt attccattgg actcgctatc ggcacgaaca gcgtcgggtg ggcggtcatc      60
actgacgagt acaaggtgcc gagcaagaag tttaaggtgc tgggaaacac cgacaggcac     120
tcgatcaaga aaatcttat cggggcccta ctcttcgact ccggagaaac cgccgaggcc      180
acccggttga agcgcacggc ccgccgtcgc tacaccaggc gcaagaaccg gatctgctac     240
ctccaggaga tattcagcaa tgagatggcg aaggtggacg actcgttttt tcacaggcta    300
gaggagtctt cctcgtgga ggaggacaag aaacacgagc gccacccat cttcggcaac      360
atcgtggatg aggtggcata tcacgagaag tacccaacca tctaccacct ccgcaaaaag   420
ctcgtggact ctaccgacaa ggccgacctc cgtctgatct acctcgcgct ggcccacatg    480
```

| | |
|---|---|
| attaagttcc gaggacactt tctgatcgag ggcgacctga acccagacaa cagcgacgtg | 540 |
| gacaagctgt tcatccaact tgtccagacc tacaatcagc tcttcgagga gaaccctatc | 600 |
| aacgcctcgg gcgtggacgc gaaggccatc ctgtccgccc gcctgagcaa gtcgcggcgg | 660 |
| ctggagaacc tgatcgccca gctccccggc gaaaaaaaga acggcctctt cggcaacctc | 720 |
| atcgcgttgt cgctggggct caccccgaac ttcaagtcca acttcgacct ggccgaggac | 780 |
| gctaaactcc agctctcgaa ggatacctac gacgacgacc tcgacaacct gctggcccag | 840 |
| atcggcgacc agtacgcgga cctttcctg gcggccaaga acctgagcga cgcgatcctc | 900 |
| cttagcgaca tactccgtgt gaacaccgag atcacgaagg ccccgctctc cgcgtccatg | 960 |
| attaagcgct acgacgagca ccaccaagac cttaccctgc ttaaggcgct ggtcaggcag | 1020 |
| cagttaccgg agaagtacaa ggagatcttt tttgatcaat ctaagaacgg ttacgccggg | 1080 |
| tacatcgacg gcggcgcgtc ccaggaggag ttctacaagt tcatcaagcc gatcttggag | 1140 |
| aaaatggacg ggaccgagga gctgctcgtg aagctcaacc gcaagacct cctccgcaag | 1200 |
| cagcgcacct tcgacaacgg gagcatcccg caccagatcc acctgggaga gctgcacgcg | 1260 |
| atcctgcgga gacaagagga cttctacccc ttcctcaagg acaaccggga gaagattgaa | 1320 |
| aaaatactta cttttcgtat cccgtactac gtcgggcccc ttgcgagggg caactccaga | 1380 |
| ttcgcgtgga tgacccgcaa gtccgaggag accatcaccc cgtggaactt cgaggaggtg | 1440 |
| gtggacaagg gcgcgtcggc ccagtcgttc atcgagcgca tgaccaactt cgacaagaac | 1500 |
| cttccgaacg agaaggtgct cccgaagcac agcctgctct acgaatattt tactgtgtac | 1560 |
| aacgagctga cgaaggtcaa gtacgttacg gaggggatga ggaagcccgc cttcctctcc | 1620 |
| ggcgagcaga gaaagccat tgtggatctc ctgttcaaga ccaaccgcaa ggtgacggtg | 1680 |
| aaacagctca agaggactac cttcaagaag atcgagtgct cgactccgt agagatcagc | 1740 |
| ggggtcgagg accgcttcaa cgcctcgctg ggcacgtacc acgacctgct aaagattatc | 1800 |
| aaggacaaag acttcctaga caatgaggag aacgaggaca ttctggagga catcgtgctg | 1860 |
| actctgacgc tgttcgaaga ccgcgagatg atcgaggagc ggcttaagac gtacgcccac | 1920 |
| ctgttcgacg acaaggtgat gaagcagttg aaacggcggc gctacaccgg gtggggccgc | 1980 |
| ctctcccgca agctcatcaa cggcatccgc gacaagcagt cggggaagac gatcctggac | 2040 |
| ttcctcaaga gcgacggctt cgccaaccga aacttcatgc agctaatcca cgacgacagc | 2100 |
| ctgacgttca aggaggacat ccagaaggcc caagtgagcg gccagggaga ctcgctacac | 2160 |
| gagcatatcg ccaacctggc tggcagcccg gcgattaaga aaggaatcct ccaaaccgtc | 2220 |
| aaagtggtgg acgagctggt gaaggtgatg ggccgccaca gcccgagaa cattgtgatc | 2280 |
| gagatggcgc gggagaacca gacgacgcag aagggccaaa aaatagcag ggaaaggatg | 2340 |
| aagcgaatag aggaggggat caaggagctg gggagccaga ttctcaaaga gcacccggtc | 2400 |
| gagaacacac agctccagaa cgagaagctg tacctctact acctccaaaa cggccgcgat | 2460 |
| atgtacgtgg accaggaact agacatcaac cggctgagcg actatgacgt ggaccacatc | 2520 |
| gtgccgcagt ccttcctcaa ggacgactcg attgacaaca agtgctcac tagatccgac | 2580 |
| aagaacagag gcaagagcga taacgtcccg tcggaggagg tcgtcaagaa aatgaaaaac | 2640 |
| tactggcggc agctcctaaa cgccaagctc atcacgcagc gtaagttcga caacctgacg | 2700 |
| aaggcggagc gggcgggct gagcgagctg gacaaagcgg ggttcatcaa gcggcagctc | 2760 |
| gttgagacgc ggcagatcac aaagcacgtc gcgcaaatcc tcgactcccg catgaacacc | 2820 |

```
aagtacgacg agaacgacaa gctcatccgg gaggtgaagg tcattaccct taaatcgaag    2880
ctcgtcagcg actttcgtaa ggacttccag ttctacaagg tcagagagat caacaactac    2940
caccacgccc acgacgccta tctgaacgcc gtggtgggca ccgcgcttat taagaagtac    3000
cccaagctgg agtccgagtt cgtgtacggc gactacaagg tttatgacgt caggaagatg    3060
atcgccaagt cggaacagga gatcggaaaa gctaccgcca atatttcttc tatagcaac    3120 atcatgaact tcttcaaaac cgagatcacc ctcgccaacg gcgagatccg gaagcgcccg    3180
ctcatcgaga ccaacgggga gaccggggag atcgtctggg acaaggggcg ggacttcgct    3240
actgtccgaa aggtgctctc catgccacaa gtgaatatcg tcaagaaaac agaggtgcag    3300
accggagggt tcagtaagga gtccatcctg cccaagcgga actccgacaa gctaattgct    3360
cgcaaaaagg attgggatcc taaaaaatat ggcggcttcg actcgcccac ggtcgcctac    3420
tctgtgctgg tcgtggcgaa ggtggagaag ggcaagtcca agaagctcaa gagcgtcaag    3480
gagctgctgg ggatcacgat catggagcgt agttcgtttg agaagaatcc catcgacttc    3540
ctggaggcta agggctacaa ggaggtcaaa aaggacctca tcattaagct gccgaagtac    3600
agcctcttcg agctggagaa cgggcggaag cgtatgctcg cctccgctgg ggagttacaa    3660
aagggggaac agctggcgct gccgtctaag tacgtcaact tcctgtacct ggcctcccac    3720
tacgagaagc tcaaggggtc gccggaggac aacgagcaga agcagctctt cgtagagcag    3780
cacaagcact acctggacga gatcatcgag cagatttcag agttctcaaa gcgggtcatc    3840
ctcgccgacg ccaacctgga caaggtgctc tcggcctaca acaagcaccg ggacaagccg    3900
atccgcgaac aggccgaaaa catcatccac ctgttcacgc tcaccaacct cggtgccccg    3960
gcggccttca gtactttga cacgaccatc gaccggaagc gctatacctc gacgaaggag    4020
gtgctggacg ccaccctgat ccaccagtcc atcaccgggc tttacgagac ccggatcgac    4080
ctctcgcagc ta                                                        4092

<210> SEQ ID NO 7
<211> LENGTH: 4101
<212> TYPE: DNA
<213> ORGANISM: Artificial
<220> FEATURE:
<223> OTHER INFORMATION: Cas9 polynucleotide

<400> SEQUENCE: 7
gacaagaagt atagtattgg actcgccatc ggaaccaact ctgtggggtg gctgtatt      60 acagatgaat ataaggtgcc atccaaaaag tttaaagttc tgggcaatac tgatagacac    120
tcaatcaaga gaatctgat aggtgcactt ctgtttgata gtggagagac tgccgaggca    180
accagactta aaaggactgc aagaagaaga tataccagaa gaaagaatag gatttgctat    240
ttgcaggaaa tcttcagcaa cgaaatggcc aaggttgatg actcattttt ccataggttg    300
gaggagagtt tccttgtgga ggaagataag aagcacgaaa gacacccaat tttcgggaat    360
atagtggacg aggtggctta tcatgagaag tatcccacta tctaccacct gagaaagaaa    420
cttgtggact caaccgataa ggctgatctt aggcttatat acttggccct tgcacatatg    480
atcaaattca ggggccattt tcttatcgaa ggcgatctta tcccgataa ctcagatgtg    540 gacaagctgt ttatacaact tgtgcaaacc tacaatcaac tcttcgagga aatcccatt    600 aacgcctccg gcgtggatgc aaaagccata ctgtcagcca gactgagcaa agtaggaga    660 ctggagaatc ttatagccca actgcccggt gaaaagaaga tgggctctt cggaaatctg    720 atcgctcttt cattggggtt gacacccaac tttaagagta actttgactt ggcagaagat    780
```

```
gcaaagttgc agctcagtaa agacacatat gacgatgacc ttgacaatct cttggcacaa    840 atagggatc  aatacgctga cctttcctc  gctgccaaga acctcagcga cgctatactg    900
ttgtccgaca ttcttagggt taataccgaa attacaaagg ccctcttag  tgcaagtatg    960 atcaaaaggt atgatgagca tcaccaagac cttacactgc tgaaggctct ggttagacag   1020
caactccctg aaaagtataa ggaaatattc ttcgaccaaa gtaagaacgg gtacgccggt   1080
tatattgatg ggggcgcaag tcaagaagaa ttttacaaat tcatcaagcc aattcttgaa   1140
aagatggacg ggactgagga attgctggtg aaactgaata gagaggacct tcttagaaaa   1200
cagaggacat ttgacaatgg gtccatccca caccagattc atctggggga actccacgca   1260
atattgagga gacaagaaga ctttttaccca ttccttaagg ataatagaga gaaaatcgaa   1320
aaaatcctga ctttcaggat tccttactat gttgggccac tggccagggg gaactcaaga   1380
ttcgcttgga tgacaaggaa gtcagaagaa accataaccc cttggaattt tgaagaggtg   1440
gttgataagg gggcatcagc ccagtctttc atagagagga tgaccaactt tgataaaaat   1500
cttccaaatg agaaggtttt gccaaaacat agtctttgt  acgagtactt tactgtttat   1560
aacgaattga ccaaggtgaa gtatgtgacc gagggaatga ggaagccagc attttgtcc   1620 ggggagcaaa agaaagcaat cgttgatctt ctcttcaaga ccaacagaaa agtgaccgtg   1680
aaacaactga aggaagacta cttcaaaaag atagaatgtt tcgattcagt ggaaattagc   1740
ggtgttgaag acaggttcaa tgcttcattg ggtacttacc acgacctgtt gaagataatc   1800
aaagacaagg actttctcga taatgaggag aacgaagaca tcttggaaga cattgtgctt   1860
acactcactt tgtttgagga cagggaaatg attgaggaaa gactcaaaac ttacgctcat   1920
ttgtttgatg ataaggttat gaaacaacta aaaagaagaa ggtacaccgg ctggggaaga   1980
ttgagtagga aactgatcaa cggtattaga gataaacaat ccggaaagac tatcctcgat   2040
ttccttaaga gtgatggctt tgcaaatagg aatttatgc  agctgattca tgacgactca   2100
cttaccttca aagaagacat ccaaaaagct caggtgtctg gcaaggcga  cagtctgcat   2160 gaacatatag ctaacttggc tgggagtccc gccatcaaga aggggatact tcaaacagtt   2220
aaagttgtgg acgaattggt gaaggtaatg ggaaggcaca agcctgaaaa tatagtgata   2280
gaaatggcaa gggaaaatca aacaacccag aagggacaga agaacagtag ggaaaggatg   2340
aaaaggatag aagaggggat caaagagctt ggtagccaga tcctcaagga acatccagtg   2400
gagaataccc aacttcaaaa cgagaaactc tatttgtact acttgcagaa cggaagagat   2460
atgtatgtgg accaagagct tgatattaac aggctgagcg attatgacgt tgaccacata   2520
gtgccccaat cattcctcaa ggatgactct attgataata aggtgctgac aaggagtgac   2580
aagaatagag ggaaatccga caacgttcca tccgaggaag ttgtgaagaa gatgaagaac   2640
tactggaggc agttgctgaa cgctaagctc attacccaga ggaaattcga taacctgacc   2700
aaagcagaga gaggcgggct gagcgaactc gataaagcag gtttcatcaa gagacaactc   2760
gtggagacta ggcaaattac taagcacgtg gctcaaatac tcgacagcag gatgaacaca   2820
aagtacgacg agaacgacaa gctcattaga gaggttaagg ttattactct gaaaagtaaa   2880
ttggttagcg atttcagaaa ggatttccaa ttctataagg ttagagagat caacaattat   2940
catcatgcac atgatgccta tctgaatgct gtggttggta cagcccttat caagaagtac   3000
cctaagctag agagcgagtt tgtgtacgga gattataagg tgtatgatgt gaggaaaatg   3060
atcgctaaaa gtgagcaaga gattggaaag gctaccgcca atacttctt  ttattccaat   3120
```

```
attatgaatt tcttcaagac agaaatcacc ctggctaacg gcgagataag gaagaggccg    3180
cttatcgaaa ctaatgggga gacaggcgaa atagtgtggg acaaagggag ggatttcgca    3240
actgtgagga aggttttgag catgcctcag gtgaatatcg ttaagaaaac cgaagttcaa    3300
actggagggt tctctaagga aagcattctc cccaagagga actccgacaa gctgattgct    3360
agaaagaaag actgggaccc caagaagtat ggcggattcg actcacccac tgtggcatat    3420
agcgttctcg tggtggcaaa ggttgaaaag ggtaaatcca aaaaactcaa atccgtgaag    3480
gaactccttg gcataactat tatggaaagg agtagctttg aaaagaatcc catcgacttt    3540
ctcgaagcta agggctataa ggaagttaag aaggaccctta taatcaaact tccaaaatac    3600
tcccttttgt agttggaaaa cggcagaaag agaatgttgg ccagtgccgg ggagcttcaa    3660
aagggcaacg aactggctct gcctagcaaa tatgtgaact ttttgtatct ggcatcacac    3720
tacgagaaac ttaaaggctc tcctgaggac aacgagcaaa acagctctt tgttgaacag    3780
cataagcact acctcgacga gattattgag cagatcagcg agttctcaaa gagagttatt    3840
ctggctgacg ctaatcttga caaggttttg tccgcttaca caaacacag gataagcca    3900
atcagggagc aggcagaaaa cataatccat ctctttaccc tgacaaacct cggtgccccc    3960
gctgctttca gtattttga tactaccatt gacaggaaga gatatacttc cactaaggaa    4020
gtgctcgacg caaccctcat acaccaaagt atcacaggcc tctatgaaac taggatagat    4080
ttgtctcaac ttgggggcga t                                             4101
```

<210> SEQ ID NO 8
<211> LENGTH: 4101
<212> TYPE: DNA
<213> ORGANISM: Artificial
<220> FEATURE:
<223> OTHER INFORMATION: Cas9 polynucleotide

<400> SEQUENCE: 8

```
gacaaaaagt attccatcgg gcttgctatc ggaaccaact ctgtggggtg ggcagttatt      60
accgacgaat acaaggtgcc cagcaagaag tttaaggttc tggggaacac agatagacat     120
agcataaaga aaaacctgat aggcgcactg ttgttcgact ccggggaaac agccgaagct     180
accaggctga agagaactgc aagaagaagg tacaccagaa gaaaaaacag aatatgttat     240
ctccaagaga ttttctctaa cgagatggcc aaggtggacg actcattctt tcacagactg     300
gaagaatctt tccttgtgga agaagataag aaacacgaga ggcaccctat ttttggcaat     360
atcgtggatg aggtggctta ccacgaaaaa taccctacaa tataccacct caggaaaaaa     420
ttggttgata gtacagacaa ggccgacctc aggctcatct atttggccct ggcccatatg     480
attaaattca gggggcactt tctcatcgag ggagatttga accccgacaa cagtgatgtt     540
gataagctct ttattcagct cgtgcagact acaatcagt tgtttgagga aaaccccatt     600
aatgcttccg gggtggacgc caaggcaatc ctttctgcaa gactctcaaa gtcaaggaga     660
ctcgaaaatc tgatagcaca gcttccagga gagaagaaga cgggctctt tggaaacctg     720
atcgctctgt cactcggact cacacccaat ttcaaaagca tttttgattt ggcagaggac     780
gctaagctgc aactcagtaa ggataccac gacgatgact ggataatct gctcgcacaa     840
attggggacc agtatgcaga cctgtttctc gcagctaaga acttgagtga cgccatattg     900
ctcagtgaca tcctcagggt taataccgag attacaaaag ctccactctc tgcaagcatg     960
atcaagaggt atgacgagca ccatcaagac ctgacactcc ttaaggcgtt ggttaggcag    1020
caacttcctg aaaagtataa ggaaatcttc ttcgatcaaa gcaaaaacgg ctacgccggc    1080
```

```
tatatagacg ggggagcatc ccaagaagaa ttttataagt tcataaaacc tatattggag    1140
aagatggacg ggacagagga attgctcgtg aaactgaaca gggaggatct cctcaggaag    1200
caaaggacct tcgacaatgg ctccatccca catcagattc acctcggcga actgcacgca    1260
atactgagaa gacaagagga cttttatcct ttcctgaagg acaacaggga gaaaatcgag    1320
aaaatcttga cattcagaat cccatactac gttgggcctc tggccagagg taacagtagg    1380
ttcgcctgga tgactaggaa atcagaggag actattacac cctggaactt tgaagaagtt    1440
gttgataagg gagcttcagc acaatcattc atcgaaagaa tgacaaactt tgacaaaaat    1500
ctgcctaatg agaaagtgct cccaaaacat tccctgctgt atgagtattt taccgtttat    1560
aacgagctta ccaaggtgaa atacgttact gaaggtatga gaaagccagc ttttctttca    1620
ggggagcaaa agaaggctat cgtggatctt ctctttaaga ccaacagaaa ggttaccgtg    1680
aagcagctta aggaagacta ctttaaaaag atcgagtgtt ttgactcagt ggaaataagc    1740
ggtgttgaag atagattcaa cgcatccttg ggaacttatc atgatcttct taagataatc    1800
aaggataaag actttctcga caacgaggaa aacgaagata tactggagga catagttctg    1860
acacttactt tgttcgagga tagggagatg atcgaggaaa gactgaaaac atatgctcac    1920
cttttcgacg acaaagttat gaaacaactc aagagaagga gatatacagg gtgggggaga    1980
ttgagcagga aactgattaa tggtatcaga gacaaacagt caggaaaaac aatactcgac    2040
tttttgaaat cagacgggtt cgcaaatagg aatttcatgc agcttataca cgacgattca    2100 cttacttta aagaggacat tcaaaaggct caagttagtg acaaggtga ctccctccac    2160 gaacacatcg caaatctcgc tggcagccct gcaattaaga agggtatact ccagacagtt    2220
aaggttgttg acgagctggt taaagtgatg gaagacaca aacccgagaa catagtgata    2280
gagatggcca gggaaaacca aaccactcaa aaagggcaga aaaattccag agagaggatg    2340
aaaaggattg aagaaggtat caaggagctg ggtagccaaa ttctgaaaga acatcctgtg    2400
gaaaacactc aactccagaa tgagaaactc tatctgtact atctgcaaaa tgggagagat    2460
atgtatgtgg accaggaact ggacataaac aggctctcag attacgatgt ggatcatatc    2520
gtgccacagt ccttcttaa ggatgatagc atcgacaata aggtgcttac caggtccgac    2580
aagaacaggg gaaagtcaga taacgtgcct tctgaagaag ttgttaaaaa gatgaagaac    2640
tactggagac agctgcttaa cgctaagctc ataacacaga gaagtttga acttgacc    2700 aaggccgaga gaggcggact ctcagaattg gataaggcag ggttcataaa aaggcagctg    2760
gtggaaacaa ggcagataac taaacatgtg gctcagatcc tcgatagtag gatgaataca    2820
aaatacgatg agaacgacaa gctcataagg gaggttaaag tgataactct gaaatccaaa    2880
ctggttagcg attttaggaa ggatttccag ttttacaaag ttagggagat caacaattat    2940
catcacgccc acgatgccta cttgaacgca gttgtgggta ctgcacttat caaaaagtac    3000
cctaagctgg aatccgagtt tgttatgga gactataagt tgtacgacgt tagaaaaatg    3060
attgcaaagt cagagcagga gatagggaaa gccactgcaa aatatttctt ttatagcaat    3120
atcatgaatt tctttaagac agaaatcaca ctggccaatg ggaaataag gaagaggccc    3180 ctgatcgaaa ctaatggcga gacaggggag attgtgtggg ataaaggtag ggactttgca    3240
acagtgagga aagtgctgag catgccccaa gttaatatcg ttaaaaagac cgaggttcaa    3300 acaggggct ttagtaagga aagcattttg cccaagagga atagtgacaa attgattgct    3360
aggaaaaaag attgggaccc caaaaagtat ggcggatttg atagccccac tgttgcttac    3420
```

```
tccgtgctcg tggttgcaaa ggtggagaag ggaaagagca agaaactgaa gtcagttaag    3480
gaactccttg gtatcactat catggaaaga agctcctttg agaagaaccc tattgacttc    3540
ctggaggcta agggtacaa agaggttaag aaagacctta tcattaaatt gcccaaatat    3600
agtcttttcg agcttgaaaa cggaagaaag aggatgcttg catccgctgg cgaattgcaa    3660
aagggcaatg agcttgctct cccttccaag tatgtgaact tcctttatct tgcctcacac    3720
tatgaaaaac tcaaaggttc acccgaagac aacgaacaaa agcaactatt tgtgaacaa    3780 cacaagcact acctggacga aatcattgag caaatttctg agttttcaaa aagggtaatc    3840
ttggctgacg caaatctcga caaagttttg tcagcttaca caaacatag agataagcca    3900 attagagagc aagctgagaa tatcatccat ctgtttaccc tgactaacct tggagcgcct    3960
gctgctttta atatttcga caccacaatc gacaggaaga ggtacactag cactaaggaa    4020
gttctcgacg ccaccctcat ccaccagagt attacaggcc tgtacgagac aagaattgat    4080
ctttctcaac ttggtggtga c                                             4101

<210> SEQ ID NO 9
<211> LENGTH: 4101
<212> TYPE: DNA
<213> ORGANISM: Artificial
<220> FEATURE:
<223> OTHER INFORMATION: Cas9 polynucleotide

<400> SEQUENCE: 9
gataagaagt actcaatcgg tctggcaatc ggaaccaact ctgtgggttg ggcagtgatt     60
acagatgagt ataaggtgcc aagcaaaaaa ttcaaggtgc tgggtaatac cgacagacac    120
agcattaaga gaatttgat tggagcactc ctctttgact caggggaaac agcagaggca    180
acaaggctga gaggacagc aaggcggagg tacacaaggc ggaaaaacag gatatgctac    240
ctccaggaaa tctttagcaa cgagatggct aaagtggatg atagcttttt ccatagactc    300
gaagaatcct tcttgttga agaggacaaa agcatgaaa ggcatcccat cttcggcaat    360
atagttgatg aggttgcata ccatgagaag taccccacaa tctaccacct cagaaagaaa    420
cttgtggact ccacagataa agcagacctg aggctcatat acctcgcact cgcacacatg    480
atcaagttca gagggcactt tctcatcgaa ggtgacctga atccagataa ttcagatgtg    540
gataaactgt ttatacagct ggtgcaaaca tacaaccaac ttttcgagga aaacccaatc    600
aatgcctccg gtgttgatgc aaaggccatc ctgtcagcaa gactcagcaa agcaggcgg    660 ctcgaaaacc tcatcgccca gcttcccggt gaaaagaaga acgggctctt tggtaatctc    720
atcgcattga gccttggtct tactccaaac ttcaagagca attttgatct ggcagaggat    780
gctaaactgc aactctcaaa ggacacatat gacgatgacc ttgacaatct gttggcccag    840 atcgggacc aatatgcaga cctcttcctg gccgcaaaga atcgtcaga tgcaatcctc    900 ttgtccgaca tactgagagt aaacactgag atcacaaagg cacctctgtc cgcctccatg    960
attaagagat acgatgagca tcaccaggat ctgactttgc tcaaagccct cgttagacag    1020
cagttgccag aaaagtacaa agaaatattc tttgatcaat caaaaaacgg atatgcaggg    1080
tacatcgacg tggggcaag ccaggaagag ttctacaaat tcatcaaacc tatcctggaa    1140
aagatggatg ggacagaaga gctgctggtt aagctgaata gggaagacct cctcagaaag    1200
cagaggacat tgataacgg agcatccct catcaaatcc acctcggtga actccatgct    1260
atcctgagaa ggcaggaaga cttttatcca ttttgaagg acaatagga gaaaatcgaa    1320 aaaatcctga cattcagaat cccatactac gttggtcctc tggcaagagg taacagtagg    1380
```

```
ttcgcatgga tgacaaggaa aagcgaggag acaatcacac cctggaattt tgaggaagtt    1440
gttgacaagg gtgccagcgc acaatccttt atcgaaagaa tgacaaattt cgacaagaat    1500
ctgcctaacg aaaaggttct cccaaagcat tcactcctgt acgaatattt tacagtttat    1560
aacgaactga ctaaagttaa atacgttacc gagggtatga ggaagccagc attccttttcc   1620 ggggaacaga agaaagctat tgtggacctc ctgttcaaga caaatagaaa agtgacagtt    1680
aagcaactca aagaggatta cttcaaaaag atcgaatgtt ttgactctgt ggagatcagc    1740
ggggtggagg atagattcaa cgccagcctg gtacatatc atgatctcct gaaaatcatt     1800
aaagacaagg acttccttga caacgaggag aacgaggaca ttctggaaga cattgttctg    1860
accctcacac tctttgagga tagggagatg attgaggaaa gactgaagac ctacgcccac    1920
ctctttgacg ataaagtgat gaaacagctc aagagaagaa ggtatacagg ttgggggaga    1980
ctgagcagga agttgatcaa tgggattagg acaaacagt ccgggaaaac aatcctcgat     2040
tttctgaagt cagacggttt cgcaaacaga aattttatgc agctcattca cgatgacagc    2100
ttgacattca aggaagacat ccaaaaggct caagtgagcg gccaagggga tagcctccac    2160
gagcatattg caaatctggc aggttcacca gccatcaaaa agggcatact tcagacagtt    2220
aaggttgtgg acgaattggt taaagttatg ggcaggcata agccagagaa tatcgttatc    2280
gaaatggcaa gggagaacca aacaactcaa aaagggcaga aaaatagcag agagaggatg    2340
aaaagaatcg aggaagggat caaggaactt gggtcccaaa tcctcaagga gcacccagtt    2400
gaaaatactc aactgcaaaa cgagaagctc tatctctact atctccaaaa cgggagggat    2460
atgtatgttg accaggagct ggatattaac agactgtcag attatgatgt tgatcatatc    2520 gtgcccagt cattcctgaa ggacgattcc atcgacaaca aagttctcac aaggtccgat    2580
aaaaacaggg gcaagtccga taacgttcca agcgaagaag tggtgaaaaa gatgaaaaac    2640
tattggagac aacttctgaa tgcaaagttg attactcaga gaaagtttga caacctcaca    2700
aaagcagaaa gaggcgggct tagcgaactc gataaggcag ggtttatcaa aagacagctg    2760
gttgagacaa ggcagatcac aaaacatgtg gcacagatcc ttgactcaag gatgaatacc    2820
aagtatgatg agaatgataa gttgatcagg gaggttaaag ttatcacact caaatccaaa    2880
ctggtgtcag acttcaggaa agactttcaa ttttataagg tgagggagat caataactac    2940
caccatgcac atgacgccta cctgaacgca gtggtgggta cagcattgat taaaaaatac    3000
cctaagctgg agtctgagtt tgtgtacggg gactacaagg tgtacgacgt gagggaaatg    3060
atagccaagt ccgagcagga gatcgggaaa gcaacagcta gtatttctt ttacagtaat     3120 atcatgaatt tctttaaaac tgagattact ctggcaaacg gggagatcag gaaaagaccc    3180
ctcatcgaga ctaatggtga aacaggtgag atcgtttggg acaaggggag ggattttgct    3240
actgttagaa aagttctgag tatgccacaa gtgaatattg tgaaaaagac agaagttcag    3300
acaggtgggt tctccaaaga atccatcctg cccaagagaa attcagacaa gctcatcgca    3360
agaaagaagg actgggaccc taagaagtac ggaggatttg acagcccac cgtggcctat    3420 tccgtgcttg ttgtggcaaa ggtggagaaa gggaagagca aaaaactgaa atccgtgaaa    3480
gaactgctgg gaattaccat catggaaaga agctccttg agaagaaccc aatcgacttc     3540
ctggaagcaa aaggatataa ggaagtgaaa aaggacctca ttatcaagct cccaaaatac    3600
tcacttttcg agttggagaa cggtagaaag aggatgctgg caagcgcagg gaacttcag    3660 aaaggcaatg agctggcatt gccatcaaag tatgtgaact tcctctactt ggccagccat    3720
```

| | |
|---|---|
| tacgagaaac ttaaaggtag cccagaagat aacgagcaaa acagctctt tgtggaacag | 3780 |
| cataagcatt atctggatga gatcatgaaa caaatctcag agttttccaa gagagttatc | 3840 |
| ctcgcagatg caaacctgga taaggttctc tcagcctata ataagcatag agacaagcca | 3900 |
| attagagagc aagcagagaa cattatccac ttgttcactc ttacaaacct gggggcacca | 3960 |
| gccgccttca atatttcga tacaacaata gacagaaaga ggtataccag caccaaagaa | 4020 |
| gttctcgacg ccacactgat ccatcaatca atcacaggcc tttacgaaac taggatcgac | 4080 |
| ttgtcacaac tgggtgggga t | 4101 |

<210> SEQ ID NO 10
<211> LENGTH: 3307
<212> TYPE: DNA
<213> ORGANISM: Artificial
<220> FEATURE:
<223> OTHER INFORMATION: Cas9 polynucleotide

<400> SEQUENCE: 10

| | |
|---|---|
| gagcaaggac acctacgacg acgacttgga caacctattg cccagatag gtgaccagta | 60 |
| tgcagacctc ttccttgcgg ccaagaactt gagtgacgct atactgctca gtgacatcct | 120 |
| gagggtgaac actgagatca ctaaggcccc tctctctgcc tcaatgatta agcgttacga | 180 |
| cgagcatcac caggatctca ccctgcttaa ggcccttgtt cggcagcagc tccctgagaa | 240 |
| gtacaaggag atatttttg accagtctaa gaacggctac gccggttaca ttgacggtgg | 300 |
| ggcaagccag gaggagttct acaagttcat caagccgatc cttgagaaga tggacggcac | 360 |
| cgaggagcta cttgtcaagt tgaaccggga agacctgctc cggaaacagc gtacattcga | 420 |
| caacggcagc atccctcacc agatccacct gggcgaacta cacgccatcc tccgacgtca | 480 |
| ggaggacttc tatccattct tgaaagataa cagggaaaaa atcgaaaaaa tacttacgtt | 540 |
| tcgaatacct tactacgtgg ggccccttgc tcggggaaac tccagattcg catggatgac | 600 |
| caggaagtca gaggagacca tcacaccctg aactttgag gaggtggttg acaaaggtgc | 660 |
| ttctgcccag tccttcattg agcggatgac taacttcgac aagaacctgc caacgagaa | 720 |
| ggtgctgcca agcacagcc tgctctacga atactttact gtgtacaatg agctgacgaa | 780 |
| ggtgaagtac gtgacagagg ggatgcggaa gccgcttttc ctgagcggcg agcaaaaaaa | 840 |
| agcaatcgtg gacctactgt tcaagaccaa ccgaaaggtg acagtgaagc agctcaagga | 900 |
| ggactacttc aaaaaaatcg agtgcttcga ctctgttgag ataagcggcg tggaggaccg | 960 |
| attcaacgcc tcattgggaa cctatcacga cctgctcaag atcattaagg acaaggactt | 1020 |
| cctggataat gaggagaatg aggacatcct ggaggatatt gtgctgaccc ttactctatt | 1080 |
| cgaggacagg gagatgatcg aggagcgact caagacctac gctcacctgt tcgacgacaa | 1140 |
| ggttatgaag caattgaagc gtaggcgata cacggggtgg ggaagactct cccgaaaact | 1200 |
| gataaacggc atcagggaca gcagtcagg gaagacgatc ttggacttcc tgaaatccga | 1260 |
| cgggttcgcc aaccgcaact tcatgcagct cattcacgac gactcactaa cgttcaaaga | 1320 |
| ggacattcag aaggctcaag tcagtggaca aggcgactcc ctgcacgagc acattgcaaa | 1380 |
| ccttgcggga tccccggcga ttaaaaaggg cattctccaa acggttaagg tggtggacga | 1440 |
| gctggtgaag gtgatgggcc gacacaagcc tgagaacatc gtgatcgaga tggccaggga | 1500 |
| gaaccagact acccagaagg gtcagaagaa ctctcgggaa cgtatgaagc gtattgagga | 1560 |
| ggggattaag gagttgggct ctcaaatcct caaggagcac cctgtggaga acactcagct | 1620 |
| ccaaaacgag aagctgtacc tgtactacct gcaaaacggg cgcgatatgt acgtggatca | 1680 |

```
ggagttggac atcaacaggc ttagcgatta cgacgtggac cacatcgtgc cacagtcatt    1740
cttaaaggac gacagcatcg acaacaaggt tctgacgagg agcgacaaga atcgagggaa    1800
aagtgacaat gttccatccg aggaggtggt caagaaaatg aagaactatt ggcgtcagct    1860
tctgaacgcc aagctcatca cccagcggaa attcgacaac ctgactaagg ctgagcgagg    1920
cggactctcc gagcttgaca aggctggctt catcaagcgg cagttggtcg aaacccgaca    1980
gataacgaag cacgttgccc agatacttga ctcccgtatg aacaccaagt acgacgagaa    2040
cgacaagctc atcagggagg tgaaggtcat taccccttaag tccaaactcg tcagcgactt    2100
tcgtaaggac ttccagttct acaaggtgcg cgagatcaat aactaccacc acgcacacga    2160
cgcctacctg aacgcagtgg ttggaaccgc gttgattaaa aagtaccccca agttggagtc    2220 ggagttcgtt tacggggact acaaggtgta cgacgttcgg aagatgatcg ccaagtctga    2280
acaggagatc gggaaagcaa ccgccaagta tttcttctat agcaacatca tgaacttctt    2340
taaaaccgag atcacacttg ccaatggcga gatccgtaag aggccgctga tcgagacaaa    2400
tggggagact ggcgagatcg tgtgggacaa gggccgcgac ttcgcaaccg ttcggaaagt    2460
cttgtccatg cctcaagtca acatcgtcaa gaagactgag gtgcaaacag gcgggttctc    2520
gaaggagtcc atactgccca gaggaactc agacaagctc atagcacgca aaaaagactg    2580
ggatccaaag aaatacggcg ggttcgactc gccgacagtc gcatactccg tgttagtggt    2640
ggctaaagtg gaaaagggga agtccaagaa gctcaagtcc gtcaaggagt tgctcgggat    2700
caccattatg gaacggtcct cattcgagaa gaatcccatt gacttcctag aggcgaaggg    2760
ctacaaagag gtcaaaaagg acctaattat taagctcccc aagtattcac tcttcgaact    2820
tgaaaatggt cgtaagcgga tgttggcaag cgctggagag cttcagaagg ggaacgagct    2880
tgcactgcct tccaagtacg tgaacttcct gtacctcgcc tctcattacg agaagttgaa    2940
gggctcaccg gaggacaacg agcagaagca gttgttcgtg gagcagcaca agcactacct    3000
cgacgagatc attgagcaga taagtgagtt cagcaaacgg gtgatccttg ccgacgctaa    3060
cctggacaag gtgctgagcg cctacaacaa gcacagagac aagccgatcc gagagcaagc    3120
ggagaacatc atacacctgt tcaccctcac gaacctcggg gctcccgcag ccttcaaata    3180
ttttgacacg accatcgacc gtaaacgcta cactagcacg aaggaggtgc tggacgctac    3240
ccttatccac cagtccatca ccggcctgta cgagacgaga atcgacttgt cgcagctcgg    3300
tggtgac                                                               3307
```

<210> SEQ ID NO 11
<211> LENGTH: 4101
<212> TYPE: DNA
<213> ORGANISM: Artificial
<220> FEATURE:
<223> OTHER INFORMATION: Cas9 polynucleotide

<400> SEQUENCE: 11

```
gacaaaaaat actcaattgg tctggcaatt gggaccaaca gtgtcggatg ggccgtgatt      60
accgacgagt acaaggtgcc gtccaaaaaa ttcaaggtgc ttgggaacac cgaccgccac     120
tcgatcaaga aaaacctaat cggtgcgttg cttttcgaca gtggggagac cgccgaggca     180
acacgcttaa aacgcacagc taggaggaga tatacacggc gcaagaaccg aatatgctac     240
ttacaggaga tattctccaa tgagatggcg aaggtggacg actctttctt ccatcggctt     300
gaggaatcct tcctggtcga ggaggacaag aagcacgagc gacacccgat attcgggaac     360
```

```
atcgttgatg aggtggcgta ccacgagaag tacccaacga tataccactt acgcaagaag    420
ctcgtggact ctacggacaa ggccgacttg cgccttatct acttggcact ggcccacatg    480
attaagttcc gaggccactt ccttatcgag ggtgacctga accccgataa ctccgacgtg    540
gacaagctct tcatccaact cgtccagaca tacaaccagc tattcgagga gaatcctatc    600
aacgcctctg gggtggacgc taaagctatc ctctcagccc gcctgtcaaa gtcgaggagg    660
ttggagaacc taatcgccca gcttccaggc gagaagaaaa atgggctgtt cggaaacctt    720
atcgcactct cactgggcct aaccccgaac ttcaagtcca acttcgacct ggcagaggac    780
gcgaaattgc agttgtcgaa agacacctat gacgatgacc tggacaacct gttggcccag    840
ataggggacc agtacgccga cctgttccta gcggccaaga acctgtccga cgccatcttg    900
ctgtcggata tactgcgggt gaacaccgag atcactaaag cacctctctc cgccagcatg    960
attaagcgtt acgacgagca ccaccaagat ttgaccctgc taaaggcact tgtacggcag   1020
cagcttcccg agaagtacaa ggagatctttt tcgaccaaa gcaagaacgg ctacgccggg   1080
tacatcgacg gaggtgccag ccaggaggag ttctacaagt tcattaagcc catcctggag   1140
aagatggacg ggactgagga actacttgtg aagctgaacc gggaagactt actacggaag   1200
cagcgtacct tcgacaacgg ttctatccca catcagatcc atcttgggga gttgcacgcg   1260
atcctgcgac gccaggagga ctttttacccc ttcctgaaag acaaccgcga gaaaatcgag   1320
aagatactga ccttcagaat accttactac gtcggacccc ttgcgcgagg caactcaaga   1380
ttcgcgtgga tgaccaggaa atcagaggag accatcacac cctggaattt cgaggaggtg   1440
gttgacaagg gtgcctccgc ccagtccttt atcgaacgaa tgaccaactt cgacaagaac   1500
ttgcccaacg agaaggtgct ccccaaacac agcctcctct acgaatattt cacagtgtac   1560
aacgagctta ctaaagttaa gtatgttact gagggcatga ggaaacccgc cttcctgtca   1620
ggcgagcaga agaaagctat tgtggacctc ctttttcaaga ccaaccggaa ggtgacagtg   1680
aagcagctca aggaggacta cttcaagaag atagagtgct tcgacagcgt ggagatcagc   1740
ggggtggagg acagattcaa tgcctctctc ggaacatacc acgacttgct aagatcatc   1800 aaggacaagg acttcctcga caacgaggaa aacgaggata ttctggagga tattgttctg   1860
actcttaccc tgttcgagga ccgggagatg atcgaggagc gtctcaagac ctacgcccac   1920
ctgttcgacg acaaagttat gaagcagctc aagcgtcgga gatataccgg atggggccgt   1980
ctgtctcgga agctcatcaa cgggatcagg gacaagcagt cagggaagac gatcttagac   2040
ttccttaagt ctgacggctt cgccaacagg aacttcatgc agttgatcca cgacgacagc   2100
cttaccttca aggaggacat ccagaaggcc caagtgagtg gccagggtga cagcctccac   2160
gagcatattg ctaatcttgc gggttcccca gcgattaaaa agggcatact tcaaaccgtt   2220
aaggtggtgg acgagcttgt caaggtgatg gggcgacaca gcccgagaa catcgtgatc   2280 gagatggcca gggagaacca gaccacccag aaggggcaga gaatagccga gaacgcatg   2340 aagcgcatcg aggaggggat taaggagcta gggagccaga tcctcaagga acatcccgtc   2400
gagaacaccc agctccagaa cgagaagcta tacctctact acttgcaaaa cgggagggat   2460
atgtacgtgg atcaggagtt ggacattaac cgcctaagcg actacgacgt agatcacatc   2520
gtgcctcagt cattcctcaa agacgacagc attgacaaca agtcttgac ccgatccgac   2580 aagaaccgag gaaaatccga caatgtgccc tcagaggagg tcgtcaagaa aatgaagaac   2640
tattggaggc agctacttaa cgccaaactc ataacccagc ggaagttcga caacctgaca   2700
aaggctgagc gggtgtgggct cagcgagctt gacaaggctg gcttcatcaa gcggcagttg   2760
```

```
gtggagacaa gacagataac gaagcacgtg gctcagatcc tggactctcg catgaacacg    2820
aagtacgacg agaacgacaa attgatccgc gaggtcaagg ttattacgct caagagcaaa    2880
cttgtcagcg atttccgcaa ggacttccag ttctacaagg tgagggagat taacaactac    2940
caccatgcac atgatgccta cttgaacgca gtggtgggga ccgcgcttat aaaaagtac    3000 cctaagttgg agtcagagtt cgtttatggg gactacaagg tgtacgacgt ccggaagatg    3060
attgcaaagt ctgaacagga aatcgggaag gccaccgcca aatatttctt ctacagtaac    3120
attatgaatt ttttttaagac tgaaattact ctcgcaaacg gcgagatcag gaagcgtccc    3180
ctcatcgaga caaacgggga gaccggggag atagtctggg acaaggggcg ggacttcgct    3240
acggtgagga aggtgctctc gatgccacaa gtgaacatcg tcaaaaagac agaggtgcag    3300
accggtggct tctcaaagga gtcaatcctg ccaaaacgta acagcgacaa gctcatcgcc    3360
cgcaagaaag actgggaccc taagaagtat ggtgggttcg actcaccgac ggtcgcatac    3420
tccgttctgg tcgtggcaaa ggtggaaaag ggcaagtcca aaaaactgaa atccgtgaag    3480
gagttgcttg gcattaccat catggaacgc agcagcttcg agaagaaccc cattgacttc    3540
ctggaggcta aagggtacaa ggaggtcaag aaagatttaa ttattaagct acctaagtac    3600
agcttgttcg agctggagaa cggccgaaaa cgaatgctcg catccgccgg gaacttcaa    3660 aagggcaacg agcttgcgct gccctccaag tacgtgaact tcctgtactt ggcatcccac    3720
tacgagaaac tcaagggtag cccagaggac aacgagcaga agcagctatt cgtggagcag    3780
cacaagcact acctcgacga gataatcgag cagatcagtg agttcagtaa gcgggtgata    3840
ctcgcggacg ccaacttgga caaggtgctt agtgcctaca caagcaccg tgacaagccc    3900 atccgagaac aggctgagaa catcatccac cttttcactc tgacaaacct cggtgctccc    3960
gccgccttca aatacttcga cactaccatc gacaggaagc gctacacatc tacgaaggaa    4020
gttcttgacg ctacgcttat tcatcagtct atcacagggc tgtacgagac aaggatcgac    4080
cttagccaac tcggcgggga t                                             4101
```

<210> SEQ ID NO 12
<211> LENGTH: 5499
<212> TYPE: DNA
<213> ORGANISM: Artificial
<220> FEATURE:
<223> OTHER INFORMATION: base editor

<400> SEQUENCE: 12

```
ggttcgaaga agagaagaat taaacaagat tcttcggaga caggccccgt tgccgttgac      60
cccacgctgc ggaggcggat tgagccccac gagttcgagg ttttcttcga cccaagggag     120
ctgaggaaag agacatgcct cctctacgag atcaactggg gcgggcggca cagcatctgg     180 aggcataccct cgcagaacac caacaagcat gtggaggtta atttcattga agttcaca     240 actgagaggt acttctgccc caacactagg tgctcgatta cttggttcct gagctggagc     300
ccatgcgggg agtgcagccg cgcgatcaca gagttcctgt cccgctaccc ccacgtgacg     360
ctcttcatct acattgcccg gctgtaccat catgccgatc cacggaatag gcaggggctg     420
cgggatctga tcagcagcgg ggtgacgatt cagatcatga ccgagcagga gtcggggtac     480
tgctggcgga acttcgtgaa ttactccccc tccaacgagg cgcactggcc caggtatcca     540
catctctggg tccggctgta tgtgctggag ctgtactgca tcatcctcgg cctgccccca     600
tgcctcaaca tcctcaggcg gaagcagccc cagctgacgt tcttcacgat cgctctgcaa     660
```

```
tcgtgccact accagaggct gccccctcat atcctctggg ctaccggcct caagtcggga    720
ggctcttccg gcgggagcag cggctcggaa cgccaggta cctcggagtc ggctacacca    780
gagagttccg gcgggtccag cgggggcagc gacaagaagt acagcatcgg gctggcgatc    840
gggaccaact ccgtcggctg ggctgtgatt accgacgagt acaaggtgcc atccaagaag    900
ttcaaggtcc tcggcaacac tgaccggcac agcattaaga agaacctgat tggggcgctg    960
ctgttcgatt cgggggagac tgcggaggcg accaggctga agcggactgc gcgccggagg   1020
tacaccagga ggaagaatcg gatctgctac ctccaggaga ttttctcgaa tgagatggcc   1080
aaggtggacg attccttctt ccatcgcctg gaggagtcgt tcctcgttga ggaggacaag   1140
aagcatgaga ggcatcccat tttcgggaat atcgttgacg aggtggctta ccatgagaag   1200
tacccgacca tctaccatct gcggaagaag ctcgtcgatt cgaccgataa ggccgacctg   1260
cggctgatct acctggccct cgcgcacatg attaagttcc ggggccattt cctcatcgag   1320
ggcgacctca acccgacaa ctcggacgtg ataagctct tcattcagct cgtgcagaca   1380
tacaaccagc tcttcgagga gaatcccatt aacgcctcgg gggtcgacgc taaggctatt   1440
ctctcggctc ggctgtcgaa gtcgcgccgg ctggagaatc tcattgccca gctcccaggc   1500
gagaagaaga acggctctt cggcaacctg attgccctgt cgctggggct cacaccgaat   1560
ttcaagtcga acttcgacct cgccgaggac gctaagctcc agctcagcaa ggatacttac   1620
gatgatgacc tcgataacct gctcgcccag attgggatc agtacgcgga tctgttcctc   1680
gcggccaaga atctcagcga tgctattctc ctgtcggaca ttctccgcgt caacacagag   1740
attactaagg ccccactgtc ggcgagcatg attaagaggt acgatgagca tcatcaggac   1800
ctgacactgc tcaaggcgct ggtccggcag cagctccccg agaagtacaa ggagatttc   1860
ttcgatcagt caaagaatgg gtacgcgggc tacattgatg gcgcgcgtc ccaggaggag   1920
ttctacaagt tcattaagcc catcctggag aagatggacg ggaccgagga gctgctggtg   1980
aagctcaatc gggaggacct gctccggaag cagcgcacat cgacaatgg ctcgattcct   2040
caccagattc acctgggcga gctgcacgcc attctccgca ggcaggagga cttctacccg   2100
ttcctcaagg acaaccgcga gaagatcgag aagatcctga ccttccggat tccatactac   2160
gtggggccgc tcgcgcgggg gaactcccgg ttcgcgtgga tgactcgcaa gtccgaagaa   2220
acgattacac cgtggaattt cgaggaggtc gtcgacaagg gcgctagtgc gcagtcattc   2280
attgagagga tgaccaattt cgataagaac ctgcctaacg agaaggtgct gccgaagcat   2340
tcgctgctct acgagtactt caccgtttac aatgagctga ccaaggtgaa gtatgtgact   2400
gagggcatga ggaagccagc gttcctgagc ggcgagcaga agaaggctat cgtggacctg   2460
ctcttcaaga ctaaccggaa ggtgactgtg aagcagctca aggaggacta cttcaagaag   2520
attgagtgct tcgattccgt tgagattagc ggggtggagg atcggttcaa tgcttcgctc   2580
gggacatacc acgatctcct gaagatcatt aaggataagg acttcctcga caacgaggag   2640
aacgaggaca ttctcgaaga tattgtcctg accctcaccc tcttcgagga tcgggagatg   2700
atcgaggaga ggctcaagac atacgctcat ctgttcgatg ataaggtcat gaagcagctg   2760
aagcgcaggc ggtacacagg gtgggggcgg ctgagccgga agctgatcaa cgggattcgg   2820
gataagcagt ccgggaagac aattctcgac ttcctcaagt ccgacgggtt cgctaaccgg   2880
aacttcatgc agctcattca tgatgactcg ctgacattca aggaggatat tcagaaggcg   2940
caggtttcgg ggcagggcga ctcgctccac gagcatattg cgaatctggc gggctccccc   3000
gcgattaaga agggcattct gcaaaccgtc aaggtggttg atgagctggt caaggtcatg   3060
```

```
gggcggcata agccagagaa tattgtcatc gagatggcgc gggagaatca gaccacacag    3120
aaggggcaga agaactcacg ggagcggatg aagcgcatcg aggagggcat caaggagctg    3180
gggtcgcaga tcctgaagga gcatcccgtg gagaacactc agctgcaaaa tgagaagctg    3240
tacctctact acctccagaa cgggagggac atgtatgtgg atcaggagct ggatattaat    3300
aggctgagcg attacgatgt cgaccacatt gtcccacagt cgttcctgaa ggacgacagc    3360
attgacaaca aggtgctgac ccgctcggat aagaacaggg gcaagagcga taatgttcca    3420
agcgaggagg ttgtgaagaa gatgaagaac tactggcggc agctcctgaa cgcgaagctc    3480
atcacacagc ggaagttcga caacctcacc aaggctgagc gcggggggcct gagcgagctg    3540 gacaaggcgg ggttcattaa gaggcagctg gtcgagacac ggcagattac aaagcatgtt    3600
gcgcagattc tcgattcccg gatgaacacc aagtacgatg agaacgataa gctgattcgg    3660
gaggtcaagg taattaccct gaagtccaag ctggtgtccg acttcaggaa ggacttccag    3720
ttctacaagg ttcgggagat caacaactac caccacgcgc atgatgccta cctcaacgcg    3780
gtcgtgggga ccgctctcat caagaagtac ccaaagctgg agtcagagtt cgtctacggg    3840
gattacaagg tttacgacgt gcggaagatg atcgctaaga gcgagcagga gattggcaag    3900
gctaccgcta agtacttctt ctactccaac atcatgaact tcttcaagac agagattacc    3960
ctcgcgaatg gcgagatccg gaagaggccc ctcatcgaga caaatgggga gacaggggag    4020
attgtctggg ataaggggcg ggatttcgcg accgtccgga aggtcctgtc gatgcccag    4080 gttaatattg tcaagaagac tgaggtccag actggcggct tctcaaagga gtcgattctc    4140
ccaaagagga actccgataa gctcattgct cggaagaagg attgggaccc caagaagtac    4200
gggggattcg actccccccac tgttgcttac tctgttctgg ttgttgctaa ggtggagaag    4260
gggaagtcga agaagctgaa gagcgtgaag gagctgctcg ggattacaat tatggagagg    4320
tcatccttcg agaagaatcc catcgacttc ctggaggcca agggctacaa ggaggtgaag    4380
aaggacctga ttattaagct gcccaagtac tcgctcttcg agctggagaa tgggcggaag    4440
cggatgctgg cgtccgcggg ggagctgcaa aaggggaacg agctggcgct ccctccaag    4500 tatgtgaact tcctctacct ggcgtcgcac tacgagaagc tgaaggggtc cccagaggat    4560
aatgagcaga agcagctctt cgtcgagcag cataagcact acctggacga gattatcgag    4620
cagattagcg agttctcgaa gcgggtcatc ctcgcggatg cgaacctgga taaggtgctc    4680
agcgcctaca ataagcaccg ggacaagccg attcgggagc aggcggagaa tattattcac    4740
ctcttcacac tcaccaacct cggggcacca gctgcgttca gtacttcga cactactatc    4800 gaccggaagc ggtacacctc gacgaaggag gtgctcgacg ccaccctcat tcaccagtcg    4860
atcacaggcc tgtacgagac acggattgac ctgtcccagc tcgggggcga cagcggcggg    4920
tcgggcgggt cggcggctc aaccaacctg tcggatatta ttgagaagga gacaggcaag    4980
cagctggtta ttcaggagtc gatcctgatg ctcccgagg aggtgaggga ggtcatcggg    5040
aacaagccag agtcggatat tctcgtgcac accgcgtacg acgagtcgac agacgagaac    5100
gttatgctgc tcacatcgga cgcgccagag tacaagcct gggcgctggt aattcaggat    5160
tcaaatggcg agaacaagat caagatgctg tccgggggca gcggcgggtc cggggggctcg    5220 accaacctct ccgatataat tgagaaggaa accggcaagc agctcgttat tcaggagtcg    5280
attctgatgc tccccgagga ggtcgaggag gtaattggga ataagccgga gtcggatatt    5340
ctggtgcaca ctgcttacga tgagagcaca gacgagaatg ttatgctgct gaccagcgac    5400
```

```
gctcctgagt acaagccgtg ggcgctggtt attcaggatt ccaatgggga gaacaagatt    5460
aagatgctgg gatctaagaa gagaagaatt aaacaagat                           5499

<210> SEQ ID NO 13
<211> LENGTH: 5499
<212> TYPE: DNA
<213> ORGANISM: Artificial
<220> FEATURE:
<223> OTHER INFORMATION: base editor

<400> SEQUENCE: 13
ggttcgaaga agagaagaat taaacaagat tcttctgaga ctggccccgt tgctgttgac      60
cccacgctcc gccgccgcat tgagccccac gagttcgagg ttttcttcga cccacgcgag    120
ctgcggaagg agacatgcct cctgtacgag attaattggg gagggcggca ttcgatttgg    180
cggcacacct cgcagaatac aaacaagcac gttgaggtga acttcatcga agttcaca     240 accgagcggt acttctgccc caatacgcgg tgctcaatta cttggttcct gtcctggagc    300
ccctgcgggg agtgctccag ggcgatcaca gagttcctgt cccggtatcc acacgtcacc    360
ctcttcatct acatcgctcg gctctaccac catgctgatc cccgcaaccg ccaggggctc    420
cgcgacctca tttcgtcggg cgtgaccatc cagatcatga cggagcagga gagcggctac    480
tgctggcgca atttcgtcaa ctactcaccc tccaacgagg ctcactggcc tcggtatccc    540
cacctctggg tgcggctcta cgtgctggag ctgtactgca ttattctggg cctcccacca    600
tgcctcaata tcctccgccg gaagcagcca cagctcacct tcttcaccat tgctctccag    660
tcctgccatt accagcggct ccctccacat atcctctggg ccactggcct caagtccggc    720
gggtcgagcg gcgggtcgag cggctcagag acacccggta cctcggagtc ggccacacca    780
gagtcgtccg gcggcagcag cggcggctca gacaagaagt actccattgg cctggcgatt    840
gggacaaact cggtggggtg ggccgtgatt acggatgagt acaaggttcc aagcaagaag    900
ttcaaggtcc tcgggaacac agatcggcat tcgattaaga gaatctcat ggggcgctc     960 ctcttcgact cgggggagac agcggaggct accaggctca gcggacagc caggcggcgg   1020 tacacaaggc ggaagaatcg catctgctac ctccaggaga ttttctcgaa tgagatggcg   1080
aaggtggacg acagcttctt ccatcggctg gaggagtcct tcctggtgga ggaggataag   1140
aagcacgaga ggcatccaat tttcgggaac atcgtggacg aggttgcgta ccatgagaag   1200
taccctacaa tctaccatct gcggaagaag ctggttgact ccacagacaa ggcggacctg   1260
aggctgatct acctcgctct ggcccacatg attaagttcc gcgggcattt cctgatcgag   1320
ggggacctga atcccgacaa ttcggatgtg acaagctct catccagct ggtgcagacc     1380 tacaaccagc tgttcgagga gaatcccatc aatgcgtcgg gcgttgacgc taaggccatt   1440
ctgtccgcta ggctgtcgaa gagcaggagg ctggagaacc tgatcgccca gctgccaggc   1500
gagaagaaga tgggctcttc gggaatctg attgcgctct ccctggggct gacaccgaac    1560
ttcaagagca atttcgatct ggctgaggac gcgaagctcc agctctcgaa ggacacttac   1620
gacgatgacc tcgataacct cctcgcgcag atcgggacc agtacgctga tctcttcctc    1680
gccgctaaga acctctcgga tgctatcctg ctctccgaca ttctccgggt taataccgag   1740
attacaaagg ccccactgtc ggcgtccatg atcaagcggt acgatgagca tcatcaggat   1800
ctcacccctg ccaaggccct cgtgcggcag cagctgcccg agaagtacaa ggagattttc   1860
ttcgaccaga gcaagaatgg gtacgctggc tacattgacg gcggggcctc acaggaggag   1920
ttctacaagt tcatcaagcc aatcctggag aagatggatg gacagagga gctgctggtg   1980
```

```
aagctcaacc gggaggatct gctcaggaag cagcggacgt tcgacaacgg gtcgattccc    2040
catcagatcc acctggggga gctgcacgcg atcctgcgcc ggcaggagga tttctaccct    2100
ttcctgaagg ataatcggga gaagatcgag aagattctca ccttccggat tccctactac    2160
gtcgggccac tcgcgcgggg caatagcagg ttcgcctgga tgacacgaa gagcgaggag    2220 acaatcaccc cctggaactt cgaggaggtt gtcgacaagg gggcgtccgc ccagtcattc    2280
attgagcgga tgaccaattt cgacaagaat ctgccaaatg agaaggttct cccaaagcat    2340
agcctcctct acgagtactt cactgtttac aacgagctga ccaaggtgaa gtatgtgacc    2400
gagggcatgc ggaagcccgc gttcctgtcc ggcgagcaga agaaggccat tgtggacctc    2460
ctgttcaaga ccaatcgcaa ggtcacagtc aagcagctca aggaggatta cttcaagaag    2520
atcgagtgct tcgactcggt tgagattagc ggggtggagg atcggttcaa cgcgagcctc    2580
ggcacttacc acgacctcct gaagatcatc aaggataagg acttcctcga caacgaggag    2640
aacgaggata ttctggagga catcgtgctc accctgacgc tgttcgagga tcggagatg    2700 atcgaggagc gcctgaagac ctacgctcat ctcttcgatg ataaggtcat gaagcagctg    2760
aagaggaggc ggtacaccgg tgggggccgc ctgagcagga agctcattaa cgggatcagg    2820
gacaagcaga gcggcaagac catcctggac ttcctcaaga gcgatggctt cgccaaccgg    2880
aatttcatgc agctcatcca cgacgactcc ctcaccttca aggaggacat tcagaaggct    2940
caggtcagcg ccagggcga ctcgctgcat gagcacatcg ctaacctggc gggcagccca    3000
gccatcaaga agggcatcct ccagacagtg aaggtcgtgg atgagctggt gaaggtcatg    3060
ggccggcata agcccgagaa tattgtgatt gagatggcgc gggagaatca gaccactcag    3120
aagggccaga agaactcgcg ggagcgcatg aagaggatcg aggaggggat taaggagctg    3180
ggcagccaga ttctcaagga gcaccccgtg gagaataccc agctccagaa cgagaagctg    3240
tacctctact acctccagaa tgggcggac atgtatgttg atcaggagct ggacatcaat    3300
cgcctctcgg attacgacgt ggaccacatc gtgccccaga gcttcctgaa ggatgatagc    3360
atcgacaata aggtcctgac ccgctccgac aagaatcgcg gcaagagcga caacgtgccg    3420
agcgaggagg tcgtgaagaa gatgaagaac tactggcggc agctgctgaa cgcgaagctc    3480
attacacagc ggaagttcga taacctgacg aaggcggaga ggggcggcct ctccgagctg    3540
gacaaggcgg gcttcattaa gaggcagctc gtggagactc gccagatcac caagcacgtg    3600
gctcagatcc tcgatagccg gatgaatacg aagtacgatg agaatgacaa gctcatccgg    3660
gaggtgaagg taatcaccct gaagtcaaag ctcgttagcg atttccggaa ggacttccag    3720
ttctacaagg tgcgggagat taacaactac catcatgcgc acgatgcgta cctcaatgcg    3780
gtggtgggca cagccctgat taagaagtac cccaagctgg agagcgagtt cgtctacggg    3840
gactacaagg tgtacgatgt tcggaagatg atcgccaaga gcgagcagga gattgggaag    3900
gccaccgcta agtacttctt ctactcgaat attatgaatt tcttcaagac cgagatcaca    3960
ctcgctaatg gggagattcg gaagcggccc ctcatcgaga ctaacgggga gactggcgag    4020
attgtgtggg acaaggggcg cgacttcgct accgtgcgca aggtcctctc gatgccccag    4080
gttaatattg ttaagaagac agaggtgcag acgggcgggt tctccaagga gtctatcctg    4140
ccgaagcgga actcggacaa gctgatcgcc cgcaagaagg attgggaccc caagaagtac    4200
gggggattcg atagcccaac cgtggcttac agcgtcctgg tggtcgccaa ggttgagaag    4260
gggaagtcga agaagctcaa gagcgttaag gagctgctgg gcatcaccat catggagcgg    4320
```

```
tccagcttcg agaagaatcc tatcgacttc ctggaggcta aggggtacaa ggaggtcaag    4380
aaggacctga tcattaagct gcccaagtac tctctgttcg agctggagaa cgggaggaag    4440
cggatgctgg cgtctgctgg cgagctacag aagggcaatg agctggcgct cccctcgaag    4500
tatgtcaact tcctctacct ggcttcccat tacgagaagc tgaagggctc gcccgaggat    4560
aatgagcaga agcagctctt cgtggagcag cacaagcact acctcgacga gatcattgag    4620
cagatttcgg agttctcgaa gcgggtcatt ctcgcggacg cgaacctcga caaggtcctc    4680
tcggcgtaca acaagcaccg ggacaagccc atccgggagc aggccgagaa cattatccac    4740
ctcttcacac tgaccaacct cggcgctccc gccgcgttca agtacttcga caccaccatt    4800
gaccgcaaga gatacacatc caccaaggag gtgctggacg cgaccctcat ccaccagagc    4860
atcacaggcc tctacgagac acggatcgac ctctcgcagc tcggggggcga tagcggcggg    4920 tctgggggct ccggcgggtc gacaaacctc agcgatatta tcgagaagga gactgggaag    4980
cagctggtaa ttcaggagtc aatcctcatg ctcccagagg aggtggagga ggttatcggg    5040
aacaagccgg agtcggacat tctcgtgcac acggcgtacg atgagtccac tgacgagaat    5100
gtgatgctcc tcacctccga tgcgcccgag tacaagcccct gggcgctcgt gattcaggac    5160
tccaacggcg agaataagat caagatgctc agcggggggct ccggcggcag cggcggctcg    5220
acaaacctga gcgatattat tgagaaggag acagggaagc agctggtaat ccaggagagc    5280
attctcatgc tccccgagga ggtcgaggag gtaattggga ataagcccga gagcgatatt    5340
ctcgtgcata cagcgtacga tgagtcgaca gatgagaacg tgatgctcct cacatccgac    5400
gctccagagt acaagccgtg ggcgctcgtt attcaggatt ccaatgggga gaacaagatt    5460
aagatgctcg gatctaagaa gagaagaatt aaacaagat                          5499
```

<210> SEQ ID NO 14
<211> LENGTH: 5499
<212> TYPE: DNA
<213> ORGANISM: Artificial
<220> FEATURE:
<223> OTHER INFORMATION: base editor

<400> SEQUENCE: 14

```
ggttcgaaga agagaagaat taaacaagat agcagcgaga caggcccagt tgccgtggac      60
cctactctga ggaggcgcat tgagcccccat gagttcgagg tgttcttcga ccccccgcgag    120 ctaaggaagg agacatgcct cctctacgag atcaactggg gcgggcggca ttcgatctgg     180
cggcatacaa gccagaacac caataagcac gtggaggtca acttcatcga gaagttcacc     240
accgagaggt acttctgccc aaacacgcgg tgctctatca catggttcct gtcgtggtcg     300
ccatgcgggg agtgctcgcg ggcgattact gagttcctgt cgcgctaccc acacgtcacc     360
ctgttcatct acattgcgcg cctgtaccat catgctgacc ccaggaatag gcagggctc      420 cgggacctga tttcctctgg ggtcacaatt cagatcatga ccgagcagga gtcgggtac      480 tgctggcgga acttcgttaa ctacagccca tccaacgagg cgcactggcc acggtatcca     540
cacctgtggg ttcggctcta cgtcctggag ctgtactgca tcatcctcgg gctgccacca     600
tgcctgaaca ttctgcggcg gaagcagccg cagctcacgt tcttcactat tgctctccag     660
agctgccact accagaggct gccacccac attctgtggg cgaccgggct gaagtccggc     720
ggctccagcg gcgggtcgtc aggctcagag acaccaggta cctccgagtc agccaccccc     780
gagtcgtcgg gcgcagctc gggcggctcg gacaagaagt actcgatcgg cctggcgatt     840
ggcacaaaca gcgtggggtg ggctgtgatc actgatgagt acaaggtgcc atcgaagaag     900
```

```
ttcaaggtgc tgggaaatac agaccggcat tcgatcaaga agaatctcat tggcgctctc    960
ctcttcgatt ccggcgagac tgctgaggcg acccgcctga agcgcaccgc ccggcggcgc   1020
tacactcggc ggaagaatag gatttgctac ctccaggaga ttttctcgaa tgagatggcc   1080
aaggtggatg acagcttctt ccaccgcctg gaggagtcgt tcctggtcga ggaggacaag   1140
aagcatgagc ggcaccctat cttcgggaat atcgttgatg aggtcgccta ccacgagaag   1200
taccccacta tctaccatct ccgcaagaag ctcgtgaca gcacagataa ggccgacctc   1260
cgcctgatct acctcgccct cgcgcacatg attaagttcc gggggcactt cctcattgag   1320
ggggatctga atcccgataa ctccgacgtg gacaagctgt tcatccagct ggtgcagaca   1380
tacaaccagc tgttcgagga gaatcccatc aacgcgagcg gcgtggacgc taaggccatt   1440
ctgtcggcta ggctctcgaa gtcgaggcgg ctggagaacc tgattgcgca gctccccggc   1500
gagaagaaga acgggctgtt cgggaatctc atcgccctct ccctcggcct cacaccaaac   1560
ttcaagagca atttcgacct ggctgaggac gctaagctgc aactctcaaa ggatacatac   1620
gatgacgacc tggacaatct cctggctcag atcggcgacc agtacgctga cctgttcctc   1680
gcggccaaga atctgtcgga cgcgattctc ctcagcgaca tcctgcgcgt caataccgag   1740
attacgaagg ctccactgtc tgcgtcaatg attaagcggt acgatgagca tcaccaggat   1800
ctgaccctcc tgaaggcgct cgtgcggcag cagctgcccg agaagtacaa ggagattttc   1860
ttcgatcaga gcaagaatgg ctacgccggc tacatcgacg ggggcgcgag ccaggaggag   1920
ttctacaagt tcatcaagcc catcctggag aagatggacg gcaccgagga gctactcgtg   1980
aagctcaatc gggaggatct cctccggaag cagcggacat tcgataacgg gtctatccca   2040
caccagatcc acctcggcga gctgcatgcg attctgcggc ggcaggagga tttctaccct   2100
ttcctgaagg acaaccggga gaagatcgag aagatcctca cattccggat tccatactac   2160
gtcggccccc tggcgagggg caatagccgg ttcgcgtgga tgacaaggaa gtccgaggag   2220
actattaccc cgtggaattt cgaggaggtg gttgacaagg gcgcttccgc gcagagcttc   2280
attgagcgga tgacaaactt cgacaagaat ctcccccaacg agaaggtcct gccgaagcat   2340
agcctcctgt acgagtactt caccgtctac aatgagctaa ctaaggtcaa gtatgtgaca   2400
gagggcatga ggaagccagc cttcctctca ggcgagcaga agaaggccat tgtggacctc   2460
ctgttcaaga caaccgcaa ggtgacagtg aagcagctga aggaggatta cttcaagaag   2520
attgagtgct tcgactcagt ggagatttca ggcgtggagg atcggttcaa cgcgagcctg   2580
gggacttacc acgacctgct gaagattatt aaggacaagg acttcctgga taacgaggag   2640
aatgaggaca tcctggagga tattgtgctc accctcaccc tgttcgagga cagggagatg   2700
attgaggaga ggctcaagac ctacgcgcac ctgttcgatg acaaggtcat gaagcagctg   2760
aagaggcggc gctacactgg gtggggccgc ctgtcgcgga agctgatcaa cggcattcgg   2820
gataagcagt ccgggaagac cattctggat tccctgaagt cggacggctt cgccaacagg   2880
aatttcatgc agctgatcca cgacgactcc ctcaccttca aggaggacat tcagaaggcc   2940
caggttagcg gccaggggga ctcactccac gagcatattg ccaatctggc cggctctcca   3000
gctatcaaga agggcatcct gcaaacagtt aaggttgttg acgagctggt taaggtcatg   3060 ggcggcata agcccgagaa cattgtcatc gagatggctc gggagaacca gacaactcag   3120
aagggccaga agaactccag ggagcgcatg aagcggattg aggagggcat taaggagctg   3180
gggtcccaga tcctcaagga gcaccctgtc gagaacactc agctgcaaaa cgagaagctc   3240
```

```
tacctgtact acctccagaa cgggcgggat atgtatgtgg atcaggagct ggacatcaac      3300
aggctctccg actacgacgt ggatcacatt gtcccacagt ctttcctcaa ggatgattcc      3360
atcgacaaca aggtgctgac gcgcagcgac aagaataggg ggaagtcgga caacgttccg      3420
agcgaggagg tcgtgaagaa gatgaagaat tactggaggc agctcctgaa tgcgaagctg      3480
atcactcaga ggaagttcga caatctgaca aaggcggaga ggggcgggct ctcggagctg      3540
gataaggcgg gcttcatcaa gcggcagctc gttgaaaccc ggcagatcac caagcatgtc      3600
gcccagatcc tcgatagccg catgaacacc aagtacgatg agaacgacaa gctcattcgg      3660
gaggttaagg tcattacgct gaagtccaag ctcgtcagcg acttcaggaa ggatttccag      3720
ttctacaagg ttcgggagat taacaactac caccacgcgc atgatgcgta cctgaacgct      3780
gttgtcggca ctgctctcat caagaagtac ccaaagctgg agtccgagtt cgtctacggg      3840
gactacaagg tctacgatgt ccggaagatg atcgccaagt cggagcagga gatcgggaag      3900
gctactgcga agtacttctt ctacagcaac attatgaatt tcttcaagac ggagattacg      3960
ctggcgaacg gggagattag gaagaggccc ctcattgaga ctaatgggga cagggcgag       4020 attgtttggg acaagggccg cgacttcgcg actgtgcgga aggtcctgtc catgccacag      4080
gtgaatattg ttaagaagac agaggtgcag actgggggct ctcgaaggga gagcattctc      4140
ccaaagcgga acagcgataa gctcatcgcg cgcaagaagg attgggaccc taagaagtac      4200
ggcggcttcg attctcccac tgtggcctac tccgttctcg tggttgccaa ggttgagaag      4260
gggaagtcga agaagctgaa gtcggtcaag gagctgctcg ggattacaat catggagcgg      4320
agcagcttcg agaagaaccc tattgatttc ctggaggcca agggctacaa ggaggttaag      4380
aaggatctca ttatcaagct ccctaagtac tctctgttcg agctggagaa tggccggaag      4440
aggatgctgc cctcggctgg cgagctacag aaggggaatg agctggccct cccgtcgaag      4500
tatgtgaatt tcctgtacct cgcgtcgcac tacgagaagc tcaagggcag cccggaggat      4560
aatgagcaga agcagctctt cgtggagcag cataagcact acctggacga gatcattgag      4620
cagatcagcg agttctcgaa gcgggttatt ctggctgatg ctaacctgga caaggttctg      4680
agcgcctaca ataagcatcg cgacaagccg attcgcgagc aggcggagaa tattatccac      4740
ctgttcaccc tcactaacct cggggctccc gcggccttca agtacttcga taccacaata      4800
gataggaagc ggtacacctc gacgaaggag gtcctcgacg ccacactcat ccatcagtcg      4860
attacaggcc tgtacgagac acggattgac ctctcgcagc tgggcggcga tagcggcggg      4920
tccggcggga gcgggggctc gaccaatctg tcggacatca ttgagaagga accgggaag       4980 cagctggtta tccaggagtc catcctcatg ctcccggagg aggttgagga ggtaatcggg      5040
aataagccag agtctgacat cctcgtccac acagcgtacg atgagtcgac agacgagaat      5100
gtcatgctcc tcactagcga tgcgcccgag tacaagcctt gggcgctggt cattcaggat      5160
agcaacggcg agaataagat taagatgctg agcggcgggt cgggaggctc tggcgggtcc      5220
acgaacctgt ctgacatcat cgagaaggag acaggcaagc agctcgtgat ccaggagagc      5280
attctgatgc tgccggagga ggtggaggag gtaattggca ataagcccga gtctgatatt      5340
ctggtgcaca cagcgtacga cgagagcacg gatgagaatg tcatgctcct gacatccgat      5400
gctcctgagt acaagccgtg ggcgctcgtg attcaggact caaatgggga gaacaagatt      5460
aagatgctcg gatctaagaa gagaagaatt aaacaagat                              5499

<210> SEQ ID NO 15
<211> LENGTH: 5499
```

<212> TYPE: DNA
<213> ORGANISM: Artificial
<220> FEATURE:
<223> OTHER INFORMATION: base editor

<400> SEQUENCE: 15

```
ggttcgaaga agagaagaat taaacaagat tcctcggaga ccggcccgt  ggcggtggac    60
ccgacgctca ggaggcgcat cgagccgcac gagttcgagg tgttttcga  cccgcgcgag   120
ttgcgcaagg aaacctgcct gctctacgag atcaactggg gcggccgaca ttcgatctgg   180
cggcacacca gccagaacac caacaagcac gtggaggtca acttcatcga gaagttcacc   240
accgagcgct acttctgccc gaacacgcgg tgctcgatca cgtggttcct ctcctggtcg   300
ccctgcggcg agtgctcgcg ggccatcacc gagttcctgt cccgctaccc gcacgtcacg   360
ctcttcatct acatcgcccg gctgtaccac cacgccgacc cccggaaccg caggggctg    420
cgggatctca tctcctcggg cgtcacgatc cagatcatga ccgaacagga gtcgggctac   480
tgctggcgga acttcgtgaa ctactcgccg agcaacgagg cccactggcc gcgctacccg   540
cacctgtggg tccggctgta cgtgctggag ctgtactgca tcatcctcgg cctaccgccg   600
tgcctcaaca tctccgccg  gaagcagccg cagctcacat tcttcaccat cgcccttcag   660
agctgccact accagcgcct gccgccgcac atcctgtggg ccaccgggct caagagcggc   720
ggttccagcg gcggctcgtc tggctccgag actcccggca ccagcgagag cgcgacgccc   780
gagtcgagcg gcggttcatc tggcgggagc gacaagaagt attccatagg cctggctatc   840
ggcaccaaca gcgtgggctg gccgtcatc  accgacgagt acaaagtgcc gagtaaaaag   900
ttcaaagtgc tcggcaacac cgaccgccac tccataaaga aaaacctgat cggggcgctc   960
ctgttcgaca cgggcgagac ggcggaggcc accgcttga  aacgcacggc ccgacggcgc  1020
tacacgcggc gcaagaaccg gatctgttac ctacaggaga ttttctctaa cgagatggcg  1080
aaggtggacg actcgttctt tcaccgcctc gaagagtcct tcctcgtgga ggaggacaag  1140
aaacacgagc gccacccgat cttcggcaac atcgtggacg aggtggccta ccacgagaag  1200
tacccgacca tctaccacct ccggaagaaa ctcgtggaca gcacggacaa ggccgacctg  1260
aggctcatct acctcgccct ggcgcacatg attaagttcc ggggccactt cctgatcgag  1320
ggcgacctga acccggacaa cagcgacgtg gacaagctgt tcatccagct agtccagacc  1380
tacaaccagc ttttcgagga aaaccccatc aacgccagcg gggtggacgc gaaggcgatc  1440
ctgtccgccc ggctgagcaa gtcccggcgg ctggagaacc tcatcgcgca gttgcccggc  1500
gagaagaaga acgggctgtt cgggaacctg atcgccctct ccctggggct caccccgaac  1560
ttcaagtcca acttcgacct cgccgaggac gccaaactac agctgagcaa ggacacctac  1620
gacgacgacc tcgacaacct gctggcccag atcgggacc  agtacgcaga cctgttcctc  1680
gccgccaaga acctctccga cgccatcctg ctgtcggaca tcctgcgggt gaacacggag  1740
atcacgaagg ccccgctctc ggcctcgatg attaaacgct acgacgagca ccaccaggac  1800
ttgaccctcc tcaaggcgct ggtccgccag cagcttcccg agaagtacaa ggaaatcttt  1860
ttcgatcaga gcaagaacgg gtacgccggg tacatcgacg gcggggcgtc ccaggaggag  1920
ttctacaagt tcatcaagcc catcctggag aaaatggacg gaccgaggga gctgctcgtg  1980
aagctcaacc gcgaagattt gctccgcaag cagcgcacgt tcgacaacgg gtcgatcccg  2040
caccagatcc acctgggcga gctgcacgcg atcctcaggc gtcaggaaga cttctacccc  2100
ttcctcaagg acaaccgcga gaagatagag aagattctga ccttcagaat tccttattac  2160
```

```
gtgggcccgc tggctcgggg caactcgcgc ttcgcctgga tgacgcgcaa gtccgaggag    2220
accatcaccc cgtggaactt cgaggaggtg gtggataagg gtgcctcggc ccagtccttc    2280
atcgagcgga tgaccaactt cgacaagaac ctgccgaacg agaaggtgct ccccaagcac    2340
agcctgctct acgaatattt cacggtgtac aacgagctga cgaaggtcaa gtacgtgacc    2400
gagggaatga ggaaacctgc attcctctcc ggggagcaga agaaagccat agtcgacctc    2460
ctgttcaaga ccaaccggaa ggtcaccgtc aagcagctca aggaggacta cttcaagaag    2520
atcgagtgct tcgattcagt ggagatcagc ggcgtcgagg accggttcaa cgccagcctg    2580
ggcacctacc acgacctgct caagatcatc aaggacaagg acttcctcga caacgaggag    2640
aacgaggaca tcctggagga catcgtgctg accctgacgc tcttcgagga ccgcgagatg    2700
atcgaggagc gcctcaagac ctacgcccac ctgttcgacg acaaggtgat gaagcagctc    2760
aagcggcgga gatatactgg gtggggccgc ctctcccgga agctcattaa cggtatcagg    2820
gataagcagt ccgggaagac gatcctcgac ttcctcaagt cggacgggtt cgccaaccgc    2880
aacttcatgc agctcatcca cgacgactcc ctgacgttca aggaggacat ccagaaggcc    2940
caagtgtctg gtcaaggtga ctcgctccac gagcacatcg ccaacctcgc gggcagcccg    3000
gccatcaaga agggaatact ccagaccgtc aaggtggtgg acgagctggt gaaggtcatg    3060
ggccgccaca agccggagaa catcgtcatc gagatggcgc gggagaacca gaccacgcag    3120
aaggggcaga aaatagccgt gagcgcatg aagcgcatcg aggagggat taaggagttg    3180
ggcagccaga tcctcaagga gcaccctgtg gagaacacgc agttgcaaaa cgagaagctc    3240
tacctgtact acctccagaa cgggagggat atgtacgtgg accaagaact ggacatcaac    3300
cgcctgtccg actacgacgt ggaccacatc gtgccgcaga gcttcctcaa ggacgacagc    3360
atcgacaaca aggtgctcac ccggtccgac aagaatcggg gcaagtccga caacgtgccc    3420
agcgaggagg tcgtcaaaaa gatgaaaaac tactggcgac aactactgaa cgccaagctc    3480
atcacccagc gcaagttcga caacctcaca aaagccgagc gcggcgggtt gagcgagctg    3540
gacaaggccg ggttcatcaa gcgccagctc gtcgagacgc gccagatcac gaagcacgtc    3600
gcgcagatac tcgacagccg gatgaacacc aagtacgacg agaacgacaa gctcatccgg    3660
gaggtgaagg tcatcacccc tcaagtcgaa gctcgtgagcg acttccgcaa ggacttccag    3720
ttctacaagg tccgggagat caacaactac caccacgccc acgatgctta tcttaacgcc    3780
gtggtgggga cggccctcat taagaaatac ccgaagctgg agtcggagtt cgtgtacggc    3840
gactacaagg tgtacgacgt caggaagatg atcgccaagt ccgaacagga gatcgggaag    3900
gccacggcga atacttcttc tacagcaac atcatgaact tcttcaagac cgagatcacc    3960
ctcgccaacg gcgagatccg caagcgcccg ctcatcgaga cgaacgggga gaccggcgag    4020
atcgtctggg acaagggcg cgacttcgcc actgtgcgga aggtgctgtc gatgcccag    4080
gtcaacatcg tcaagaagac ggaggtccag acgggcgggt tcagcaagga gagcatcctg    4140
ccgaagcgca acagcgacaa gctgatcgcc cgcaaaaagg actgggatcc aaaaaagtac    4200
ggcggcttcg acagccccac cgtcgcctac agcgtcctcg tcgtcgctaa agtcgagaag    4260
ggcaagtcca aaaagctcaa gagcgtcaag gagctgctcg gatcaccat catgagcgg    4320
tccagcttcg agaagaaccc aattgatttc ctggagcga agggctacaa ggaggtcaag    4380
aaagacctca tcataaagct gccgaagtac tcactcttcg agctggagaa cgggcgcaag    4440
cggatgctgg cgtcggccgg agagctccaa aagggcaacg agctggcgct gccgagcaag    4500
tacgtgaact tcctctacct ggcgtcccac tacgagaagc tcaagggcag tccagaggat    4560
```

```
aacgagcaga agcagctatt cgtggagcag cacaagcact acctggacga gatcatcgag    4620
cagatcagcg agttctccaa gcgcgtcatc ctggcggacg ccaacctgga caaggtgctg    4680
tccgcgtaca acaagcaccg cgacaagccg atccgcgagc aagccgagaa catcatccac    4740
ctgttcaccc tcacgaacct cggggcaccc gccgccttca aatatttcga cacgaccatc    4800
gaccgcaagc gctacaccag cacgaaggag gtgctcgacg ccaccctgat ccaccagagc    4860
atcaccgggc tgtacgagac ccgcatcgac ctctcgcagc tcggcgggga cagcggtggc    4920
tcgggcggct cgggcgggag caccaacctg agcgacatca tcgagaagga cacgggcaag    4980
cagctcgtga tccaggagtc catcctcatg ctcccggagg aggtcgagga ggtgatcggc    5040
aacaagccag agtcggacat cctggtgcac accgcgtacg acgagtccac cgacgagaac    5100
gtcatgctgc tcaccagcga cgccccagag tacaagccct gggccctggt catacaggac    5160
tcgaacgggg agaacaagat caagatgctc tctggcggca gcggcgggag cggcggctcg    5220
accaacctca gcgacatcat cgagaaggag accggcaagc agttggtgat ccaggagagc    5280
atactgatgc tccccgagga ggtggaggag gtgatcggca acaagccgga gtcggacatc    5340
ctggtgcaca cggcgtacga cgagagcacg gacgagaacg tgatgctgct gacgtctgat    5400
gcgcccgagt acaagccctg ggccctggtg atccaggaca gcaacgggga gaacaagatc    5460
aagatgctgg gatctaagaa gagaagaatt aaacaagat                           5499

<210> SEQ ID NO 16
<211> LENGTH: 5499
<212> TYPE: DNA
<213> ORGANISM: Artificial
<220> FEATURE:
<223> OTHER INFORMATION: base editor

<400> SEQUENCE: 16
ggttcgaaga agagaagaat taaacaagat tcgtccgaga ccggcccccgt ggctgtggac      60 ccgacccttc gcagacgtat cgagccccac gagttcgagg tgttctttga cccgagggaa     120
ctccggaagg agacgtgcct gctctacgag atcaactggg gaggaagaca ctccatctgg     180
cggcacacct cgcagaacac gaacaagcac gtggaggtca acttcatcga aagttcacg      240 actgagcggt acttctgtcc gaacacgcgc tgctcgatca catggttcct gtcttggagc     300
ccgtgcgggg agtgctctcg ggccattacc gagttcctct cccgctaccc gcacgtcacg     360
ctgttcatct acattgcgcg gctataccac cacgccgatc cacggaaccg ccagggcctc     420
cgcgacctta tcagctccgg cgtgacgatc cagatcatga ccgagcaaga gtccgggtac     480
tgctggcgca acttcgtcaa ctactcaccg tccaacgagg cgcactggcc gcgttaccct     540
catctctggg tccggctgta cgtgctggag ctgtactgca taatcctggg cctgccgcct     600
tgcctgaaca tcctcaggcg gaagcagccc caacttacat tttcaccat gcgctccag      660 tcctgccact accagcgtct gccgcccac atcctgtggg ccaccggctt gaagtccggt     720
ggctcgtccg gcggctccag cgggagcgag acgccgggca ccagcgagtc cgccacgcct     780
gagtccagcg gcggctccag cggcggttcg gacaagaagt acagtattgg attggccatc     840
gggacgaaca gcgtgggctg ggccgtcatc accgacgagt acaaggtgcc atccaagaag     900
tttaaggttc tggggaatac cgaccgccac tcgatcaaga aaatctcat cggggcgctg     960 cttttcgaca gcgcgagac ggcggaagcg acgcggctca agcggacggc tcgtcgccgt    1020
tacacccggc gtaagaaccg catctgttac ctccaggaga tattcagcaa cgagatggcg    1080
```

-continued

```
aaggtggacg actccttttt ccaccgtctt gaggagtcct tcctggtcga ggaggacaag    1140
aagcacgagc gccacccgat cttcgggaac atcgtggacg aggtggccta ccacgagaag    1200
taccccacga tctaccacct ccgcaaaaaa ctcgtggact caactgacaa ggccgatttg    1260
aggcttatct acctcgccct cgcccacatg attaagttcc gtgggcactt cctaatcgag    1320
ggtgacctca accccgacaa ctctgacgtg acaagctgt tcatccagct tgtgcagacc     1380
tacaatcagc tctttgagga gaatccgatc aacgcatctg gtgtggacgc aaaggccatc    1440
ctcagcgcgc ggctgagcaa gtctaggcgg ttggagaacc tgatcgccca actgcccggc    1500
gagaagaaaa atggcctctt cggcaacctg atcgccctgt cgctggggct cacgccgaac    1560
ttcaagagta actttgacct ggcggaggac gctaagctcc agctatctaa ggacacatac    1620
gacgacgacc tggacaacct gctggcccag atcggcgacc agtacgccga cctcttccta    1680
gccgccaaga acctgtccga cgccatcctc ctcagcgaca tcctgcgcgt gaacacggag    1740
atcacgaagg ctccgctcag cgcctccatg attaagcggt acgacgagca ccaccaagac    1800
ctaactttac tcaaagccct cgtgcggcag cagcttcccg agaagtacaa agagatattt    1860
tttgatcagt ccaagaacgg ttatgcgggc tacatcgacg gcggcgcgag ccaggaggag    1920
ttctacaagt tcatcaagcc catcctggag aagatggacg gcacggagga gctgctcgtg    1980
aagctcaacc gtgaagacct cctgcgaaag cagcgaacct tcgacaacgg ttcgatcccg    2040
caccagatcc acctcgggga gctgcacgcc atcctgaggc gacaggagga cttctaccct    2100
ttcctaaagg acaaccgcga gaagattgaa aaaatcctga cgtttcgcat accctactac    2160
gtcggcccgc tggcgcgcgg caactcccgg ttcgcctgga tgacccgtaa gagcgaggag    2220
acgatcaccc cgtggaactt cgaggaggtc gtggacaagg gcgcgagcgc gcagagcttc    2280
atcgagcgca tgaccaactt cgacaagaac ctcccgaacg agaaggtgct cccaaagcac    2340
tccctcctgt acgagtattt caccgtgtac aacgagttga caaaggtgaa gtacgtgacg    2400
gagggaatgc ggaagcctgc gttcctctcg ggcgagcaga agaaggcaat cgtgacctg    2460 ctcttcaaga ccaaccggaa ggtgacggtg aagcagctca aggaggacta cttcaaaaaa    2520
atcgagtgct tcgactccgt ggagataagc ggcgtggagg accgattcaa cgcctccctc    2580
ggcacctacc acgacctcct taagatcatc aaggacaagg acttcctgga caacgaggag    2640
aacgaggaca tcctggagga catcgtgctc accctgaccc tcttcgagga ccgggagatg    2700
atcgaggagc gcctcaagac gtacgcccac ttgttcgacg acaaggtgat gaagcagctc    2760
aagcggcggc gatacaccgg gtggggccgc ctatcccgca aacttatcaa cggcatccgc    2820
gacaagcagt ccggcaagac gatcctggat ttcctcaagt cggacgggtt cgccaaccgg    2880
aacttcatgc agctcatcca cgacgacagc ctcacgttca aggaggacat ccagaaggcc    2940
caagtgagcg gtcaagggga cagcctccac gagcacattg cgaaccttgc tgggagccct    3000
gcgatcaaga aggggatatt gcaaaccgtg aaggtcgtgg acgagttggt gaaggtcatg    3060
gggcgacaca agcccgagaa catcgtgatc gagatggccg ggaaaatca gaccacgcag    3120 aagggccaaa aaaacagccg cgagcggatg aagcggatcg aggagggcat caaggagctg    3180
gggtcgcaga tcctcaagga gcacccggtg agaacacgc agctccagaa cgagaagctg    3240
tacctctatt acctacagaa cgggcgggat atgtacgtgg accaggagct agacatcaac    3300
cgcctgtccg actacgacgt ggaccatatc gtcccgcagt cgttcttgaa ggacgacagc    3360
atcgacaaca aggtgctcac aagatcggat aagaatcgag gcaagtccga caacgtgccc    3420
tcggaggagg tggtcaagaa aatgaaaaac tactggcggc agttgctgaa cgccaagctc    3480
```

```
attacgcagc ggaagttcga caacctgacg aaggctgaac gtggtgggct cagcgagcta   3540
gacaaggcgg ggttcatcaa gcggcagctc gtcgagaccc ggcagatcac caagcacgtg   3600
gcgcagatcc tggactcgcg catgaacacc aagtacgacg agaacgacaa gctcatccgt   3660
gaggtgaagg tcatcaccct taagtctaag ctggtcagtg acttccgcaa ggacttccag   3720
ttctacaagg tccgggagat caacaactac caccacgcgc acgacgccta cctcaacgcg   3780
gtggtgggga cggcgcttat taagaaatat cccaagctgg aaagcgagtt cgtttacggc   3840
gactacaagg tgtacgacgt ccgcaagatg atcgcaaagt cggaacagga aatcggaaag   3900
gcgacggcca atatttctt ttactccaac atcatgaatt ttttaagac ggagatcacc   3960
ctggcgaacg gggagatccg caagcggccc ctcatcgaga ccaacgggga gacgggcgag   4020
atcgtctggg acaagggccg ggacttcgcc accgtgcgga aggtgctttc tatgcctcaa   4080
gtcaatatcg tcaaaaagac agaggtgcag accggcgggt tcagcaagga gtctatcctg   4140
ccgaagcgca actcggacaa gctcatcgcg cgcaagaaag actgggaccc caaaaaatat   4200
ggcgggttcg actcgccgac cgtcgcctac agcgtcctcg tggtggctaa ggtcgagaag   4260
ggcaagagca aaaagctaaa gtcggtgaag gagctgctgg gcatcaccat catggagcgc   4320
tcgtctttcg agaagaatcc aatcgacttc ctagaggcga aggggtacaa ggaggtcaaa   4380
aaggatctta tcatcaaact gccgaagtac agtctgttcg agctggagaa cgggcggaag   4440
cggatgctgg ctagtgcggg cgagttgcag aagggcaacg agttggcact gccctccaag   4500
tacgtgaact tcctgtacct ggcctcccac tacgagaagc tcaaggggag ccccgaggac   4560
aacgagcaga agcagctatt cgtcgagcag cacaagcact acctggacga gatcatcgag   4620
cagatcagtg agttctccaa gcgggtcatc ctcgcggacg ccaacctgga caaggtgctg   4680
agcgcgtaca acaagcacag ggacaagcca atcagggaac aggccgagaa catcatccac   4740
ctgttcaccc tgaccaacct gggtgcaccg gctgccttca gtactttgga cacgaccatc   4800
gaccggaagc gctacacctc cacgaaggag gtgctggacg ccacgctgat ccaccagagc   4860
atcaccgggc tctacgagac acggatcgac ctgagccagc ttggcgggga ctcgggcggc   4920
agcggcggta gcggcgggag caccaacctc tccgacatca tcgagaagga gacggggaag   4980
cagttggtga tccaggagag catcctcatg ctgccggagg aggtcgagga ggtgatcggg   5040
aacaagccgg agtcggacat tctcgtgcac acagcctacg acgagtccac cgacgagaac   5100
gtcatgctcc tgacctcgga cgccccggag tacaagccct gggcgctggt gatccaggac   5160
agcaacggcg agaacaagat caagatgctg tccggcggca gcggtggcag cggcgggagc   5220
accaacctga gcgacatcat cgagaaggag acaggcaagc agctcgtgat ccaggagtcg   5280
atactgatgc tccccgagga ggtcgaggag gtcatcggga acaagcccga gtcagacatc   5340
ctcgtgcaca ccgcctacga cgagagcacg gacgagaacg tgatgctcct gacctccgac   5400
gcaccggagt acaagcccctg ggccctggtc atccaggaca gcaacggcga gaacaagatc   5460
aagatgctcg gatctaagaa gagaagaatt aaacaagat                          5499

<210> SEQ ID NO 17
<211> LENGTH: 5499
<212> TYPE: DNA
<213> ORGANISM: Artificial
<220> FEATURE:
<223> OTHER INFORMATION: base editor
```

<400> SEQUENCE: 17

```
ggttcgaaga agagaagaat taaacaagat tcatccgaga cggggcccgt cgccgtggac      60
cccacgctca gacgccggat cgagccccac gagttcgagg tcttttttcga cccgagagag     120
ctacgaaagg agacctgcct gctgtacgag atcaactggg gcgggcggca ttcgatctgg     180
cggcacacga gccagaacac gaacaagcac gtggaggtca acttcatcga gaagttcacg     240
acggagcggt acttctgccc caacacccgc tgctctatca cctggttcct gtcgtggagc     300
ccgtgcggcg agtgcagccg cgccatcacg gagttcctca gccgctatcc gcacgtgacc     360
ctgttcatct acatcgcgcg gctctaccac cacgccgacc cacgcaaccg caggggctg      420
cgcgacttaa tcagctccgg ggtcacgatc cagatcatga cggaacaaga gtccggctat     480
tgctggcgca acttcgtcaa ctacagcccg agtaacgagg cccactggcc gcgctacccg     540
cacctctggg tccggctgta cgtcctggag ctgtactgca tcatattggg gctcccgccg     600
tgtctcaaca tcctccggcg gaagcagccc cagctcacat tctttactat agccttgcag     660
tcgtgccact accagcgcct cccgccgcac atcctctggg cgaccgggct taagagcggt     720
ggctccagcg gcggtagcag cggcagcgag acgcccggca cgagcgagtc tgccactcca     780
gaatcatctg gcggctccag cggcggttcc gacaaaaagt attccattgg actcgctatc     840
ggcacgaaca gcgtcgggtg ggcggtcatc actgacgagt acaaggtgcc gagcaagaag     900
tttaaggtgc tgggaaacac cgacaggcac tcgatcaaga aaaatcttat cggggcccta     960
ctcttcgact ccggagaaac cgccgaggcc acccggttga agcgcacggc ccgccgtcgc    1020
tacaccaggc gcaagaaccg gatctgctac ctccaggaga tattcagcaa tgagatggcg    1080
aaggtggacg actcgttttt tcacaggcta gaggagtctt tcctcgtgga ggaggacaag    1140
aaacacgagc gccacccccat cttcggcaac atcgtggatg aggtggcata tcacgagaag    1200
tacccaacca tctaccacct ccgcaaaaag ctcgtggact ctaccgacaa ggccgacctc    1260
cgtctgatct acctcgcgct ggcccacatg attaagttcc gaggacactt tctgatcgag    1320
ggcgacctga acccagacaa cagcgacgtg acaagctgt tcatccaact tgtccagacc    1380
tacaatcagc tcttcgagga aaccctatc aacgcctcgg gcgtggacgc gaaggccatc    1440
ctgtccgccc gcctgagcaa gtcgcggcgg ctggagaacc tgatcgccca gctccccggc    1500
gaaaaaaaga acggcctctt cggcaacctc atcgcgttgt cgctggggct caccccgaac    1560
ttcaagtcca acttcgacct ggccgaggac gctaaactcc agctctcgaa ggatacctac    1620
gacgacgacc tcgacaacct gctggcccag atcggcgacc agtacgcgga ccttttcctg    1680
gcggccaaga acctgagcga cgcgatcctc cttagcgaca tactccgtgt gaacaccgag    1740
atcacgaagg ccccgctctc cgcgtccatg attaagcgct acgacgagca ccaccaagac    1800
cttaccctgc ttaaggcgct ggtcaggcag cagttaccgg agaagtacaa ggagatcttt    1860
tttgatcaat ctaagaacgg ttacgccggg tacatcgacg gcggcgcgtc ccaggaggag    1920
ttctacaagt tcatcaagcc gatcttggag aaaatggacg ggaccgagga gctgctcgtg    1980
aagctcaacc gcgaagacct cctccgcaag cagcgcacct tcgacaacgg gagcatcccg    2040
caccagatcc acctgggaga gctgcacgcg atcctgcgga gacaagagga cttctacccc    2100
ttcctcaagg acaaccggga gaagattgaa aaaatactta ctttcgtat cccgtactac    2160
gtcgggcccc ttgcgagggg caactccaga ttcgcgtgga tgaccgcaa gtccgaggag    2220
accatcaccc cgtggaactt cgaggaggtg gtggacaagg gcgcgtcggc ccagtcgttc    2280
```

```
atcgagcgca tgaccaactt cgacaagaac cttccgaacg agaaggtgct cccgaagcac    2340
agcctgctct acgaatattt tactgtgtac aacgagctga cgaaggtcaa gtacgttacg    2400
gaggggatga ggaagcccgc cttcctctcc ggcgagcaga agaaagccat tgtggatctc    2460
ctgttcaaga ccaaccgcaa ggtgacggtg aaacagctca agaggacta cttcaagaag    2520 atcgagtgct tcgactccgt agagatcagc ggggtcgagg accgcttcaa cgcctcgctg    2580
ggcacgtacc acgacctgct aaagattatc aaggacaaag acttcctaga caatgaggag    2640
aacgaggaca ttctggagga catcgtgctg actctgacgc tgttcgaaga ccgcgagatg    2700
atcgaggagc ggcttaagac gtacgcccac ctgttcgacg acaaggtgat gaagcagttg    2760
aaacggcggc gctacaccgg gtggggccgc ctctcccgca agctcatcaa cggcatccgc    2820
gacaagcagt cggggaagac gatcctggac ttcctcaaga gcgacggctt cgccaaccga    2880
aacttcatgc agctaatcca cgacgacagc ctgacgttca aggaggacat ccagaaggcc    2940
caagtgagcg gccagggaga ctcgctacac gagcatatcg ccaacctggc tggcagcccg    3000
gcgattaaga aaggaatcct ccaaaccgtc aaagtggtgg acgagctggt gaaggtgatg    3060
ggccgccaca agcccgagaa cattgtgatc gagatggcgc gggagaacca gacgacgcag    3120
aagggccaaa aaaatagcag ggaaaggatg aagcgaatag aggaggggat caaggagctg    3180
gggagccaga ttctcaaaga gcacccggtc gagaacacac agctccagaa cgagaagctg    3240
tacctctact acctccaaaa cggccgcgat atgtacgtgg accaggaact agacatcaac    3300
cggctgagcg actatgacgt ggaccacatc gtgccgcagt ccttcctcaa ggacgactcg    3360
attgacaaca agtgctcac tagatccgac aagaacagag gcaagagcga taacgtcccg    3420
tcggaggagg tcgtcaagaa aatgaaaaac tactggcggc agctcctaaa cgccaagctc    3480
atcacgcagc gtaagttcga caacctgacg aaggcggagc ggggcgggct gagcgagctg    3540
gacaaagcgg ggttcatcaa gcggcagctc gttgagacgc ggcagatcac aaagcacgtc    3600
gcgcaaatcc tcgactcccg catgaacacc aagtacgacg agaacgacaa gctcatccgg    3660
gaggtgaagg tcattaccct taaatcgaag ctcgtcagcg actttcgtaa ggacttccag    3720
ttctacaagg tcagagagat caacaactac caccacgccc acgacgccta tctgaacgcc    3780
gtggtgggca ccgcgcttat taagaagtac cccaagctgg agtccgagtt cgtgtacggc    3840
gactacaagg tttatgacgt caggaagatg atcgccaagt cggaacagga gatcggaaaa    3900
gctaccgcca aatatttctt ctatagcaac atcatgaact tcttcaaaac cgagatcacc    3960
ctcgccaacg gcgagatccg gaagcgcccg ctcatcgaga ccaacgggga gaccggggag    4020
atcgtctggg acaaggggcg ggacttcgct actgtccgaa aggtgctctc catgccacaa    4080
gtgaatatcg tcaagaaaac agaggtgcag accggagggt tcagtaagga gtccatcctg    4140
cccaagcgga actccgacaa gctaattgct cgcaaaaagg attgggatcc taaaaaatat    4200
ggcggcttcg actcgcccac ggtcgcctac tctgtgctgg tcgtggcgaa ggtggagaag    4260
ggcaagtcca agaagctcaa gagcgtcaag gagctgctgg ggatcacgat catggagcgt    4320
agttcgtttg agaagaatcc catcgacttc ctggaggcta agggctacaa ggaggtcaaa    4380
aaggacctca tcattaagct gccgaagtac agcctcttcg agctggagaa cgggcggaag    4440
cgtatgctcg cctccgctgg ggagttacaa aaggggaacg agctggcgct gccgtctaag    4500
tacgtcaact tcctgtacct ggcctcccac tacgagaagc tcaaggggtc gccggaggac    4560
aacgagcaga agcagctctt cgtagagcag cacaagcact acctggacga gatcatcgag    4620
cagatttcag agttctcaaa gcgggtcatc ctcgccgacg ccaacctgga caaggtgctc    4680
```

| | |
|---|---|
| tcggcctaca acaagcaccg ggacaagccg atccgcgaac aggccgaaaa catcatccac | 4740 |
| ctgttcacgc tcaccaacct cggtgccccg gcggccttca agtactttga cacgaccatc | 4800 |
| gaccggaagc gctatacctc gacgaaggag gtgctggacg ccaccctgat ccaccagtcc | 4860 |
| atcaccgggc tttacgagac ccggatcgac ctctcgcagc taggcgggga ctcgggcggc | 4920 |
| tcgggcggct ccggcgggag caccaacctg tccgacatca tcgagaagga gacggggaag | 4980 |
| cagctcgtca tccaggagtc gatcctcatg ctccccgagg aggtcgagga ggtgatcggc | 5040 |
| aacaagccgg agtccgacat cctggtccac acggcgtacg acgagagcac ggacgagaac | 5100 |
| gtgatgctcc tgacctccga cgccccggag tacaagccct gggcgctcgt catccaggac | 5160 |
| agcaacggcg agaacaagat caagatgctc tccggcggct ccggcggcag cggagggagc | 5220 |
| acgaacctca gcgacatcat cgagaaggag accggcaagc agctcgtgat ccaggagtcc | 5280 |
| atcctcatgc tgccggagga ggtggaggag gtgatcggca acaagccgga gtcggacata | 5340 |
| ctcgtgcaca ccgcgtatga cgagagcacc gacgagaacg tgatgctgct gacaagcgac | 5400 |
| gcgccagagt acaagccctg ggccctcgtg atccaggact ccaacggcga gaacaagatt | 5460 |
| aagatgctgg gatctaagaa gagaagaatt aaacaagat | 5499 |

<210> SEQ ID NO 18
<211> LENGTH: 5499
<212> TYPE: DNA
<213> ORGANISM: Artificial
<220> FEATURE:
<223> OTHER INFORMATION: base editor

<400> SEQUENCE: 18

| | |
|---|---|
| ggatctaaga agagaagaat taaacaagat tcatcagaga caggaccagt tgccgttgac | 60 |
| cccacccctta ggagaagaat agaaccccac gagtttgaag tgttttcga cccaagagaa | 120 |
| ttgaggaagg aaacatgtct tctgtatgag ataaattggg gaggtaggca cagcatttgg | 180 |
| agacatacca gccagaatac aaacaagcat gttgaggtga atttattga aaagttcact | 240 |
| accgaaagat atttttgtcc aaacactaga gtgtagtataa cctggttct cagttggagc | 300 |
| ccatgtgggg aatgtagcag ggcaatcacc gagtttctct caagatacc tcacgtgacc | 360 |
| ttgtttatct acatagccag actttatcat cacgcagacc caagaaacag acaaggtctg | 420 |
| agagatttga tttcttcagg agtgactatt cagatcatga ccgaacaaga gagcggttac | 480 |
| tgctggagaa actttgttaa ttattcacct agtaacgaag cacattggcc tagatacccct | 540 |
| cacctgtggg ttaggctcta cgtgttggaa ctctattgca ttattcttgg cttgcctccc | 600 |
| tgcctgaaca tactgagaag gaagcagccc caactcacat tcttcactat agctctgcaa | 660 |
| agttgtcact accagaggct ccctcctcac atcctgtggg ccacaggttt gaagtcaggg | 720 |
| ggctccagtg gaggtagttc aggctccgag actccaggaa cttccgagtc agctacaccc | 780 |
| gaatccagcg gtggtagttc tggcggcagt gacaagaagt atagtattgg actcgccatc | 840 |
| ggaaccaact ctgtggggtg ggctgttatt acagatgaat ataaggtgcc atccaaaaag | 900 |
| tttaaagttc tgggcaatac tgatagacac tcaatcaaga gaatctgat aggtgcactt | 960 |
| ctgtttgata gtggagagac tgccgaggca accagactta aaggactgc aagaagaaga | 1020 |
| tataccagaa gaaagaatag gatttgctat ttgcaggaaa tcttcagcaa cgaaatggcc | 1080 |
| aaggttgatg actcattttt ccataggttg gaggagagtt tcttgtgga ggaagataag | 1140 |
| aagcacgaaa gacacccaat tttcgggaat atagtggacg aggtggctta tcatgagaag | 1200 |

```
tatcccacta tctaccacct gagaaagaaa cttgtggact caaccgataa ggctgatctt    1260
aggcttatat acttggccct tgcacatatg atcaaattca ggggccattt tcttatcgaa    1320
ggcgatctta atcccgataa ctcagatgtg acaagctgt ttatacaact tgtgcaaacc     1380
tacaatcaac tcttcgagga gaatcccatt aacgcctccg gcgtggatgc aaaagccata   1440
ctgtcagcca gactgagcaa agtaggaga ctggagaatc ttatagccca actgcccggt    1500
gaaaagaaga atgggctctt cggaaatctg atcgctcttt cattggggtt gacacccaac   1560
tttaagagta actttgactt ggcagaagat gcaaagttgc agctcagtaa agacacatat   1620
gacgatgacc ttgacaatct cttggcacaa ataggggatc aatacgctga cctttttcctc 1680 gctgccaaga acctcagcga cgctatactg ttgtccgaca ttcttagggt taataccgaa   1740
attacaaagg cccctcttag tgcaagtatg atcaaaaggt atgatgagca tcaccaagac   1800
cttacactgc tgaaggctct ggttagacag caactccctg aaaagtataa ggaaatattc   1860
ttcgaccaaa gtaagaacgg gtacgccggt tatattgatg ggggcgcaag tcaagaagaa   1920
ttttacaaat tcatcaagcc aattcttgaa agatggacg ggactgagga attgctggtg    1980
aaactgaata gagaggacct tcttagaaaa cagaggacat tgacaatgg gtccatccca    2040 caccagattc atctggggga actccacgca atattgagga gacaagaaga cttttaccca   2100
ttccttaagg ataatagaga gaaaatcgaa aaaatcctga ctttcaggat tccttactat   2160
gttgggccac tggccagggg gaactcaaga ttcgcttgga tgacaaggaa gtcagaagaa   2220
accataaccc cttggaattt tgaagaggtg gttgataagg gggcatcagc ccagtctttc   2280
atagagagga tgaccaactt tgataaaaat cttccaaatg agaaggtttt gccaaaacat   2340
agtcttttgt acgagtactt tactgtttat aacgaattga ccaaggtgaa gtatgtgacc   2400
gagggaatga ggaagccagc attttttgtcc ggggagcaaa agaaagcaat cgttgatctt  2460
ctcttcaaga ccaacagaaa agtgaccgtg aaacaactga aggaagacta cttcaaaaag   2520
atagaatgtt tcgattcagt ggaaattagc ggtgttgaag acaggttcaa tgcttcattg   2580
ggtacttacc acgacctgtt gaagataatc aaagacaagg actttctcga taatgaggag   2640
aacgaagaca tcttggaaga cattgtgctt acactcactt tgtttgagga cagggaaatg   2700
attgaggaaa gactcaaaac ttacgctcat ttgtttgatg ataaggttat gaaacaacta   2760
aaaagaagaa ggtacaccgg ctggggaaga ttgagtagga aactgatcaa cggtattaga   2820
gataaacaat ccggaaagac tatcctcgat ttccttaaga gtgatggctt tgcaaatagg   2880
aattttatgc agctgattca tgacgactca cttaccttca aagaagacat ccaaaaagct   2940
caggtgtctg gcaaggcga cagtctgcat gaacatatag ctaacttggc tgggagtccc   3000
gccatcaaga aggggatact tcaaacagtt aaagttgtgg acgaattggt gaaggtaatg   3060
ggaaggcaca agcctgaaaa tatagtgata gaaatggcaa gggaaaatca aacaacccag   3120
aagggacaga agaacagtag ggaaggatg aaaaggatag aagagggat caaagagctt     3180 ggtagccaga tcctcaagga acatccagtg agaataccc aacttcaaaa cgagaaactc    3240
tatttgtact acttgcagaa cggaagagat atgtatgtgg accaagagct tgatattaac   3300
aggctgagcg attatgacgt tgaccacata gtgccccaat cattcctcaa ggatgactct   3360
attgataata aggtgctgac aaggagtgac aagaatagag ggaaatccga caacgttcca   3420
tccgaggaag ttgtgaagaa gatgaagaac tactggaggc agttgctgaa cgctaagctc   3480
attcccagag gaaattcga taacctgacc aaagcagaga gaggcgggct gagcgaactc   3540
gataaagcag gtttcatcaa gagacaactc gtggagacta ggcaaattac taagcacgtg   3600
```

```
gctcaaatac tcgacagcag gatgaacaca aagtacgacg agaacgacaa gctcattaga    3660
gaggttaagg ttattactct gaaaagtaaa ttggttagcg atttcagaaa ggatttccaa    3720
ttctataagg ttagagagat caacaattat catcatgcac atgatgccta tctgaatgct    3780
gtggttggta cagcccttat caagaagtac cctaagctag agagcgagtt tgtgtacgga    3840
gattataagg tgtatgatgt gaggaaaatg atcgctaaaa gtgagcaaga gattggaaag    3900
gctaccgcca aatacttctt ttattccaat attatgaatt tcttcaagac agaaatcacc    3960
ctggctaacg gcgagataag gaagaggccg cttatcgaaa ctaatgggga gacaggcgaa    4020
atagtgtggg acaaagggag ggatttcgca actgtgagga aggttttgag catgcctcag    4080
gtgaatatcg ttaagaaaac cgaagttcaa actggagggt tctctaagga aagcattctc    4140
cccaagagga actccgacaa gctgattgct agaaagaaag actgggaccc caagaagtat    4200
ggcggattcg actcacccac tgtggcatat agcgttctcg tggtggcaaa ggttgaaaag    4260
ggtaaatcca aaaaactcaa atccgtgaag gaactccttg gcataactat tatggaaagg    4320
agtagctttg aaaagaatcc catcgacttt ctcgaagcta agggctataa ggaagttaag    4380
aaggacctta taatcaaact tccaaaatac tcccttttg agttggaaaa cggcagaaag    4440
agaatgttgg ccagtgccgg ggagcttcaa aagggcaacg aactggctct gcctagcaaa    4500
tatgtgaact ttttgtatct ggcatcacac tacgagaaac ttaaaggctc tcctgaggac    4560
aacgagcaaa acagctctt tgttaacag cataagcact acctcgacga gattattgag    4620
cagatcagcg agttctcaaa gagagttatt ctggctgacg ctaatcttga caaggttttg    4680
tccgcttaca acaaacacag ggataagcca atcagggagc aggcagaaaa cataatccat    4740
ctctttaccc tgacaaacct cggtgccccc gctgctttca agtattttga tactaccatt    4800
gacaggaaga gatatacttc cactaaggaa gtgctcgacg caacccctcat acaccaaagt    4860
atcacaggcc tctatgaaac taggatagat ttgtctcaac ttggggggcga ttccggaggt    4920
tctgggggct ccggagggag tactaatctg agtgatataa ttgaaaagga aaccggaaag    4980
caactcgtta tccaggaatc catacttatg ttgcccgaag aggtggaaga ggttattggt    5040
aataagcctg aaagtgatat tttggttcac actgcctacg acgaatccac tgacgagaac    5100
gtgatgctgc tgacctctga cgctcccgag tataagcctt gggctctggt aattcaagac    5160
tccaacggag aaaataagat caaaatgctt tcagggggga gtggtggttc cggcggtagt    5220
actaacctca gcgatattat tgagaaggaa accggcaagc aactagttat acaagagagt    5280
attctcatgc tgcctgagga agttgaagag gttataggaa acaagcccga gtctgatatt    5340
ctggttcaca ctgcctatga cgaaagtaca gacgaaaacg tgatgcttct tacatccgac    5400
gcacccgaat acaaaccctg ggcactcgtg attcaagact ctaacgggga aaacaagatt    5460
aaaatgctcg gatctaagaa gagaagaatt aaacaagat                           5499
```

<210> SEQ ID NO 19
<211> LENGTH: 5499
<212> TYPE: DNA
<213> ORGANISM: Artificial
<220> FEATURE:
<223> OTHER INFORMATION: base editor

<400> SEQUENCE: 19

```
ggatctaaga agagaagaat taaacaagat tcttccgaga ctggacccgt tgctgtggac      60
cctacactga ggagaaggat agagccccat gagtttgagg ttttctttga ccctagagaa     120
```

-continued

| | |
|---|---|
| cttaggaagg agacatgcct gttgtacgag attaattggg gcggcaggca cagcatatgg | 180 |
| agacacacca gtcagaacac aaataagcac gtggaggtga acttcatcga gaaattcacc | 240 |
| accgagagat attttttgccc aaacaccaga tgttcaataa cttggttcct ttcttggagc | 300 |
| ccctgtggag agtgttccag ggcaattaca gagttcctca gtaggtatcc acacgttacc | 360 |
| cttttttatct atatcgccag gctttatcac cacgctgacc caaggaatag acagggcctt | 420 |
| agggacctca tatctagcgg tgttacaatt cagataatga ctgagcaaga atctggttac | 480 |
| tgttggagaa attttgtgaa ttactcccct agcaacgagg cacactggcc aagataccca | 540 |
| cacctctggg ttaggcttta tgttctggaa ctttactgca tcatacttgg tctacctccc | 600 |
| tgtcttaaca tcctcaggag aaagcaacct caactcacat ttttcaccat agcccttcaa | 660 |
| agctgccact atcagaggtt gccaccacat attctctggg ccactgggct gaagagtgga | 720 |
| ggctcctcag ggggaagttc tggcagcgaa acaccaggta ctagcgaaag cgccaccccc | 780 |
| gaaagcagtg gaggctcctc cggcggtagc gacaaaaagt attccatcgg gcttgctatc | 840 |
| ggaaccaact ctgtggggtg ggcagttatt accgacgaat acaaggtgcc cagcaagaag | 900 |
| tttaaggttc tggggaacac agatagacat agcataaaga aaaacctgat aggcgcactg | 960 |
| ttgttcgact ccggggaaac agccgaagct accaggctga agagaactgc aagaagaagg | 1020 |
| tacaccagaa gaaaaaacag aatatgttat ctccaagaga ttttctctaa cgagatggcc | 1080 |
| aaggtggacg actcattctt tcacagactg gaagaatctt ccttgtgga agaagataag | 1140 |
| aaacacgaga ggcaccctat ttttggcaat atcgtggatg aggtggctta ccacgaaaaa | 1200 |
| tacccctacaa tataccacct caggaaaaaa ttggttgata gtacagacaa ggccgacctc | 1260 |
| aggctcatct atttggccct ggcccatatg attaaattca gggggcactt tctcatcgag | 1320 |
| ggagatttga accccgacaa cagtgatgtt gataagctct ttattcagct cgtgcagact | 1380 |
| tacaatcagt tgtttgagga aaaccccatt aatgcttccg gggtggacgc caaggcaatc | 1440 |
| ctttctgcaa gactctcaaa gtcaaggaga ctcgaaaatc tgatagcaca gcttccagga | 1500 |
| gagaagaaga acgggctctt tggaaacctg atcgctctgt cactcggact cacacccaat | 1560 |
| ttcaaaagca atttttgattt ggcagaggac gctaagctgc aactcagtaa ggatacctac | 1620 |
| gacgatgact tggataatct gctcgcacaa attggggacc agtatgcaga cctgtttctc | 1680 |
| gcagctaaga acttgagtga cgccatattg ctcagtgaca tcctcagggt taataccgag | 1740 |
| attacaaaag ctccactctc tgcaagcatg atcaagaggt atgacgagca ccatcaagac | 1800 |
| ctgacactcc ttaaggcgtt ggttaggcag caacttcctg aaaagtataa ggaaatcttc | 1860 |
| ttcgatcaaa gcaaaaacgg ctacgccggc tatatagacg ggggagcatc ccaagaagaa | 1920 |
| ttttataagt tcataaaacc tatattggag aagatggacg ggacagagga attgctcgtg | 1980 |
| aaactgaaca gggaggatct cctcaggaag caaaggacct tcgacaatgg ctccatccca | 2040 |
| catcagattc acctcggcga actgcacgca atactgagaa gacaagagga cttttatcct | 2100 |
| ttcctgaagg acaacaggga gaaaatcgag aaaatcttga cattcagaat cccatactac | 2160 |
| gttgggcctc tggccagagg taacagtagg ttcgcctgga tgactaggaa atcagaggag | 2220 |
| actattacac cctggaactt tgaagaagtt gttgataagg gagcttcagc acaatcattc | 2280 |
| atcgaaagaa tgacaaactt tgacaaaaat ctgcctaatg agaaagtgct cccaaaacat | 2340 |
| tccctgctgt atgagtattt taccgtttat aacgagctta ccaaggtgaa atacgttact | 2400 |
| gaaggtatga gaaagccagc ttttctttca ggggagcaaa agaaggctat cgtggatctt | 2460 |
| ctctttaaga ccaacagaaa ggttaccgtg aagcagctta aggaagacta ctttaaaaag | 2520 |

```
atcgagtgtt ttgactcagt ggaaataagc ggtgttgaag atagattcaa cgcatccttg   2580
ggaacttatc atgatcttct taagataatc aaggataaag actttctcga caacgaggaa   2640
aacgaagata tactggagga catagttctg acacttactt tgttcgagga tagggagatg   2700
atcgaggaaa gactgaaaac atatgctcac cttttcgacg acaaagttat gaacaactc    2760 aagagaagga gatatacagg gtggggggaga ttgagcagga aactgattaa tggtatcaga  2820
gacaaacagt caggaaaaac aatactcgac tttttgaaat cagacgggtt cgcaaatagg   2880
aatttcatgc agcttataca cgacgattca cttactttta aagaggacat tcaaaaggct   2940
caagttagtg acaaggtgac tccctccac gaacacatcg caaatctcgc tggcagccct    3000
gcaattaaga agggtatact ccagacagtt aaggttgttg acgagctggt taaagtgatg   3060
ggaagacaca aacccgagaa catagtgata gagatggcca gggaaaacca aaccactcaa   3120
aaagggcaga aaaattccag agagaggatg aaaaggattg aagaaggtat caaggagctg   3180
ggtagccaaa ttctgaaaga acatcctgtg gaaaacactc aactccagaa tgagaaactc   3240
tatctgtact atctgcaaaa tgggagagat atgtatgtgg accaggaact ggacataaac   3300
aggctctcag attacgatgt ggatcatatc gtgccacagt cctttcttaa ggatgatagc   3360
atcgacaata aggtgcttac caggtccgac aagaacaggg gaaagtcaga taacgtgcct   3420
tctgaagaag ttgttaaaaa gatgaagaac tactggagac agctgcttaa cgctaagctc   3480
ataacacaga ggaagtttga aacttgacc aaggccgaga gaggcggact ctcagaattg    3540
gataaggcag ggttcataaa aaggcagctg gtggaaacaa ggcagataac taaacatgtg   3600
gctcagatcc tcgatagtag gatgaataca aaatacgatg agaacgacaa gctcataagg   3660
gaggttaaag tgataactct gaaatccaaa ctggttagcg attttaggaa ggatttccag   3720
ttttacaaag ttagggagat caacaattat catcacgccc acgatgccta cttgaacgca   3780
gttgtgggta ctgcacttat caaaaagtac cctaagctgg aatccgagtt tgtttatgga   3840
gactataagg tgtacgacgt tagaaaaatg attgcaaagt cagagcagga gatagggaaa   3900
gccactgcaa atatttctt ttatagcaat atcatgaatt tctttaagac agaaatcaca    3960
ctggccaatg gggaaataag gaagaggccc ctgatcgaaa ctaatggcga gacaggggag   4020
attgtgtggg ataaaggtag ggactttgca acagtgagga agtgctgag catgcccaa    4080 gttaatatcg ttaaaagac cgaggttcaa acagggggct ttagtaagga aagcattttg    4140
cccaagagga atagtgacaa attgattgct aggaaaaaag attgggaccc caaaaagtat   4200
ggcggatttg atagccccac tgttgcttac tccgtgctcg tggttgcaaa ggtggagaag   4260
ggaaagagca agaaactgaa gtcagttaag gaactccttg gtatcactat catggaaaga   4320
agctcctttg agaagaaccc tattgacttc ctggaggcta aagggtacaa agaggttaag   4380
aaagacctta tcattaaatt gcccaaatat agtcttttcg agcttgaaaa cggaagaaag   4440
aggatgcttg catccgctgg cgaattgcaa aagggcaatg agcttgctct cccttccaag   4500
tatgtgaact tcctttatct tgcctcacac tatgaaaaac tcaaaggttc acccgaagac   4560
aacgaacaaa agcaactatt tgtggaacaa cacaagcact acctggacga aatcattgag   4620
caaatttctg agttttcaaa aagggtaatc ttggctgacg caaatctcga caaagttttg   4680
tcagcttaca caaacatag agataagcca attagagagc aagctgagaa tatcatccat   4740
ctgtttaccc tgactaacct tggagcgcct gctgctttta aatatttcga caccacaatc   4800
gacaggaaga ggtacactag cactaaggaa gttctcgacg ccaccctcat ccaccagagt   4860
```

```
attacaggcc tgtacgagac aagaattgat ctttctcaac ttggtggtga cagcggcggt   4920
agtgggggtt caggggcag  tactaacctc agcgatataa ttgaaaagga aaccgggaaa   4980
cagcttgtta ttcaagagtc tatcctcatg ctgcccgaag aagtggagga agtgattggt   5040
aacaaacccg aatccgacat tctggttcat acagcatacg acgagtctac cgatgagaac   5100
gttatgcttc tcaccagtga tgcccctgag tacaagcctt gggccttggt aattcaagac   5160
tccaacgggg agaacaagat caagatgctt agcggtggca gtgggggaag cggcggtagt   5220
acaaatctgt ccgacatcat agaaaaggag actgggaaac aactcgtgat acaagagtct   5280
attcttatgc ttcctgaaga agttgaagaa gtgatcggta ataagcccga atcagacata   5340
ctcgttcata ccgcatacga cgaatctacc gatgagaacg tgatgctcct cacatccgat   5400
gctcccgagt acaaaccttg ggctctcgtg atacaggact ctaatgggga aaataagata   5460
aaaatgcttg gatctaagaa gagaagaatt aaacaagat                          5499
```

<210> SEQ ID NO 20
<211> LENGTH: 5499
<212> TYPE: DNA
<213> ORGANISM: Artificial
<220> FEATURE:
<223> OTHER INFORMATION: base editor

<400> SEQUENCE: 20

```
ggatctaaga agagaagaat taaacaagat agcagcgaga caggaccagt tgccgttgac     60
cctacattga agaagaatt  tgaaccccac gagtttgaag tgttttcga  tcccagggaa    120 ctcagaaaag agacttgcct cctgtatgag atcaactggg gtgggaggca cagcatctgg    180
aggcacacct cacagaacac taacaaacac gttgaagtga atttcattga gaagttcact    240
accgagaggt acttctgccc aaatacaagg tgttccatca cttggtttct ttcctggagc    300
ccatgtggtg aatgttcaag gcaatcaca  gagttttgt  caagatacc  acacgttacc    360 ctctttatat atatcgcaag actgtaccac cacgccgatc aaggaatag  acaagggctt    420 agggaccta  tatcctccgg ggttactatc cagattatga ctgaacagga agcgggtac     480 tgttggagga atttcgtgaa ttattcccca tcaaacgaag cacactggcc aagatacccca   540 cacctgtggg tgaggcttta tgtgttggag ctatactgca tcatcctggg gctcccacct    600
tgtcttaata ttttgagaag aaaacaacca caactcacct ttttcacaat cgctctccag    660
agctgccatt atcaaaggct gccccctcac atcttgtggg ctactgggct gaaatccggg    720
ggtagctccg ggggttccag tgggtccgaa acacctggga cttcagaatc cgcaacacct    780
gagagcagcg ggggcagcag cggcggaagt gataagaagt actcaatcgg tctggcaatc    840
ggaaccaact ctgtgggttg ggcagtgatt acagatgagt ataaggtgcc aagcaaaaaa    900
ttcaaggtgc tgggtaatac cgacagacac agcattaaga gaatttgat  tggagcactc    960 ctctttgact caggggaaac agcagaggca acaaggctga gaggacagc  aaggcggagg   1020 tacacaaggc ggaaaaacag gatatgctac ctccaggaaa tctttagcaa cgagatggct   1080
aaagtggatg atagcttttt ccatagactc gaagaatcct tcttgttga  agaggacaaa   1140 aagcatgaaa ggcatcccat cttcggcaat atagttgatg aggttgcata ccatgagaag   1200
taccccacaa tctaccacct cagaaagaaa cttgtggact ccacagataa agcagacctg   1260
aggctcatat acctcgcact cgcacacatg atcaagttca gagggcactt tctcatcgaa   1320
ggtgacctga atcagataa  ttcagatgtg gataaactgt ttatacagct ggtgcaaaca   1380
tacaaccaac ttttcgagga aaacccaatc aatgcctccg gtgttgatgc aaaggccatc   1440
```

```
ctgtcagcaa gactcagcaa aagcaggcgg ctcgaaaacc tcatcgccca gcttcccggt    1500
gaaaagaaga acgggctctt tggtaatctc atcgcattga gccttggtct tactccaaac    1560
ttcaagagca attttgatct ggcagaggat gctaaactgc aactctcaaa ggacacatat    1620
gacgatgacc ttgacaatct gttggcccag atcggggacc aatatgcaga cctcttcctg    1680
gccgcaaaga atctgtcaga tgcaatcctc ttgtccgaca tactgagagt taacactgag    1740
atcacaaagg cacctctgtc cgcctccatg attaagagat acgatgagca tcaccaggat    1800
ctgactttgc tcaaagccct cgttagacag cagttgccag aaaagtacaa agaaatattc    1860
tttgatcaat caaaaaacgg atatgcaggg tacatcgacg gtggggcaag ccaggaagag    1920
ttctacaaat tcatcaaacc tatcctggaa aagatggatg ggacagaaga gctgctggtt    1980
aagctgaata gggaagacct cctcagaaag cagaggacat tgataacgg gagcatccct     2040 catcaaatcc acctcggtga actccatgct atcctgagaa ggcaggaaga cttttatcca    2100
tttttgaagg acaataggga gaaaatcgaa aaaatcctga cattcagaat cccatactac    2160
gttggtcctc tggcaagagg taacagtagg ttcgcatgga tgacaaggaa aagcgaggag    2220
acaatcacac cctggaattt tgaggaagtt gttgacaagg gtgccagcgc acaatccttt    2280
atcgaaagaa tgacaaattt cgacaagaat ctgcctaacg aaaaggttct cccaaagcat    2340
tcactcctgt acgaatattt tacagtttat aacgaactga ctaaagttaa atacgttacc    2400
gagggtatga ggaagccagc attcctttcc ggggaacaga agaaagctat tgtggacctc    2460
ctgttcaaga caaatagaaa agtgacagtt aagcaactca agaggatta cttcaaaaag    2520 atcgaatgtt ttgactctgt ggagatcagc ggggtggagg atagattcaa cgccagcctg    2580
ggtacatatc atgatctcct gaaaatcatt aaagacaagg acttccttga caacgaggag    2640
aacgaggaca ttctggaaga cattgttctg accctcacac tctttgagga tagggagatg    2700
attgaggaaa gactgaagac ctacgcccac ctctttgacg ataaagtgat gaaacagctc    2760
aagagaagaa ggtatacagg ttgggggaga ctgagcagga agttgatcaa tgggattagg    2820
gacaaacagt ccgggaaaac aatcctcgat tttctgaagt cagacggttt cgcaaacaga    2880
aattttatgc agctcattca cgatgacagc ttgacattca aggaagacat ccaaaaggct    2940
caagtgagcg ccaaggggga tagcctccac gagcatattg caaatctggc aggttcacca    3000
gccatcaaaa agggcatact tcagacagtt aaggttgtgg acgaattggt taaagttatg    3060
ggcaggcata agccagagaa tatcgttatc gaaatggcaa gggagaacca aacaactcaa    3120
aaagggcaga aaatagcag agagaggatg aaaagaatcg aggaagggat caaggaactt    3180
gggtcccaaa tcctcaagga gcacccagtt gaaaatactc aactgcaaaa cgagaagctc    3240
tatctctact atctccaaaa cgggagggat atgtatgttg accaggagct ggatattaac    3300
agactgtcag attatgatgt tgatcatatc gtgccccagt cattcctgaa ggacgattcc    3360
atcgacaaca aagttctcac aaggtccgat aaaaacaggg gcaagtccga taacgttcca    3420
agcgaagaag tggtgaaaaa gatgaaaaac tattggagac aacttctgaa tgcaaagttg    3480
attactcaga gaaagtttga caacctcaca aaagcagaaa gaggcgggct tagcgaactc    3540
gataaggcag ggtttatcaa aagacagctg gttgagacaa ggcagatcac aaaacatgtg    3600
gcacagatcc ttgactcaag gatgaatacc aagtatgatg agaatgataa gttgatcagg    3660
gaggttaaag ttatcacact caaatccaaa ctggtgtcag acttcaggaa agactttcaa    3720
ttttataagg tgagggagat caataactac caccatgcac atgacgccta cctgaacgca    3780
```

| | |
|---|---:|
| gtggtgggta cagcattgat taaaaaatac cctaagctgg agtctgagtt tgtgtacggg | 3840 |
| gactacaagg tgtacgacgt gaggaaaatg atagccaagt ccgagcagga gatcgggaaa | 3900 |
| gcaacagcta agtatttctt ttacagtaat atcatgaatt tctttaaaac tgagattact | 3960 |
| ctggcaaacg gggagatcag gaaaagaccc ctcatcgaga ctaatggtga acaggtgag | 4020 |
| atcgtttggg acaaggggag ggattttgct actgttagaa aagttctgag tatgccacaa | 4080 |
| gtgaatattg tgaaaaagac agaagttcag acaggtgggt tctccaaaga atccatcctg | 4140 |
| cccaagagaa attcagacaa gctcatcgca agaaagaagg actgggaccc taagaagtac | 4200 |
| ggaggatttg acagccccac cgtggcctat tccgtgcttg ttgtggcaaa ggtggagaaa | 4260 |
| gggaagagca aaaaactgaa atccgtgaaa gaactgctgg gaattaccat catggaaaga | 4320 |
| agctcctttg agaagaaccc aatcgacttc ctggaagcaa aaggatataa ggaagtgaaa | 4380 |
| aaggacctca ttatcaagct cccaaaatac tcacttttcg agttggagaa cggtagaaag | 4440 |
| aggatgctgg caagcgcagg ggaacttcag aaaggcaatg agctggcatt gccatcaaag | 4500 |
| tatgtgaact tcctctactt ggccagccat tacgagaaac ttaaaggtag cccagaagat | 4560 |
| aacgagcaaa aacagctctt tgtggaacag cataagcatt atctggatga gatcatagaa | 4620 |
| caaatctcag agttttccaa gagagttatc ctcgcagatg caaacctgga taaggttctc | 4680 |
| tcagcctata ataagcatag agacaagcca attagagagc aagcagagaa cattatccac | 4740 |
| ttgttcactc ttacaaacct gggggcacca gccgccttca atatttcga tacaacaata | 4800 |
| gacagaaaga ggtataccag caccaaagaa gttctcgacg ccacactgat ccatcaatca | 4860 |
| atcacaggcc tttacgaaac taggatcgac ttgtcacaac tgggtgggga tagcggtgga | 4920 |
| tcagggggct ccggtggttc aacaaatctc tccgacataa tcgaaaaaga gactggcaaa | 4980 |
| cagctcgtga tccaagagag catcctgatg ctgccagaag aggtgaaaga agtgatcggt | 5040 |
| aacaaaccag agagtgacat actggttcac actgcttacg atgagagcac agatgagaac | 5100 |
| gtgatgctgc ttacaagcga tgcacctgag tacaaaccct gggctctggt tatccaagac | 5160 |
| tccaacggag agaacaagat taaaatgctg agcggtggta gcggggggtag cggcggaagc | 5220 |
| actaacctca gcgacataat cgagaaagag acaggtaaac agctcgtgat tcaggaatcc | 5280 |
| atcctcatgc tcccagagga agtggaggaa gttatcggca acaaaccaga atcagacatc | 5340 |
| ctggttcata cagcctatga cgagagcact gacgaaaatg tgatgctgct caccagcgac | 5400 |
| gcacccgagt acaaaccttg ggcactcgtg atacaggatt caaatggcga aaataagatt | 5460 |
| aagatgctgg gatctaagaa gagaagaatt aaacaagat | 5499 |

<210> SEQ ID NO 21
<211> LENGTH: 5469
<212> TYPE: DNA
<213> ORGANISM: Artificial
<220> FEATURE:
<223> OTHER INFORMATION: base editor

<400> SEQUENCE: 21

| | |
|---|---:|
| ggatctaaga agagaagaat taaacaagat tcaagtgaga cgggcccggt cgcggtggac | 60 |
| cccacgctcc gacggcgtat cgagcccac gagttcgagg tgttttttcga cccgcgcgag | 120 |
| cttcgtaagg agacctgctt gctttacgag atcaactggg gaggacggca ctccatctgg | 180 |
| cggcacacct cgcagaacac caacaagcac gtcgaggtca actttatcga gaaattcaca | 240 |
| accgagcgct acttctgccc caacacacgg tgttcaatca catggttcct gagctggtcg | 300 |
| ccttgcggag agtgctcacg cgccatcacg gagttcctgt ctcgctaccc gcacgtcacc | 360 |

```
ctctttatct atatcgcacg cctctaccac cacgccgatc cgcgtaatcg ccaggggttg    420
cgcgacctaa tctcatccgg cgtaaccatt cagatcatga ccgaacaaga atctggttac    480
tgctggagga atttcgtaaa ctactccccg tcgaacgagg cccactggcc ccgctatccc    540
caccttgggg tgcgccttta cgtgctggag ctgtactgca tcatactcgg tcttcctcct    600
tgcctgaaca tccttcggcg aaagcagccg cagttgactt tcttcaccat tgcacttcaa    660
agctgccact accagcgtct ccctccacat attctctggg cgaccggctt gaagtctggt    720
ggttcaagcg gaggctcatc tggcagcgaa actccgggca cttccgagtc agctactcct    780
gagtctagcg gcgggtcgtc aggagggtct gacaagaaat acagtattgg ccttgcaatt    840
gggactaact ctgtgggatg ggccgtgatt acagacgagt acaaggtgcc gagcaagaag    900
tttaaggtgc ttgggaacac cgaccggcac tcgattaaga agaacctaat aggggcactt    960
ctgttcgact ccggagaaac cgcagaggcc acccgcctta acgcaccgc acgacgacga   1020 tacacccggc gtaagaaccg gatctgctat ctacaggaaa tcttcagtaa tgagatggca   1080
aaggtggatg acagcttttt tcacaggctt gaggagtcgt tcctagttga ggaggacaaa   1140
aagcacgaac gccatcccat cttcgggaac atcgtggatg aggtcgccta ccacgagaag   1200
tacccgacca tctaccacct ccgcaagaaa ctcgtggaca gcacagacaa ggctgacctg   1260
cgactgatct acttagccct ggcccacatg attaagttcc ggggtcactt cctaatcgag   1320
ggagacctca acccgataa cagtgacgtg gacaagctct catccaact tgtgcagacc   1380 tacaaccagt tgttcgagga gaaccctatc aacgccagcg gggtggacgc gaaagctatc   1440
ctgtccgcca ggctgtcgaa gtctaggcgt ctggagaacc taatcgctca gctaccgggc   1500 gaaaaaaga atggactgtt cggcaacctc atagccctga gcctgggggct gacgcccaac   1560 ttcaaaagca acttcgacct ggccgaggac gccaagctcc aattgagcaa ggacacctac   1620
gacgacgact tggacaacct attggcccag ataggtgacc agtatgcaga cctcttcctt   1680
gcggccaaga acttgagtga cgctatactg ctcagtgaca tcctgagggt gaacactgag   1740
atcactaagg cccctctctc tgcctcaatg attaagcgtt acgacgagca tcaccaggat   1800 ctcacctgc ttaaggccct tgttcggcag cagctccctg agaagtacaa ggagatattt   1860
tttgaccagt ctaagaacgg ctacgccggt tacattgacg gtggggcaag ccaggaggag   1920
ttctacaagt tcatcaagcc gatccttgag aagatggacg caccgaggaa gctacttgtc   1980
aagttgaacc gggaagacct gctccggaaa cagcgtacat tcgacaacgg cagcatccct   2040
caccagatcc acctgggcga actacacgcc atcctccgac gtcaggagga cttctatcca   2100
ttcttgaaag ataacagggga aaaaatcgaa aaaatactta cgtttcgaat accttactac   2160
gtggggcccc ttgctcgggg aaactccaga ttcgcatgga tgaccaggaa gtcagaggag   2220
accatcacac cctggaactt tgaggaggtg gttgacaaag gtgcttctgc ccagtccttc   2280
attgagcgga tgactaactt cgacaagaac ctgcccaacg agaaggtgct gccaaagcac   2340
agcctgctct acgaatactt tactgtgtac aatgagctga cgaaggtgaa gtacgtgaca   2400
gaggggatgc ggaagcccgc tttcctgagc ggcgagcaaa aaaagcaat cgtggaccta   2460 ctgttcaaga ccaaccgaaa ggtgacagtg aagcagctca aggaggacta cttcaaaaaa   2520
atcgagtgct tcgactctgt tgagataagc ggcgtggagg accgattcaa cgcctcattg   2580
ggaacctatc acgacctgct caagatcatt aaggacaagg acttcctgga taatgaggag   2640
aatgaggaca tcctggagga tattgtgctg acccttactc tattcgagga cagggagatg   2700
```

```
atcgaggagc gactcaagac ctacgctcac ctgttcgacg acaaggttat gaagcaattg    2760
aagcgtaggc gatacacggg gtggggaaga ctctcccgaa aactgataaa cggcatcagg    2820
gacaagcagt cagggaagac gatcttggac ttcctgaaat ccgacgggtt cgccaaccgc    2880
aacttcatgc agctcattca cgacgactca ctaacgttca aagaggacat tcagaaggct    2940
caagtcagtg acaaggcga ctccctgcac gagcacattg caaaccttgc gggctccccg    3000
gcgattaaaa agggcattct ccaaacggtt aaggtggtgg acgagctggt gaaggtgatg    3060
ggccgacaca agcctgagaa catcgtgatc gagatggcca gggagaacca gactacccag    3120
aagggtcaga agaactctcg ggaacgtatg aagcgtattg aggaggggat taaggagttg    3180
ggctctcaaa tcctcaagga gcaccctgtg agaacactc agctccaaaa cgagaagctg    3240
tacctgtact acctgcaaaa cgggcgcgat atgtacgtgg atcaggagtt ggacatcaac    3300
aggcttagcg attacgacgt ggaccacatc gtgccacagt cattcttaaa ggacgacagc    3360
atcgacaaca aggttctgac gaggagcgac aagaatcgag ggaaaagtga caatgttcca    3420
tccgaggagg tggtcaagaa aatgaagaac tattggcgtc agcttctgaa cgccaagctc    3480
atcacccagc ggaaattcga caacctgact aaggctgagc gaggcggact ctccgagctt    3540
gacaaggctg gcttcatcaa gcggcagttg gtcgaaaccc gacagataac gaagcacgtt    3600
gcccagatac ttgactcccg tatgaacacc aagtacgacg agaacgacaa gctcatcagg    3660
gaggtgaagg tcattaccct taagtccaaa ctcgtcagcg acttcgtaa ggacttccag    3720 ttctacaagg tgcgcgagat caataactac caccacgcac acgacgccta cctgaacgca    3780
gtggttggaa ccgcgttgat taaaaagtac cccaagttgg agtcggagtt cgtttacggg    3840
gactacaagg tgtacgacgt tcggaagatg atcgccaagt ctgaacagga gatcgggaaa    3900
gcaaccgcca agtatttctt ctatagcaac atcatgaact tctttaaaac cgagatcaca    3960
cttgccaatg gcgagatccg taagaggccg ctgatcgaga caaatgggga gactggcgag    4020
atcgtgtggg acaagggccg cgacttcgca accgttcgga aagtcttgtc catgcctcaa    4080
gtcaacatcg tcaagaagac tgaggtgcaa acaggcgggt tctcgaagga gtccatactg    4140
cccaagagga actcagacaa gctcatagca cgcaaaaaag actgggatcc aaagaaatac    4200
ggcgggttcg actcgccgac agtcgcatac tccgtgttag tggtggctaa agtggaaaag    4260
gggaagtcca agaagctcaa gtccgtcaag gagttgctcg ggatcaccat tatgaacgg    4320 tcctcattcg agaagaatcc cattgacttc ctagaggcga agggctacaa agaggtcaaa    4380
aaggacctaa ttattaagct ccccaagtat tcactcttcg aacttgaaaa tggtcgtaag    4440
cggatgttgg caagcgctgg agagcttcag aaggggaacg agcttgcact gccttccaag    4500
tacgtgaact tcctgtacct cgcctctcat tacgagaagt tgaagggctc accggaggac    4560
aacgagcaga agcagttgtt cgtggagcag cacaagcact acctcgacga gatcattgag    4620
cagataagtg agttcagcaa acgggtgatc cttgccgacg ctaacctgga caaggtgctg    4680
agcgcctaca caagcacag agacaagccg atccgagagc aagcggagaa catcatacac    4740
ctgttcaccc tcacgaacct cggggctccc gcagccttca atatttttga cacgaccatc    4800
gaccgtaaac gctacactag cacgaaggag gtgctggacg ctacccttat ccaccagtcc    4860
atcaccggcc tgtacgagac gagaatcgac ttgtcgcagc tcggtggtga ctctggcggt    4920
agtggaggaa gcgcgggag taccaacctc agcgacatta tcgagaagga gaccggcaag    4980
caactcgtga tccaggagag catactgatg ctcccccgagg aggtcgagga ggtgattggc    5040
aataagcccg agtccgatat actggttcat actgcgtatg acgaaagcac agacgagaac    5100
```

```
gtcatgctac ttaccagcga cgccccggag tacaagccct gggccctagt catccaagac   5160
agcaacggtg agaacaagat caagatgctt accaacctga cgacatcat tgaaaaggag    5220 accggaaagc agcttgtgat ccaggagtcc atcctaatgt tgcccgagga ggtcgaggag   5280
gtcatcggaa acaagcccga gtcggacatc ctagtgcaca ccgcctacga cgaatcgacc   5340
gacgagaacg tgatgctcct cacctccgac gcacctgagt acaagccgtg ggccctcgtt   5400
atccaagact ctaatggtga gaacaagatc aagatgctcg gatctaagaa gagaagaatt   5460
aaacaagat                                                           5469
```

<210> SEQ ID NO 22
<211> LENGTH: 5499
<212> TYPE: DNA
<213> ORGANISM: Artificial
<220> FEATURE:
<223> OTHER INFORMATION: base editor

<400> SEQUENCE: 22

```
ggatctaaga agagaagaat taaacaagat tcgtccgaga ccggcccgt cgccgttgac     60 ccgacccctcc gccgccgcat cgagccccat gagttcgagg tgtttttcga cccacgtgaa   120
ctccgcaagg aaacttgcct cctgtacgag atcaactggg gtggacgtca ctccatctgg   180
agacacacca gccagaacac gaacaagcac gtcgaggtca acttcatcga agttcacc     240 accgagcgct acttctgccc caacacgcgg tgctcgatca cgtggttcct gtcctggtcc   300
ccatgcgggg agtgcagccg cgccatcacc gagttcctct cccgatatccc gcacgtcacc  360 ctcttcatct acattgcccg gctctaccac cacgcagacc cgcgaaaccg ccagggcctc   420
cgcgacctca tatcctccgg cgtgaccata cagatcatga ccgaacagga gtctggctac   480
tgctggcgca acttcgtgaa ctacagcccc tcgaacgagg cccactggcc gcgttacccg   540
cacttgtggg tgaggctgta cgtcctggag ttgtactgca tcatcctggg cctgcctccc   600
tgcctaaaca tcctccgccg gaagcagccc agctcacgt tcttcacaat tgcgttgcaa    660
tcctgtcact accagcggct tccacctcac atccctgggg ctaccggcct caagagcggc   720
ggtagctccg gaggctcatc tgggagcgag acacccggca cttccgagtc tgcaaccccg   780
gagagtagtg gtggctcctc tggtggatct gacaaaaaat actcaattgg tctggcaatt   840
gggaccaaca gtgtcggatg gccgtgatt accgacgagt acaaggtgcc gtccaaaaaa   900
ttcaaggtgc ttgggaacac cgaccgccac tcgatcaaga aaaacctaat cggtgcgttg   960 ctttcgaca gtggggagac cgccgaggca acacgcttaa aacgcacagc taggaggaga   1020
tatacacggc gcaagaaccg aatatgctac ttacaggaga tattctccaa tgagatggcg   1080
aaggtggacg actctttctt ccatcggctt gaggaatcct tcctggtcga ggaggacaag   1140
aagcacgagc gacacccgat attcgggaac atcgttgatg aggtggcgta ccacgagaag   1200
tacccaacga tataccactt acgcaagaag ctcgtggact ctacgacaa ggccgacttg   1260 cgccttatct acttggcact ggcccacatg attaagttcc gaggccactt ccttatcgag   1320
ggtgacctga cccccgataa ctccgacgtg gacaagctct catccaact cgtccagaca   1380 tacaaccagc tattcgagga gaatccatc aacgcctctg ggtggacgc taaagctatc    1440 ctctcagccc gcctgtcaaa gtcgaggagg ttggagaacc taatcgccca gcttccaggc   1500
gagaagaaaa atgggctgtt cggaaaccttt atcgcactct cactgggcct aaccccgaac   1560
ttcaagtcca acttcgacct ggcagaggac gcgaaattgc agttgtcgaa agacacctat    1620
```

```
gacgatgacc tggacaacct gttggcccag ataggggacc agtacgccga cctgttccta      1680
gcggccaaga acctgtccga cgccatcttg ctgtcggata tactgcgggt gaacaccgag      1740
atcactaaag cacctctctc cgccagcatg attaagcgtt acgacgagca ccaccaagat      1800
ttgaccctgc taaaggcact tgtacggcag cagcttcccg agaagtacaa ggagatcttt      1860
ttcgaccaaa gcaagaacgg ctacgccggg tacatcgacg gaggtgccag ccaggaggag      1920
ttctacaagt tcattaagcc catcctggag aagatggacg ggactgagga actacttgtg      1980
aagctgaacc gggaagactt actacggaag cagcgtacct tcgacaacgg ttctatccca      2040
catcagatcc atcttgggga gttgcacgcg atcctgcgac gccaggagga cttttacccc      2100
ttcctgaaag acaaccgcga gaaaatcgag aagatactga ccttcagaat accttactac      2160
gtcggacccc ttgcgcgagg caactcaaga ttcgcgtgga tgaccaggaa atcagaggag      2220
accatcacac cctggaattt cgaggaggtg gttgacaagg gtgcctccgc ccagtccttt      2280
atcgaacgaa tgaccaactt cgacaagaac ttgcccaacg agaaggtgct ccccaaacac      2340
agcctcctct acgaatattt cacagtgtac aacgagctta ctaaagttaa gtatgttact      2400
gagggcatga ggaaacccgc cttcctgtca ggcgagcaga agaaagctat tgtggacctc      2460
cttttcaaga ccaaccggaa ggtgacagtg aagcagctca aggaggacta cttcaagaag      2520
atagagtgct tcgacagcgt ggagatcagc ggggtggagg acagattcaa tgcctctctc      2580
ggaacatacc acgacttgct taagatcatc aaggacaagg acttcctcga caacgaggaa      2640
aacgaggata ttctggagga tattgttctg actcttaccc tgttcgagga ccgggagatg      2700
atcgaggagc gtctcaagac ctacgcccac ctgttcgacg acaaagttat gaagcagctc      2760
aagcgtcgga gatataccgg atggggccgt ctgtctcgga agctcatcaa cgggatcagg      2820
gacaagcagt cagggaagac gatcttagac ttccttaagt ctgacggctt cgccaacagg      2880
aacttcatgc agttgatcca cgacgacagc cttaccttca aggaggacat ccagaaggcc      2940
caagtgagtg gccagggtga cagcctccac gagcatattg ctaatcttgc gggttccccca     3000 gcgattaaaa agggcatact tcaaaccgtt aaggtggtgg acgagcttgt caaggtgatg      3060
gggcgacaca agcccgagaa catcgtgatc gagatggcca gggagaacca gaccacccag      3120
aaggggcaga agaatagccg agaacgcatg aagcgcatcg aggagggat taaggagcta      3180 gggagccaga tcctcaagga acatcccgtc gagaacaccc agctccagaa cgagaagcta      3240
tacctctact acttgcaaaa cgggagggat atgtacgtgg atcaggagtt ggacattaac      3300
cgcctaagcg actacgacgt agatcacatc gtgcctcagt cattcctcaa agacgacagc      3360
attgacaaca aagtcttgac ccgatccgac aagaaccgag gaaaatccga caatgtgccc      3420
tcagaggagg tcgtcaagaa aatgaagaac tattggaggc agctacttaa cgccaaactc      3480
ataacccagc ggaagttcga caacctgaca aaggctgagc ggggtgggct cagcgagctt      3540
gacaaggctg gcttcatcaa gcggcagttg gtggagacaa gacagataac gaagcacgtg      3600
gctcagatcc tggactctcg catgaacacg aagtacgacg agaacgacaa attgatccgc      3660
gaggtcaagg ttattacgct caagagcaaa cttgtcagcg atttccgcaa ggacttccag      3720
ttctacaagg tgagggagat taacaactac caccatgcac atgatgccta cttgaacgca      3780
gtggtgggga ccgcgcttat taaaaagtac cctaagttgg agtcagagtt cgtttatggg      3840
gactacaagg tgtacgacgt ccggaagatg attgcaaagt ctgaacagga aatcgggaag      3900
gccaccgcca aatatttctt ctacagtaac attatgaatt tttttaagac tgaaattact      3960
ctcgcaaacg gcgagatcag gaagcgtccc ctcatcgaga caaacgggga gaccggggag      4020
```

```
atagtctggg acaagggcg ggacttcgct acggtgagga aggtgctctc gatgccacaa    4080
gtgaacatcg tcaaaaagac agaggtgcag accggtggct tctcaaagga gtcaatcctg    4140
ccaaaacgta acagcgacaa gctcatcgcc cgcaagaaag actgggaccc taagaagtat    4200
ggtgggttcg actcaccgac ggtcgcatac tccgttctgg tcgtggcaaa ggtggaaaag    4260
ggcaagtcca aaaaactgaa atccgtgaag gagttgcttg gcattaccat catggaacgc    4320
agcagcttcg agaagaaccc cattgacttc ctggaggcta aagggtacaa ggaggtcaag    4380
aaagatttaa ttattaagct acctaagtac agcttgttcg agctggagaa cggccgaaaa    4440
cgaatgctcg catccgccgg ggaacttcaa aagggcaacg agcttgcgct gccctccaag    4500
tacgtgaact tcctgtactt ggcatcccac tacgagaaac tcaagggtag cccagaggac    4560
aacgagcaga agcagctatt cgtggagcag cacaagcact acctcgacga gataatcgag    4620
cagatcagtg agttcagtaa gcgggtgata ctcgcggacg ccaacttgga caaggtgctt    4680
agtgcctaca acaagcaccg tgacaagccc atccgagaac aggctgagaa catcatccac    4740
cttttcactc tgacaaacct cggtgctccc gccgccttca atacttcga cactaccatc    4800 gacaggaagc gctacacatc tacgaaggaa gttcttgacg ctacgcttat tcatcagtct    4860
atcacagggc tgtacgagac aaggatcgac cttagccaac tcggcgggga ttccggagga    4920
agcggcggct ccggtggttc tacaaacctg tccgacatca tcgagaagga aaccggcaag    4980
cagcttgtga tccaggagag catactcatg ctccccgagg aggtcgagga ggtgatcggc    5040
aacaagcccg agtcagacat tctggtccac acagcctacg acgagtcaac cgacgagaac    5100
gtgatgctcc tgacaagcga cgcgcccgag tacaagccct gggccctggt gatccaggac    5160
tcgaatgggg agaacaagat caagatgctt agtggaggct ctggagggag cggtggatca    5220
actaacctgt ctgacattat cgaaaaggag acgggcaagc agcttgtgat ccaagaatct    5280
atcctaatgt tgccggagga ggtcgaggag gtgattggaa acaagccgga aagcgacatc    5340
ctcgtccaca ccgcctatga cgagagcacg gacgagaatg tgatgctcct gacatcagac    5400
gcgccggagt acaagccgtg ggccctggtc atacaggaca gcaacgggga gaacaagatc    5460
aagatgctag gatctaagaa gagaagaatt aaacaagat                          5499
```

<210> SEQ ID NO 23
<211> LENGTH: 3987
<212> TYPE: DNA
<213> ORGANISM: Artificial
<220> FEATURE:
<223> OTHER INFORMATION: Cas12a polynucleotide

<400> SEQUENCE: 23

```
atggccggga gcaagaagcg ccggataaag caggacacgc agttcgaggg cttcaccaac     60
ctgtaccaag tctccaagac gctccggttc gagcttatcc cgcaagggaa gaccctgaaa    120
cacatccagg aacaaggttt catcgaggag acaaggccc gcaacgacca ctacaaggag    180
ctcaagccca taatcgatcg gatctacaag acgtacgccg accagtgcct ccaactggtg    240
cagctcgact gggagaacct gagcgccgcc attgacagct accgcaagga aaagacggag    300
gagacgcgca acgcccttat tgaggagcaa gccacctacc gcaacgccat ccacgactac    360
ttcatcgggc gcaccgacaa cctgacggac gcgatcaaca gcgccacgc ggaaatctac    420 aagggccttt tcaaggccga gctcttcaac gggaaggtcc taaacagct cgggactgtc    480 acgacaaccg agcatgagaa cgccctcctt cgcagcttcg acaagttcac cacatacttc    540
```

```
tcgggcttct accggaaccg caagaacgtt ttcagcgccg aggacatctc caccgccatc    600
ccgcacagga tcgtccagga caacttcccc aagttcaagg agaactgcca catcttcacg    660
cgcctgatta cagccgtacc ttcacttcgt gagcacttcg agaacgtcaa aaaggccatc    720
gggatcttcg tctccacgtc catcgaggag gtattctctt tcccgttcta taaccagctc    780
ctgacccaga cgcagatcga cctctacaac cagctactgg gcggcatcag ccgggaggcc    840
gggaccgaga aaataaaggg cctcaacgaa gttctcaacc tggccatcca agaacgac      900 gagaccgcgc atatcatcgc atccctgccg catcgcttca ttcctttgtt caagcagata    960
ttgagcgacc ggaacaccct ctcgttcatc ctcgaagaat tcaagagcga cgaggaggtc   1020
attcagtctt tctgcaagta caagacgctc ctacggaatg agaatgtgct ggagaccgcg   1080
gaggcactct tcaatgagct gaactccatt gacctgaccc acatcttcat tagccacaag   1140
aaactggaga cgatctccag cgccctgtgc gaccactggg acactctccg caacgccctc   1200
tacgaacgcc ggatctccga acttaccggc aagataacta agtcggctaa ggagaaggtg   1260
caacggagcc tcaagcacga ggacatcaac cttcaggaaa tcatctcagc cgcgggcaag   1320
gagctgagcg aggcgtttaa gcagaaaaca tcggagatac tgagccacgc gcacgcggcc   1380
ctggatcaac cgctgccgac gactctcaag aagcaagagg agaaggaaat ccttaagtcc   1440
cagctcgact cgctgctcgg cctctatcac ttgctcgact ggttcgcggt tgatgagtcc   1500
aacgaggtgg acccggagtt ctccgcgcgc ctcacgggta ttaagctgga gatggagcca   1560
agcttaagct tctacaacaa ggcccgcaac tacgcgacca aaaaccgta ctcagtcgag   1620 aaattcaagc tgaatttcca gatgcctaca ttggcgaggg ggtgggacgt gaaccgcgag   1680
aagaacaatg gagccatcct gttcgtcaaa aatgggttgt actacctggg catcatgccc   1740
aagcagaagg gccgttacaa ggccctgtca ttcgagccta ccgagaagac ctcggagggc   1800
ttcgacaaga tgtactacga ctatttcccg gacgccgcca agatgatccc gaagtgctcc   1860
acgcagctca agccgtcac ggcccacttc cagacgcata ccacgccgat acttctgagc   1920
aacaacttca ttgagccgct agagatcacg aaggagatat acgacctaaa caaccccgaa   1980
aaggagccca gaagttcca gacagcctac gctaagaaga caggtgatca gaagggatat   2040
agggaggcac tctgcaagtg gatcgacttc acgcgcgact tcctgtcgaa atatacaaag   2100
acgaccagca ttgacctaag ttctctccgc ccatcctccc agtacaagga tctgggcgag   2160
tattatgcgg agctgaaccc attgctgtac cacatcagct tccagaggat cgccgagaag   2220
gagattatgg acgcggtgga gacggggaaa ctatacctgt tccaaatata taacaaggac   2280
ttcgctaaag ggcaccacgg gaagcccaac ctgcacacac tctactggac gggcttgttt   2340
tcgccagaaa atttggccaa gacttcgatc aagctcaacg gccaggcgga gttgttttac   2400
cgtcccaagt ctcgcatgaa gcgcatggcg catcgcctcg gagagaaaat gcttaacaag   2460
aagctcaagg atcagaagac gcccatacct gatacgttgt accaggaatt gtacgactac   2520
gtgaaccacc gcctatcgca cgacctctca gacgaggccc gcgccctcct cccaaacgtg   2580
attactaagg aggtttccca tgaaataatc aaggaccgac ggttcaccag cgacaaattt   2640
tttttccacg tgcctatcac gctcaattac caggcggcca actccccatc gaagttcaac   2700
cagcgcgtga acgcctacct taaggagcac ccggagaccc caatcatcgg gatcgaccgt   2760
ggcgagcgga acctgatcta tattacggtg atcgatagca ccgggaagat cctggagcag   2820
cgctccctga acacaatcca gcagtttgac taccagaaga aactcgacaa ccgggagaag   2880
gagcgcgtcg cagcccggca agcatggagt gtggtcggca ccataaagga cctgaaacag   2940
```

```
ggttacctaa gtcaagttat ccacgagatc gttgacctga tgatacacta tcaagccgta    3000
gtcgtgctgg agaacctcaa cttcgggttt aagtccaagc gcaccggcat cgcggagaag    3060
gcggtgtacc agcagttcga gaagatgctg atcgacaagc tgaactgcct ggtgctcaag    3120
gactaccctg cggagaaggt cggcggggtc ttgaacccgt accagctaac cgaccagttc    3180
acgagcttcg ccaaaatggg cacgcagtcc ggattcttgt tttatgtccc ggctccatat    3240
acaagtaaga tcgacccgct gacagggttt gttgacccat cgtgtggaa gaccatcaag     3300 aaccacgaga gcaggaaaca cttcttagag ggcttcgact tcctgcatta cgacgttaag    3360
acaggcgact tcatcctgca cttcaagatg aaccgcaacc tgtcgttcca gaggggcctg    3420
cccggcttca tgcccgcctg ggatatcgtc tttgagaaga tgagacgca gttcgacgcg     3480 aaggggacgc cgttcatcgc tggaaagcgg atcgtgccgg tcatcgagaa ccaccgcttc    3540
acgggtcgct accgagattt ataccccgcc aacgaactaa ttgcgctgct ggaggagaag    3600
gggatcgtgt tccgagatgg cagcaacatt ctcccgaagc tgctggagaa cgacgactcg    3660
cacgctattg acacgatggt cgccctcata cggagcgtgc ttcagatgcg gaacagtaac    3720
gctgccacgg gcgaggacta cattaactcc cccgtccgcg acctcaacgg ggtctgcttc    3780
gatagccgct tccagaaccc ggagtggcct atggatgcgg acgcgaacgg ggcctaccac    3840
atcgccctca agggccaact cctgctcaac cacttgaagg aaagcaaaga cctcaaattg    3900
cagaatggca tcagtaacca ggactggctc gcgtacatcc aggaactgag aaacgggtcc    3960
aagaagcggc gtatcaagca agattga                                         3987
```

<210> SEQ ID NO 24
<211> LENGTH: 3987
<212> TYPE: DNA
<213> ORGANISM: Artificial
<220> FEATURE:
<223> OTHER INFORMATION: Cas12a polynucleotide

<400> SEQUENCE: 24

```
atggcgggaa gcaaaaagcg ccggattaag caagacacgc agttcgaggg cttcacgaac     60
ctctaccaag tcagcaagac cctccggttc gagctgatac acagggaaa gacgctcaag    120 cacatccagg aacagggctt catcgaggag acaaggcgc gcaacgacca ctacaaggag     180
ttgaaaccga tcatcgaccg catctacaag acgtacgccg accagtgcct ccagctcgtg    240
cagctcgact gggagaacct ctccgccgcc attgactcgt accggaagga gaagactgag    300
gagacccgca acgccctgat cgaggagcaa gcaacctacc ggaacgccat ccacgactac    360
ttcatcggcc gcaccgacaa cctcaccgac gcgatcaaca gcggcacgc ggagatatac     420 aaagggctgt tcaaggcgga gctgttcaac ggcaaggtgc tcaagcagct agggacggtg    480
accacgaccg agcacgagaa cgcgctcctc cgcagcttcg acaagttcac cacctacttc    540
agcggcttct accggaaccg caagaatgtg ttcagcgcgg aggacatcag cacggccatc    600
ccgcaccgca tcgtccagga caacttcccg aagttcaagg agaactgcca tcttcacc      660 cgcctgataa ccgccgtccc ctccctgcgg gagcacttcg agaacgtcaa aaaggcaatt    720
gggatcttcg tctcgaccag cattgaggag gtgttcagct tcccttcta caaccagctc     780 ctcacccaga cgcagatcga cctgtacaat cagttgctcg gcgggataag ccgcgaggcg    840
ggaaccgaaa aaatcaaggg gctgaacgaa gtgttgaacc tcgccatcca gaagaacgac    900
gagaccgcgc acatcatcgc ctcccctgccc caccggttca tcccgctgtt caagcagatc    960
```

```
ctctctgacc ggaacaccct gtccttcatt cttgaggagt tcaagtcgga cgaggaggtc    1020
atccagagct tctgcaagta caagacgctg ctacggaacg agaacgtgct ggagacggcg    1080
gaggcactgt tcaacgagct aaacagcatc gacctcacgc acatcttcat cagtcacaag    1140
aaactggaga ccatctcctc cgcgctgtgc gaccactggg acacgctcag gaacgcgctc    1200
tacgagcgcc gaatcagtga gctgacgggc aagatcacga agtccgcgaa ggagaaggtg    1260
cagcggtccc tcaagcacga ggacatcaac ctccaggaga tcatctcagc ggctgggaaa    1320
gagctgtccg aggcgttcaa gcagaaaacg agcgaaatcc tgtcccacgc gcacgcggcc    1380
ctggatcagc tctgccgac gaccctcaag aaacaagaag aaaaggaaat cctcaagtcg    1440
cagctcgact cgctgctggg cctgtaccat ctcctcgact ggttcgccgt ggacgagagc    1500
aacgaggtgg accccgagtt ctccgcgcgg cttacgggga tcaagctgga gatggagccc    1560
agcctgtcct tctacaacaa ggcgcgcaac tacgccacca agaagcccta cagcgtggag    1620
aagttcaagc tcaacttcca gatgcccact ctcgcacgtg ggtgggacgt caaccgcgaa    1680
aaaaataatg gggcgatcct gttcgtcaag aacggcctgt actacttggg catcatgccg    1740
aaacagaagg gccgctacaa ggccctgagc ttcgaaccga ccgagaaaac gagcgagggg    1800
ttcgacaaga tgtactacga ctacttcccc gacgccgcga agatgattcc aaagtgctcc    1860
acgcagctta aggccgtgac ggcccacttc cagacgcaca cgaccccgat cctcctcagc    1920
aacaacttca tcgagcccct ggagatcacg aaggagatat acgacctgaa caacccggag    1980
aaggagccca agaaattcca gaccgcctac gccaagaaga caggcgacca aaagggttac    2040
agggaggccc tctgcaagtg gatcgacttc actaggggact tcctgtccaa gtacaccaag    2100
actacctcta tcgacctgtc cagcctccgc ccgtcgtccc agtacaaaga tttgggcgag    2160
tattacgcgg agctgaaccc actgctctac cacatcagct tccagcgcat cgcggagaag    2220
gagatcatgg acgcagtgga cgggcaag ctataccctat ttcagatata caacaaagac    2280
ttcgctaagg gacaccacgg caagcctaac ctgcacaccc tctactggac ggggctcttc    2340
agcccggaga acctcgccaa gacctcgatc aagctcaacg gccaggccga gctgttctac    2400
cggcccaagt cccgcatgaa gcggatggcc caccggctcg gggagaaaat gctcaacaag    2460
aaattgaagg accaaaaaac gccgataccc gacaccctat accaggagct gtacgactat    2520
gtgaaccacc gcctgagcca cgacctcagc gacgaggcgc gggcccttcct gccgaacgtc    2580 atcacaaagg aggtcagcca cgagatcatc aaggaccggc gcttcacctc cgacaagttt    2640
ttctttcacg tgcccatcac gctcaactac caggccgcca actcgccgtc caagttcaac    2700
cagcgcgtga acgcctacct caaggagcac cccgagaccc cgatcatcgg gattgaccga    2760
ggggagcgga acctcatcta catcaccgtc atcgacagca ccgggaagat ccttgaacag    2820
cggtcgctca acaccatcca gcagttcgac taccagaaga aactcgacaa ccgggagaag    2880
gagagagtgg cggccggcca ggcttggtcc gtcgtcggga cgattaagga cttgaaacaa    2940
ggttacctgt cgcaagtgat ccacgagatc gttgacctga tgatccacta ccaagccgtc    3000
gtggtcctgg agaacctcaa cttcggcttc aagagcaaac gaaccggcat cgcggagaag    3060
gccgtgtacc agcagttcga aaaaatgctg atcgacaagc tgaactgcct cgtgctcaag    3120 gactacccg ctgagaaggt cggcggggtg ctgaacccgt accagctcac tgaccagttc    3180
accagcttcg caaagatggg cacccagtcc ggcttcctgt tctacgtgcc tgcgccatac    3240
acctcgaaga tcgaccgct caccgggttc gtggacccct cgtctgaa gaccatcaag    3300 aaccacgaga gccgcaagca cttcctggag ggcttcgact tcctccacta cgacgtcaag    3360
```

```
accggggact tcatcctgca cttcaagatg aaccgcaacc tcagtttcca gcgcggcctg    3420
ccggggttca tgcccgcttg ggatatagtc ttcgagaaga atgagacgca gttcgacgcg    3480
aagggcaccc cgttcatcgc cgggaagcgc atcgtgccgg tcatcgagaa ccaccggttc    3540 accggcgct accgcgacct atacccggcg aacgagttga tcgccctcct ggaggagaag    3600
ggcatcgtgt ccgcgacgg ctccaacatc ctcccgaagc tgctcgaaaa cgacgactcc    3660
cacgccatcg acacgatggt cgcgctgatc cggtcggtgc tccagatgcg gaactccaac    3720
gccgcgacgg gcgaggacta catcaacagt ccggtccgcg atctgaacgg cgtctgcttc    3780
gactcccggt tccagaaccc cgagtggccg atggacgcgg acgcgaacgg cgcataccac    3840
atcgccctaa aagggcaatt gctgctcaac cacctcaagg aatccaaaga cctaaagctc    3900
cagaacggca tctccaacca ggactggctg gcgtacatcc aggaactgcg gaacgggagc    3960
aaaaaacgtc ggatcaagca agattga                                       3987
```

<210> SEQ ID NO 25
<211> LENGTH: 3987
<212> TYPE: DNA
<213> ORGANISM: Artificial
<220> FEATURE:
<223> OTHER INFORMATION: Cas12a polynucleotide

<400> SEQUENCE: 25

```
atggcgggct ccaagaaacg ccggattaag caagataccc agttcgaggg gttcacgaac      60
ctctaccaag tgagcaagac cctccgattc gaactgattc ctcaggggaa gaccctcaag     120
cacatccagg agcaagggtt catcgaggag acaaggcgc ggaacgacca ctacaaggaa     180
ctcaaaccca tcatcgaccg catctacaag acctacgccg atcagtgcct ccagctcgtg     240
cagttggact gggagaacct cagcgcggcc attgactcct accggaagga gaaaacggag     300
gagacgcgca acgcgctcat cgaggaacag gcaacctatc gcaacgccat ccacgactac     360
ttcatcggga ggactgacaa cctcactgac gcgattaaca agcgccacgc ggagatatac     420
aagggactct tcaaagcgga gctgtttaac ggcaaggttc tcaagcaact cggcactgtg     480
accacgaccg agcatgagaa cgccctgctc cgctccttcg acaagttcac cacctacttc     540
tccgggttct accgcaaccg caagaatgtc ttcagcgcgg aggacatcag cacggccatt     600
ccacatcgaa tcgtccaaga taacttcccg aagttcaagg agaactgcca catcttcacc     660
cgactcatta ctgctgtacc gtcgttacgc gaacacttcg agaacgtcaa gaaggcaatt     720
ggaatcttcg tctctacgtc aatagaggag gtgttcagct ccctttcta caaccagctc     780 cttacgcaga cccagataga cctgtacaat cagctcctcg gtgggatcag ccggaggcg     840 gggactgaga agattaaagg gctcaacgag gtcttgaacc tggccatcca aaaaaacgat     900
gagacggcgc acatcatcgc ctcgctgccc caccggttca tcccgctgtt caagcagatc     960
ctcagtgaca ggaacacctt gagctttatc ctagaggagt tcaagagcga cgaggaggtg    1020
atccagagct tctgcaagta caaaaccctg ctgaggaacg agaacgtcct ggagacggcg    1080
gaggcgctgt tcaacgagct gaactctatc gacttaactc acatattcat ctcgcacaag    1140
aagctggaga ctattagctc tgcactctgc gaccactggg acaccctccg caacgcgctc    1200
tacgagcgcc gcatctcgga gctgaccggg aagatcacca atccgcgaa ggaaaaggtc    1260 cagcgttccc tcaaacacga ggatattaac ttacaggaga ttatctcagc ggctgggaag    1320
gagttgtcag aggcgttcaa gcagaaaact tccgagatcc tgagccacgc gcacgcagcg    1380
```

```
ctcgaccagc ctctgcccac caccctcaaa aagcaggaag aaaaagagat cctcaagagc   1440
cagttggact ccctgctggg gctctatcac cttctcgact ggttcgccgt cgatgagtcg   1500
aacgaggtgg accccgagtt ctccgcccgg ctgaccggca tcaagctaga gatggagccg   1560
tccctcagct tctacaataa ggcccgcaac tacgcgacca aaaaacccta cagcgtggag   1620
aagttcaagc tgaacttcca gatgccgacc ttagcacgcg gttgggacgt aaacagggag   1680
aagaacaatg gagccatcct gttcgtcaag aacgggcttt actacctcgg gataatgccc   1740
aagcagaagg gccgctacaa ggcccttttcc ttcgagccga cggagaaaac ctccgagggg   1800
ttcgacaaga tgtactacga ctacttcccc gacgccgcca agatgatccc gaagtgctca   1860
acgcagctaa aagccgtgac cgcccacttc cagacccaca cgacgccgat cctgctgagc   1920
aacaacttca tcgagcccct tgagatcact aaggagatat acgacctgaa caaccccgag   1980
aaggagccca agaagtttca aaccgcctac gccaaaaaaa ctggcgacca aaagggctac   2040
agggaggcgc tgtgtaagtg gatcgacttc acacgcgact tcctttcgaa gtatacgaag   2100
acaacctcta ttgacctgag cagcctgcgt cctagctccc agtacaaaga tttgggcgag   2160
tactacgcgg agcttaatcc actactctac cacatctcat tccagcgcat cgctgagaag   2220
gaaatcatgg acgcggtgga gacaggcaaa ctgtacctct tccagatata caacaaagac   2280
ttcgctaagg ggcaccacgg gaagcccaac cttcatacgc tctactggac gggcctattc   2340
agccccgaaa atctggccaa gacctccatc aagctgaacg gccaagcgga gctgttctac   2400
agacccaaga gccggatgaa gcggatggcc cacaggctcg gcgagaaaat gcttaacaaa   2460
aagttgaagc accagaaaac ccctatcccc gacaccctct accaggaact gtacgactac   2520
gtgaaccaca ggctctcgca cgaccttttcc gacgaggccc gtgccctact cccgaacgtc   2580
attaccaaag aggtttcgca cgagatcatc aaggaccggc ggttcacgag cgacaagttt   2640
ttctttcacg tccccatcac ccttaactac caggcggcca actcccatc caagttcaac   2700
cagcgtgtga atgcctacct caaggagcac ccagagaccc cgatcattgg gatcgaccgg   2760
ggcgagcgga acctgatcta catcaccgtc atcgactcga cgggcaagat tcttgagcag   2820
agatcgttga ataccataca gcagttcgac taccagaaga aactcgacaa ccgcgagaag   2880
gagcgcgtgg cggcccgcca ggcgtggtcc gtcgttggga cgattaagga cttgaaacaa   2940
ggttatctgt cccaagtcat ccacgagatc gttgatctga tgatccacta tcaggcagtg   3000
gtggtgctgg agaatctcaa cttcggcttc aagagtaagc ggacgggaat cgccgagaag   3060
gccgtgtacc agcagttcga gaagatgctg atcgacaagc tcaactgcct tgtgctgaaa   3120
gactacccgg ccgagaaggt cggcggcgtc ctcaacccgt accaacttac cgaccagttc   3180
acctccttcg ccaagatggg cactcagtcc gggttcttgt tctacgtccc cgcaccttac   3240
acctctaaga tcgaccctct gactggcttc gtagatccat tcgtgtggaa gaccattaag   3300
aaccacgaga gccgcaagca cttcctggag ggcttcgact tcctgcacta cgacgtgaag   3360
accggggact tcatccttca cttcaagatg aaccggaacc tcagcttcca gcggggcctg   3420
ccggggttca tgcccgcctg ggacatcgtg ttcgagaaga cgagaccca gttcgacgcg   3480
aagggcacgc ccttcatcgc cgggaagcgt atcgtgccgg tgatcgagaa ccatcgtttc   3540
acgggtcgct accgtgacct ctacccggcg aacgagctta tcgcactcct ggaggagaag   3600
ggcatcgtct tccgggacgg ctccaacatc ctcccgaaac tgctggaaaa cgacgactct   3660
cacgccatcg acacgatggt ggccctcatc cggtccgtgc tccaaatgcg gaacagcaac   3720
gccgccaccg gtgaggacta catcaacagc ccggtccggg atctgaacgg ggtgtgcttc   3780
```

```
gattcgcggt tccagaatcc tgagtggccg atggacgcgg atgcaaacgg ggcgtaccac    3840
atcgcgctca agggccagtt acttctgaac caccttaagg agtctaaaga tttgaaactc    3900
cagaacggga tctcgaacca ggactggctg gcctacatcc aagagttgcg gaacggcagc    3960
aagaagcggc ggattaagca agattag                                        3987

<210> SEQ ID NO 26
<211> LENGTH: 1228
<212> TYPE: PRT
<213> ORGANISM: Unknown
<220> FEATURE:
<223> OTHER INFORMATION: Lachnospiraceae bacterium

<400> SEQUENCE: 26
```

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

```
Leu Glu Lys Leu Phe Lys Asn Phe Asp Glu Tyr Ser Ser Ala Gly Ile
            325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
            355                 360                 365

Ile His Leu Lys Lys Lys Ala Val Val Thr Glu Lys Tyr Glu Asp Asp
            370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
            405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
            485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
            530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
            565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
            645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
            690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
            725                 730                 735
```

-continued

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
            835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
            915                 920                 925

Ser Gly Phe Lys Asn Ser Arg Val Lys Val Glu Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
            995                 1000                1005

Gly Phe Val Asn Leu Leu Lys Thr Lys Tyr Thr Ser Ile Ala Asp
            1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

```
Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 27
<211> LENGTH: 1307
<212> TYPE: PRT
<213> ORGANISM: Acidaminococcus sp.

<400> SEQUENCE: 27

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285
```

-continued

```
Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
690                 695                 700
```

```
Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
            725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
                820                 825                 830

Arg Leu Ser His Asp Leu Ser Asp Glu Ala Arg Ala Leu Leu Pro Asn
                835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
                900                 905                 910

Asn Leu Ile Tyr Ile Thr Val Ile Asp Ser Thr Gly Lys Ile Leu Glu
                915                 920                 925

Gln Arg Ser Leu Asn Thr Ile Gln Gln Phe Asp Tyr Gln Lys Lys Leu
                930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
                980                 985                 990

Glu Asn Leu Asn Phe Gly Phe Lys Ser Lys Arg Thr Gly Ile Ala Glu
                995                 1000                1005

Lys Ala Val Tyr Gln Gln Phe Glu Lys Met Leu Ile Asp Lys Leu
        1010                1015                1020

Asn Cys Leu Val Leu Lys Asp Tyr Pro Ala Glu Lys Val Gly Gly
        1025                1030                1035

Val Leu Asn Pro Tyr Gln Leu Thr Asp Gln Phe Thr Ser Phe Ala
        1040                1045                1050

Lys Met Gly Thr Gln Ser Gly Phe Leu Phe Tyr Val Pro Ala Pro
        1055                1060                1065

Tyr Thr Ser Lys Ile Asp Pro Leu Thr Gly Phe Val Asp Pro Phe
        1070                1075                1080

Val Trp Lys Thr Ile Lys Asn His Glu Ser Arg Lys His Phe Leu
        1085                1090                1095

Glu Gly Phe Asp Phe Leu His Tyr Asp Val Lys Thr Gly Asp Phe
        1100                1105                1110
```

```
Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305

<210> SEQ ID NO 28
<211> LENGTH: 1241
<212> TYPE: PRT
<213> ORGANISM: Utyrivibrio proteoclasticus

<400> SEQUENCE: 28

Met Leu Leu Tyr Glu Asn Tyr Thr Lys Arg Asn Gln Ile Thr Lys Ser
1               5                   10                  15

Leu Arg Leu Glu Leu Arg Pro Gln Gly Lys Thr Leu Arg Asn Ile Lys
            20                  25                  30

Glu Leu Asn Leu Leu Glu Gln Asp Lys Ala Ile Tyr Ala Leu Leu Glu
        35                  40                  45

Arg Leu Lys Pro Val Ile Asp Glu Gly Ile Lys Asp Ile Ala Arg Asp
    50                  55                  60

Thr Leu Lys Asn Cys Glu Leu Ser Phe Glu Lys Leu Tyr Glu His Phe
65                  70                  75                  80

Leu Ser Gly Asp Lys Lys Ala Tyr Ala Lys Glu Ser Glu Arg Leu Lys
                85                  90                  95

Lys Glu Ile Val Lys Thr Leu Ile Lys Asn Leu Pro Glu Gly Ile Gly
            100                 105                 110

Lys Ile Ser Glu Ile Asn Ser Ala Lys Tyr Leu Asn Gly Val Leu Tyr
        115                 120                 125

Asp Phe Ile Asp Lys Thr His Lys Asp Ser Glu Glu Lys Gln Asn Ile
    130                 135                 140

Leu Ser Asp Ile Leu Glu Thr Lys Gly Tyr Leu Ala Leu Phe Ser Lys
145                 150                 155                 160
```

-continued

```
Phe Leu Thr Ser Arg Ile Thr Thr Leu Glu Gln Ser Met Pro Lys Arg
                165                 170                 175

Val Ile Glu Asn Phe Glu Ile Tyr Ala Ala Asn Ile Pro Lys Met Gln
            180                 185                 190

Asp Ala Leu Glu Arg Gly Ala Val Ser Phe Ala Ile Glu Tyr Glu Ser
        195                 200                 205

Ile Cys Ser Val Asp Tyr Tyr Asn Gln Ile Leu Ser Gln Glu Asp Ile
    210                 215                 220

Asp Ser Tyr Asn Arg Leu Ile Ser Gly Ile Met Asp Glu Asp Gly Ala
225                 230                 235                 240

Lys Glu Lys Gly Ile Asn Gln Thr Ile Ser Lys Asn Ile Lys Ile
                245                 250                 255

Lys Ser Glu His Leu Glu Glu Lys Pro Phe Arg Ile Leu Lys Gln Leu
            260                 265                 270

His Lys Gln Ile Leu Glu Glu Arg Glu Lys Ala Phe Thr Ile Asp His
        275                 280                 285

Ile Asp Ser Asp Glu Glu Val Val Gln Val Thr Lys Glu Ala Phe Glu
    290                 295                 300

Gln Thr Lys Glu Gln Trp Glu Asn Ile Lys Lys Ile Asn Gly Phe Tyr
305                 310                 315                 320

Ala Lys Asp Pro Gly Asp Ile Thr Leu Phe Ile Val Val Gly Pro Asn
                325                 330                 335

Gln Thr His Val Leu Ser Gln Leu Ile Tyr Gly Glu His Asp Arg Ile
            340                 345                 350

Arg Leu Leu Leu Glu Glu Tyr Glu Lys Asn Thr Leu Glu Val Leu Pro
        355                 360                 365

Arg Arg Thr Lys Ser Glu Asp Ala Arg Tyr Asp Lys Phe Val Asn Ala
    370                 375                 380

Val Pro Lys Lys Val Ala Lys Glu Ser His Thr Phe Asp Gly Leu Gln
385                 390                 395                 400

Lys Met Thr Gly Asp Asp Arg Leu Phe Ile Leu Tyr Arg Asp Glu Leu
                405                 410                 415

Ala Arg Asn Tyr Met Arg Ile Lys Glu Ala Tyr Gly Thr Phe Glu Arg
            420                 425                 430

Asp Ile Leu Lys Ser Arg Arg Gly Ile Lys Gly Asn Arg Asp Val Gln
        435                 440                 445

Glu Ser Leu Val Ser Phe Tyr Asp Glu Leu Thr Lys Phe Arg Ser Ala
    450                 455                 460

Leu Arg Ile Ile Asn Ser Gly Asn Asp Glu Lys Ala Asp Pro Ile Phe
465                 470                 475                 480

Tyr Asn Thr Phe Asp Gly Ile Phe Glu Lys Ala Asn Arg Thr Tyr Lys
                485                 490                 495

Ala Glu Asn Leu Cys Arg Asn Tyr Val Thr Lys Ser Pro Ala Asp Asp
            500                 505                 510

Ala Arg Ile Met Ala Ser Cys Leu Gly Thr Pro Ala Arg Leu Arg Thr
        515                 520                 525

His Trp Trp Asn Gly Glu Glu Asn Phe Ala Ile Asn Asp Val Ala Met
    530                 535                 540

Ile Arg Arg Gly Asp Glu Tyr Tyr Phe Val Leu Thr Pro Asp Val
545                 550                 555                 560

Lys Pro Val Asp Leu Lys Thr Lys Asp Glu Thr Asp Ala Gln Ile Phe
                565                 570                 575
```

```
Val Gln Arg Lys Gly Ala Lys Ser Phe Leu Gly Leu Pro Lys Ala Leu
                580                 585                 590

Phe Lys Cys Ile Leu Glu Pro Tyr Phe Glu Ser Pro Glu His Lys Asn
        595                 600                 605

Asp Lys Asn Cys Val Ile Glu Glu Tyr Val Ser Lys Pro Leu Thr Ile
        610                 615                 620

Asp Arg Arg Ala Tyr Asp Ile Phe Lys Asn Gly Thr Phe Lys Lys Thr
625                 630                 635                 640

Asn Ile Gly Ile Asp Gly Leu Thr Glu Glu Lys Phe Lys Asp Asp Cys
                645                 650                 655

Arg Tyr Leu Ile Asp Val Tyr Lys Glu Phe Ile Ala Val Tyr Thr Arg
                660                 665                 670

Tyr Ser Cys Phe Asn Met Ser Gly Leu Lys Arg Ala Asp Glu Tyr Asn
                675                 680                 685

Asp Ile Gly Glu Phe Phe Ser Asp Val Asp Thr Arg Leu Cys Thr Met
        690                 695                 700

Glu Trp Ile Pro Val Ser Phe Glu Arg Ile Asn Asp Met Val Asp Lys
705                 710                 715                 720

Lys Glu Gly Leu Leu Phe Leu Val Arg Ser Met Phe Leu Tyr Asn Arg
                725                 730                 735

Pro Arg Lys Pro Tyr Glu Arg Thr Phe Ile Gln Leu Phe Ser Asp Ser
                740                 745                 750

Asn Met Glu His Thr Ser Met Leu Leu Asn Ser Arg Ala Met Ile Gln
                755                 760                 765

Tyr Arg Ala Ala Ser Leu Pro Arg Arg Val Thr His Lys Lys Gly Ser
770                 775                 780

Ile Leu Val Ala Leu Arg Asp Ser Asn Gly Glu His Ile Pro Met His
785                 790                 795                 800

Ile Arg Glu Ala Ile Tyr Lys Met Lys Asn Asn Phe Asp Ile Ser Ser
                805                 810                 815

Glu Asp Phe Ile Met Ala Lys Ala Tyr Leu Ala Glu His Asp Val Ala
                820                 825                 830

Ile Lys Lys Ala Asn Glu Asp Ile Ile Arg Asn Arg Arg Tyr Thr Glu
        835                 840                 845

Asp Lys Phe Phe Leu Ser Leu Ser Tyr Thr Lys Asn Ala Asp Ile Ser
        850                 855                 860

Ala Arg Thr Leu Asp Tyr Ile Asn Asp Lys Val Glu Glu Asp Thr Gln
865                 870                 875                 880

Asp Ser Arg Met Ala Val Ile Val Thr Arg Asn Leu Lys Asp Leu Thr
                885                 890                 895

Tyr Val Ala Val Val Asp Glu Lys Asn Asn Val Leu Glu Glu Lys Ser
                900                 905                 910

Leu Asn Glu Ile Asp Gly Val Asn Tyr Arg Glu Leu Leu Lys Glu Arg
        915                 920                 925

Thr Lys Ile Lys Tyr His Asp Lys Thr Arg Leu Trp Gln Tyr Asp Val
        930                 935                 940

Ser Ser Lys Gly Leu Lys Glu Ala Tyr Val Glu Leu Ala Val Thr Gln
945                 950                 955                 960

Ile Ser Lys Leu Ala Thr Lys Tyr Asn Ala Val Val Val Glu Ser
                965                 970                 975

Met Ser Ser Thr Phe Lys Asp Lys Phe Ser Phe Leu Asp Glu Gln Ile
                980                 985                 990
```

```
Phe Lys Ala Phe Glu Ala Arg Leu Cys Ala Arg Met Ser Asp Leu Ser
        995                 1000                1005

Phe Asn Thr Ile Lys Glu Gly Glu Ala Gly Ser Ile Ser Asn Pro
    1010                1015                1020

Ile Gln Val Ser Asn Asn Gly Asn Ser Tyr Gln Asp Gly Val
    1025                1030                1035

Ile Tyr Phe Leu Asn Asn Ala Tyr Thr Arg Thr Leu Cys Pro Asp
    1040                1045                1050

Thr Gly Phe Val Asp Val Phe Asp Lys Thr Arg Leu Ile Thr Met
    1055                1060                1065

Gln Ser Lys Arg Gln Phe Phe Ala Lys Met Lys Asp Ile Arg Ile
    1070                1075                1080

Asp Asp Gly Glu Met Leu Phe Thr Phe Asn Leu Glu Glu Tyr Pro
    1085                1090                1095

Thr Lys Arg Leu Leu Asp Arg Lys Glu Trp Thr Val Lys Ile Ala
    1100                1105                1110

Gly Asp Gly Ser Tyr Phe Asp Lys Asp Lys Gly Glu Tyr Val Tyr
    1115                1120                1125

Val Asn Asp Ile Val Arg Glu Gln Ile Ile Pro Ala Leu Leu Glu
    1130                1135                1140

Asp Lys Ala Val Phe Asp Gly Asn Met Ala Glu Lys Phe Leu Asp
    1145                1150                1155

Lys Thr Ala Ile Ser Gly Lys Ser Val Glu Leu Ile Tyr Lys Trp
    1160                1165                1170

Phe Ala Asn Ala Leu Tyr Gly Ile Ile Thr Lys Lys Asp Gly Glu
    1175                1180                1185

Lys Ile Tyr Arg Ser Pro Ile Thr Gly Thr Glu Ile Asp Val Ser
    1190                1195                1200

Lys Asn Thr Thr Tyr Asn Phe Gly Lys Lys Phe Met Phe Lys Gln
    1205                1210                1215

Glu Tyr Arg Gly Asp Gly Asp Phe Leu Asp Ala Phe Leu Asn Tyr
    1220                1225                1230

Met Gln Ala Gln Asp Ile Ala Val
    1235                1240

<210> SEQ ID NO 29
<211> LENGTH: 1238
<212> TYPE: PRT
<213> ORGANISM: Candidatus Methanoplasma termitum

<400> SEQUENCE: 29

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
            20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Lys Phe Ile Asp Glu
    50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Lys Val Phe Leu
                85                  90                  95
```

```
Ser Glu Gln Lys Arg Met Arg Gln Glu Ile Val Ser Glu Phe Lys Lys
            100                 105                 110

Asp Asp Arg Phe Lys Asp Leu Phe Ser Lys Lys Leu Phe Ser Glu Leu
            115                 120                 125

Leu Lys Glu Glu Ile Tyr Lys Lys Gly Asn His Gln Glu Ile Asp Ala
130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
                180                 185                 190

Lys Tyr Gln Glu Ala Arg Lys Lys Tyr Pro Glu Trp Ile Ile Lys Ala
                195                 200                 205

Glu Ser Ala Leu Val Ala His Asn Ile Lys Met Asp Ile Val Phe Ser
            210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Glu Lys Ser Ser
            260                 265                 270

Lys Gly Arg Ile His Met Thr Pro Leu Phe Lys Gln Ile Leu Ser Glu
            275                 280                 285

Lys Glu Ser Phe Ser Tyr Ile Pro Asp Val Phe Thr Glu Asp Ser Gln
            290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335

Glu Tyr Asp Thr Glu Arg Ile Tyr Ile Arg Gln Ala Asp Ile Asn Arg
                340                 345                 350

Val Ser Asn Val Ile Phe Gly Glu Trp Gly Thr Leu Gly Gly Leu Met
            355                 360                 365

Arg Glu Tyr Lys Ala Asp Ser Ile Asn Asp Ile Asn Leu Glu Arg Thr
            370                 375                 380

Cys Lys Lys Val Asp Lys Trp Leu Asp Ser Lys Glu Phe Ala Leu Ser
385                 390                 395                 400

Asp Val Leu Glu Ala Ile Asp Arg Thr Gly Asn Asn Asp Ala Phe Asn
                405                 410                 415

Glu Tyr Ile Ser Lys Met Arg Thr Ala Arg Glu Lys Ile Asp Ala Ala
            420                 425                 430

Arg Lys Glu Met Lys Phe Ile Ser Glu Lys Ile Ser Gly Asp Glu Glu
            435                 440                 445

Ser Ile His Ile Ile Lys Thr Leu Leu Asp Ser Val Gln Gln Phe Leu
            450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
                485                 490                 495

Val Pro Leu Tyr Asn Lys Val Arg Asn Tyr Leu Thr Lys Asn Asn Leu
            500                 505                 510
```

```
Asn Thr Lys Lys Ile Lys Leu Asn Phe Lys Asn Pro Thr Leu Ala Asn
            515                 520                 525
Gly Trp Asp Gln Asn Lys Val Tyr Asp Tyr Ala Ser Leu Ile Phe Leu
530                 535                 540
Arg Asp Gly Asn Tyr Tyr Leu Gly Ile Ile Asn Pro Lys Arg Lys Lys
545                 550                 555                 560
Asn Ile Lys Phe Glu Gln Gly Ser Gly Asn Gly Pro Phe Tyr Arg Lys
            565                 570                 575
Met Val Tyr Lys Gln Ile Pro Gly Pro Asn Lys Asn Leu Arg Pro Val
            580                 585                 590
Phe Leu Thr Ser Thr Lys Gly Lys Lys Glu Tyr Lys Pro Ser Lys Glu
            595                 600                 605
Ile Ile Glu Gly Tyr Glu Ala Asp Lys His Ile Arg Gly Asp Lys Phe
            610                 615                 620
Asp Leu Asp Phe Cys His Lys Leu Ile Asp Phe Phe Lys Glu Ser Ile
625                 630                 635                 640
Glu Lys His Lys Asp Trp Ser Lys Phe Asn Phe Tyr Phe Ser Pro Thr
            645                 650                 655
Glu Ser Tyr Gly Asp Ile Ser Glu Phe Tyr Leu Asp Val Glu Lys Gln
            660                 665                 670
Gly Tyr Arg Met His Phe Glu Asn Ile Ser Ala Glu Thr Ile Asp Glu
            675                 680                 685
Tyr Val Glu Lys Gly Asp Leu Phe Leu Phe Gln Ile Tyr Asn Lys Asp
            690                 695                 700
Phe Val Lys Ala Ala Thr Gly Lys Lys Asp Met His Thr Ile Tyr Trp
705                 710                 715                 720
Asn Ala Ala Phe Ser Pro Glu Asn Leu Gln Asp Val Val Val Lys Leu
            725                 730                 735
Asn Gly Glu Ala Glu Leu Phe Tyr Arg Asp Lys Ser Asp Ile Lys Glu
            740                 745                 750
Ile Val His Arg Glu Gly Glu Ile Leu Val Asn Arg Thr Tyr Asn Gly
            755                 760                 765
Arg Thr Pro Val Pro Asp Lys Ile His Lys Lys Leu Thr Asp Tyr His
770                 775                 780
Asn Gly Arg Thr Lys Asp Leu Gly Glu Ala Lys Glu Tyr Leu Asp Lys
785                 790                 795                 800
Val Arg Tyr Phe Lys Ala His Tyr Asp Ile Thr Lys Asp Arg Arg Tyr
            805                 810                 815
Leu Asn Asp Lys Ile Tyr Phe His Val Pro Leu Thr Leu Asn Phe Lys
            820                 825                 830
Ala Asn Gly Lys Lys Asn Leu Asn Lys Met Val Ile Glu Lys Phe Leu
            835                 840                 845
Ser Asp Glu Lys Ala His Ile Ile Gly Ile Asp Arg Gly Glu Arg Asn
            850                 855                 860
Leu Leu Tyr Tyr Ser Ile Ile Asp Arg Ser Gly Lys Ile Ile Asp Gln
865                 870                 875                 880
Gln Ser Leu Asn Val Ile Asp Gly Phe Asp Tyr Arg Glu Lys Leu Asn
            885                 890                 895
Gln Arg Glu Ile Glu Met Lys Asp Ala Arg Gln Ser Trp Asn Ala Ile
            900                 905                 910
Gly Lys Ile Lys Asp Leu Lys Glu Gly Tyr Leu Ser Lys Ala Val His
            915                 920                 925
```

```
Glu Ile Thr Lys Met Ala Ile Gln Tyr Asn Ala Ile Val Val Met Glu
    930                 935                 940

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
                965                 970                 975

Val Phe Lys Asp Ala Pro Asp Glu Ser Pro Gly Gly Val Leu Asn Ala
            980                 985                 990

Tyr Gln Leu Thr Asn Pro Leu Glu Ser Phe Ala Lys Leu Gly Lys Gln
        995                 1000                1005

Thr Gly Ile Leu Phe Tyr Val Pro Ala Ala Tyr Thr Ser Lys Ile
    1010                1015                1020

Asp Pro Thr Thr Gly Phe Val Asn Leu Phe Asn Thr Ser Ser Lys
    1025                1030                1035

Thr Asn Ala Gln Glu Arg Lys Glu Phe Leu Gln Lys Phe Glu Ser
    1040                1045                1050

Ile Ser Tyr Ser Ala Lys Asp Gly Gly Ile Phe Ala Phe Ala Phe
    1055                1060                1065

Asp Tyr Arg Lys Phe Gly Thr Ser Lys Thr Asp His Lys Asn Val
    1070                1075                1080

Trp Thr Ala Tyr Thr Asn Gly Glu Arg Met Arg Tyr Ile Lys Glu
    1085                1090                1095

Lys Lys Arg Asn Glu Leu Phe Asp Pro Ser Lys Glu Ile Lys Glu
    1100                1105                1110

Ala Leu Thr Ser Ser Gly Ile Lys Tyr Asp Gly Gly Gln Asn Ile
    1115                1120                1125

Leu Pro Asp Ile Leu Arg Ser Asn Asn Asn Gly Leu Ile Tyr Thr
    1130                1135                1140

Met Tyr Ser Ser Phe Ile Ala Ala Ile Gln Met Arg Val Tyr Asp
    1145                1150                1155

Gly Lys Glu Asp Tyr Ile Ile Ser Pro Ile Lys Asn Ser Lys Gly
    1160                1165                1170

Glu Phe Phe Arg Thr Asp Pro Lys Arg Arg Glu Leu Pro Ile Asp
    1175                1180                1185

Ala Asp Ala Asn Gly Ala Tyr Asn Ile Ala Leu Arg Gly Glu Leu
    1190                1195                1200

Thr Met Arg Ala Ile Ala Glu Lys Phe Asp Pro Asp Ser Glu Lys
    1205                1210                1215

Met Ala Lys Leu Glu Leu Lys His Lys Asp Trp Phe Glu Phe Met
    1220                1225                1230

Gln Thr Arg Gly Asp
    1235

<210> SEQ ID NO 30
<211> LENGTH: 1281
<212> TYPE: PRT
<213> ORGANISM: Eubacterium eligens

<400> SEQUENCE: 30

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
            20                  25                  30
```

-continued

```
Gln Glu His Ile Ile Gln Asn Gly Leu Ile Gln Glu Asp Glu Leu Arg
         35                  40                  45
Gln Glu Lys Ser Thr Glu Leu Lys Asn Ile Met Asp Asp Tyr Tyr Arg
     50                  55                  60
Glu Tyr Ile Asp Lys Ser Leu Ser Gly Val Thr Asp Leu Asp Phe Thr
65                  70                  75                  80
Leu Leu Phe Glu Leu Met Asn Leu Val Gln Ser Ser Pro Ser Lys Asp
                 85                  90                  95
Asn Lys Lys Ala Leu Glu Lys Glu Gln Ser Lys Met Arg Glu Gln Ile
                100                 105                 110
Cys Thr His Leu Gln Ser Asp Ser Asn Tyr Lys Asn Ile Phe Asn Ala
                115                 120                 125
Lys Leu Leu Lys Glu Ile Leu Pro Asp Phe Ile Lys Asn Tyr Asn Gln
            130                 135                 140
Tyr Asp Val Lys Asp Lys Ala Gly Lys Leu Glu Thr Leu Ala Leu Phe
145                 150                 155                 160
Asn Gly Phe Ser Thr Tyr Phe Thr Asp Phe Phe Glu Lys Arg Lys Asn
                165                 170                 175
Val Phe Thr Lys Glu Ala Val Ser Thr Ser Ile Ala Tyr Arg Ile Val
                180                 185                 190
His Glu Asn Ser Leu Ile Phe Leu Ala Asn Met Thr Ser Tyr Lys Lys
            195                 200                 205
Ile Ser Glu Lys Ala Leu Asp Glu Ile Glu Val Ile Glu Lys Asn Asn
210                 215                 220
Gln Asp Lys Met Gly Asp Trp Glu Leu Asn Gln Ile Phe Asn Pro Asp
225                 230                 235                 240
Phe Tyr Asn Met Val Leu Ile Gln Ser Gly Ile Asp Phe Tyr Asn Glu
                245                 250                 255
Ile Cys Gly Val Val Asn Ala His Met Asn Leu Tyr Cys Gln Gln Thr
                260                 265                 270
Lys Asn Asn Tyr Asn Leu Phe Lys Met Arg Lys Leu His Lys Gln Ile
            275                 280                 285
Leu Ala Tyr Thr Ser Thr Ser Phe Glu Val Pro Lys Met Phe Glu Asp
            290                 295                 300
Asp Met Ser Val Tyr Asn Ala Val Asn Ala Phe Ile Asp Glu Thr Glu
305                 310                 315                 320
Lys Gly Asn Ile Ile Gly Lys Leu Lys Asp Ile Val Asn Lys Tyr Asp
                325                 330                 335
Glu Leu Asp Glu Lys Arg Ile Tyr Ile Ser Lys Asp Phe Tyr Glu Thr
                340                 345                 350
Leu Ser Cys Phe Met Ser Gly Asn Trp Asn Leu Ile Thr Gly Cys Val
            355                 360                 365
Glu Asn Phe Tyr Asp Glu Asn Ile His Ala Lys Gly Lys Ser Lys Glu
            370                 375                 380
Glu Lys Val Lys Lys Ala Val Lys Glu Asp Lys Tyr Lys Ser Ile Asn
385                 390                 395                 400
Asp Val Asn Asp Leu Val Glu Lys Tyr Ile Asp Glu Lys Glu Arg Asn
                405                 410                 415
Glu Phe Lys Asn Ser Asn Ala Lys Gln Tyr Ile Arg Glu Ile Ser Asn
            420                 425                 430
Ile Ile Thr Asp Thr Glu Thr Ala His Leu Glu Tyr Asp Asp His Ile
            435                 440                 445
```

```
Ser Leu Ile Glu Ser Glu Glu Lys Ala Asp Glu Met Lys Lys Arg Leu
450                 455                 460

Asp Met Tyr Met Asn Met Tyr His Trp Ala Lys Ala Phe Ile Val Asp
465                 470                 475                 480

Glu Val Leu Asp Arg Asp Glu Met Phe Tyr Ser Asp Ile Asp Asp Ile
                485                 490                 495

Tyr Asn Ile Leu Glu Asn Ile Val Pro Leu Tyr Asn Arg Val Arg Asn
            500                 505                 510

Tyr Val Thr Gln Lys Pro Tyr Asn Ser Lys Lys Ile Lys Leu Asn Phe
        515                 520                 525

Gln Ser Pro Thr Leu Ala Asn Gly Trp Ser Gln Ser Lys Glu Phe Asp
530                 535                 540

Asn Asn Ala Ile Ile Leu Ile Arg Asp Asn Lys Tyr Tyr Leu Ala Ile
545                 550                 555                 560

Phe Asn Ala Lys Asn Lys Pro Asp Lys Lys Ile Ile Gln Gly Asn Ser
                565                 570                 575

Asp Lys Lys Asn Asp Asn Asp Tyr Lys Lys Met Val Tyr Asn Leu Leu
            580                 585                 590

Pro Gly Ala Asn Lys Met Leu Pro Lys Val Phe Leu Ser Lys Lys Gly
        595                 600                 605

Ile Glu Thr Phe Lys Pro Ser Asp Tyr Ile Ile Ser Gly Tyr Asn Ala
    610                 615                 620

His Lys His Ile Lys Thr Ser Glu Asn Phe Asp Ile Ser Phe Cys Arg
625                 630                 635                 640

Asp Leu Ile Asp Tyr Phe Lys Asn Ser Ile Glu Lys His Ala Glu Trp
                645                 650                 655

Arg Lys Tyr Glu Phe Lys Phe Ser Ala Thr Asp Ser Tyr Ser Asp Ile
            660                 665                 670

Ser Glu Phe Tyr Arg Glu Val Glu Met Gln Gly Tyr Arg Ile Asp Trp
        675                 680                 685

Thr Tyr Ile Ser Glu Ala Asp Ile Asn Lys Leu Asp Glu Glu Gly Lys
    690                 695                 700

Ile Tyr Leu Phe Gln Ile Tyr Asn Lys Asp Phe Ala Glu Asn Ser Thr
705                 710                 715                 720

Gly Lys Glu Asn Leu His Thr Met Tyr Phe Lys Asn Ile Phe Ser Glu
                725                 730                 735

Glu Asn Leu Asp Lys Ile Ile Lys Leu Asn Gly Gln Ala Glu Leu Phe
            740                 745                 750

Tyr Arg Arg Ala Ser Val Lys Asn Pro Val Lys His Lys Lys Asp Ser
        755                 760                 765

Val Leu Val Asn Lys Thr Tyr Lys Asn Gln Leu Asp Asn Gly Asp Val
    770                 775                 780

Val Arg Ile Pro Ile Pro Asp Asp Ile Tyr Asn Glu Ile Tyr Lys Met
785                 790                 795                 800

Tyr Asn Gly Tyr Ile Lys Glu Ser Asp Leu Ser Glu Ala Ala Lys Glu
                805                 810                 815

Tyr Leu Asp Lys Val Glu Val Arg Thr Ala Gln Lys Asp Ile Val Lys
            820                 825                 830

Asp Tyr Arg Tyr Thr Val Asp Lys Tyr Phe Ile His Thr Pro Ile Thr
        835                 840                 845

Ile Asn Tyr Lys Val Thr Ala Arg Asn Asn Val Asn Asp Met Val Val
    850                 855                 860
```

```
Lys Tyr Ile Ala Gln Asn Asp Asp Ile His Val Ile Gly Ile Asp Arg
865                 870                 875                 880

Gly Glu Arg Asn Leu Ile Tyr Ile Ser Val Ile Asp Ser His Gly Asn
            885                 890                 895

Ile Val Lys Gln Lys Ser Tyr Asn Ile Leu Asn Asn Tyr Asp Tyr Lys
                900                 905                 910

Lys Lys Leu Val Glu Lys Glu Lys Thr Arg Glu Tyr Ala Arg Lys Asn
            915                 920                 925

Trp Lys Ser Ile Gly Asn Ile Lys Glu Leu Lys Glu Gly Tyr Ile Ser
            930                 935                 940

Gly Val Val His Glu Ile Ala Met Leu Ile Val Glu Tyr Asn Ala Ile
945                 950                 955                 960

Ile Ala Met Glu Asp Leu Asn Tyr Gly Phe Lys Arg Gly Arg Phe Lys
                965                 970                 975

Val Glu Arg Gln Val Tyr Gln Lys Phe Glu Ser Met Leu Ile Asn Lys
            980                 985                 990

Leu Asn Tyr Phe Ala Ser Lys Glu Lys Ser Val Asp Glu Pro Gly Gly
            995                1000                1005

Leu Leu Lys Gly Tyr Gln Leu Thr Tyr Val Pro Asp Asn Ile Lys
1010                1015                1020

Asn Leu Gly Lys Gln Cys Gly Val Ile Phe Tyr Val Pro Ala Ala
1025                1030                1035

Phe Thr Ser Lys Ile Asp Pro Ser Thr Gly Phe Ile Ser Ala Phe
1040                1045                1050

Asn Phe Lys Ser Ile Ser Thr Asn Ala Ser Arg Lys Gln Phe Phe
1055                1060                1065

Met Gln Phe Asp Glu Ile Arg Tyr Cys Ala Glu Lys Asp Met Phe
1070                1075                1080

Ser Phe Gly Phe Asp Tyr Asn Asn Phe Asp Thr Tyr Asn Ile Thr
1085                1090                1095

Met Gly Lys Thr Gln Trp Thr Val Tyr Thr Asn Gly Glu Arg Leu
1100                1105                1110

Gln Ser Glu Phe Asn Asn Ala Arg Arg Thr Gly Lys Thr Lys Ser
1115                1120                1125

Ile Asn Leu Thr Glu Thr Ile Lys Leu Leu Leu Glu Asp Asn Glu
1130                1135                1140

Ile Asn Tyr Ala Asp Gly His Asp Ile Arg Ile Asp Met Glu Lys
1145                1150                1155

Met Asp Glu Asp Lys Lys Ser Glu Phe Phe Ala Gln Leu Leu Ser
1160                1165                1170

Leu Tyr Lys Leu Thr Val Gln Met Arg Asn Ser Tyr Thr Glu Ala
1175                1180                1185

Glu Glu Gln Glu Asn Gly Ile Ser Tyr Asp Lys Ile Ile Ser Pro
1190                1195                1200

Val Ile Asn Asp Glu Gly Glu Phe Phe Asp Ser Asp Asn Tyr Lys
1205                1210                1215

Glu Ser Asp Asp Lys Glu Cys Lys Met Pro Lys Asp Ala Asp Ala
1220                1225                1230

Asn Gly Ala Tyr Cys Ile Ala Leu Lys Gly Leu Tyr Glu Val Leu
1235                1240                1245

Lys Ile Lys Ser Glu Trp Thr Glu Asp Gly Phe Asp Arg Asn Cys
1250                1255                1260
```

```
Leu Lys Leu Pro His Ala Glu Trp Leu Asp Phe Ile Gln Asn Lys
    1265                1270                1275

Arg Tyr Glu
    1280

<210> SEQ ID NO 31
<211> LENGTH: 1300
<212> TYPE: PRT
<213> ORGANISM: Francisella novicida

<400> SEQUENCE: 31

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
                20                  25                  30

Ala Arg Gly Leu Ile Leu Asp Asp Glu Lys Arg Ala Lys Asp Tyr Lys
            35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Val Asn Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350
```

```
Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
        370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
            435                 440                 445

Lys Tyr Leu Ser Leu Glu Thr Ile Lys Leu Ala Leu Glu Glu Phe Asn
        450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gly Lys Lys
            500                 505                 510

Asp Leu Leu Gln Ala Ser Ala Glu Asp Val Lys Ala Ile Lys Asp
            515                 520                 525

Leu Leu Asp Gln Thr Asn Asn Leu Leu His Lys Leu Lys Ile Phe His
        530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
        610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
        690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
            755                 760                 765
```

-continued

```
Ile Ser Glu Ser Tyr Ile Asp Ser Val Val Asn Gln Gly Lys Leu Tyr
770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
            805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
            885                 890                 895

Asn Asp Glu Ile Asn Leu Leu Lys Glu Lys Ala Asn Asp Val His
            900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170
```

```
Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 32
<211> LENGTH: 1206
<212> TYPE: PRT
<213> ORGANISM: Unknown
<220> FEATURE:
<223> OTHER INFORMATION: Lachnospiraceae bacterium

<400> SEQUENCE: 32

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
                20                  25                  30

Asn Asn Ile Leu Glu Ser Asp Val Lys Arg Lys Gln Asn Tyr Glu His
            35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Glu Gln Asp
        195                 200                 205

Ser Leu Phe Ile Val Glu Thr Phe Asn Lys Thr Leu Thr Gln Asp Gly
    210                 215                 220
```

```
Ile Asp Thr Tyr Asn Ser Gln Val Gly Lys Ile Asn Ser Ser Ile Asn
225                 230                 235                 240

Leu Tyr Asn Gln Lys Asn Gln Lys Ala Asn Gly Phe Arg Lys Ile Pro
                245                 250                 255

Lys Met Lys Met Leu Tyr Lys Gln Ile Leu Ser Asp Arg Glu Glu Ser
                260                 265                 270

Phe Ile Asp Glu Phe Gln Ser Asp Glu Val Leu Ile Asp Asn Val Glu
            275                 280                 285

Ser Tyr Gly Ser Val Leu Ile Glu Ser Leu Lys Ser Ser Lys Val Ser
        290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Val Ile Val Phe Glu Asn
                325                 330                 335

Trp Arg Thr Phe Asp Asp Leu Leu Asn Gln Glu Tyr Asp Leu Ala Asn
            340                 345                 350

Glu Asn Lys Lys Lys Asp Asp Lys Tyr Phe Glu Lys Arg Gln Lys Glu
        355                 360                 365

Leu Lys Lys Asn Lys Ser Tyr Ser Leu Glu His Leu Cys Asn Leu Ser
370                 375                 380

Glu Asp Ser Cys Asn Leu Ile Glu Asn Tyr Ile His Gln Ile Ser Asp
385                 390                 395                 400

Asp Ile Glu Asn Ile Ile Asn Asn Glu Thr Phe Leu Arg Ile Val
                405                 410                 415

Ile Asn Glu His Asp Arg Ser Arg Lys Leu Ala Lys Asn Arg Lys Ala
            420                 425                 430

Val Lys Ala Ile Lys Asp Phe Leu Asp Ser Ile Lys Val Leu Glu Arg
        435                 440                 445

Glu Leu Lys Leu Ile Asn Ser Ser Gly Gln Glu Leu Glu Lys Asp Leu
450                 455                 460

Ile Val Tyr Ser Ala His Glu Glu Leu Leu Val Glu Leu Lys Gln Val
465                 470                 475                 480

Asp Ser Leu Tyr Asn Met Thr Arg Asn Tyr Leu Thr Lys Lys Pro Phe
                485                 490                 495

Ser Thr Glu Lys Val Lys Leu Asn Phe Asn Arg Ser Thr Leu Leu Asn
            500                 505                 510

Gly Trp Asp Arg Asn Lys Glu Thr Asp Asn Leu Gly Val Leu Leu Leu
        515                 520                 525

Lys Asp Gly Lys Tyr Tyr Leu Gly Ile Met Asn Thr Ser Ala Asn Lys
530                 535                 540

Ala Phe Val Asn Pro Pro Val Ala Lys Thr Glu Lys Val Phe Lys Lys
545                 550                 555                 560

Val Asp Tyr Lys Leu Leu Pro Val Pro Asn Gln Met Leu Pro Lys Val
                565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
        595                 600                 605

Leu Glu Asp Cys His Asn Leu Ile Asp Phe Phe Lys Glu Ser Ile Ser
610                 615                 620

Lys His Glu Asp Trp Ser Lys Phe Gly Phe Lys Phe Asp Thr Gln Ala
625                 630                 635                 640
```

```
Ser Tyr Asn Asp Ile Ser Glu Phe Tyr Arg Glu Val Glu Lys Gln Gly
                645                 650                 655

Tyr Lys Leu Thr Tyr Thr Asp Ile Asp Glu Thr Tyr Ile Asn Asp Leu
            660                 665                 670

Ile Glu Arg Asn Glu Leu Tyr Leu Phe Gln Ile Tyr Asn Lys Asp Phe
            675                 680                 685

Ser Met Tyr Ser Lys Gly Lys Leu Asn Leu His Thr Leu Tyr Phe Met
690                 695                 700

Met Leu Phe Asp Gln Arg Asn Ile Asp Asp Val Val Tyr Lys Leu Asn
705                 710                 715                 720

Gly Glu Ala Glu Val Phe Tyr Arg Pro Ala Ser Ile Ser Glu Asp Glu
                725                 730                 735

Leu Ile Ile His Lys Ala Gly Glu Glu Ile Lys Asn Lys Asn Pro Asn
            740                 745                 750

Arg Ala Arg Thr Lys Glu Thr Ser Thr Phe Ser Tyr Asp Ile Val Lys
            755                 760                 765

Asp Lys Arg Tyr Ser Lys Asp Lys Phe Thr Leu His Ile Pro Ile Thr
            770                 775                 780

Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
                805                 810                 815

Gly Glu Arg Asn Leu Leu Tyr Val Val Ile Asp Ser Lys Gly Asn
                820                 825                 830

Ile Leu Glu Gln Ile Ser Leu Asn Ser Ile Ile Asn Lys Glu Tyr Asp
            835                 840                 845

Ile Glu Thr Asp Tyr His Ala Leu Leu Asp Glu Arg Glu Gly Gly Arg
            850                 855                 860

Asp Lys Ala Arg Lys Asp Trp Asn Thr Val Glu Asn Ile Arg Asp Leu
865                 870                 875                 880

Lys Ala Gly Leu Tyr Leu Gln Val Val Asn Val Val Ala Lys Leu Val
                885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
            915                 920                 925

Lys Met Leu Ile Asp Lys Leu Asn Tyr Leu Val Ile Asp Lys Ser Arg
            930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
                965                 970                 975

Val Ile Tyr Tyr Val Pro Ala Tyr Leu Thr Ser Lys Ile Asp Pro Thr
            980                 985                 990

Thr Gly Phe Ala Asn Leu Phe Tyr  Met Lys Cys Glu Asn Val Glu Lys
            995                 1000                1005

Ser Lys Arg Phe Phe Asp Gly Phe Asp Phe Ile Arg Phe Asn Ala
            1010                1015                1020

Leu Glu Asn Val Phe Glu Phe Gly Phe Asp Tyr Arg Ser Phe Thr
            1025                1030                1035

Gln Arg Ala Cys Gly Ile Asn Ser Lys Trp Thr Val Cys Thr Asn
            1040                1045                1050
```

```
Gly Glu Arg Ile Ile Lys Tyr Arg Asn Pro Asp Lys Asn Asn Met
    1055                1060                1065

Phe Asp Glu Lys Val Val Val Thr Asp Glu Met Lys Asn Leu
    1070                1075                1080

Phe Glu Gln Tyr Lys Ile Pro Tyr Glu Asp Gly Arg Asn Val Lys
    1085                1090                1095

Asp Met Ile Ile Ser Asn Glu Glu Ala Glu Phe Tyr Arg Arg Leu
    1100                1105                1110

Tyr Arg Leu Leu Gln Gln Thr Leu Gln Met Arg Asn Ser Thr Ser
    1115                1120                1125

Asp Gly Thr Arg Asp Tyr Ile Ile Ser Pro Val Lys Asn Lys Arg
    1130                1135                1140

Glu Ala Tyr Phe Asn Ser Glu Leu Ser Asp Gly Ser Val Pro Lys
    1145                1150                1155

Asp Ala Asp Ala Asn Gly Ala Tyr Asn Ile Ala Arg Lys Gly Leu
    1160                1165                1170

Trp Val Leu Glu Gln Ile Arg Gln Lys Ser Glu Gly Glu Lys Ile
    1175                1180                1185

Asn Leu Ala Met Thr Asn Ala Glu Trp Leu Glu Tyr Ala Gln Thr
    1190                1195                1200

His Leu Leu
    1205

<210> SEQ ID NO 33
<211> LENGTH: 1233
<212> TYPE: PRT
<213> ORGANISM: Unknown
<220> FEATURE:
<223> OTHER INFORMATION: Lachnospiraceae bacterium

<400> SEQUENCE: 33

Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
                20                  25                  30

Arg Glu Gln Lys Leu Leu Glu Gln Asp Ala Ala Phe Arg Lys Leu Val
            35                  40                  45

Glu Thr Val Thr Pro Ile Val Asp Asp Cys Ile Arg Lys Ile Ala Asp
        50                  55                  60

Asn Ala Leu Cys His Phe Gly Thr Glu Tyr Asp Phe Ser Cys Leu Gly
65                  70                  75                  80

Asn Ala Ile Ser Lys Asn Asp Ser Lys Ala Ile Lys Lys Glu Thr Glu
                85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
        115                 120                 125

Thr Leu Thr Ser Phe Val Gln Asp Asp Ala Asp Lys Arg Val Leu Ile
    130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190
```

-continued

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
        210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
            275                 280                 285

Ser Asn Asp Ser Asp Ala Arg Ser Ile Leu Glu Lys Ile Leu Lys Asp
        290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
                340                 345                 350

Glu Ser Lys Arg Ile Ser Glu Leu Met Glu Thr Leu Ser Pro Lys Glu
            355                 360                 365

Arg Lys Glu Ser Lys Lys Arg Leu Glu Gly Leu Glu Glu His Ile Arg
        370                 375                 380

Lys Ser Thr Tyr Thr Phe Asp Glu Leu Asn Arg Tyr Ala Glu Lys Asn
385                 390                 395                 400

Val Met Ala Ala Tyr Ile Ala Ala Val Glu Glu Ser Cys Ala Glu Ile
                405                 410                 415

Met Arg Lys Glu Lys Asp Leu Arg Thr Leu Leu Ser Lys Glu Asp Val
            420                 425                 430

Lys Ile Arg Gly Asn Arg His Asn Thr Leu Ile Val Lys Asn Tyr Phe
        435                 440                 445

Asn Ala Trp Thr Val Phe Arg Asn Leu Ile Arg Ile Leu Arg Arg Lys
        450                 455                 460

Ser Glu Ala Glu Ile Asp Ser Asp Phe Tyr Asp Val Leu Asp Asp Ser
465                 470                 475                 480

Val Glu Val Leu Ser Leu Thr Tyr Lys Gly Glu Asn Leu Cys Arg Ser
                485                 490                 495

Tyr Ile Thr Lys Lys Ile Gly Ser Asp Leu Lys Pro Glu Ile Ala Thr
            500                 505                 510

Tyr Gly Ser Ala Leu Arg Pro Asn Ser Arg Trp Trp Ser Pro Gly Glu
        515                 520                 525

Lys Phe Asn Val Lys Phe His Thr Ile Val Arg Arg Asp Gly Arg Leu
        530                 535                 540

Tyr Tyr Phe Ile Leu Pro Lys Gly Ala Lys Pro Val Glu Leu Glu Asp
545                 550                 555                 560

Met Asp Gly Asp Ile Glu Cys Leu Gln Met Arg Lys Ile Pro Asn Pro
                565                 570                 575

Thr Ile Phe Leu Pro Lys Leu Val Phe Lys Asp Pro Glu Ala Phe Phe
            580                 585                 590

Arg Asp Asn Pro Glu Ala Asp Glu Phe Val Phe Leu Ser Gly Met Lys
        595                 600                 605

```
Ala Pro Val Thr Ile Thr Arg Glu Thr Tyr Glu Ala Tyr Arg Tyr Lys
    610                 615                 620
Leu Tyr Thr Val Gly Lys Leu Arg Asp Gly Glu Val Ser Glu Glu
625                 630                 635                 640
Tyr Lys Arg Ala Leu Leu Gln Val Leu Thr Ala Tyr Lys Glu Phe Leu
                    645                 650                 655
Glu Asn Arg Met Ile Tyr Ala Asp Leu Asn Phe Gly Phe Lys Asp Leu
            660                 665                 670
Glu Glu Tyr Lys Asp Ser Ser Glu Phe Ile Lys Gln Val Glu Thr His
        675                 680                 685
Asn Thr Phe Met Cys Trp Ala Lys Val Ser Ser Gln Leu Asp Asp
690                 695                 700
Leu Val Lys Ser Gly Asn Gly Leu Leu Phe Glu Ile Trp Ser Glu Arg
705                 710                 715                 720
Leu Glu Ser Tyr Tyr Lys Tyr Gly Asn Glu Lys Val Leu Arg Gly Tyr
                725                 730                 735
Glu Gly Val Leu Leu Ser Ile Leu Lys Asp Glu Asn Leu Val Ser Met
            740                 745                 750
Arg Thr Leu Leu Asn Ser Arg Pro Met Leu Val Tyr Arg Pro Lys Glu
        755                 760                 765
Ser Ser Lys Pro Met Val Val His Arg Asp Gly Ser Arg Val Val Asp
770                 775                 780
Arg Phe Asp Lys Asp Gly Lys Tyr Ile Pro Pro Glu Val His Asp Glu
785                 790                 795                 800
Leu Tyr Arg Phe Phe Asn Asn Leu Leu Ile Lys Glu Lys Leu Gly Glu
                805                 810                 815
Lys Ala Arg Lys Ile Leu Asp Asn Lys Lys Val Lys Val Lys Val Leu
            820                 825                 830
Glu Ser Glu Arg Val Lys Trp Ser Lys Phe Tyr Asp Glu Gln Phe Ala
        835                 840                 845
Val Thr Phe Ser Val Lys Lys Asn Ala Asp Cys Leu Asp Thr Thr Lys
850                 855                 860
Asp Leu Asn Ala Glu Val Met Glu Gln Tyr Ser Glu Ser Asn Arg Leu
865                 870                 875                 880
Ile Leu Ile Arg Asn Thr Thr Asp Ile Leu Tyr Tyr Leu Val Leu Asp
                885                 890                 895
Lys Asn Gly Lys Val Leu Lys Gln Arg Ser Leu Asn Ile Ile Asn Asp
            900                 905                 910
Gly Ala Arg Asp Val Asp Trp Lys Glu Arg Phe Arg Gln Val Thr Lys
        915                 920                 925
Asp Arg Asn Glu Gly Tyr Asn Glu Trp Asp Tyr Ser Arg Thr Ser Asn
930                 935                 940
Asp Leu Lys Glu Val Tyr Leu Asn Tyr Ala Leu Lys Glu Ile Ala Glu
945                 950                 955                 960
Ala Val Ile Glu Tyr Asn Ala Ile Leu Ile Ile Glu Lys Met Ser Asn
                965                 970                 975
Ala Phe Lys Asp Lys Tyr Ser Phe Leu Asp Asp Val Thr Phe Lys Gly
            980                 985                 990
Phe Glu Thr Lys Lys Leu Ala Lys  Leu Ser Asp Leu His  Phe Arg Gly
        995                 1000                1005
Ile Lys  Asp Gly Glu Pro Cys  Ser Phe Thr Asn Pro  Leu Gln Leu
    1010                1015                1020
```

Cys Gln Asn Asp Ser Asn Lys Ile Leu Gln Asp Gly Val Ile Phe
    1025                1030                1035

Met Val Pro Asn Ser Met Thr Arg Ser Leu Asp Pro Asp Thr Gly
    1040                1045                1050

Phe Ile Phe Ala Ile Asn Asp His Asn Ile Arg Thr Lys Lys Ala
    1055                1060                1065

Lys Leu Asn Phe Leu Ser Lys Phe Asp Gln Leu Lys Val Ser Ser
    1070                1075                1080

Glu Gly Cys Leu Ile Met Lys Tyr Ser Gly Asp Ser Leu Pro Thr
    1085                1090                1095

His Asn Thr Asp Asn Arg Val Trp Asn Cys Cys Cys Asn His Pro
    1100                1105                1110

Ile Thr Asn Tyr Asp Arg Glu Thr Lys Lys Val Glu Phe Ile Glu
    1115                1120                1125

Glu Pro Val Glu Glu Leu Ser Arg Val Leu Glu Glu Asn Gly Ile
    1130                1135                1140

Glu Thr Asp Thr Glu Leu Asn Lys Leu Asn Glu Arg Glu Asn Val
    1145                1150                1155

Pro Gly Lys Val Val Asp Ala Ile Tyr Ser Leu Val Leu Asn Tyr
    1160                1165                1170

Leu Arg Gly Thr Val Ser Gly Val Ala Gly Gln Arg Ala Val Tyr
    1175                1180                1185

Tyr Ser Pro Val Thr Gly Lys Lys Tyr Asp Ile Ser Phe Ile Gln
    1190                1195                1200

Ala Met Asn Leu Asn Arg Lys Cys Asp Tyr Tyr Arg Ile Gly Ser
    1205                1210                1215

Lys Glu Arg Gly Glu Trp Thr Asp Phe Val Ala Gln Leu Ile Asn
    1220                1225                1230

<210> SEQ ID NO 34
<211> LENGTH: 1227
<212> TYPE: PRT
<213> ORGANISM: Unknown
<220> FEATURE:
<223> OTHER INFORMATION: Lachnospiraceae bacterium

<400> SEQUENCE: 34

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

```
Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560
```

```
Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Asn Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
            820                 825                 830

Asp Arg Gly Glu Arg Asn Leu Leu Tyr Ile Val Val Val Asp Gly Lys
            835                 840                 845

Gly Asn Ile Val Glu Gln Tyr Ser Leu Asn Glu Ile Ile Asn Asn Phe
    850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
            915                 920                 925

Asn Ser Gly Phe Lys Asn Ser Arg Val Lys Val Glu Lys Gln Val Tyr
    930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
                965                 970                 975
```

```
Ile Thr Asn Lys Phe Glu Ser Phe Lys Ser Met Ser Thr Gln Asn Gly
                980                 985                 990

Phe Ile Phe Tyr Ile Pro Ala Trp Leu Thr Ser Lys Ile Asp Pro Ser
            995                1000                1005

Thr Gly Phe Val Asn Leu Leu Lys Thr Lys Tyr Thr Ser Ile Ala
        1010                1015                1020

Asp Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ser Asn Lys Glu Trp Leu
    1205                1210                1215

Glu Tyr Ala Gln Thr Ser Val Lys His
    1220                1225

<210> SEQ ID NO 35
<211> LENGTH: 1264
<212> TYPE: PRT
<213> ORGANISM: Leptospira inadai

<400> SEQUENCE: 35

Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
            20                  25                  30

Lys Lys Gly Phe Leu Lys Lys Asp Lys Ile Arg Ala Glu Asp Tyr Lys
        35                  40                  45

Ala Val Lys Lys Ile Ile Asp Lys Tyr His Arg Ala Tyr Ile Glu Glu
    50                  55                  60

Val Phe Asp Ser Val Leu His Gln Lys Lys Lys Asp Lys Thr Arg
65                  70                  75                  80

Phe Ser Thr Gln Phe Ile Lys Glu Ile Lys Glu Phe Ser Glu Leu Tyr
                85                  90                  95
```

```
Tyr Lys Thr Glu Lys Asn Ile Pro Asp Lys Glu Arg Leu Glu Ala Leu
            100                 105                 110

Ser Glu Lys Leu Arg Lys Met Leu Val Gly Ala Phe Lys Gly Glu Phe
            115                 120                 125

Ser Glu Glu Val Ala Glu Lys Tyr Asn Lys Asn Leu Phe Ser Lys Glu
        130                 135                 140

Leu Ile Arg Asn Glu Ile Glu Lys Phe Cys Thr Asp Glu Arg
145                 150                 155                 160

Lys Gln Val Ser Asn Phe Lys Ser Phe Thr Thr Tyr Phe Thr Gly Phe
                165                 170                 175

His Ser Asn Arg Gln Asn Ile Tyr Ser Asp Lys Lys Ser Thr Ala
                180                 185                 190

Ile Gly Tyr Arg Ile Ile His Gln Asn Leu Pro Lys Phe Leu Asp Asn
            195                 200                 205

Leu Lys Ile Ile Glu Ser Ile Gln Arg Arg Phe Lys Asp Phe Pro Trp
        210                 215                 220

Ser Asp Leu Lys Lys Asn Leu Lys Lys Ile Asp Lys Asn Ile Lys Leu
225                 230                 235                 240

Thr Glu Tyr Phe Ser Ile Asp Gly Phe Val Asn Val Leu Asn Gln Lys
                245                 250                 255

Gly Ile Asp Ala Tyr Asn Thr Ile Leu Gly Gly Lys Ser Glu Glu Ser
            260                 265                 270

Gly Glu Lys Ile Gln Gly Leu Asn Glu Tyr Ile Asn Leu Tyr Arg Gln
        275                 280                 285

Lys Asn Asn Ile Asp Arg Lys Asn Pro Leu Asn Val Lys Ile Leu Phe
290                 295                 300

Lys Gln Ile Leu Gly Asp Arg Glu Thr Lys Ser Phe Ile Pro Glu Ala
305                 310                 315                 320

Phe Pro Asp Asp Gln Ser Val Leu Asn Ser Ile Thr Glu Phe Ala Lys
                325                 330                 335

Tyr Leu Lys Leu Asp Lys Lys Lys Ser Ile Ile Ala Glu Leu Lys
            340                 345                 350

Lys Phe Leu Ser Ser Phe Asn Arg Tyr Glu Leu Asp Gly Ile Tyr Leu
        355                 360                 365

Ala Asn Asp Asn Ser Leu Ala Ser Ile Ser Thr Phe Leu Phe Asp Asp
370                 375                 380

Trp Ser Phe Ile Lys Lys Ser Val Ser Phe Lys Tyr Asp Glu Ser Val
385                 390                 395                 400

Gly Asp Pro Lys Lys Ile Lys Ser Pro Leu Lys Tyr Glu Lys Glu
            405                 410                 415

Lys Glu Lys Trp Leu Lys Gln Lys Tyr Tyr Thr Ile Ser Phe Leu Asn
            420                 425                 430

Asp Ala Ile Glu Ser Tyr Ser Lys Ser Gln Asp Glu Lys Arg Val Lys
            435                 440                 445

Ile Arg Leu Glu Ala Tyr Phe Ala Glu Phe Lys Ser Lys Asp Asp Ala
            450                 455                 460

Lys Lys Gln Phe Asp Leu Leu Glu Arg Ile Glu Glu Ala Tyr Ala Ile
465                 470                 475                 480

Val Glu Pro Leu Leu Gly Ala Glu Tyr Pro Arg Asp Arg Asn Leu Lys
                485                 490                 495

Ala Asp Lys Lys Glu Val Gly Lys Ile Lys Asp Phe Leu Asp Ser Ile
            500                 505                 510
```

-continued

```
Lys Ser Leu Gln Phe Phe Leu Lys Pro Leu Ser Ala Glu Ile Phe
            515                 520                 525

Asp Glu Lys Asp Leu Gly Phe Tyr Asn Gln Leu Glu Gly Tyr Glu
530                 535                 540

Glu Ile Asp Ile Ser Gly His Leu Tyr Asn Lys Val Arg Asn Tyr Leu
545                 550                 555                 560

Thr Gly Lys Ile Tyr Ser Lys Glu Lys Phe Lys Leu Asn Phe Glu Asn
                565                 570                 575

Ser Thr Leu Leu Lys Gly Trp Asp Glu Asn Arg Glu Val Ala Asn Leu
            580                 585                 590

Cys Val Ile Phe Arg Glu Asp Gln Lys Tyr Tyr Leu Gly Val Met Asp
            595                 600                 605

Lys Glu Asn Asn Thr Ile Leu Ser Asp Ile Pro Lys Val Lys Pro Asn
610                 615                 620

Glu Leu Phe Tyr Glu Lys Met Val Tyr Lys Leu Ile Pro Thr Pro His
625                 630                 635                 640

Met Gln Leu Pro Arg Ile Ile Phe Ser Ser Asp Asn Leu Ser Ile Tyr
                645                 650                 655

Asn Pro Ser Lys Ser Ile Leu Lys Ile Arg Glu Ala Lys Ser Phe Lys
                660                 665                 670

Glu Gly Lys Asn Phe Lys Leu Lys Asp Cys His Lys Phe Ile Asp Phe
            675                 680                 685

Tyr Lys Glu Ser Ile Ser Lys Asn Glu Asp Trp Ser Arg Phe Asp Phe
            690                 695                 700

Lys Phe Ser Lys Thr Ser Ser Tyr Glu Asn Ile Ser Glu Phe Tyr Arg
705                 710                 715                 720

Glu Val Glu Arg Gln Gly Tyr Asn Leu Asp Phe Lys Lys Val Ser Lys
                725                 730                 735

Phe Tyr Ile Asp Ser Leu Val Glu Asp Gly Lys Leu Tyr Leu Phe Gln
                740                 745                 750

Ile Tyr Asn Lys Asp Phe Ser Ile Phe Ser Lys Gly Lys Pro Asn Leu
            755                 760                 765

His Thr Ile Tyr Phe Arg Ser Leu Phe Ser Lys Glu Asn Leu Lys Asp
            770                 775                 780

Val Cys Leu Lys Leu Asn Gly Glu Ala Glu Met Phe Phe Arg Lys Lys
785                 790                 795                 800

Ser Ile Asn Tyr Asp Glu Lys Lys Arg Glu Gly His His Pro Glu
                805                 810                 815

Leu Phe Glu Lys Leu Lys Tyr Pro Ile Leu Lys Asp Lys Arg Tyr Ser
                820                 825                 830

Glu Asp Lys Phe Gln Phe His Leu Pro Ile Ser Leu Asn Phe Lys Ser
            835                 840                 845

Lys Glu Arg Leu Asn Phe Asn Leu Lys Val Asn Glu Phe Leu Lys Arg
850                 855                 860

Asn Lys Asp Ile Asn Ile Ile Gly Ile Asp Arg Gly Glu Arg Asn Leu
865                 870                 875                 880

Leu Tyr Leu Val Met Ile Asn Gln Lys Gly Glu Ile Leu Lys Gln Thr
                885                 890                 895

Leu Leu Asp Ser Met Gln Ser Gly Lys Gly Arg Pro Glu Ile Asn Tyr
            900                 905                 910

Lys Glu Lys Leu Gln Glu Lys Glu Ile Glu Arg Asp Lys Ala Arg Lys
            915                 920                 925
```

Ser Trp Gly Thr Val Glu Asn Ile Lys Glu Leu Lys Glu Gly Tyr Leu
930                935                940

Ser Ile Val Ile His Gln Ile Ser Lys Leu Met Val Glu Asn Asn Ala
945                950                955                960

Ile Val Val Leu Glu Asp Leu Asn Ile Gly Phe Lys Arg Gly Arg Gln
                965                970                975

Lys Val Glu Arg Gln Val Tyr Gln Lys Phe Glu Lys Met Leu Ile Asp
            980                985                990

Lys Leu Asn Phe Leu Val Phe Lys Glu Asn Lys Pro Thr Glu Pro Gly
        995                1000               1005

Gly Val Leu Lys Ala Tyr Gln Leu Thr Asp Glu Phe Gln Ser Phe
    1010               1015               1020

Glu Lys Leu Ser Lys Gln Thr Gly Phe Leu Phe Tyr Val Pro Ser
    1025               1030               1035

Trp Asn Thr Ser Lys Ile Asp Pro Arg Thr Gly Phe Ile Asp Phe
    1040               1045               1050

Leu His Pro Ala Tyr Glu Asn Ile Glu Lys Ala Lys Gln Trp Ile
    1055               1060               1065

Asn Lys Phe Asp Ser Ile Arg Phe Asn Ser Lys Met Asp Trp Phe
    1070               1075               1080

Glu Phe Thr Ala Asp Thr Arg Lys Phe Ser Glu Asn Leu Met Leu
    1085               1090               1095

Gly Lys Asn Arg Val Trp Val Ile Cys Thr Thr Asn Val Glu Arg
    1100               1105               1110

Tyr Phe Thr Ser Lys Thr Ala Asn Ser Ser Ile Gln Tyr Asn Ser
    1115               1120               1125

Ile Gln Ile Thr Glu Lys Leu Lys Glu Leu Phe Val Asp Ile Pro
    1130               1135               1140

Phe Ser Asn Gly Gln Asp Leu Lys Pro Glu Ile Leu Arg Lys Asn
    1145               1150               1155

Asp Ala Val Phe Phe Lys Ser Leu Leu Phe Tyr Ile Lys Thr Thr
    1160               1165               1170

Leu Ser Leu Arg Gln Asn Asn Gly Lys Lys Gly Glu Glu Glu Lys
    1175               1180               1185

Asp Phe Ile Leu Ser Pro Val Val Asp Ser Lys Gly Arg Phe Phe
    1190               1195               1200

Asn Ser Leu Glu Ala Ser Asp Asp Glu Pro Lys Asp Ala Asp Ala
    1205               1210               1215

Asn Gly Ala Tyr His Ile Ala Leu Lys Gly Leu Met Asn Leu Leu
    1220               1225               1230

Val Leu Asn Glu Thr Lys Glu Glu Asn Leu Ser Arg Pro Lys Trp
    1235               1240               1245

Lys Ile Lys Asn Lys Asp Trp Leu Glu Phe Val Trp Glu Arg Asn
    1250               1255               1260

Arg

<210> SEQ ID NO 36
<211> LENGTH: 1373
<212> TYPE: PRT
<213> ORGANISM: Moraxella bovoculi

<400> SEQUENCE: 36

Met Leu Phe Gln Asp Phe Thr His Leu Tyr Pro Leu Ser Lys Thr Val
1               5                   10                  15

```
Arg Phe Glu Leu Phe Ile Asp Arg Thr Leu Glu His Ile His Ala Lys
                20                  25                  30

Asn Phe Leu Ser Gln Asp Glu Thr Met Ala Asp Met His Gln Lys Val
                35                  40                  45

Lys Val Ile Leu Asp Asp Tyr His Arg Asp Phe Ile Ala Asp Met Met
 50                  55                  60

Gly Glu Val Lys Leu Thr Lys Leu Ala Glu Phe Tyr Asp Val Tyr Leu
 65                  70                  75                  80

Lys Phe Arg Lys Asn Pro Lys Asp Asp Glu Leu Gln Lys Ala Gln Leu
                85                  90                  95

Lys Asp Leu Gln Ala Val Leu Arg Lys Glu Ile Val Lys Pro Ile Gly
                100                 105                 110

Asn Gly Gly Lys Tyr Lys Ala Gly Tyr Asp Arg Leu Phe Gly Ala Lys
                115                 120                 125

Leu Phe Lys Asp Gly Lys Glu Leu Gly Asp Leu Ala Lys Phe Val Ile
130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
                180                 185                 190

His Glu Asn Leu Pro Arg Phe Ile Asp Asn Leu Gln Ile Leu Thr Thr
                195                 200                 205

Ile Lys Gln Lys His Ser Ala Leu Tyr Asp Gln Ile Ile Asn Glu Leu
                210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
                260                 265                 270

Glu Leu Ile Asn Ser His His Asn Gln His Cys His Lys Ser Glu Arg
                275                 280                 285

Ile Ala Lys Leu Arg Pro Leu His Lys Gln Ile Leu Ser Asp Gly Met
290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
                340                 345                 350

Tyr Val Glu His Lys Asn Leu Asn Glu Leu Ser Lys Gln Ala Phe Gly
                355                 360                 365

Asp Phe Ala Leu Leu Gly Arg Val Leu Asp Gly Tyr Tyr Val Asp Val
                370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
                420                 425                 430
```

His Asp Asp Glu Ser Val Gln Ala Gly Lys Leu Gly Gln Tyr Phe Lys
            435                 440                 445

His Gly Leu Ala Gly Val Asp Asn Pro Ile Gln Lys Ile His Asn Asn
450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
            485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
            515                 520                 525

Asn Phe Tyr Gly Glu Phe Gly Val Leu Tyr Asp Glu Leu Ala Lys Ile
530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
            565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
            595                 600                 605

Val Phe Asp Asn Ala Pro Asn Thr Gly Lys Ser Ile Tyr Gln Lys Met
610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
            645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
            675                 680                 685

Lys Lys Phe Glu Gly Ala Ile Gly Asp Ile Gln Leu Phe Lys Lys Asp
            690                 695                 700

Lys Lys Gly Arg Glu Val Pro Ile Ser Glu Lys Asp Leu Phe Lys Asp
705                 710                 715                 720

Ile Asn Gly Ile Phe Ser Ser Lys Pro Lys Leu Glu Met Glu Asp Phe
            725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
            755                 760                 765

Glu Asn Phe Tyr Asn Asn His Pro Lys Phe Lys Lys Asp Leu Val Arg
            770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
            805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
            835                 840                 845

```
Gln Leu Tyr Leu Phe Gln Ile Tyr Asn Lys Asp Phe Ser Pro Lys Ala
    850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
                900                 905                 910

Arg Ala Gly Glu Val Leu Glu Asn Lys Asn Pro Asp Asn Pro Lys Lys
                915                 920                 925

Arg Gln Phe Val Tyr Asp Ile Ile Lys Asp Lys Arg Tyr Thr Gln Lys
    930                 935                 940

Asp Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
                980                 985                 990

Leu Tyr Leu Thr Val Ile Asn Ser Lys Gly Glu Ile Leu Glu Gln Cys
    995                 1000                1005

Ser Leu Asn Asp Ile Thr Thr Ala Ser Ala Asn Gly Thr Gln Met
    1010                1015                1020

Thr Thr Pro Tyr His Lys Ile Leu Asp Lys Arg Glu Ile Glu Arg
    1025                1030                1035

Leu Asn Ala Arg Val Gly Trp Gly Glu Ile Glu Thr Ile Lys Glu
    1040                1045                1050

Leu Lys Ser Gly Tyr Leu Ser His Val Val His Gln Ile Ser Gln
    1055                1060                1065

Leu Met Leu Lys Tyr Asn Ala Ile Val Val Leu Glu Asp Leu Asn
    1070                1075                1080

Phe Gly Phe Lys Arg Gly Arg Phe Lys Val Glu Lys Gln Ile Tyr
    1085                1090                1095

Gln Asn Phe Glu Asn Ala Leu Ile Lys Lys Leu Asn His Leu Val
    1100                1105                1110

Leu Lys Asp Lys Ala Asp Asp Glu Ile Gly Ser Tyr Lys Asn Ala
    1115                1120                1125

Leu Gln Leu Thr Asn Asn Phe Thr Asp Leu Lys Ser Ile Gly Lys
    1130                1135                1140

Gln Thr Gly Phe Leu Phe Tyr Val Pro Ala Trp Asn Thr Ser Lys
    1145                1150                1155

Ile Asp Pro Glu Thr Gly Phe Val Asp Leu Leu Lys Pro Arg Tyr
    1160                1165                1170

Glu Asn Ile Gln Ala Ser Gln Ala Phe Phe Gly Lys Phe Asp Lys
    1175                1180                1185

Ile Cys Tyr Asn Ala Asp Lys Asp Tyr Phe Glu Phe His Ile Asp
    1190                1195                1200

Tyr Ala Lys Phe Thr Asp Lys Ala Lys Asn Ser Arg Gln Ile Trp
    1205                1210                1215

Thr Ile Cys Ser His Gly Asp Lys Arg Tyr Val Tyr Asp Lys Thr
    1220                1225                1230

Ala Asn Gln Asn Lys Gly Ala Ala Lys Gly Ile Asn Val Asn Asp
    1235                1240                1245
```

```
Ile Leu Lys Ser Leu Phe Ala Arg His His Ile Asn Glu Lys Gln
    1250                1255                1260

Pro Asn Leu Val Met Asp Ile Cys Gln Asn Asn Asp Lys Glu Phe
    1265                1270                1275

His Lys Ser Leu Met Tyr Leu Leu Lys Thr Leu Leu Ala Leu Arg
    1280                1285                1290

Tyr Ser Asn Ala Ser Ser Asp Glu Asp Phe Ile Leu Ser Pro Val
    1295                1300                1305

Ala Asn Asp Glu Gly Val Phe Phe Asn Ser Ala Leu Ala Asp Asp
    1310                1315                1320

Thr Gln Pro Gln Asn Ala Asp Ala Asn Gly Ala Tyr His Ile Ala
    1325                1330                1335

Leu Lys Gly Leu Trp Leu Leu Asn Glu Leu Lys Asn Ser Asp Asp
    1340                1345                1350

Leu Asn Lys Val Lys Leu Ala Ile Asp Asn Gln Thr Trp Leu Asn
    1355                1360                1365

Phe Ala Gln Asn Arg
    1370

<210> SEQ ID NO 37
<211> LENGTH: 1352
<212> TYPE: PRT
<213> ORGANISM: Unknown
<220> FEATURE:
<223> OTHER INFORMATION: Parcubacteria bacterium

<400> SEQUENCE: 37

Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
                20                  25                  30

Lys Ile Asn Lys Val Phe Glu Lys Asp Gln Thr Ile Asp Asp Ser Tyr
            35                  40                  45

Asn Gln Ala Lys Phe Tyr Phe Asp Ser Leu His Gln Lys Phe Ile Asp
        50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
                100                 105                 110

Arg Leu Gln Lys Glu Ile Asn Asp Ala Glu Asp Ile Ile Gln Lys Glu
            115                 120                 125

Lys Glu Lys Ile Tyr Lys Asp Val Arg Thr Leu Phe Asp Asn Glu Ala
        130                 135                 140

Glu Ser Trp Lys Thr Tyr Tyr Gln Gly Arg Glu Val Asp Gly Lys Lys
145                 150                 155                 160

Ile Thr Glu Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
                180                 185                 190

Lys Glu Lys Glu Phe Gln Ala Lys Asn Gln Pro Ser Leu Phe Val Glu
            195                 200                 205

Glu Lys Glu Asn Pro Gly Gln Leu Arg Tyr Ile Phe Asp Ser Phe Asp
        210                 215                 220
```

-continued

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
            245                 250                 255

Asn Phe Ile Ile Phe His Gln Asn Thr Lys Val Phe Arg Asp Lys Tyr
                260                 265                 270

Lys Asn Asn His Thr Asp Leu Gly Phe Asp Glu Glu Asn Ile Phe Glu
            275                 280                 285

Ile Glu Arg Tyr Lys Asn Cys Leu Leu Gln Arg Glu Ile Glu His Ile
        290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
    530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
625                 630                 635                 640

-continued

Lys Glu Gly Arg Leu Tyr Leu Gly Ile Met His Lys Asn His Arg Lys
              645                 650                 655

Leu Phe Gln Ser Met Gly Asn Ala Lys Gly Asp Asn Ala Asn Arg Tyr
              660                 665                 670

Gln Lys Met Ile Tyr Lys Gln Ile Ala Asp Ala Ser Lys Asp Val Pro
              675                 680                 685

Arg Leu Leu Leu Thr Ser Lys Lys Ala Met Glu Lys Phe Lys Pro Ser
              690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
              725                 730                 735

Asn Cys Ile Pro Gln Tyr Ser Asn Trp Ser Phe Tyr Asp Phe Gln Phe
              740                 745                 750

Gln Asp Thr Gly Lys Tyr Gln Asn Ile Lys Glu Phe Thr Asp Asp Val
              755                 760                 765

Gln Lys Tyr Gly Tyr Lys Ile Ser Phe Arg Asp Ile Asp Asp Glu Tyr
              770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
              805                 810                 815

Leu Tyr Phe Glu His Ile Leu Ser Ala Glu Asn Leu Asn Asp Pro Val
              820                 825                 830

Phe Lys Leu Ser Gly Met Ala Glu Ile Phe Gln Arg Gln Pro Ser Val
              835                 840                 845

Asn Glu Arg Glu Lys Ile Thr Thr Gln Lys Asn Gln Cys Ile Leu Asp
850                 855                 860

Lys Gly Asp Arg Ala Tyr Lys Tyr Arg Arg Tyr Thr Glu Lys Lys Ile
865                 870                 875                 880

Met Phe His Met Ser Leu Val Leu Asn Thr Gly Lys Gly Glu Ile Lys
              885                 890                 895

Gln Val Gln Phe Asn Lys Ile Ile Asn Gln Arg Ile Ser Ser Ser Asp
              900                 905                 910

Asn Glu Met Arg Val Asn Val Ile Gly Ile Asp Arg Gly Glu Lys Asn
              915                 920                 925

Leu Leu Tyr Tyr Ser Val Val Lys Gln Asn Gly Glu Ile Ile Glu Gln
              930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
              965                 970                 975

Val Lys Ile Lys Asp Leu Lys Lys Gly Tyr Ile Ser His Val Ile His
              980                 985                 990

Lys Ile Cys Gln Leu Ile Glu Lys Tyr Ser Ala Ile Val Val Leu Glu
              995                1000                1005

Asp Leu Asn Met Arg Phe Lys Gln Ile Arg Gly Gly Ile Glu Arg
              1010                1015                1020

Ser Val Tyr Gln Gln Phe Glu Lys Ala Leu Ile Asp Lys Leu Gly
              1025                1030                1035

Tyr Leu Val Phe Lys Asp Asn Arg Asp Leu Arg Ala Pro Gly Gly
              1040                1045                1050

Val Leu Asn Gly Tyr Gln Leu Ser Ala Pro Phe Val Ser Phe Glu
1055                1060                1065

Lys Met Arg Lys Gln Thr Gly Ile Leu Phe Tyr Thr Gln Ala Glu
1070                1075                1080

Tyr Thr Ser Lys Thr Asp Pro Ile Thr Gly Phe Arg Lys Asn Val
1085                1090                1095

Tyr Ile Ser Asn Ser Ala Ser Leu Asp Lys Ile Lys Glu Ala Val
1100                1105                1110

Lys Lys Phe Asp Ala Ile Gly Trp Asp Gly Lys Glu Gln Ser Tyr
1115                1120                1125

Phe Phe Lys Tyr Asn Pro Tyr Asn Leu Ala Asp Glu Lys Tyr Lys
1130                1135                1140

Asn Ser Thr Val Ser Lys Glu Trp Ala Ile Phe Ala Ser Ala Pro
1145                1150                1155

Arg Ile Arg Arg Gln Lys Gly Glu Asp Gly Tyr Trp Lys Tyr Asp
1160                1165                1170

Arg Val Lys Val Asn Glu Glu Phe Glu Lys Leu Leu Lys Val Trp
1175                1180                1185

Asn Phe Val Asn Pro Lys Ala Thr Asp Ile Lys Gln Glu Ile Ile
1190                1195                1200

Lys Lys Ile Lys Ala Gly Asp Leu Gln Gly Glu Lys Glu Leu Asp
1205                1210                1215

Gly Arg Leu Arg Asn Phe Trp His Ser Phe Ile Tyr Leu Phe Asn
1220                1225                1230

Leu Val Leu Glu Leu Arg Asn Ser Phe Ser Leu Gln Ile Lys Ile
1235                1240                1245

Lys Ala Gly Glu Val Ile Ala Val Asp Glu Gly Val Asp Phe Ile
1250                1255                1260

Ala Ser Pro Val Lys Pro Phe Phe Thr Thr Pro Asn Pro Tyr Ile
1265                1270                1275

Pro Ser Asn Leu Cys Trp Leu Ala Val Glu Asn Ala Asp Ala Asn
1280                1285                1290

Gly Ala Tyr Asn Ile Ala Arg Lys Gly Val Met Ile Leu Lys Lys
1295                1300                1305

Ile Arg Glu His Ala Lys Lys Asp Pro Glu Phe Lys Lys Leu Pro
1310                1315                1320

Asn Leu Phe Ile Ser Asn Ala Glu Trp Asp Glu Ala Ala Arg Asp
1325                1330                1335

Trp Gly Lys Tyr Ala Gly Thr Thr Ala Leu Asn Leu Asp His
1340                1345                1350

<210> SEQ ID NO 38
<211> LENGTH: 1260
<212> TYPE: PRT
<213> ORGANISM: Porphyromonas crevioricanis

<400> SEQUENCE: 38

Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
            20                  25                  30

Lys Ala Gly Ile Leu Lys Glu Asp Glu His Arg Ala Glu Ser Tyr Arg
        35                  40                  45

Arg Val Lys Lys Ile Ile Asp Thr Tyr His Lys Val Phe Ile Asp Ser
    50                  55                  60

```
Ser Leu Glu Asn Met Ala Lys Met Gly Ile Glu Asn Glu Ile Lys Ala
 65                  70                  75                  80

Met Leu Gln Ser Phe Cys Glu Leu Tyr Lys Asp His Arg Thr Glu
                 85                  90                  95

Gly Glu Asp Lys Ala Leu Asp Lys Ile Arg Ala Val Leu Arg Gly Leu
                100                 105                 110

Ile Val Gly Ala Phe Thr Gly Val Cys Gly Arg Arg Glu Asn Thr Val
                115                 120                 125

Gln Asn Glu Lys Tyr Glu Ser Leu Phe Lys Glu Lys Leu Ile Lys Glu
        130                 135                 140

Ile Leu Pro Asp Phe Val Leu Ser Thr Glu Ala Glu Ser Leu Pro Phe
145                 150                 155                 160

Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
                180                 185                 190

Lys Pro Gln Ser Thr Ala Ile Ala Tyr Arg Leu Ile His Glu Asn Leu
        195                 200                 205

Pro Lys Phe Ile Asp Asn Ile Leu Val Phe Gln Lys Ile Lys Glu Pro
        210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
                260                 265                 270

Ile Gly Lys Ile Val Thr Glu Gly Asp Gly Glu Met Lys Gly Leu Asn
        275                 280                 285

Glu His Ile Asn Leu Tyr Asn Gln Gln Arg Gly Arg Glu Asp Arg Leu
        290                 295                 300

Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
                340                 345                 350

Thr Gln Gln Leu Met Thr Ser Ile Ser Glu Tyr Asp Leu Ser Arg Ile
        355                 360                 365

Tyr Val Arg Asn Asp Ser Gln Leu Thr Asp Ile Ser Lys Lys Met Leu
        370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
                420                 425                 430

Cys Ile Ala Phe Leu Asp Asn Val Arg Asp Cys Arg Val Asp Thr Tyr
        435                 440                 445

Leu Ser Thr Leu Gly Gln Lys Glu Gly Pro His Gly Leu Ser Asn Leu
        450                 455                 460

Val Glu Asn Val Phe Ala Ser Tyr His Glu Ala Glu Gln Leu Leu Ser
465                 470                 475                 480
```

-continued

```
Phe Pro Tyr Pro Glu Glu Asn Asn Leu Ile Gln Asp Lys Asp Asn Val
                485                 490                 495
Val Leu Ile Lys Asn Leu Leu Asp Asn Ile Ser Asp Leu Gln Arg Phe
            500                 505                 510
Leu Lys Pro Leu Trp Gly Met Gly Asp Glu Pro Asp Lys Asp Glu Arg
        515                 520                 525
Phe Tyr Gly Glu Tyr Asn Tyr Ile Arg Gly Ala Leu Asp Gln Val Ile
    530                 535                 540
Pro Leu Tyr Asn Lys Val Arg Asn Tyr Leu Thr Arg Lys Pro Tyr Ser
545                 550                 555                 560
Thr Arg Lys Val Lys Leu Asn Phe Gly Asn Ser Gln Leu Leu Ser Gly
                565                 570                 575
Trp Asp Arg Asn Lys Glu Lys Asp Asn Ser Cys Val Ile Leu Arg Lys
            580                 585                 590
Gly Gln Asn Phe Tyr Leu Ala Ile Met Asn Asn Arg His Lys Arg Ser
        595                 600                 605
Phe Glu Asn Lys Met Leu Pro Glu Tyr Lys Glu Gly Glu Pro Tyr Phe
    610                 615                 620
Glu Lys Met Asp Tyr Lys Phe Leu Pro Asp Pro Asn Lys Met Leu Pro
625                 630                 635                 640
Lys Val Phe Leu Ser Lys Lys Gly Ile Glu Ile Tyr Lys Pro Ser Pro
                645                 650                 655
Lys Leu Leu Glu Gln Tyr Gly His Gly Thr His Lys Lys Gly Asp Thr
            660                 665                 670
Phe Ser Met Asp Asp Leu His Glu Leu Ile Asp Phe Phe Lys His Ser
        675                 680                 685
Ile Glu Ala His Glu Asp Trp Lys Gln Phe Gly Phe Lys Phe Ser Asp
    690                 695                 700
Thr Ala Thr Tyr Glu Asn Val Ser Ser Phe Tyr Arg Glu Val Glu Asp
705                 710                 715                 720
Gln Gly Tyr Lys Leu Ser Phe Arg Lys Val Ser Glu Ser Tyr Val Tyr
                725                 730                 735
Ser Leu Ile Asp Gln Gly Lys Leu Tyr Leu Phe Gln Ile Tyr Asn Lys
            740                 745                 750
Asp Phe Ser Pro Cys Ser Lys Gly Thr Pro Asn Leu His Thr Leu Tyr
        755                 760                 765
Trp Arg Met Leu Phe Asp Glu Arg Asn Leu Ala Asp Val Ile Tyr Lys
    770                 775                 780
Leu Asp Gly Lys Ala Glu Ile Phe Phe Arg Glu Lys Ser Leu Lys Asn
785                 790                 795                 800
Asp His Pro Thr His Pro Ala Gly Lys Pro Ile Lys Lys Lys Ser Arg
                805                 810                 815
Gln Lys Lys Gly Glu Glu Ser Leu Phe Glu Tyr Asp Leu Val Lys Asp
            820                 825                 830
Arg Arg Tyr Thr Met Asp Lys Phe Gln Phe His Val Pro Ile Thr Met
        835                 840                 845
Asn Phe Lys Cys Ser Ala Gly Ser Lys Val Asn Asp Met Val Asn Ala
    850                 855                 860
His Ile Arg Glu Ala Lys Asp Met His Val Ile Gly Ile Asp Arg Gly
865                 870                 875                 880
Glu Arg Asn Leu Leu Tyr Ile Cys Val Ile Asp Ser Arg Gly Thr Ile
                885                 890                 895
```

```
Leu Asp Gln Ile Ser Leu Asn Thr Ile Asn Asp Ile Asp Tyr His Asp
                900                 905                 910

Leu Leu Glu Ser Arg Asp Lys Asp Arg Gln Gln Glu His Arg Asn Trp
                915                 920                 925

Gln Thr Ile Glu Gly Ile Lys Glu Leu Lys Gln Gly Tyr Leu Ser Gln
                930                 935             940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
                980                 985                 990

Asn Tyr Leu Val Asp Lys Lys Lys Arg Pro Glu Asp Ile Gly Gly Leu
                995                 1000                1005

Leu Arg Ala Tyr Gln Phe Thr Ala Pro Phe Lys Ser Phe Lys Glu
                1010            1015                1020

Met Gly Lys Gln Asn Gly Phe Leu Phe Tyr Ile Pro Ala Trp Asn
                1025            1030            1035

Thr Ser Asn Ile Asp Pro Thr Thr Gly Phe Val Asn Leu Phe His
                1040            1045            1050

Val Gln Tyr Glu Asn Val Asp Lys Ala Lys Ser Phe Phe Gln Lys
                1055            1060            1065

Phe Asp Ser Ile Ser Tyr Asn Pro Lys Lys Asp Trp Phe Glu Phe
                1070            1075            1080

Ala Phe Asp Tyr Lys Asn Phe Thr Lys Lys Ala Glu Gly Ser Arg
                1085            1090            1095

Ser Met Trp Ile Leu Cys Thr His Gly Ser Arg Ile Lys Asn Phe
                1100            1105            1110

Arg Asn Ser Gln Lys Asn Gly Gln Trp Asp Ser Glu Glu Phe Ala
                1115            1120            1125

Leu Thr Glu Ala Phe Lys Ser Leu Phe Val Arg Tyr Glu Ile Asp
                1130            1135            1140

Tyr Thr Ala Asp Leu Lys Thr Ala Ile Val Asp Glu Lys Gln Lys
                1145            1150            1155

Asp Phe Phe Val Asp Leu Leu Lys Leu Phe Lys Leu Thr Val Gln
                1160            1165            1170

Met Arg Asn Ser Trp Lys Glu Lys Asp Leu Asp Tyr Leu Ile Ser
                1175            1180            1185

Pro Val Ala Gly Ala Asp Gly Arg Phe Phe Asp Thr Arg Glu Gly
                1190            1195            1200

Asn Lys Ser Leu Pro Lys Asp Ala Asp Ala Asn Gly Ala Tyr Asn
                1205            1210            1215

Ile Ala Leu Lys Gly Leu Trp Ala Leu Arg Gln Ile Arg Gln Thr
                1220            1225            1230

Ser Glu Gly Gly Lys Leu Lys Leu Ala Ile Ser Asn Lys Glu Trp
                1235            1240            1245

Leu Gln Phe Val Gln Glu Arg Ser Tyr Glu Lys Asp
                1250            1255            1260

<210> SEQ ID NO 39
<211> LENGTH: 1324
<212> TYPE: PRT
<213> ORGANISM: Prevotella disiens
```

-continued

```
<400> SEQUENCE: 39

Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Val Lys Lys Thr Ala Leu Arg
            100                 105                 110

Asn Lys Cys Thr Ser Ile Gln Arg Ala Met Arg Glu Ala Ile Ser Gln
            115                 120                 125

Ala Phe Leu Lys Ser Pro Gln Lys Leu Leu Ala Ile Lys Asn Leu
    130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Gly Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
        275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Asp Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
        355                 360                 365

Tyr Arg Asn Phe Ser Ile Asp Glu Ala Ile Asp Ala Gln Asn Ala Glu
    370                 375                 380

Leu Gln Thr Phe Asn Asn Tyr Glu Leu Ile Ala Asn Ala Leu Arg Ala
385                 390                 395                 400

Lys Ile Lys Lys Glu Thr Lys Gln Gly Arg Lys Ser Phe Glu Lys Tyr
                405                 410                 415
```

```
Glu Glu Tyr Ile Asp Lys Lys Val Lys Ala Ile Asp Ser Leu Ser Ile
            420                 425                 430

Gln Glu Ile Asn Glu Leu Val Glu Asn Tyr Val Ser Glu Phe Asn Ser
            435                 440                 445

Asn Ser Gly Asn Met Pro Arg Lys Val Glu Asp Tyr Phe Ser Leu Met
        450                 455                 460

Arg Lys Gly Asp Phe Gly Ser Asn Asp Leu Ile Glu Asn Ile Lys Thr
465                 470                 475                 480

Lys Leu Ser Ala Ala Glu Lys Leu Leu Gly Thr Lys Tyr Gln Glu Thr
                485                 490                 495

Ala Lys Asp Ile Phe Lys Lys Asp Glu Asn Ser Lys Leu Ile Lys Glu
            500                 505                 510

Leu Leu Asp Ala Thr Lys Gln Phe Gln His Phe Ile Lys Pro Leu Leu
            515                 520                 525

Gly Thr Gly Glu Glu Ala Asp Arg Asp Leu Val Phe Tyr Gly Asp Phe
530                 535                 540

Leu Pro Leu Tyr Glu Lys Phe Glu Glu Leu Thr Leu Leu Tyr Asn Lys
545                 550                 555                 560

Val Arg Asn Arg Leu Thr Gln Lys Pro Tyr Ser Lys Asp Lys Ile Arg
                565                 570                 575

Leu Cys Phe Asn Lys Pro Lys Leu Met Thr Gly Trp Val Asp Ser Lys
            580                 585                 590

Thr Glu Lys Ser Asp Asn Gly Thr Gln Tyr Gly Gly Tyr Leu Phe Arg
            595                 600                 605

Lys Lys Asn Glu Ile Gly Glu Tyr Asp Tyr Phe Leu Gly Ile Ser Ser
            610                 615                 620

Lys Ala Gln Leu Phe Arg Lys Asn Glu Ala Val Ile Gly Asp Tyr Glu
625                 630                 635                 640

Arg Leu Asp Tyr Tyr Gln Pro Lys Ala Asn Thr Ile Tyr Gly Ser Ala
                645                 650                 655

Tyr Glu Gly Glu Asn Ser Tyr Lys Glu Asp Lys Lys Arg Leu Asn Lys
            660                 665                 670

Val Ile Ile Ala Tyr Ile Glu Gln Ile Lys Gln Thr Asn Ile Lys Lys
            675                 680                 685

Ser Ile Ile Glu Ser Ile Ser Lys Tyr Pro Asn Ile Ser Asp Asp Asp
            690                 695                 700

Lys Val Thr Pro Ser Ser Leu Leu Glu Lys Ile Lys Lys Val Ser Ile
705                 710                 715                 720

Asp Ser Tyr Asn Gly Ile Leu Ser Phe Lys Ser Phe Gln Ser Val Asn
            725                 730                 735

Lys Glu Val Ile Asp Asn Leu Leu Lys Thr Ile Ser Pro Leu Lys Asn
            740                 745                 750

Lys Ala Glu Phe Leu Asp Leu Ile Asn Lys Asp Tyr Gln Ile Phe Thr
            755                 760                 765

Glu Val Gln Ala Val Ile Asp Glu Ile Cys Lys Gln Lys Thr Phe Ile
            770                 775                 780

Tyr Phe Pro Ile Ser Asn Val Glu Leu Glu Lys Glu Met Gly Asp Lys
785                 790                 795                 800

Asp Lys Pro Leu Cys Leu Phe Gln Ile Ser Asn Lys Asp Leu Ser Phe
                805                 810                 815

Ala Lys Thr Phe Ser Ala Asn Leu Arg Lys Lys Arg Gly Ala Glu Asn
            820                 825                 830
```

```
Leu His Thr Met Leu Phe Lys Ala Leu Met Glu Gly Asn Gln Asp Asn
        835                 840                 845

Leu Asp Leu Gly Ser Gly Ala Ile Phe Tyr Arg Ala Lys Ser Leu Asp
850                 855                 860

Gly Asn Lys Pro Thr His Pro Ala Asn Glu Ala Ile Lys Cys Arg Asn
865             870                 875                     880

Val Ala Asn Lys Asp Lys Val Ser Leu Phe Thr Tyr Asp Ile Tyr Lys
                885                 890                 895

Asn Arg Arg Tyr Met Glu Asn Lys Phe Leu Phe His Leu Ser Ile Val
            900                 905                 910

Gln Asn Tyr Lys Ala Ala Asn Asp Ser Ala Gln Leu Asn Ser Ser Ala
            915                 920                 925

Thr Glu Tyr Ile Arg Lys Ala Asp Asp Leu His Ile Ile Gly Ile Asp
    930                 935                 940

Arg Gly Glu Arg Asn Leu Leu Tyr Tyr Ser Val Ile Asp Met Lys Gly
945                 950                 955                 960

Asn Ile Val Glu Gln Asp Ser Leu Asn Ile Ile Arg Asn Asn Asp Leu
                965                 970                 975

Glu Thr Asp Tyr His Asp Leu Leu Asp Lys Arg Glu Lys Glu Arg Lys
            980                 985                 990

Ala Asn Arg Gln Asn Trp Glu Ala  Val Glu Gly Ile Lys  Asp Leu Lys
        995                 1000                1005

Lys Gly Tyr Leu Ser Gln Ala  Val His Gln Ile Ala  Gln Leu Met
    1010                1015                1020

Leu Lys Tyr Asn Ala Ile Ile  Ala Leu Glu Asp Leu  Gly Gln Met
    1025                1030                1035

Phe Val Thr Arg Gly Gln Lys  Ile Glu Lys Ala Val  Tyr Gln Gln
    1040                1045                1050

Phe Glu Lys Ser Leu Val Asp  Lys Leu Ser Tyr Leu  Val Asp Lys
    1055                1060                1065

Lys Arg Pro Tyr Asn Glu Leu  Gly Gly Ile Leu Lys  Ala Tyr Gln
    1070                1075                1080

Leu Ala Ser Ser Ile Thr Lys  Asn Asn Ser Asp Lys  Gln Asn Gly
    1085                1090                1095

Phe Leu Phe Tyr Val Pro Ala  Trp Asn Thr Ser Lys  Ile Asp Pro
    1100                1105                1110

Val Thr Gly Phe Thr Asp Leu  Leu Arg Pro Lys Ala  Met Thr Ile
    1115                1120                1125

Lys Glu Ala Gln Asp Phe Phe  Gly Ala Phe Asp Asn  Ile Ser Tyr
    1130                1135                1140

Asn Asp Lys Gly Tyr Phe Glu  Phe Glu Thr Asn Tyr  Asp Lys Phe
    1145                1150                1155

Lys Ile Arg Met Lys Ser Ala  Gln Thr Arg Trp Thr  Ile Cys Thr
    1160                1165                1170

Phe Gly Asn Arg Ile Lys Arg  Lys Lys Asp Lys Asn  Tyr Trp Asn
    1175                1180                1185

Tyr Glu Glu Val Glu Leu Thr  Glu Glu Phe Lys Lys  Leu Phe Lys
    1190                1195                1200

Asp Ser Asn Ile Asp Tyr Glu  Asn Cys Asn Leu Lys  Glu Glu Ile
    1205                1210                1215

Gln Asn Lys Asp Asn Arg Lys  Phe Phe Asp Asp Leu  Ile Lys Leu
    1220                1225                1230
```

```
Leu Gln Leu Thr Leu Gln Met Arg Asn Ser Asp Asp Lys Gly Asn
    1235                1240                1245

Asp Tyr Ile Ile Ser Pro Val Ala Asn Ala Glu Gly Gln Phe Phe
    1250                1255                1260

Asp Ser Arg Asn Gly Asp Lys Lys Leu Pro Leu Asp Ala Asp Ala
    1265                1270                1275

Asn Gly Ala Tyr Asn Ile Ala Arg Lys Gly Leu Trp Asn Ile Arg
    1280                1285                1290

Gln Ile Lys Gln Thr Lys Asn Lys Asp Asp Leu Asn Leu Ser Ile
    1295                1300                1305

Ser Ser Thr Glu Trp Leu Asp Phe Val Arg Glu Lys Pro Tyr Leu
    1310                1315                1320

Lys

<210> SEQ ID NO 40
<211> LENGTH: 1484
<212> TYPE: PRT
<213> ORGANISM: Unknown
<220> FEATURE:
<223> OTHER INFORMATION: Peregrinibacteria bacterium
<220> FEATURE:
<221> NAME/KEY: misc_feature
<222> LOCATION: (1073)..(1073)
<223> OTHER INFORMATION: Xaa can be any naturally occurring amino acid

<400> SEQUENCE: 40

Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
                20                  25                  30

Lys Asp His Leu Glu Tyr Asp Lys Leu Gln Thr Phe Leu Lys Asp
            35                  40                  45

Gln Asn Ile Asp Asp Ala Tyr Gln Ala Leu Lys Pro Gln Phe Asp Glu
50                  55                  60

Ile His Glu Glu Phe Ile Thr Asp Ser Leu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
    130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
        195                 200                 205

Phe Cys Asp Asn Val Ile Gln Phe Lys His Ile Ile Lys Arg Lys Lys
    210                 215                 220

Asp Gly Thr Val Glu Lys Thr Glu Arg Lys Thr Glu Tyr Leu Asn Ala
225                 230                 235                 240
```

```
Tyr Gln Tyr Leu Lys Asn Asn Asn Lys Ile Thr Gln Ile Lys Asp Ala
                245                 250                 255

Glu Thr Glu Lys Met Ile Glu Ser Thr Pro Ile Ala Glu Lys Ile Phe
                260                 265                 270

Asp Val Tyr Tyr Phe Ser Ser Cys Leu Ser Gln Lys Gln Ile Glu Glu
                275                 280                 285

Tyr Asn Arg Ile Ile Gly His Tyr Asn Leu Leu Ile Asn Leu Tyr Asn
                290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
                340                 345                 350

Glu Ala Asn Lys Ser Arg Asn Glu Gly Lys Glu Ser His Ser Val Glu
                355                 360                 365

Glu Ile Ile Asn Lys Ala Gln Glu Ala Ile Asn Lys Tyr Phe Lys Ser
                370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
                405                 410                 415

Met Asn Thr Ile Ser Asp Lys Tyr Phe Ala Asn Tyr His Asp Leu Gln
                420                 425                 430

Asp Arg Leu Lys Glu Ala Lys Val Phe Gln Lys Ala Asp Lys Lys Ser
                435                 440                 445

Glu Asp Asp Ile Lys Ile Pro Glu Ala Ile Glu Leu Ser Gly Leu Phe
                450                 455                 460

Gly Val Leu Asp Ser Leu Ala Asp Trp Gln Thr Thr Leu Phe Lys Ser
465                 470                 475                 480

Ser Ile Leu Ser Asn Glu Lys Leu Lys Ile Ile Thr Asp Ser Gln Thr
                485                 490                 495

Pro Ser Glu Ala Leu Leu Lys Met Ile Phe Asn Asp Ile Glu Lys Asn
                500                 505                 510

Met Glu Ser Phe Leu Lys Glu Thr Asn Asp Ile Ile Thr Leu Lys Lys
                515                 520                 525

Tyr Lys Gly Asn Lys Glu Gly Thr Glu Lys Ile Lys Gln Trp Phe Asp
                530                 535                 540

Tyr Thr Leu Ala Ile Asn Arg Met Leu Lys Tyr Phe Leu Val Lys Glu
545                 550                 555                 560

Asn Lys Ile Lys Gly Asn Ser Leu Asp Thr Asn Ile Ser Glu Ala Leu
                565                 570                 575

Lys Thr Leu Ile Tyr Ser Asp Asp Ala Glu Trp Phe Lys Trp Tyr Asp
                580                 585                 590

Ala Leu Arg Asn Tyr Leu Thr Gln Lys Pro Gln Asp Glu Ala Lys Glu
                595                 600                 605

Asn Lys Leu Lys Leu Asn Phe Asp Asn Pro Ser Leu Ala Gly Gly Trp
                610                 615                 620

Asp Val Asn Lys Glu Cys Ser Asn Phe Cys Val Ile Leu Lys Asp Lys
625                 630                 635                 640

Asn Glu Lys Lys Tyr Leu Ala Met Ile Lys Lys Gly Glu Asn Thr Leu
                645                 650                 655
```

```
Phe Gln Lys Glu Trp Thr Glu Gly Arg Gly Lys Asn Leu Thr Lys Lys
            660                 665                 670

Ser Asn Pro Leu Phe Glu Ile Asn Asn Cys Glu Ile Leu Ser Lys Met
            675                 680                 685

Glu Tyr Asp Phe Trp Ala Asp Val Ser Lys Met Ile Pro Lys Cys Ser
            690                 695                 700

Thr Gln Leu Lys Ala Val Val Asn His Phe Lys Gln Ser Asp Asn Glu
705                 710                 715                 720

Phe Ile Phe Pro Ile Gly Tyr Lys Val Thr Ser Gly Glu Lys Phe Arg
                725                 730                 735

Glu Glu Cys Lys Ile Ser Lys Gln Asp Phe Glu Leu Asn Asn Lys Val
            740                 745                 750

Phe Asn Lys Asn Glu Leu Ser Val Thr Ala Met Arg Tyr Asp Leu Ser
            755                 760                 765

Ser Thr Gln Glu Lys Gln Tyr Ile Lys Ala Phe Gln Lys Glu Tyr Trp
            770                 775                 780

Glu Leu Leu Phe Lys Gln Glu Lys Arg Asp Thr Lys Leu Thr Asn Asn
785                 790                 795                 800

Glu Ile Phe Asn Glu Trp Ile Asn Phe Cys Asn Lys Lys Tyr Ser Glu
                805                 810                 815

Leu Leu Ser Trp Glu Arg Lys Tyr Lys Asp Ala Leu Thr Asn Trp Ile
                820                 825                 830

Asn Phe Cys Lys Tyr Phe Leu Ser Lys Tyr Pro Lys Thr Thr Leu Phe
            835                 840                 845

Asn Tyr Ser Phe Lys Glu Ser Glu Asn Tyr Asn Ser Leu Asp Glu Phe
850                 855                 860

Tyr Arg Asp Val Asp Ile Cys Ser Tyr Lys Leu Asn Ile Asn Thr Thr
865                 870                 875                 880

Ile Asn Lys Ser Ile Leu Asp Arg Leu Val Glu Glu Gly Lys Leu Tyr
                885                 890                 895

Leu Phe Glu Ile Lys Asn Gln Asp Ser Asn Asp Gly Lys Ser Ile Gly
                900                 905                 910

His Lys Asn Asn Leu His Thr Ile Tyr Trp Asn Ala Ile Phe Glu Asn
            915                 920                 925

Phe Asp Asn Arg Pro Lys Leu Asn Gly Glu Ala Glu Ile Phe Tyr Arg
930                 935                 940

Lys Ala Ile Ser Lys Asp Lys Leu Gly Ile Val Lys Gly Lys Lys Thr
945                 950                 955                 960

Lys Asn Gly Thr Trp Ile Ile Lys Asn Tyr Arg Phe Ser Lys Glu Lys
                965                 970                 975

Phe Ile Leu His Val Pro Ile Thr Leu Asn Phe Cys Ser Asn Asn Glu
            980                 985                 990

Tyr Val Asn Asp Ile Val Asn Thr Lys Phe Tyr Asn Phe Ser Asn Leu
            995                 1000                1005

His Phe Leu Gly Ile Asp Arg Gly Glu Lys His Leu Ala Tyr Tyr
            1010                1015                1020

Ser Leu Val Asn Lys Asn Gly Glu Ile Val Asp Gln Gly Thr Leu
            1025                1030                1035

Asn Leu Pro Phe Thr Asp Lys Asp Gly Asn Gln Arg Ser Ile Lys
            1040                1045                1050

Lys Glu Lys Tyr Phe Tyr Asn Lys Gln Glu Asp Lys Trp Glu Ala
            1055                1060                1065
```

```
Lys Glu Val Asp Xaa Trp Asn Tyr Asn Asp Leu Leu Asp Ala Met
    1070            1075                1080

Ala Ser Asn Arg Asp Met Ala Arg Lys Asn Trp Gln Arg Ile Gly
    1085            1090                1095

Thr Ile Lys Glu Ala Lys Asn Gly Tyr Val Ser Leu Val Ile Arg
    1100            1105                1110

Lys Ile Ala Asp Leu Ala Val Asn Asn Glu Arg Pro Ala Phe Ile
    1115            1120                1125

Val Leu Glu Asp Leu Asn Thr Gly Phe Lys Arg Ser Arg Gln Lys
    1130            1135                1140

Ile Asp Lys Ser Val Tyr Gln Lys Phe Glu Leu Ala Leu Ala Lys
    1145            1150                1155

Lys Leu Asn Phe Leu Val Asp Lys Asn Ala Lys Arg Asp Glu Ile
    1160            1165                1170

Gly Ser Pro Thr Lys Ala Leu Gln Leu Thr Pro Pro Val Asn Asn
    1175            1180                1185

Tyr Gly Asp Ile Glu Asn Lys Lys Gln Ala Gly Ile Met Leu Tyr
    1190            1195                1200

Thr Arg Ala Asn Tyr Thr Ser Gln Thr Asp Pro Ala Thr Gly Trp
    1205            1210                1215

Arg Lys Thr Ile Tyr Leu Lys Ala Gly Pro Glu Thr Thr Tyr
    1220            1225                1230

Lys Lys Asp Gly Lys Ile Lys Asn Lys Ser Val Lys Asp Gln Ile
    1235            1240                1245

Ile Glu Thr Phe Thr Asp Ile Gly Phe Asp Gly Lys Asp Tyr Tyr
    1250            1255                1260

Phe Glu Tyr Asp Lys Gly Glu Phe Val Asp Glu Lys Thr Gly Glu
    1265            1270                1275

Ile Lys Pro Lys Lys Trp Arg Leu Tyr Ser Gly Glu Asn Gly Lys
    1280            1285                1290

Ser Leu Asp Arg Phe Arg Gly Glu Arg Glu Lys Asp Lys Tyr Glu
    1295            1300                1305

Trp Lys Ile Asp Lys Ile Asp Ile Val Lys Ile Leu Asp Asp Leu
    1310            1315                1320

Phe Val Asn Phe Asp Lys Asn Ile Ser Leu Leu Lys Gln Leu Lys
    1325            1330                1335

Glu Gly Val Glu Leu Thr Arg Asn Asn Glu His Gly Thr Gly Glu
    1340            1345                1350

Ser Leu Arg Phe Ala Ile Asn Leu Ile Gln Gln Ile Arg Asn Thr
    1355            1360                1365

Gly Asn Asn Glu Arg Asp Asn Asp Phe Ile Leu Ser Pro Val Arg
    1370            1375                1380

Asp Glu Asn Gly Lys His Phe Asp Ser Arg Glu Tyr Trp Asp Lys
    1385            1390                1395

Glu Thr Lys Gly Glu Lys Ile Ser Met Pro Ser Ser Gly Asp Ala
    1400            1405                1410

Asn Gly Ala Phe Asn Ile Ala Arg Lys Gly Ile Ile Met Asn Ala
    1415            1420                1425

His Ile Leu Ala Asn Ser Asp Ser Lys Asp Leu Ser Leu Phe Val
    1430            1435                1440

Ser Asp Glu Glu Trp Asp Leu His Leu Asn Asn Lys Thr Glu Trp
    1445            1450                1455
```

```
Lys Lys Gln Leu Asn Ile Phe  Ser Ser Arg Lys Ala  Met Ala Lys
    1460                1465                1470

Arg Lys  Lys Lys Arg Pro Ala  Ala Thr Lys Lys
    1475                1480

<210> SEQ ID NO 41
<211> LENGTH: 1245
<212> TYPE: PRT
<213> ORGANISM: Porphyromonas macacae

<400> SEQUENCE: 41

Met Lys Thr Gln His Phe Phe Glu Asp Phe Thr Ser Leu Tyr Ser Leu
1                5                  10                  15

Ser Lys Thr Ile Arg Phe Glu Leu Lys Pro Ile Gly Lys Thr Leu Glu
                20                  25                  30

Asn Ile Lys Lys Asn Gly Leu Ile Arg Arg Asp Glu Gln Arg Leu Asp
            35                  40                  45

Asp Tyr Glu Lys Leu Lys Lys Val Ile Asp Glu Tyr His Glu Asp Phe
        50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Ile Ser Glu Ala Arg Ala Lys Ile Glu
                85                  90                  95

Lys Thr Met Arg Asp Thr Leu Ala Lys Ala Phe Ser Glu Asp Glu Arg
            100                 105                 110

Tyr Lys Ser Ile Phe Lys Lys Glu Leu Val Lys Lys Asp Ile Pro Val
        115                 120                 125

Trp Cys Pro Ala Tyr Lys Ser Leu Cys Lys Lys Phe Asp Asn Phe Thr
130                 135                 140

Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
            180                 185                 190

Met Gly Ala Asp Leu Tyr Leu Glu Met Met Glu Asn Leu Arg Asn Val
        195                 200                 205

Trp Pro Ser Phe Val Lys Thr Pro Asp Asp Leu Cys Asn Leu Lys Thr
210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
        275                 280                 285

Ser Phe Ile Ser Asp Thr Leu Glu Asn Asp Asp Gln Val Phe Cys Val
290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
            340                 345                 350
```

```
Lys Asn Ile Phe Asp Arg Trp Asn Tyr Ile Ser Asp Ala Ile Arg Arg
            355                 360                 365

Lys Thr Glu Val Leu Met Pro Arg Lys Lys Glu Ser Val Glu Arg Tyr
    370                 375                 380

Ala Glu Lys Ile Ser Lys Gln Ile Lys Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
            420                 425                 430

Tyr Leu Val Ser Asp Gly Glu Val Ile Leu Tyr Glu Glu Gly Ser Asn
            435                 440                 445

Ile Trp Asp Glu Val Leu Ile Ala Phe Arg Asp Leu Gln Val Ile Leu
            450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
                485                 490                 495

Phe Asp Leu Leu Ser Gly Thr Gly Ala Glu Ile Arg Arg Asp Ser Ser
            500                 505                 510

Phe Tyr Ala Leu Tyr Thr Asp Arg Met Asp Lys Leu Lys Gly Leu Leu
            515                 520                 525

Lys Met Tyr Asp Lys Val Arg Asn Tyr Leu Thr Lys Lys Pro Tyr Ser
            530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
            595                 600                 605

Met Glu Tyr Lys Gln Ile Ala Glu Pro Met Leu Met Leu Pro Lys Val
            610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
            660                 665                 670

Thr Val His Glu Trp Lys Leu Phe Asn Phe Ser Phe Ser Pro Thr Glu
            675                 680                 685

Gln Tyr Arg Asn Ile Gly Glu Phe Phe Asp Glu Val Arg Glu Gln Ala
            690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
            755                 760                 765
```

Gly Gly Glu Leu Phe Tyr Arg Lys Ala Ser Leu His Met Gln Asp Thr
770             775                 780

Thr Val His Pro Lys Gly Ile Ser Ile His Lys Lys Asn Leu Asn Lys
785             790                 795                 800

Lys Gly Glu Thr Ser Leu Phe Asn Tyr Asp Leu Val Lys Asp Lys Arg
            805                 810                 815

Phe Thr Glu Asp Lys Phe Phe His Val Pro Ile Ser Ile Asn Tyr
            820                 825                 830

Lys Asn Lys Lys Ile Thr Asn Val Asn Gln Met Val Arg Asp Tyr Ile
            835                 840                 845

Ala Gln Asn Asp Asp Leu Gln His Gly Ile Asp Arg Gly Glu Arg Asn
850                 855                 860

Leu Leu Tyr Ile Ser Arg Ile Asp Thr Arg Gly Asn Leu Leu Glu Gln
865             870                 875                 880

Phe Ser Leu Asn Val Ile Glu Ser Asp Lys Gly Asp Leu Arg Thr Asp
                885                 890                 895

Tyr Gln Lys Ile Leu Gly Asp Arg Glu Gln Glu Arg Leu Arg Arg Arg
            900                 905                 910

Gln Glu Trp Lys Ser Ile Glu Ser Ile Lys Asp Leu Lys Asp Gly Tyr
    915                 920                 925

Met Ser Gln Val Val His Lys Ile Cys Asn Met Val Val Glu His Lys
930                 935                 940

Ala Ile Val Val Leu Glu Asn Leu Asn Leu Ser Phe Met Lys Gly Arg
945                 950                 955                 960

Lys Lys Val Glu Lys Ser Val Tyr Glu Lys Phe Glu Arg Met Leu Val
                965                 970                 975

Asp Lys Leu Asn Tyr Leu Val Val Asp Lys Lys Asn Leu Ser Asn Glu
            980                 985                 990

Pro Gly Gly Leu Tyr Ala Ala Tyr Gln Leu Thr Asn Pro Leu Phe Ser
    995                 1000                1005

Phe Glu Glu Leu His Arg Tyr Pro Gln Ser Gly Ile Leu Phe Phe
    1010                1015                1020

Val Asp Pro Trp Asn Thr Ser Leu Thr Asp Pro Ser Thr Gly Phe
    1025                1030                1035

Val Asn Leu Leu Gly Arg Ile Asn Tyr Thr Asn Val Gly Asp Ala
    1040                1045                1050

Arg Lys Phe Phe Asp Arg Phe Asn Ala Ile Arg Tyr Asp Gly Lys
    1055                1060                1065

Gly Asn Ile Leu Phe Asp Leu Asp Leu Ser Arg Phe Asp Val Arg
    1070                1075                1080

Val Glu Thr Gln Arg Lys Leu Trp Thr Leu Thr Thr Phe Gly Ser
    1085                1090                1095

Arg Ile Ala Lys Ser Lys Lys Ser Gly Lys Trp Met Val Glu Arg
    1100                1105                1110

Ile Glu Asn Leu Ser Leu Cys Phe Leu Glu Leu Phe Glu Gln Phe
    1115                1120                1125

Asn Ile Gly Tyr Arg Val Glu Lys Asp Leu Lys Lys Ala Ile Leu
    1130                1135                1140

Ser Gln Asp Arg Lys Glu Phe Tyr Val Arg Leu Ile Tyr Leu Phe
    1145                1150                1155

Asn Leu Met Met Gln Ile Arg Asn Ser Asp Gly Glu Glu Asp Tyr
    1160                1165                1170

```
Ile Leu Ser Pro Ala Leu Asn Glu Lys Asn Leu Gln Phe Asp Ser
    1175                1180                1185

Arg Leu Ile Glu Ala Lys Asp Leu Pro Val Asp Ala Asp Ala Asn
    1190                1195                1200

Gly Ala Tyr Asn Val Ala Arg Lys Gly Leu Met Val Val Gln Arg
    1205                1210                1215

Ile Lys Arg Gly Asp His Glu Ser Ile His Arg Ile Gly Arg Ala
    1220                1225                1230

Gln Trp Leu Arg Tyr Val Gln Glu Gly Ile Val Glu
    1235                1240                1245

<210> SEQ ID NO 42
<211> LENGTH: 1250
<212> TYPE: PRT
<213> ORGANISM: Smithella sp.

<400> SEQUENCE: 42

Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
            20                  25                  30

Glu Gln Lys Gly Leu Leu Lys Lys Asp Glu Asp Arg Ala Glu Lys Tyr
        35                  40                  45

Lys Lys Val Lys Asn Ile Ile Asp Glu Tyr His Lys Asp Phe Ile Glu
50                  55                  60

Lys Ser Leu Asn Gly Leu Lys Leu Asp Gly Leu Glu Lys Tyr Lys Thr
65                  70                  75                  80

Leu Tyr Leu Lys Gln Glu Lys Asp Asp Lys Asp Lys Lys Ala Phe Asp
                85                  90                  95

Lys Glu Lys Glu Asn Leu Arg Lys Gln Ile Ala Asn Ala Phe Arg Asn
            100                 105                 110

Asn Glu Lys Phe Lys Thr Leu Phe Ala Lys Glu Leu Ile Lys Asn Asp
        115                 120                 125

Leu Met Ser Phe Ala Cys Glu Glu Asp Lys Lys Asn Val Lys Glu Phe
130                 135                 140

Glu Ala Phe Thr Thr Tyr Phe Thr Gly Phe His Gln Asn Arg Ala Asn
145                 150                 155                 160

Met Tyr Val Ala Asp Glu Lys Arg Thr Ala Ile Ala Ser Arg Leu Ile
                165                 170                 175

His Glu Asn Leu Pro Lys Phe Ile Asp Asn Ile Lys Ile Phe Glu Lys
            180                 185                 190

Met Lys Lys Glu Ala Pro Glu Leu Leu Ser Pro Phe Asn Gln Thr Leu
        195                 200                 205

Lys Asp Met Lys Asp Val Ile Lys Gly Thr Thr Leu Glu Glu Ile Phe
    210                 215                 220

Ser Leu Asp Tyr Phe Asn Lys Thr Leu Thr Gln Ser Gly Ile Asp Ile
225                 230                 235                 240

Tyr Asn Ser Val Ile Gly Gly Arg Thr Pro Glu Glu Gly Lys Thr Lys
                245                 250                 255

Ile Lys Gly Leu Asn Glu Tyr Ile Asn Thr Asp Phe Asn Gln Lys Gln
            260                 265                 270

Thr Asp Lys Lys Lys Arg Gln Pro Lys Phe Lys Gln Leu Tyr Lys Gln
        275                 280                 285
```

```
Ile Leu Ser Asp Arg Gln Ser Leu Ser Phe Ile Ala Glu Ala Phe Lys
    290                 295                 300

Asn Asp Thr Glu Ile Leu Glu Ala Ile Glu Lys Phe Tyr Val Asn Glu
305                 310                 315                 320

Leu Leu His Phe Ser Asn Glu Gly Lys Ser Thr Asn Val Leu Asp Ala
                325                 330                 335

Ile Lys Asn Ala Val Ser Asn Leu Glu Ser Phe Asn Leu Thr Lys Met
            340                 345                 350

Tyr Phe Arg Ser Gly Ala Ser Leu Thr Asp Val Ser Arg Lys Val Phe
        355                 360                 365

Gly Glu Trp Ser Ile Ile Asn Arg Ala Leu Asp Asn Tyr Tyr Ala Thr
    370                 375                 380

Thr Tyr Pro Ile Lys Pro Arg Glu Lys Ser Glu Lys Tyr Glu Arg
385                 390                 395                 400

Lys Glu Lys Trp Leu Lys Gln Asp Phe Asn Val Ser Leu Ile Gln Thr
                405                 410                 415

Ala Ile Asp Glu Tyr Asp Asn Glu Thr Val Lys Gly Lys Asn Ser Gly
            420                 425                 430

Lys Val Ile Ala Asp Tyr Phe Ala Lys Phe Cys Asp Asp Lys Glu Thr
        435                 440                 445

Asp Leu Ile Gln Lys Val Asn Glu Gly Tyr Ile Ala Val Lys Asp Leu
    450                 455                 460

Leu Asn Thr Pro Cys Pro Glu Asn Glu Lys Leu Gly Ser Asn Lys Asp
465                 470                 475                 480

Gln Val Lys Gln Ile Lys Ala Phe Met Asp Ser Ile Met Asp Ile Met
                485                 490                 495

His Phe Val Arg Pro Leu Ser Leu Lys Asp Thr Asp Lys Glu Lys Asp
            500                 505                 510

Glu Thr Phe Tyr Ser Leu Phe Thr Pro Leu Tyr Asp His Leu Thr Gln
        515                 520                 525

Thr Ile Ala Leu Tyr Asn Lys Val Arg Asn Tyr Leu Thr Gln Lys Pro
    530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                565                 570                 575

Arg Lys Asp Asn Leu Tyr Tyr Leu Gly Ile Met Asp Lys Arg His Asn
            580                 585                 590

Arg Ile Phe Arg Asn Val Pro Lys Ala Asp Lys Lys Asp Phe Cys Tyr
        595                 600                 605

Glu Lys Met Val Tyr Lys Leu Leu Pro Gly Ala Asn Lys Met Leu Pro
    610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                645                 650                 655

Phe Asn Leu Asn His Cys His Lys Leu Ile Asp Phe Phe Lys Asp Ser
            660                 665                 670

Ile Asn Lys His Glu Asp Trp Lys Asn Phe Asp Phe Arg Phe Ser Ala
        675                 680                 685

Thr Ser Thr Tyr Ala Asp Leu Ser Gly Phe Tyr His Glu Val Glu His
    690                 695                 700
```

```
Gln Gly Tyr Lys Ile Ser Phe Gln Ser Val Ala Asp Ser Phe Ile Asp
705                 710                 715                 720

Asp Leu Val Asn Glu Gly Lys Leu Tyr Leu Phe Gln Ile Tyr Asn Lys
            725                 730                 735

Asp Phe Ser Pro Phe Ser Lys Gly Lys Pro Asn Leu His Thr Leu Tyr
            740                 745                 750

Trp Lys Met Leu Phe Asp Glu Asn Asn Leu Lys Asp Val Val Tyr Lys
            755                 760                 765

Leu Asn Gly Glu Ala Glu Val Phe Tyr Arg Lys Lys Ser Ile Ala Glu
            770                 775                 780

Lys Asn Thr Thr Ile His Lys Ala Asn Glu Ser Ile Ile Asn Lys Asn
785                 790                 795                 800

Pro Asp Asn Pro Lys Ala Thr Ser Thr Phe Asn Tyr Asp Ile Val Lys
            805                 810                 815

Asp Lys Arg Tyr Thr Ile Asp Lys Phe Gln Phe His Ile Pro Ile Thr
            820                 825                 830

Met Asn Phe Lys Ala Glu Gly Ile Phe Asn Met Asn Gln Arg Val Asn
            835                 840                 845

Gln Phe Leu Lys Ala Asn Pro Asp Ile Asn Ile Ile Gly Ile Asp Arg
850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
            885                 890                 895

Val Asp Tyr His Asn Leu Leu Asp Lys Lys Glu Gly Asp Arg Ala Thr
            900                 905                 910

Ala Arg Gln Glu Trp Gly Val Ile Glu Thr Ile Lys Glu Leu Lys Glu
            915                 920                 925

Gly Tyr Leu Ser Gln Val Ile His Lys Leu Thr Asp Leu Met Ile Glu
930                 935                 940

Asn Asn Ala Ile Ile Val Met Glu Asp Leu Asn Phe Gly Phe Lys Arg
945                 950                 955                 960

Gly Arg Gln Lys Val Glu Lys Gln Val Tyr Gln Lys Phe Glu Lys Met
            965                 970                 975

Leu Ile Asp Lys Leu Asn Tyr Leu Val Asp Lys Asn Lys Lys Ala Asn
            980                 985                 990

Glu Leu Gly Gly Leu Leu Asn Ala Phe Gln Leu Ala Asn Lys Phe Glu
            995                 1000                1005

Ser Phe Gln Lys Met Gly Lys Gln Asn Gly Phe Ile Phe Tyr Val
    1010                1015                1020

Pro Ala Trp Asn Thr Ser Lys Thr Asp Pro Ala Thr Gly Phe Ile
    1025                1030                1035

Asp Phe Leu Lys Pro Arg Tyr Glu Asn Leu Asn Gln Ala Lys Asp
    1040                1045                1050

Phe Phe Glu Lys Phe Asp Ser Ile Arg Leu Asn Ser Lys Ala Asp
    1055                1060                1065

Tyr Phe Glu Phe Ala Phe Asp Phe Lys Asn Phe Thr Glu Lys Ala
    1070                1075                1080

Asp Gly Gly Arg Thr Lys Trp Thr Val Cys Thr Thr Asn Glu Asp
    1085                1090                1095

Arg Tyr Gln Trp Asn Arg Ala Leu Asn Asn Asn Arg Gly Ser Gln
    1100                1105                1110
```

```
Glu Lys Tyr Asp Ile Thr Ala Glu Leu Lys Ser Leu Phe Asp Gly
    1115                1120                1125

Lys Val Asp Tyr Lys Ser Gly Lys Asp Leu Lys Gln Gln Ile Ala
    1130                1135                1140

Ser Gln Glu Ser Ala Asp Phe Phe Lys Ala Leu Met Lys Asn Leu
    1145                1150                1155

Ser Ile Thr Leu Ser Leu Arg His Asn Asn Gly Glu Lys Gly Asp
    1160                1165                1170

Asn Glu Gln Asp Tyr Ile Leu Ser Pro Val Ala Asp Ser Lys Gly
    1175                1180                1185

Arg Phe Phe Asp Ser Arg Lys Ala Asp Asp Met Pro Lys Asn
    1190                1195                1200

Ala Asp Ala Asn Gly Ala Tyr His Ile Ala Leu Lys Gly Leu Trp
    1205                1210                1215

Cys Leu Glu Gln Ile Ser Lys Thr Asp Asp Leu Lys Lys Val Lys
    1220                1225                1230

Leu Ala Ile Ser Asn Lys Glu Trp Leu Glu Phe Val Gln Thr Leu
    1235                1240                1245

Lys Gly
    1250

<210> SEQ ID NO 43
<211> LENGTH: 166
<212> TYPE: PRT
<213> ORGANISM: Escherichia coli

<400> SEQUENCE: 43

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
                20                  25                  30

Leu Val His Asn Asn Arg Val Ile Gly Glu Gly Trp Asn Arg Pro Ile
                35                  40                  45

Gly Arg His Asp Pro Thr Ala His Ala Glu Ile Met Ala Leu Arg Gln
50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
                100                 105                 110

Ala Gly Ser Leu Met Asp Val Leu His His Pro Gly Met Asn His Arg
            115                 120                 125

Val Glu Ile Thr Glu Gly Ile Leu Ala Asp Glu Cys Ala Ala Leu Leu
        130                 135                 140

Ser Asp Phe Phe Arg Met Arg Arg Gln Glu Ile Lys Ala Gln Lys Lys
145                 150                 155                 160

Ala Gln Ser Ser Thr Asp
                165

<210> SEQ ID NO 44
<211> LENGTH: 166
<212> TYPE: PRT
<213> ORGANISM: Artificial
<220> FEATURE:
<223> OTHER INFORMATION: adenosine deaminase
```

<400> SEQUENCE: 44

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 45
<211> LENGTH: 166
<212> TYPE: PRT
<213> ORGANISM: Artificial
<220> FEATURE:
<223> OTHER INFORMATION: adenosine deaminase

<400> SEQUENCE: 45

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val Leu Asn Asn Arg Val Ile Gly Glu Gly Trp Asn Arg Ser Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165

-continued

```
<210> SEQ ID NO 46
<211> LENGTH: 166
<212> TYPE: PRT
<213> ORGANISM: Artificial
<220> FEATURE:
<223> OTHER INFORMATION: adenosine deaminase

<400> SEQUENCE: 46

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
            165

<210> SEQ ID NO 47
<211> LENGTH: 166
<212> TYPE: PRT
<213> ORGANISM: Artificial
<220> FEATURE:
<223> OTHER INFORMATION: adenosine deaminase

<400> SEQUENCE: 47

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140
```

```
Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 48
<211> LENGTH: 167
<212> TYPE: PRT
<213> ORGANISM: Artificial
<220> FEATURE:
<223> OTHER INFORMATION: adenine deaminase

<400> SEQUENCE: 48

Met Ser Glu Val Glu Phe Ser His Glu Tyr Trp Met Arg His Ala Leu
1               5                   10                  15

Thr Leu Ala Lys Arg Ala Arg Asp Glu Arg Glu Val Pro Val Gly Ala
            20                  25                  30

Val Leu Val Leu Asn Asn Arg Val Ile Gly Glu Gly Trp Asn Arg Ala
        35                  40                  45

Ile Gly Leu His Asp Pro Thr Ala His Ala Glu Ile Met Ala Leu Arg
50                  55                  60

Gln Gly Gly Leu Val Met Gln Asn Tyr Arg Leu Tyr Asp Ala Thr Leu
65                  70                  75                  80

Tyr Ser Thr Phe Glu Pro Cys Val Met Cys Ala Gly Ala Met Ile His
                85                  90                  95

Ser Arg Ile Gly Arg Val Val Phe Gly Val Arg Asn Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
130                 135                 140

Leu Cys Arg Phe Phe Arg Met Pro Arg Arg Val Phe Asn Ala Gln Lys
145                 150                 155                 160

Lys Ala Gln Ser Ser Thr Asp
                165

<210> SEQ ID NO 49
<211> LENGTH: 167
<212> TYPE: PRT
<213> ORGANISM: Artificial
<220> FEATURE:
<223> OTHER INFORMATION: adenine deaminase

<400> SEQUENCE: 49

Met Ser Glu Val Glu Phe Ser His Glu Tyr Trp Met Arg His Ala Leu
1               5                   10                  15

Thr Leu Ala Lys Arg Ala Arg Asp Glu Arg Glu Val Pro Val Gly Ala
            20                  25                  30

Val Leu Val Leu Asn Asn Arg Val Ile Gly Glu Gly Trp Asn Arg Ala
        35                  40                  45

Ile Gly Leu His Asp Pro Thr Ala His Ala Glu Ile Met Ala Leu Arg
50                  55                  60

Gln Gly Gly Leu Val Met Gln Asn Tyr Arg Leu Ile Asp Ala Thr Leu
65                  70                  75                  80

Tyr Val Thr Phe Glu Pro Cys Val Met Cys Ala Gly Ala Met Ile His
                85                  90                  95
```

```
Ser Arg Ile Gly Arg Val Val Phe Gly Val Arg Asn Ser Lys Arg Gly
            100                 105                 110

Ala Ala Gly Ser Leu Met Asn Val Leu Asn Tyr Pro Gly Met Asn His
        115                 120                 125

Arg Val Glu Ile Thr Glu Gly Ile Leu Ala Asp Glu Cys Ala Ala Leu
    130                 135                 140

Leu Cys Asp Phe Tyr Arg Met Pro Arg Gln Val Phe Asn Ala Gln Lys
145                 150                 155                 160

Lys Ala Gln Ser Ser Ile Asn
                165

<210> SEQ ID NO 50
<211> LENGTH: 228
<212> TYPE: PRT
<213> ORGANISM: Rattus norvegicus

<400> SEQUENCE: 50

Ser Ser Glu Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45

Ile Trp Arg His Thr Ser Gln Asn Thr Asn Lys His Val Glu Val Asn
    50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
            100                 105                 110

Ile Tyr Ile Ala Arg Leu Tyr His His Ala Asp Pro Arg Asn Arg Gln
        115                 120                 125

Gly Leu Arg Asp Leu Ile Ser Ser Gly Val Thr Ile Gln Ile Met Thr
    130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Pro Gln Leu Thr Phe Phe Thr Ile Ala
        195                 200                 205

Leu Gln Ser Cys His Tyr Gln Arg Leu Pro Pro His Ile Leu Trp Ala
    210                 215                 220

Thr Gly Leu Lys
225

<210> SEQ ID NO 51
<211> LENGTH: 199
<212> TYPE: PRT
<213> ORGANISM: Homo sapiens

<400> SEQUENCE: 51

Met Glu Ala Ser Pro Ala Ser Gly Pro Arg His Leu Met Asp Pro His
1               5                   10                  15
```

```
Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
            115                 120                 125

Ile Tyr Asp Tyr Asp Pro Leu Tyr Lys Glu Ala Leu Gln Met Leu Arg
        130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
                180                 185                 190

Ile Leu Gln Asn Gln Gly Asn
            195
```

```
<210> SEQ ID NO 52
<211> LENGTH: 621
<212> TYPE: DNA
<213> ORGANISM: Petromyzon marinus

<400> SEQUENCE: 52
acagatgcag agtatgtgag aattcacgaa aagctggaca tctataccct caagaagcag      60
ttctttaaca ataagaagtc tgtgagccat aggtgctacg tgctgttcga gctgaagaga     120
aggggtgaaa gaagggcatg ttttggggg tatgctgtga caagcccca gtctggaact      180 gagagaggca ttcacgccga aattttcagc atcagaaagg tggaggaata cctgagggat     240
aaccctggac agtttacaat taattggtat tctagctggt ctccatgcgc tgactgtgcc     300
gagaagatcc tggaatggta caaccaggag ctgagaggaa atggccatac cctgaagatt     360
tgggcctgca agctgtacta tgaaaagaac gcaagaaatc agatcggact gtggaacctg     420
agggataatg tgtggggct gaacgtgatg gtgtccgagc actatcagtg ctgtagaaag     480
attttcattc agtcctcaca taatcagctg aacgagaata atggctgga aaagactctg      540 aagagggctg agaagagaag gtccgaactg tcaattatga tccaggtgaa gatcctgcac     600
accactaagt cacctgccgt g                                              621
```

```
<210> SEQ ID NO 53
<211> LENGTH: 160
<212> TYPE: PRT
<213> ORGANISM: Artificial
<220> FEATURE:
<223> OTHER INFORMATION: cytosine deaminase

<400> SEQUENCE: 53

Phe Glu Arg Asn Tyr Asp Pro Arg Glu Leu Arg Lys Glu Thr Tyr Leu
1               5                   10                  15
```

```
Leu Tyr Glu Ile Lys Trp Gly Lys Ser Gly Lys Leu Trp Arg His Trp
             20                  25                  30

Cys Gln Asn Asn Arg Thr Gln His Ala Glu Val Tyr Phe Leu Glu Asn
         35                  40                  45

Ile Phe Asn Ala Arg Arg Phe Asn Pro Ser Thr His Cys Ser Ile Thr
 50                  55                  60

Trp Tyr Leu Ser Trp Ser Pro Cys Ala Glu Cys Ser Gln Lys Ile Val
 65                  70                  75                  80

Asp Phe Leu Lys Glu His Pro Asn Val Leu Glu Ile Tyr Val Ala Arg
                 85                  90                  95

Leu Tyr Tyr His Glu Asp Glu Arg Asn Arg Gln Gly Leu Arg Asp Leu
            100                 105                 110

Val Asn Ser Gly Val Thr Ile Arg Ile Met Asp Leu Pro Asp Tyr Asn
            115                 120                 125

Tyr Cys Trp Lys Thr Phe Val Ser Asp Gln Gly Gly Asp Glu Asp Tyr
130                 135                 140

Trp Pro Gly His Phe Ala Pro Trp Ile Lys Gln Tyr Ser Leu Lys Leu
145                 150                 155                 160

<210> SEQ ID NO 54
<211> LENGTH: 207
<212> TYPE: PRT
<213> ORGANISM: Artificial
<220> FEATURE:
<223> OTHER INFORMATION: cytosine deaminase

<400> SEQUENCE: 54

Thr Asp Ala Glu Tyr Val Arg Ile His Glu Lys Leu Asp Ile Tyr Thr
 1               5                  10                  15

Phe Lys Lys Gln Phe Ser Asn Asn Lys Lys Ser Val Ser His Arg Cys
             20                  25                  30

Tyr Val Leu Phe Glu Leu Lys Arg Arg Gly Glu Arg Arg Ala Cys Phe
         35                  40                  45

Trp Gly Tyr Ala Val Asn Lys Pro Gln Ser Gly Thr Glu Arg Gly Ile
 50                  55                  60

His Ala Glu Ile Phe Ser Ile Arg Lys Val Glu Glu Tyr Leu Arg Asp
65                  70                  75                  80

Asn Pro Gly Gln Phe Thr Ile Asn Trp Tyr Ser Ser Trp Ser Pro Cys
                 85                  90                  95

Ala Asp Cys Ala Glu Lys Ile Leu Glu Trp Tyr Asn Gln Glu Leu Arg
            100                 105                 110

Gly Asn Gly His Thr Leu Lys Ile Trp Val Cys Lys Leu Tyr Tyr Glu
            115                 120                 125

Lys Asn Ala Arg Asn Gln Ile Gly Leu Trp Asn Leu Arg Asp Asn Gly
130                 135                 140

Val Gly Leu Asn Val Met Val Ser Glu His Tyr Gln Cys Cys Arg Lys
145                 150                 155                 160

Ile Phe Ile Gln Ser Ser His Asn Gln Leu Asn Glu Asn Arg Trp Leu
                165                 170                 175

Glu Lys Thr Leu Lys Arg Ala Glu Lys Arg Arg Ser Glu Leu Ser Ile
            180                 185                 190

Met Phe Gln Val Lys Ile Leu His Thr Thr Lys Ser Pro Ala Val
            195                 200                 205

<210> SEQ ID NO 55
```

<211> LENGTH: 228
<212> TYPE: PRT
<213> ORGANISM: Artificial
<220> FEATURE:
<223> OTHER INFORMATION: cytosine deaminase

<400> SEQUENCE: 55

```
Ser Ser Lys Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45

Ile Trp Arg His Thr Ser Gln Asn Thr Asn Lys His Val Glu Val Asn
    50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro Asn Val Thr Leu Phe
            100                 105                 110

Ile Tyr Ile Ala Arg Leu Tyr His Leu Ala Asn Pro Arg Asn Arg Gln
        115                 120                 125

Gly Leu Arg Asp Leu Ile Ser Ser Gly Val Thr Ile Gln Ile Met Thr
    130                 135                 140

Glu Gln Glu Ser Gly Tyr Cys Trp His Asn Phe Val Asn Tyr Ser Pro
145                 150                 155                 160

Ser Asn Glu Ser His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Ser Gln Leu Thr Ser Phe Thr Ile Ala
        195                 200                 205

Leu Gln Ser Cys His Tyr Gln Arg Leu Pro Pro His Ile Leu Trp Ala
    210                 215                 220

Thr Gly Leu Lys
225
```

<210> SEQ ID NO 56
<211> LENGTH: 162
<212> TYPE: PRT
<213> ORGANISM: Artificial
<220> FEATURE:
<223> OTHER INFORMATION: cytosine deaminase

<400> SEQUENCE: 56

```
Ser Phe Glu Arg Asn Tyr Asp Pro Arg Glu Leu Arg Lys Glu Thr Tyr
1               5                   10                  15

Leu Leu Tyr Glu Ile Lys Trp Gly Lys Ser Gly Lys Leu Trp Arg His
            20                  25                  30

Trp Cys Gln Asn Asn Arg Thr Gln His Ala Glu Val Tyr Phe Leu Glu
        35                  40                  45

Asn Ile Phe Asn Ala Arg Arg Phe Asn Pro Ser Thr His Cys Ser Ile
    50                  55                  60

Thr Trp Tyr Leu Ser Trp Ser Pro Cys Ala Glu Cys Ser Gln Lys Ile
65                  70                  75                  80
```

```
Val Asp Phe Leu Lys Glu His Pro Asn Val Asn Leu Glu Ile Tyr Val
                85                  90                  95

Ala Arg Leu Tyr Tyr Pro Glu Asn Glu Arg Asn Arg Gln Gly Leu Arg
            100                 105                 110

Asp Leu Val Asn Ser Gly Val Thr Ile Arg Ile Met Asp Leu Pro Asp
        115                 120                 125

Tyr Asn Tyr Cys Trp Lys Thr Phe Val Ser Asp Gln Gly Gly Asp Glu
    130                 135                 140

Asp Tyr Trp Pro Gly His Phe Ala Pro Trp Ile Lys Gln Tyr Ser Leu
145                 150                 155                 160

Lys Leu

<210> SEQ ID NO 57
<211> LENGTH: 229
<212> TYPE: PRT
<213> ORGANISM: Rattus norvegicus

<400> SEQUENCE: 57

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro Pro His Ile Leu Trp
    210                 215                 220

Ala Thr Gly Leu Lys
225

<210> SEQ ID NO 58
<211> LENGTH: 198
<212> TYPE: PRT
<213> ORGANISM: Homo sapiens
```

<400> SEQUENCE: 58

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195
```

<210> SEQ ID NO 59
<211> LENGTH: 197
<212> TYPE: PRT
<213> ORGANISM: Artificial
<220> FEATURE:
<223> OTHER INFORMATION: cytosine deaminase

<400> SEQUENCE: 59

```
Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Ile Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140
```

```
Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
            165                 170                 175

Arg Arg Ile Leu Leu Pro Leu Tyr Glu Val Asp Asp Leu Arg Asp Ala
            180                 185                 190

Phe Arg Thr Cys Thr
        195

<210> SEQ ID NO 60
<211> LENGTH: 83
<212> TYPE: PRT
<213> ORGANISM: Bacillus phage

<400> SEQUENCE: 60

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Leu Asn Lys Ile
65                  70                  75                  80

Lys Met Leu

<210> SEQ ID NO 61
<211> LENGTH: 1592
<212> TYPE: DNA
<213> ORGANISM: Medicago truncatula

<400> SEQUENCE: 61
actgttaata attttaaac gtcagcgcac taaaaaaacg aaaagacgga cacgtgaaaa      60
taaaaaacac acactagttt atgacgcaat actattttac ttatgatttg ggtacattag    120
acaaaaccgt gaaagagatg tatcagctat gaaacctgta tacttcaata cagagactta    180
ctcatatcgg atacgtacgc acgaagtatc atattaatta tttttaatttt taataaaatat  240 tttatcggat acttatgtga tactctacat atacacaagg atatttctaa gatactttat    300
agatacgtat cctagaaaaa catgaagagt aaaaaagtga acaatgttg taaaaattca     360 ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttctttaa tgatgtttct ctcaatatca catcatatga     540
aaatgtaata tgatttataa gaaaattttt aaaaaattta ttttaataat cacatgtact    600
attttttaaa aattgtatct tttataataa tacaataata aagagtaatc agtgttaatt    660
tttcttcaaa tataagttttt attataaatc attgttaacg tatcataagt cattaccgta   720
tcgtatctta attttttttt aaaaaccgct aattcacgta cccgtattgt attgtacccg    780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgtttaa ttggaagagg tgccgttggc gtaatataac     960
agccaatcga ttttttgctat aaaagcaaat caggtaaact aaacttcttc attcttttct   1020
```

| | | |
|---|---|---|
| tccccatcgc tacaaaaccg gttcctttgg aaaagagatt cattcaaacc tagcacccaa | 1080 | |
| ttccgtttca aggtataatc tactttctat tcttcgatta ttttattatt attagctact | 1140 | |
| atcgtttaat cgatctttc ttttgatccg tcaaatttaa attcaattag gttttgttc | 1200 | |
| ttttctttca tctgattgaa atccttctga attgaaccgt ttacttgatt ttactgttta | 1260 | |
| ttgtatgatt taatcctttg tttttcaaag acagtcttta gattgtgatt aggggttcat | 1320 | |
| ataaatttt agatttggat ttttgtattg tatgattcaa aaaatacgtc ctttaattag | 1380 | |
| attagtacat ggatattttt tacccgattt attgattgtc agggagaatt tgatgagcaa | 1440 | |
| gttttttga tgtctgttgt aaattgaatt gattataatt gctgatctgc tgcttccagt | 1500 | |
| tttcataacc catattcttt taaccttgtt gtacacacaa tgaaaaattg gtgattgatt | 1560 | |
| catttgtttt tctttgtttt ggattataca gg | 1592 | |

<210> SEQ ID NO 62
<211> LENGTH: 2000
<212> TYPE: DNA
<213> ORGANISM: Zea mays

<400> SEQUENCE: 62

| | | |
|---|---|---|
| gtcgtgcccc tctctagaga taaagagcat tgcatgtcta aagtataaaa aattaccaca | 60 | |
| tattttttg tcacacttat ttgaagtgta gtttatctat ctctatacat atatttaaac | 120 | |
| ttcactctac aaataatata gtctataata ctaaaataat attagtgttt tagaggatca | 180 | |
| tataaataaa ctgctagaca tggtctaaag gataattgaa tattttgaca atctacagtt | 240 | |
| ttatcttttt agtgtgcatg tgatctctct gttttttttg caaatagctt gacctatata | 300 | |
| atacttcatc cattttatta gtacatccat ttaggattta gggttgatgg tttctataga | 360 | |
| ctaatttta gtacatccat tttattcttt ttagtctcta aatttttta aactaaaact | 420 | |
| ctatttagt tttttattta ataatttaga tataaaatga aataaaataa attgactaca | 480 | |
| aataaaacaa atacccttta agaaataaaa aaactaagca aacatttttc ttgtttcgag | 540 | |
| tagataatga caggctgttc aacgccgtcg acgagtctaa cggacaccaa ccagcgaacc | 600 | |
| agcagcgtcg cgtcgggcca agcgaagcag acggcacggc atctctgtag ctgcctctgg | 660 | |
| accctctcg agagttccgc tccaccgttg gacttgctcc gctgtcggca tccagaaatt | 720 | |
| gcgtggcgga gcggcagacg tgaggcggca cggcaggcgg cctcttcctc ctctcacggc | 780 | |
| accggcagct acgggggatt ccttccccac cgctccttcg ctttcccttc ctcgcccgcc | 840 | |
| gtaataaata gacacccct ccacaccctc ttttcccaac ctcgtgttcg ttcggagcgc | 900 | |
| acacacacgc aaccagatct ccccccaaatc cagccgtcgg cacctccgct tcaaggtacg | 960 | |
| ccgctcatcc tccccccccc cctctctcta ccttctctag atcggcgatc cggtccatgg | 1020 | |
| ttagggcccg gtagttctac ttctgttcat gtttgtgtta gagcaaacat gttcatgttc | 1080 | |
| atgtttgtga tgatgtggtc tggttgggcg gtcgttctag atcggagtag gatactgttt | 1140 | |
| caagctacct ggtggattta ttaattttgt atctgtatgt gtgtgccata catcttcata | 1200 | |
| gttacgagtt taagatgatg gatggaaata tcgatctagg ataggtatac atgttgatgc | 1260 | |
| gggttttact gatgcatata cagagatgct tttttctcg cttggttgtg atgatatggt | 1320 | |
| ctggttgggc ggtcgttcta gatcggagta gaatactgtt tcaaactacc tggtggattt | 1380 | |
| attaaaggat aaagggtcgt tctagatcgg agtagaatac tgtttcaaac tacctggtgg | 1440 | |
| atttattaaa ggatctgtat gtatgtgcct acatcttcat agttacgagt ttaagatgat | 1500 | |
| ggatggaaat atcgatctag gataggtata catgttgatg cgggttttac tgatgcatat | 1560 | |

```
acagagatgc ttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggatttttt    1920
agccctgcct tcatacgcta tttatttgct tggtactgtt tcttttgtcc gatgctcacc    1980
ctgttgtttg gtgatacttc                                                2000
```

<210> SEQ ID NO 63
<211> LENGTH: 1594
<212> TYPE: DNA
<213> ORGANISM: Medicago truncatula

<400> SEQUENCE: 63

```
actgttaata atttttaaac gtcagcgcac taaaaaaacg aaaagacgga cacgtgaaaa     60
taaaaaacac acactagttt atgacgcaat actattttac ttatgatttg ggtacattag    120
acaaaaccgt gaaagagatg tatcagctat gaaacctgta tacttcaata cagagactta    180
ctcatatcgg atacgtacgc acgaagtatc atattaatta ttttaatttt taataaaatat   240 tttatcggat acttatgtga tactctacat atacacaagg atatttctaa gatactttat    300
agatacgtat cctagaaaaa catgaagagt aaaaaagtga acaatgttg taaaaattca     360 ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttctttta tgatgtttct ctcaatatca catcatatga     540
aaatgtaata tgatttataa gaaaatttt aaaaaattta ttttaataat cacatgtact     600 atttttttaaa aattgtatct tttataataa tacaataata aagagtaatc agtgttaatt   660
tttcttcaaa tataagtttt attataaatc attgttaacg tatcataagt cattaccgta    720
tcgtatctta atttttttt aaaaaccgct aattcacgta cccgtattgt attgtacccg     780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagg tgccgttggc gtaatataac    960
agccaatcga tttttgctat aaaagcaaat caggtaaact aaacttcttc attcttttct   1020
tccccatcgc tacaaaaccg gttcctttgg aaaagagatt cattcaaacc tagcacccaa   1080
ttccgtttca aggtataatc tactttctat tcttcgatta ttttattatt attagctact   1140
atcgtttaat cgatctttc ttttgatccg tcaaatttaa attcaattag ggtttgttc     1200 ttttctttca tctgattgaa atccttctga attgaaccgt ttacttgatt ttactgttta   1260
ttgtatgatt taatcctttg ttttcaaag acagtcttta gattgtgatt agggtttcat    1320 ataaatttt agattggat ttttgtattg tatgattcaa aaaatacgtc ctttaattag     1380
attagtacat ggatatttt tacccgattt attgattgtc agggagaatt tgatgagcaa    1440
gtttttttga tgtctgttgt aaattgaatt gattataatt gctgatctgc tgcttccagt   1500
tttcataacc catattcttt taaccttgtt gtacacacaa tgaaaaattg gtgattgatt   1560
catttgtttt tctttgtttt ggattataca gggt                               1594
```

<210> SEQ ID NO 64
<211> LENGTH: 19
<212> TYPE: DNA
<213> ORGANISM: Artificial
<220> FEATURE:
<223> OTHER INFORMATION: RNA spacer
<220> FEATURE:
<221> NAME/KEY: misc_feature
<222> LOCATION: (1)..(19)
<223> OTHER INFORMATION: wherein n is A, C, T or G

<400> SEQUENCE: 64
nnnnnnnnnn nnnnnnnnn                                                    19

<210> SEQ ID NO 65
<211> LENGTH: 22
<212> TYPE: DNA
<213> ORGANISM: Artificial
<220> FEATURE:
<223> OTHER INFORMATION: DNA target strand
<220> FEATURE:
<221> NAME/KEY: misc_feature
<222> LOCATION: (4)..(22)
<223> OTHER INFORMATION: wherein n is A, C, T or G

<400> SEQUENCE: 65
aaannnnnnn nnnnnnnnnn nn                                                22

<210> SEQ ID NO 66
<211> LENGTH: 22
<212> TYPE: DNA
<213> ORGANISM: Artificial
<220> FEATURE:
<223> OTHER INFORMATION: DNA non-target strand
<220> FEATURE:
<221> NAME/KEY: misc_feature
<222> LOCATION: (4)..(22)
<223> OTHER INFORMATION: wherein n is A, C, T or G

<400> SEQUENCE: 66
tttnnnnnnn nnnnnnnnnn nn                                                22

<210> SEQ ID NO 67
<211> LENGTH: 1367
<212> TYPE: PRT
<213> ORGANISM: Artificial
<220> FEATURE:
<223> OTHER INFORMATION: Cas9 polypeptide

<400> SEQUENCE: 67

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

```
Glu Arg His Pro Ile Phe Gly Asn Ile Val Asp Val Ala Tyr His
            115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525
```

```
Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
                580                 585                 590

Tyr His Asp Leu Leu Lys Ile Ile Lys Asp Lys Asp Phe Leu Asp Asn
                595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
                660                 665                 670

Gln Ser Gly Lys Thr Ile Leu Asp Phe Leu Lys Ser Asp Gly Phe Ala
    675                 680                 685

Asn Arg Asn Phe Met Gln Leu Ile His Asp Asp Ser Leu Thr Phe Lys
690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
                740                 745                 750

His Lys Pro Glu Asn Ile Val Ile Glu Met Ala Arg Glu Asn Gln Thr
                755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Leu Lys Asp
    835                 840                 845

Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Gln Ile Thr Lys
                915                 920                 925

His Val Ala Gln Ile Leu Asp Ser Arg Met Asn Thr Lys Tyr Asp Glu
    930                 935                 940
```

```
Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
        980                 985                 990

Gly Thr Ala Leu Ile Lys Lys Tyr Pro Lys Leu Glu Ser Glu Phe Val
        995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335
```

```
Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 68
<211> LENGTH: 1367
<212> TYPE: PRT
<213> ORGANISM: Artificial
<220> FEATURE:
<223> OTHER INFORMATION: Cas9 polypeptide

<400> SEQUENCE: 68

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335
```

```
Leu Val Arg Gln Gln Leu Pro Glu Lys Tyr Lys Glu Ile Phe Phe Asp
                340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
        450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
        530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
            690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750
```

```
His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
        770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Ala Asp
            835                 840                 845

Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Ala Leu Glu Ser Glu Phe Val
            995                1000                1005

Tyr Gly Asp Tyr Lys Val Tyr Asp Val Arg Lys Met Ile Ala Lys
   1010                1015                1020

Ser Glu Gln Glu Ile Gly Lys Ala Thr Ala Lys Tyr Phe Phe Tyr
   1025                1030                1035

Ser Asn Ile Met Asn Phe Phe Lys Thr Glu Ile Thr Leu Ala Asn
   1040                1045                1050

Gly Glu Ile Arg Lys Ala Pro Leu Ile Glu Thr Asn Gly Glu Thr
   1055                1060                1065

Gly Glu Ile Val Trp Asp Lys Gly Arg Asp Phe Ala Thr Val Arg
   1070                1075                1080

Lys Val Leu Ser Met Pro Gln Val Asn Ile Val Lys Lys Thr Glu
   1085                1090                1095

Val Gln Thr Gly Gly Phe Ser Lys Glu Ser Ile Leu Pro Lys Arg
   1100                1105                1110

Asn Ser Asp Lys Leu Ile Ala Arg Lys Lys Asp Trp Asp Pro Lys
   1115                1120                1125

Lys Tyr Gly Gly Phe Asp Ser Pro Thr Val Ala Tyr Ser Val Leu
   1130                1135                1140

Val Val Ala Lys Val Glu Lys Gly Lys Ser Lys Lys Leu Lys Ser
   1145                1150                1155
```

| Val | Lys | Glu | Leu | Leu | Gly | Ile | Thr | Ile | Met | Glu | Arg | Ser | Ser | Phe |
| | 1160 | | | | 1165 | | | | 1170 | | | | | |

| Glu | Lys | Asn | Pro | Ile | Asp | Phe | Leu | Glu | Ala | Lys | Gly | Tyr | Lys | Glu |
| 1175 | | | | 1180 | | | | | 1185 | | | | | |

| Val | Lys | Lys | Asp | Leu | Ile | Ile | Lys | Leu | Pro | Lys | Tyr | Ser | Leu | Phe |
| 1190 | | | | | 1195 | | | | 1200 | | | | | |

| Glu | Leu | Glu | Asn | Gly | Arg | Lys | Arg | Met | Leu | Ala | Ser | Ala | Gly | Glu |
| 1205 | | | | | 1210 | | | | 1215 | | | | | |

| Leu | Gln | Lys | Gly | Asn | Glu | Leu | Ala | Leu | Pro | Ser | Lys | Tyr | Val | Asn |
| 1220 | | | | | 1225 | | | | | 1230 | | | | |

| Phe | Leu | Tyr | Leu | Ala | Ser | His | Tyr | Glu | Lys | Leu | Lys | Gly | Ser | Pro |
| 1235 | | | | | 1240 | | | | | 1245 | | | | |

| Glu | Asp | Asn | Glu | Gln | Lys | Gln | Leu | Phe | Val | Glu | Gln | His | Lys | His |
| 1250 | | | | | 1255 | | | | | 1260 | | | | |

| Tyr | Leu | Asp | Glu | Ile | Ile | Glu | Gln | Ile | Ser | Glu | Phe | Ser | Lys | Arg |
| 1265 | | | | | 1270 | | | | | 1275 | | | | |

| Val | Ile | Leu | Ala | Asp | Ala | Asn | Leu | Asp | Lys | Val | Leu | Ser | Ala | Tyr |
| 1280 | | | | | 1285 | | | | | 1290 | | | | |

| Asn | Lys | His | Arg | Asp | Lys | Pro | Ile | Arg | Glu | Gln | Ala | Glu | Asn | Ile |
| 1295 | | | | | 1300 | | | | | 1305 | | | | |

| Ile | His | Leu | Phe | Thr | Leu | Thr | Asn | Leu | Gly | Ala | Pro | Ala | Ala | Phe |
| 1310 | | | | | 1315 | | | | | 1320 | | | | |

| Lys | Tyr | Phe | Asp | Thr | Thr | Ile | Asp | Arg | Lys | Arg | Tyr | Thr | Ser | Thr |
| 1325 | | | | | 1330 | | | | | 1335 | | | | |

| Lys | Glu | Val | Leu | Asp | Ala | Thr | Leu | Ile | His | Gln | Ser | Ile | Thr | Gly |
| 1340 | | | | | 1345 | | | | | 1350 | | | | |

| Leu | Tyr | Glu | Thr | Arg | Ile | Asp | Leu | Ser | Gln | Leu | Gly | Gly | Asp | |
| 1355 | | | | | 1360 | | | | | 1365 | | | | |

<210> SEQ ID NO 69
<211> LENGTH: 5355
<212> TYPE: DNA
<213> ORGANISM: Artificial
<220> FEATURE:
<223> OTHER INFORMATION: adenosine base editor construct

<400> SEQUENCE: 69

| | |
|---|---|
| atggcgggaa gcaaaaaacg gcggattaag caagattctg aggtcgagtt tagccacgag | 60 |
| tattggatgc gccatgcctt gacgcttgcg aaacgtgctt gggatgaacg cgaagtccca | 120 |
| gtcggagccg tgctcgtgca caataaccga gtcattggtg agggatgaa tcgtccaatc | 180 |
| gggcggcatg acccgacggc tcatgctgag atcatggctc tcagacaggg tggcttggtg | 240 |
| atgcagaact atagactcat tgatgccaca ctctacgtca ctctcgaacc gtgcgtaatg | 300 |
| tgcgcgggtg caatgattca ttccagaatt ggccgtgtcg tcttcggtgc gcgggacgcg | 360 |
| aagaccggag cggctggcag cctcatggac gtgcttcacc atcctggtat gaaccaccgg | 420 |
| gtagagatca ccgagggat tctcgcagac gagtgcgctg cccttctctc cgatttcttc | 480 |
| cgcatgaggc gacaggagat taaggccag aagaaagccc aatcatcgac tgattcgggt | 540 |
| ggcagctcgg gtggttctag tggttcagaa acaccgggca aagcgaatc cgcaacccct | 600 |
| gaatctagcg gtgggagttc tggagggtcg tcagaggttg agtttagcca cgaatattgg | 660 |
| atgcgccatg ccctgacttt ggctaagcgc gctcggacg agcgcgaagt accggtggga | 720 |
| gcggtgttag tgcttaacaa tcgggtcatt ggtgaaggct ggaatcgcgc aattggcctg | 780 |

| | |
|---|---|
| catgatccga cggcgcacgc tgagataatg gctctccgtc aaggaggtct agtgatgcag | 840 |
| aactacaggc ttatcgacgc gacactatat gtcacattcg agccctgcgt gatgtgtgcc | 900 |
| ggggcgatga tccactccag aatcgggcga gtcgtcttcg gcgtcaggaa cgccaagacc | 960 |
| ggcgcggctg gtcgctgat ggacgtgctc cattaccctg gatgaaccca tcgcgttgag | 1020 |
| atcactgagg gcatactcgc cgatgagtgt gcggccctac tttgctattt cttccgaatg | 1080 |
| ccacgtcaag tattcaacgc tcagaagaag gctcagtcat ccactgacag cggtgggagc | 1140 |
| agcggcggtt catcgggcag cgagactcct ggaacgtcgg aatcggctac gcccgagagc | 1200 |
| agtggcggta gttcgggcgg cagtgacaag aagtacagca tcgggctggc catcgggacc | 1260 |
| aactccgtcg gctgggctgt gattaccgac gagtacaagg tgccatccaa gaagttcaag | 1320 |
| gtcctcggca acactgaccg gcacagcatt aagaagaacc tgattggggc gctgctgttc | 1380 |
| gattcggggg agactgcgga ggcgaccagg ctgaagcgga ctgcgcgccg gaggtacacc | 1440 |
| aggaggaaga atcggatctg ctacctccag gagattttct cgaatgagat ggccaaggtg | 1500 |
| gacgattcct tcttccatcg cctggaggag tcgttcctcg ttgaggagga caagaagcat | 1560 |
| gagaggcatc ccattttcgg gaatatcgtt gacgaggtgg cttaccatga gaagtacccg | 1620 |
| accatctacc atctgcggaa gaagctcgtc gattcgaccg ataaggccga cctgcggctg | 1680 |
| atctacctgg ccctcgcgca catgattaag ttccggggcc atttcctcat cgagggcgac | 1740 |
| ctcaacccgc acaactcgga cgtggataag ctcttcattc agctcgtgca gacatacaac | 1800 |
| cagctcttcg aggagaatcc cattaacgcc tcggggtcg acgctaaggc tattctctcg | 1860 |
| gctcggctgt cgaagtcgcg ccggctggag aatctcattg cccagctccc aggcgagaag | 1920 |
| aagaacggcc tcttcggcaa cctgattgcc ctgtcgctgg ggctcacacc gaatttcaag | 1980 |
| tcgaacttcg acctcgccga ggacgctaag ctccagctca gcaaggatac ttacgatgat | 2040 |
| gacctcgata acctgctcgc ccagattggg gatcagtacg cggatctgtt cctcgcggcc | 2100 |
| aagaatctca gcgatgctat tctcctgtcg gacattctcc gcgtcaacac agagattact | 2160 |
| aaggccccac tgtcggcgag catgattaag aggtacgatg agcatcatca ggacctgaca | 2220 |
| ctgctcaagg cgctggtccg gcagcagctc cccgagaagt acaaggagat tttcttcgat | 2280 |
| cagtcaaaga atgggtacgc gggctacatt gatggcggcg cgtcccagga ggagttctac | 2340 |
| aagttcatta agcccatcct ggagaagatg gacgggaccg aggagctgct ggtgaagctc | 2400 |
| aatcgggagg acctgctccg gaagcagcgc acattcgaca atggctcgat tcctcaccag | 2460 |
| attcacctgg gcgagctgca cgccattctc cgcaggcagg aggacttcta cccgttcctc | 2520 |
| aaggacaacc gcgagaagat cgagaagatc ctgaccttcc ggattccata ctacgtgggg | 2580 |
| ccgctcgcgc gggggaactc ccggttcgcg tggatgactc gcaagtccga agaaacgatt | 2640 |
| acaccgtgga atttcgagga ggtcgtcgac aagggcgcta gtgcgcagtc attcattgag | 2700 |
| aggatgacca atttcgataa gaacctgcct aacgagaagg tgctgccgaa gcattcgctg | 2760 |
| ctctacgagt acttcaccgt ttacaatgag ctgaccaagg tgaagtatgt gactgagggc | 2820 |
| atgaggaagc cagcgttcct gagcggcgag cagaagaagg ctatcgtgga cctgctcttc | 2880 |
| aagactaacc ggaaggtgac tgtgaagcag ctcaaggagg actacttcaa gaagattgag | 2940 |
| tgcttcgatt ccgttgagat tagcggggtg gaggatcggt tcaatgcttc gctcgggaca | 3000 |
| taccacgatc tcctgaagat cattaaggat aaggacttcc tcgacaacga ggagaacgag | 3060 |
| gacattctcg aagatattgt cctgaccctc accctcttcg aggatcggga gatgatcgag | 3120 |
| gagaggctca agacatacgc tcatctgttc gatgataagg tcatgaagca gctgaagcgc | 3180 |

```
aggcggtaca cagggtgggg gcggctgagc cggaagctga tcaacgggat tcgggataag    3240
cagtccggga agacaattct cgacttcctc aagtccgacg ggttcgctaa ccggaacttc    3300
atgcagctca ttcatgatga ctcgctgaca ttcaaggagg atattcagaa ggcgcaggtt    3360
tcggggcagg gcgactcgct ccacgagcat attgcgaatc tggcgggctc ccccgcgatt    3420
aagaagggca ttctgcaaac cgtcaaggtg gttgatgagc tggtcaaggt catgggcgg    3480
cataagccag agaatattgt catcgagatg gcgcgggaga atcagaccac acagaagggg    3540
cagaagaact cacgggagcg gatgaagcgc atcgaggagg catcaagga gctggggtcg    3600
cagatcctga aggagcatcc cgtggagaac actcagctgc aaaatgagaa gctgtacctc    3660
tactacctcc agaacgggag ggacatgtat gtggatcagg agctggatat taataggctg    3720
agcgattacg atgtcgacca cattgtccca cagtcgttcc tgaaggacga cagcattgac    3780
aacaaggtgc tgacccgctc ggataagaac aggggcaaga gcgataatgt tccaagcgag    3840
gaggttgtga agaagatgaa gaactactgg cggcagctcc tgaacgcgaa gctcatcaca    3900
cagcggaagt tcgacaacct caccaaggct gagcgcgggg gcctgagcga gctggacaag    3960
gcggggttca ttaagaggca gctggtcgag acacggcaga ttacaaagca tgttgcgcag    4020
attctcgatt cccggatgaa caccaagtac gatgagaacg ataagctgat tcgggaggtc    4080
aaggtaatta ccctgaagtc caagctggtg tccgacttca ggaaggactt ccagttctac    4140
aaggttcggg agatcaacaa ctaccaccac gcgcatgatg cctacctcaa cgcggtcgtg    4200
gggaccgctc tcatcaagaa gtacccaaag ctggagtcag agttcgtcta cggggattac    4260
aaggtttacg acgtgcggaa gatgatcgct aagagcgagc aggagattgg caaggctacc    4320
gctaagtact tcttctactc caacatcatg aacttcttca agacagagat taccctcgcg    4380
aatggcgaga tccggaagag gccctcatc gagacaaatg gggagacagg ggagattgtc    4440
tgggataagg gcgggatttc gcgaccgtc cggaaggtcc tgtcgatgcc ccaggttaat    4500
attgtcaaga agactgaggt ccagactggc ggcttctcaa aggagtcgat tctcccaaag    4560
aggaactccg ataagctcat tgctcggaag aaggattggg accccaagaa gtacggggga    4620
ttcgactccc ccactgttgc ttactctgtt ctggttgttg ctaaggtgga aaggggaag    4680
tcgaagaagc tgaagagcgt gaaggagctg ctcgggatta caattatgga gaggtcatcc    4740
ttcgagaaga tcccatcga cttcctggag gccaagggct acaaggaggt gaagaaggac    4800
ctgattatta agctgcccaa gtactcgctc ttcgagctgg agaatgggcg gaagcggatg    4860
ctggcgtccg cggggagct gcaaaagggg aacgagctgc cgctccctc caagtatgtg    4920
aacttcctct acctggcgtc gcactacgag aagctgaagg gtccccaga ggataatgag    4980
cagaagcagc tcttcgtcga gcagcataag cactacctgg acgagattat cgagcagatt    5040
agcgagttct cgaagcgggt catcctcgcg gatgcgaacc tggataaggt gctcagcgcc    5100
tacaataagc accgggacaa gccgattcgg gagcaggcgg agaatattat tcacctcttc    5160
acactcacca acctcgggc accagctgcg ttcaagtact cgacactac tatcgaccgg    5220
aagcggtaca cctcgacgaa ggaggtgctc gacgccaccc tcattcacca gtcgatcaca    5280
ggcctgtacg agacacggat tgacctgtcc cagctcgggg gcgacggatc taagaagaga    5340
agaattaaac aagat                                                    5355
```

<210> SEQ ID NO 70
<211> LENGTH: 5358
<212> TYPE: DNA

<213> ORGANISM: Artificial
<220> FEATURE:
<223> OTHER INFORMATION: adenosine base editor construct

<400> SEQUENCE: 70

```
atggcgggca gcaagaaacg ccggattaag caagattccg aagtcgagtt ctcacacgaa      60
tattggatga gacacgcgct tacactagct aaaagggcgt gggacgagcg ggaagtacct     120
gttggtgccg ttctagtgca caacaatcgg tcatcggtg aaggttggaa taggccgatt      180
ggcagacatg atcctacagc acacgctgag atcatggcgc tgcgccaggg aggactcgtt     240
atgcagaact acagactaat tgacgctacc ctctatgtca ctttggaacc atgtgtaatg     300
tgtgctgggg ctatgatcca ctccagaatt ggtagagtag tctttggcgc aagggatgct     360
aagaccggag ccgctggttc attgatggac gtcctgcacc atcccggtat gaaccatcgc     420
gttgagatta ctgagggcat tctggctgac gagtgtgccg cgctcttgtc agatttttt      480
cgaatgagga gacaggagat taaggcacag aagaaggcac agtcaagtac ggatagcgga     540
ggatcatctg gtggaagtag cggctcagag acacctggaa catcagagtc tgcaacacct     600
gaaagttccg gcgggtctag cggcggatct tcagaagttg agtttagtca cgaatattgg     660
atgcgtcacg ctttgacect tgccaagcgc gcccgcgacg agcgcgaagt tcccgttgga     720
gcagttctag tgctcaacaa ccgtgttatt ggtgaaggtt ggaacagggc tattggacta     780
catgacccca ccgctcatgc tgagattatg cccttcgac aaggcgggct tgtgatgcag      840
aactacaggc ttattgacgc taccctctat gttactttcg agccatgtgt catgtgtgcg     900
ggagcaatga tacacagtag aatcgggcgg tggtgttcg gggttcggaa cgcaaagact      960
ggagcggctg ggtcattgat ggatgtgttg cattatccag ggatgaacca cagagttgag    1020
attacgagg gcatattagc tgacgagtgt gctgccctcc tctgctactt cttcagaatg     1080
ccaagacaag tgtttaacgc ccagaagaag gctcaatcct ccacagactc tggaggatct    1140
agtggcggtt caagtgggtc tgaaacacct gggacatccg agagtgctac tcccgaatca    1200
tcaggaggtt catctggagg atctgacaag aagtatagta ttggactcgc tatcggaacc    1260
aactctgtgg ggtgggctgt tattacagat gaatataagg tgccatccaa aaagtttaaa    1320
gttctgggca atactgatag acactcaatc aagaagaatc tgataggtgc acttctgttt    1380
gatagtggag agactgccga ggcaaccaga cttaaaagga ctgcaagaag aagatatacc    1440
agaagaaaga ataggatttg ctatttgcag gaaatcttca gcaacgaaat ggccaaggtt    1500
gatgactcat ttttccatag gttggaggag agttttcttg tggaggaaga taagaagcac    1560
gaaagacacc caattttcgg gaatatagtg gacgaggtgg cttatcatga aagtatccc    1620
actatctacc acctgagaaa gaaacttgtg gactcaaccg ataaggctga tcttaggctt    1680
atatacttgg cccttgcaca tatgatcaaa ttcaggggcc attttcttat cgaaggcgat    1740
cttaatcccg ataactcaga tgtggacaag ctgtttatac aacttgtgca aacctacaat    1800
caactcttcg aggagaatcc cattaacgcc tccggcgtgg atgcaaaagc atactgtca    1860
gccagactga gcaaaagtag gagactggag aatcttatag cccaactgcc cggtgaaaag    1920
aagaatgggc tcttcggaaa tctgatcgct ctttcattgg ggttgacacc caactttaag    1980
agtaactttg acttggcaga agatgcaaag ttgcagctca gtaaagacac atatgacgat    2040
gaccttgaca atctcttggc acaaataggg gatcaatacg ctgaccttt cctcgctgcc    2100
aagaacctca gcgacgctat actgttgtcc gacattctta gggttaatac cgaaattaca    2160
aaggcccctc ttagtgcaag tatgatcaaa aggtatgatg agcatcacca agaccttaca    2220
```

```
ctgctgaagg ctctggttag acagcaactc cctgaaaagt ataaggaaat attcttcgac    2280
caaagtaaga acgggtacgc cggttatatt gatggggggcg caagtcaaga agaattttac   2340
aaattcatca agccaattct tgaaaagatg gacgggactg aggaattgct ggtgaaactg    2400
aatagagagg accttcttag aaaacagagg acatttgaca atgggtccat cccacaccag    2460
attcatctgg gggaactcca cgcaatattg aggagacaag aagactttta cccattcctt    2520
aaggataata gagagaaaat cgaaaaaatc ctgactttca ggattcctta ctatgttggg    2580
ccactggcca gggggaactc aagattcgct tggatgacaa ggaagtcaga agaaaccata    2640
accccttgga attttgaaga ggtggttgat aaggggggcat cagcccagtc tttcatagag    2700
aggatgacca actttgataa aaatcttcca aatgagaagg ttttgccaaa acatagtctt    2760
ttgtacgagt actttactgt ttataacgaa ttgaccaagg tgaagtatgt gaccgaggga    2820
atgaggaagc cagcattttt gtccggggag caaaagaaag caatcgttga tcttctcttc    2880
aagaccaaca gaaaagtgac cgtgaaacaa ctgaaggaag actacttcaa aaagatagaa    2940
tgtttcgatt cagtggaaat tagcggtgtt gaagacaggt tcaatgcttc attgggtact    3000
taccacgacc tgttgaagat aatcaaagac aaggactttc tcgataatga ggagaacgaa    3060
gacatcttgg aagacattgt gcttacactc actttgtttg aggacaggga atgattgag    3120 gaaagactca aaacttacgc tcatttgttt gatgataagg ttatgaaaca actaaaaaga    3180
agaaggtaca ccggctgggg aagattgagt aggaaactga tcaacggtat tagagataaa    3240
caatccggaa agactatcct cgatttcctt aagagtgatg gctttgcaaa taggaatttt    3300
atgcagctga ttcatgacga ctcacttacc ttcaaagaag acatccaaaa agctcaggtg    3360
tctgggcaag cgacagtct gcatgaacat atagctaact ggctgggag tcccgccatc    3420 aagaaggga tacttcaaac agttaaagtt gtggacgaat ggtgaaggt aatgggaagg    3480 cacaagcctg aaaatatagt gatagaaatg gcaaggaaa atcaaacaac ccagaaggga    3540
cagaagaaca gtagggaaag gatgaaaagg atagaagagg ggatcaaaga gcttggtagc    3600
cagatcctca aggaacatcc agtggagaat acccaacttc aaaacgagaa actctatttg    3660
tactacttgc agaacggaag agatatgtat gtggaccaag agcttgatat taacaggctg    3720
agcgattatg acgttgacca catagtgccc caatcattcc tcaaggatga ctctattgat    3780
aataaggtgc tgacaaggag tgacaagaat agagggaaat ccgacaacgt tccatccgag    3840
gaagttgtga agaagatgaa gaactactgg aggcagttgc tgaacgctaa gctcattacc    3900
cagaggaaat tcgataacct gaccaaagca gagagaggcg ggctgagcga actcgataaa    3960
gcaggtttca tcaagagaca actcgtggag actaggcaaa ttactaagca cgtggctcaa    4020
atactcgaca gcaggatgaa cacaaagtac gacgagaaca caagctcat tagagaggtt    4080 aaggttatta ctctgaaaag taaattggtt agcgatttca gaaaggattt ccaattctat    4140
aaggttagag agatcaacaa ttatcatcat gcacatgatg cctatctgaa tgctgtggtt    4200
ggtacagccc ttatcaagaa gtaccctaag ctagagagcg agtttgtgta cggagattat    4260
aaggtgtatg atgtgaggaa aatgatcgct aaaagtgagc aagagattgg aaaggctacc    4320
gccaaatact tcttttattc caatattatg aatttcttca gacagaaat caccctggct    4380 aacggcgaga taaggaagag gccgcttatc gaaactaatg gggagacagg cgaaatagtg    4440
tgggacaaag ggagggattt cgcaactgtg aggaaggttt tgagcatgcc tcaggtgaat    4500
atcgttaaga aaaccgaagt tcaaactgga gggttctcta aggaaagcat tctccccaag    4560
```

```
aggaactccg acaagctgat tgctagaaag aaagactggg accccaagaa gtatggcgga    4620
ttcgactcac ccactgtggc atatagcgtt ctcgtggtgg caaaggttga aaagggtaaa    4680
tccaaaaaac tcaaatccgt gaaggaactc cttggcataa ctattatgga aaggagtagc    4740
tttgaaaaga atcccatcga cttctcgaa gctaagggct ataaggaagt taagaaggac    4800
cttataatca aacttccaaa atactccctt tttgagttgg aaaacggcag aaagagaatg    4860
ttggccagtg ccggggagct tcaaaagggc aacgaactgg ctctgcctag caaatatgtg    4920
aactttttgt atctggcatc acactacgag aaacttaaag gctctcctga ggacaacgag    4980
caaaaacagc tctttgttga acagcataag cactacctcg acgagattat tgagcagatc    5040
agcgagttct caaagagagt tattctggct gacgctaatc ttgacaaggt tttgtccgct    5100
tacaacaaac acagggataa gccaatcagg agcaggcag aaaacataat ccatctcttt    5160
accctgacaa acctcggtgc ccccgctgct ttcaagtatt ttgatactac cattgacagg    5220
aagagatata cttccactaa ggaagtgctc gacgcaaccc tcatacacca aagtatcaca    5280
ggcctctatg aaactaggat agatttgtct caacttgggg gcgatggatc taagaagaga    5340
agaattaaac aagattga                                                  5358

<210> SEQ ID NO 71
<211> LENGTH: 5358
<212> TYPE: DNA
<213> ORGANISM: Artificial
<220> FEATURE:
<223> OTHER INFORMATION: adenosine base editor construct

<400> SEQUENCE: 71
atggcgggca gcaagaaacg ccggattaag caagattccg aagtcgagtt ctcacacgaa      60
tattggatga gacacgcgct tacactagct aaaagggcgt gggacgagcg ggaagtacct     120
gttggtgccg ttctagtgca caacaatcgg gtcatcggtg aaggttggaa taggccgatt     180
ggcagacatg atcctacagc acacgctgag atcatggcgc tgcgccaggg aggactcgtt     240
atgcagaact acagactaat tgacgctacc ctctatgtca ctttggaacc atgtgtaatg     300
tgtgctgggg ctatgatcca ctccagaatt ggtagagtag tctttggcgc aagggatgct     360
aagaccggag ccgctggttc attgatggac gtcctgcacc atcccggtat gaaccatcgc     420
gttgagatta ctgagggcat tctggctgac gagtgtgccg cgctcttgtc agatttttt     480
cgaatgagga gacaggagat taaggcacag aagaaggcac agtcaagtac ggatagcgga     540
ggatcatctg gtggaagtag cggctcagag acacctggaa catcagagtc tgcaacacct     600
gaaagttccg gcgggtctag cggcggatct tcagaagttg agtttagtca cgaatattgg     660
atgcgtcacg cttgacccct tgccaagcgc gcccgcgacg agcgcgaagt tcccgttgga     720
gcagttctag tgctcaacaa ccgtgttatt ggtgaaggt ggaacagggc tattggacta     780
catgacccca ccgctcatgc tgagattatg gcccttcgac aaggcgggct tgtgatgcag     840
aactacaggc ttattgacgc taccctctat gttactttcg agccatgtgt catgtgtgcg     900
ggagcaatga tacacagtag aatcgggcgg gtggtgttcg gggttcggaa cgcaaagact     960
ggagcggctg gtcattgat ggatgtgttc cattatccag ggatgaacca cagagttgag    1020
attacagagg gcatattagc tgacgagtgt gctgccctcc tctgctactt cttcagaatg    1080
ccaagacaag tgtttaacgc ccagaagaag gctcaatcct ccacagactc tggaggatct    1140
agtggcggtt caagtgggtc tgaaacacct gggacatccg agagtgctac tcccgaatca    1200
tcaggaggtt catctggagg atctgacaag aaatacagta ttggccttgc aattgggact    1260
```

```
aactctgtgg gatgggccgt gattacagac gagtacaagg tgccgagcaa gaagtttaag   1320
gtgcttggga acaccgaccg gcactcgatt aagaagaacc taatagggc acttctgttc    1380
gactccggag aaaccgcaga ggccacccgc cttaaacgca ccgcacgacg acgatacacc   1440
cggcgtaaga accggatctg ctatctacag gaaatcttca gtaatgagat ggcaaaggtg   1500
gatgacagct tttttcacag gcttgaggag tcgttcctag ttgaggagga caaaaagcac   1560
gaacgccatc ccatcttcgg gaacatcgtg gatgaggtcg cctaccacga gaagtacccg   1620
accatctacc acctccgcaa gaaactcgtg gacagcacag acaaggctga cctgcgactg   1680
atctacttag ccctggccca catgattaag ttccggggtc acttcctaat cgagggagac   1740
ctcaaccccg ataacagtga cgtggacaag ctcttcatcc aacttgtgca gacctacaac   1800
cagttgttcg aggagaaccc tatcaacgcc agcggggtgg acgcgaaagc tatcctgtcc   1860
gccaggctgt cgaagtctag gcgtctggag aacctaatcg ctcagctacc gggcgaaaaa   1920
aagaatggac tgttcggcaa cctcatagcc ctgagcctgg ggctgacgcc caacttcaaa   1980
agcaacttcg acctggccga ggacgccaag ctccaattga gcaaggacac ctacgacgac   2040
gacttggaca acctattggc ccagataggt gaccagtatg cagacctctt ccttgcggcc   2100
aagaacttga gtgacgctat actgctcagt gacatcctga gggtgaacac tgagatcact   2160
aaggccctc tctctgcctc aatgattaag cgttacgacg agcatcacca ggatctcacc    2220
ctgcttaagg cccttgttcg gcagcagctc cctgagaagt acaaggagat atttttgac    2280
cagtctaaga acggctacgc cggttacatt gacggtgggg caagccagga ggagttctac   2340
aagttcatca agccgatcct tgagaagatg gacggcaccg aggagctact tgtcaagttg   2400
aaccgggaag acctgctccg gaaacagcgt acattcgaca acggcagcat ccctcaccag   2460
atccacctgg gcgaactaca cgccatcctc cgacgtcagg aggacttcta tccattcttg   2520
aaagataaca gggaaaaaat cgaaaaaata cttacgtttc gaatacctta ctacgtgggg   2580
cccttgctc ggggaaactc cagattcgca tggatgacca ggaagtcaga ggagaccatc    2640
acacctgga actttgagga ggtggttgac aaaggtgctt ctgcccagtc cttcattgag    2700
cggatgacta acttcgacaa gaacctgccc aacgagaagg tgctgccaaa gcacagcctg   2760
ctctacgaat actttactgt gtacaatgag ctgacgaagg tgaagtacgt gacagagggg   2820
atgcggaagc ccgcttttcct gagcggcgag caaaaaaaag caatcgtgga cctactgttc   2880
aagaccaacc gaaaggtgac agtgaagcag ctcaaggagg actacttcaa aaaaatcgag   2940
tgcttcgact ctgttgagat aagcggcgtg gaggaccgat tcaacgcctc attgggaacc   3000
tatcacgacc tgctcaagat cattaaggac aaggacttcc tggataatga ggagaatgag   3060
gacatcctgg aggatattgt gctgacccct actctattcg aggacaggga gatgatcgag   3120
gagcgactca agacctacgc tcacctgttc gacgacaagg ttatgaagca attgaagcgt   3180
aggcgataca cggggtgggg aagactctcc cgaaaactga taaacggcat cagggacaag   3240
cagtcaggga agacgatctt ggacttcctg aaatccgacg ggttcgccaa ccgcaacttc   3300
atgcagctca ttcacgacga ctcactaacg ttcaaagagg acattcagaa ggctcaagtc   3360
agtggacaag gcgactccct gcacgagcac attgcaaacc ttgcgggctc cccggcgatt   3420
aaaaagggca ttctccaaac ggttaaggtg gtggacgagc tggtgaaggt gatgggccga   3480
cacaagcctg agaacatcgt gatcgagatg gccaggagga accagactac ccagaagggt   3540
cagaagaact ctcgggaacg tatgaagcgt attgaggagg ggattaagga gttgggctct   3600
```

-continued

| | |
|---|---|
| caaatcctca aggagcaccc tgtggagaac actcagctcc aaaacgagaa gctgtacctg | 3660 |
| tactacctgc aaaacgggcg cgatatgtac gtggatcagg agttggacat caacaggctt | 3720 |
| agcgattacg acgtggacca catcgtgcca cagtcattct taaaggacga cagcatcgac | 3780 |
| aacaaggttc tgacgaggag cgacaagaat cgagggaaaa gtgacaatgt tccatccgag | 3840 |
| gaggtggtca agaaaatgaa gaactattgg cgtcagcttc tgaacgccaa gctcatcacc | 3900 |
| cagcggaaat cgacaacct gactaaggct gagcgaggcg gactctccga gcttgacaag | 3960 |
| gctggcttca tcaagcggca gttggtcgaa acccgacaga taacgaagca cgttgcccag | 4020 |
| atacttgact cccgtatgaa caccaagtac gacgagaacg acaagctcat cagggaggtg | 4080 |
| aaggtcatta cccttaagtc caaactcgtc agcgactttc gtaaggactt ccagttctac | 4140 |
| aaggtgcgcg agatcaataa ctaccaccac gcacacgacg cctacctgaa cgcagtggtt | 4200 |
| ggaaccgcgt tgattaaaaa gtaccccaag ttggagtcgg agttcgttta cggggactac | 4260 |
| aaggtgtacg acgttcggaa gatgatcgcc aagtctgaac aggagatcgg gaaagcaacc | 4320 |
| gccaagtatt tcttctatag caacatcatg aacttcttta aaaccgagat cacacttgcc | 4380 |
| aatggcgaga tccgtaagag gccgctgatc gagacaaatg gggagactgg cgagatcgtg | 4440 |
| tgggacaagg gccgcgactt cgcaaccgtt cggaaagtct tgtccatgcc tcaagtcaac | 4500 |
| atcgtcaaga agactgaggt gcaaacaggc gggttctcga aggagtccat actgcccaag | 4560 |
| aggaactcag acaagctcat agcacgcaaa aaagactggg atccaaagaa atacggcggg | 4620 |
| ttcgactcgc cgacagtcgc atactccgtg ttagtggtgg ctaaagtgga aaaggggaag | 4680 |
| tccaagaagc tcaagtccgt caaggagttg ctcgggatca ccattatgga acggtcctca | 4740 |
| ttcgagaaga atcccattga cttcctagag gcgaagggct acaaagaggt caaaaaggac | 4800 |
| ctaattatta agctccccaa gtattcactc ttcgaacttg aaaatggtcg taagcggatg | 4860 |
| ttggcaagcg ctggagagct tcagaagggg aacgagcttg cactgccttc caagtacgtg | 4920 |
| aacttcctgt acctcgcctc tcattacgag aagttgaagg gctcaccgga ggacaacgag | 4980 |
| cagaagcagt tgttcgtgga gcagcacaag cactacctcg acgagatcat tgagcagata | 5040 |
| agtgagttca gcaaacgggt gatccttgcc gacgctaacc tggacaaggt gctgagcgcc | 5100 |
| tacaacaagc acagagacaa gccgatccga gagcaagcgg agaacatcat acacctgttc | 5160 |
| accctcacga acctcgggc tcccgcagcc ttcaaatatt ttgacacgac catcgaccgt | 5220 |
| aaacgctaca ctagcacgaa ggaggtgctg gacgctaccc ttatccacca gtccatcacc | 5280 |
| ggcctgtacg agacgagaat cgacttgtcg cagctcggtg gtgacggatc taagaagaga | 5340 |
| agaattaaac aagattga | 5358 |

<210> SEQ ID NO 72
<211> LENGTH: 20
<212> TYPE: DNA
<213> ORGANISM: Artificial
<220> FEATURE:
<223> OTHER INFORMATION: CRISPR spacer

<400> SEQUENCE: 72
cagatcacaa acttcaaatg                                            20

<210> SEQ ID NO 73
<211> LENGTH: 20
<212> TYPE: DNA
<213> ORGANISM: Artificial
<220> FEATURE:
<223> OTHER INFORMATION: CRISPR spacer

```
<400> SEQUENCE: 73
agccctcctt gcgctgcaag                                                20

<210> SEQ ID NO 74
<211> LENGTH: 20
<212> TYPE: DNA
<213> ORGANISM: Artificial
<220> FEATURE:
<223> OTHER INFORMATION: CRISPR spacer

<400> SEQUENCE: 74
gaaatcacgg ttgagtgtga                                                20

<210> SEQ ID NO 75
<211> LENGTH: 133
<212> TYPE: DNA
<213> ORGANISM: Homo sapiens

<400> SEQUENCE: 75
gtaagtatca aggttacaag acaggtttaa ggagaccaat agaaactggg cttgtcgaga     60
cagagaagac tcttgcgttt ctgataggca cctattggtc ttactgacat ccactttgcc   120
tttctctcca cag                                                      133

<210> SEQ ID NO 76
<211> LENGTH: 99
<212> TYPE: DNA
<213> ORGANISM: Simian virus 40

<400> SEQUENCE: 76
gtaagtttag tcttttgtc ttttatttca ggtcccggat ccggtggtgg tgcaaatcaa     60
agaactgctc ctcagtggat gttgccttta cttctaggc                           99
```

OPTIMIZED CRISPR-CAS NUCLEASES AND BASE EDITORS AND METHODS OF USE THEREOF

STATEMENT REGARDING ELECTRONIC FILING OF A SEQUENCE LISTING

A Sequence Listing in ASCII text format, submitted under 37 C.F.R. § 1.821, entitled 1499-8WO_ST25.txt, 427,717 bytes in size, generated on Oct. 20, 2020 and filed via EFS-Web, is provided in lieu of a paper copy. This Sequence Listing is hereby incorporated herein by reference into the specification for its disclosures.

STATEMENT OF PRIORITY

This application claims the benefit, under 35 U.S.C. § 119(e), of U.S. Provisional Application No. 62/925,422 filed on Oct. 24, 2019, the entire contents of which is incorporated by reference herein.

FIELD OF THE INVENTION

This invention relates to codon optimized CRISPR-Cas nucleases and nucleic acid constructs encoding base editors comprising a CRISPR-Cas nuclease and a deaminase domain, wherein the nucleic acid constructs are optimized for expression in a plant. The invention further relates to methods of modifying nucleic acids using the nucleic acid constructs.

BACKGROUND OF THE INVENTION

Gene editing is the process of utilizing a site-directed nuclease to introduce variation at targeted genomic locations. The most widely utilized nuclease for gene editing, Cas9, can introduce mutations at a genomic region upstream of an NGG motif (e.g., PAM). These mutations generated are typically insertions or deletions of a few base pairs, but the final sequence achieved can be unpredictable. As a result, obtaining precise genomic alterations using Cas9 editing has been difficult, and for the most part, use of these tools has been for the removal of protein function. As an alternative to Cas9 gene editing, targeted base editing has recently been developed by fusing deaminase protein domains to a disabled nuclease. The most commonly used version for modifying cytosine residues, cytosine base editors (CBE), comprise an Apobec1 domain, which functions to deaminate the cytosine residues within a targeting window. In addition, the base editors can include uracil glycosylase inhibitor (UGI) domains to help facilitate the repair of the modification towards a non-cytosine base change. In mammalian systems, these modification tools have been engineered to produce a very specific cytosine to thymine (C→T) change, through multiple different base editor iterations. In contrast to mammalian systems, the use of base editor cassettes for gene modification in plants has been limited and their efficacy has been low. For example, with the exception of rice, use of CBE base editors in plants has provided low editing efficiency.

To make base editing more useful across a greater number of plant species, new base editing tools are needed.

SUMMARY OF THE INVENTION

Base editing can provide modifications of specific nucleotides within a targeting window. The type of change introduced is reliant on the type of nuclease introduced and the repair profile of the target organism. For example, cytosine base editors (CBEs) provide a base change from C→T and adenine base editors (ABEs) provide a base change from A→G. These base changes limit the type of modification that can be designed and recovered. Further, while base editing has been demonstrated in plants, the editing efficiency is low (e.g., base edits are recovered at low rates). The only plant species that has exhibited a high level of editing is rice; however, even for rice the amount of base editing recovered has been quite variable, from 0% to about 80%. In maize, base edits have been recovered at a low frequency of about 10% frequency, and for wheat the efficiency of editing is even lower at less than 2%. Currently, base editing in plants relies on the use of base editing gene cassettes employed in mammalian systems that are placed into a plant-compatible cloning vector. To enhance efficacy of base editor constructs in planta, the present invention provides base editor expression cassettes in which the components have been codon optimized to increase the efficiency of base editor activity in plants.

One aspect of the invention provides a nucleic acid construct encoding a CRISPR-Cas nuclease, wherein the CRISPR-Cas nuclease is codon optimized for expression in a plant and comprises the nucleotide sequence of any one of SEQ ID NOs:1-11 and 23-25.

A second aspect provides a nucleic acid construct encoding a CRISPR-Cas nuclease operably associated with a promoter, wherein the promoter is associated with an intron. In some embodiments, the nucleic acid construct encoding a CRISPR-Cas nuclease is operably associated with a promoter region, wherein the promoter region comprises an intron. In some embodiments, the CRISPR-Cas nuclease operably associated with a promoter/promoter region may be codon optimized for expression in a plant.

A third aspect of the invention provides a nucleic acid construct encoding a CRISPR-Cas nuclease and a deaminase domain (e.g., a base editor), wherein the CRISPR-Cas nuclease is codon optimized for expression in a plant, and optionally, the deaminase domain is codon optimized for expression in a plant. In some aspects, a nucleic acid construct of the invention encoding a base editor comprises the nucleotide sequence of any one of SEQ ID NOs: 12-22.

A fourth aspect of the invention provides a method of modifying a target nucleic acid, comprising contacting a cell or a cell free system comprising the target nucleic acid with: (a) a nucleic acid construct of the invention, or an expression cassette or vector comprising the same; and (b) a guide nucleic acid (e.g., CRISPR RNA, CRISPR DNA, crRNA, crDNA), under conditions, wherein the nucleic acid construct is expressed and forms a complex with the guide nucleic acid, the complex then hybridizing to the target nucleic acid, thereby modifying the target nucleic acid.

A fifth aspect of the invention provides a method of editing a target nucleic acid, comprising contacting a cell or a cell free system comprising the target nucleic acid with: (a) a nucleic acid construct encoding an optimized CRISPR-Cas nuclease of the invention and an adenine deaminase (e.g., a base editor), or an expression cassette or vector comprising the same; and (b) a guide nucleic acid, under conditions wherein the nucleic acid construct is expressed and the CRISPR-Cas nuclease forms a complex with the guide nucleic acid, the complex hybridizing to the target nucleic acid, wherein the adenine deaminase domain converts an adenosine (A) to a guanine (G) in the target nucleic acid, thereby editing the target nucleic acid to produce a mutation (e.g., a point mutation) in the target nucleic acid.

A sixth aspect of the invention provides a method of editing a target nucleic acid, comprising contacting a cell or a cell free system comprising the target nucleic acid with: (a) a nucleic acid construct encoding an optimized CRISPR-Cas nuclease of the invention and an cytosine deaminase (e.g., a base editor), or an expression cassette or vector comprising the same; and (b) a guide nucleic acid under conditions wherein the nucleic acid construct is expressed and the CRISPR-Cas nuclease forms a complex with the guide nucleic acid, the complex hybridizing to the target nucleic acid, wherein the cytosine deaminase domain converts a cytosine (C) to a thiamine (T) in the target nucleic acid, thereby editing the target nucleic acid to produce a (point) mutation.

The invention further provides expression cassettes and/or vectors comprising the nucleic acid constructs of the invention, and cells comprising polypeptides, fusion proteins and/or nucleic acid constructs of the invention. Additionally, the invention provides kits comprising the nucleic acid constructs of the invention and expression cassettes, vectors and/or cells comprising the same.

These and other aspects of the invention are set forth in more detail in the description of the invention below.

SEQUENCES

SEQ ID NOs:1-11 are exemplary nucleotide sequences encoding Cas9 nucleases of the invention codon optimized for use in plants.

SEQ ID NOs:12-22 and SEQ ID NOs: 69-71 are exemplary nucleotide sequences encoding base editors of the invention.

SEQ ID NOs: 23-25 are exemplary nucleotide sequences encoding Cas12a nucleases of the invention that are codon optimized for use in plants.

SEQ ID NOs:26-42 are example Cas12a amino acid sequences useful with this invention.

SEQ ID NOs:43-49 are example adenine deaminase amino acid sequences useful with this invention.

SEQ ID NOs:50-59 are example cytosine deaminase amino acid sequences useful with this invention.

SEQ ID NO:60 is an exemplary uracil-DNA glycosylase inhibitor (UGI) useful with this invention.

SEQ ID NO:61-63 are exemplary regulatory sequences encoding a promoter and intron.

SEQ ID NOs: 64-66 provide an example of a protospacer adjacent motif position for a Type V CRISPR-Cas12a nuclease.

SEQ ID NOs: 67-68 provide exemplary nucleotide sequences encoding non-natural Cas9 nucleases.

SEQ ID NOs: 69-71 provide exemplary nucleic acid constructs comprising codon optimized polynucleotides encoding base editors that include a CRISPR-Cas9 nuclease and an adenine deaminase domain.

SEQ ID NOs: 72-73 provide exemplary

DETAILED DESCRIPTION

Figure 1:
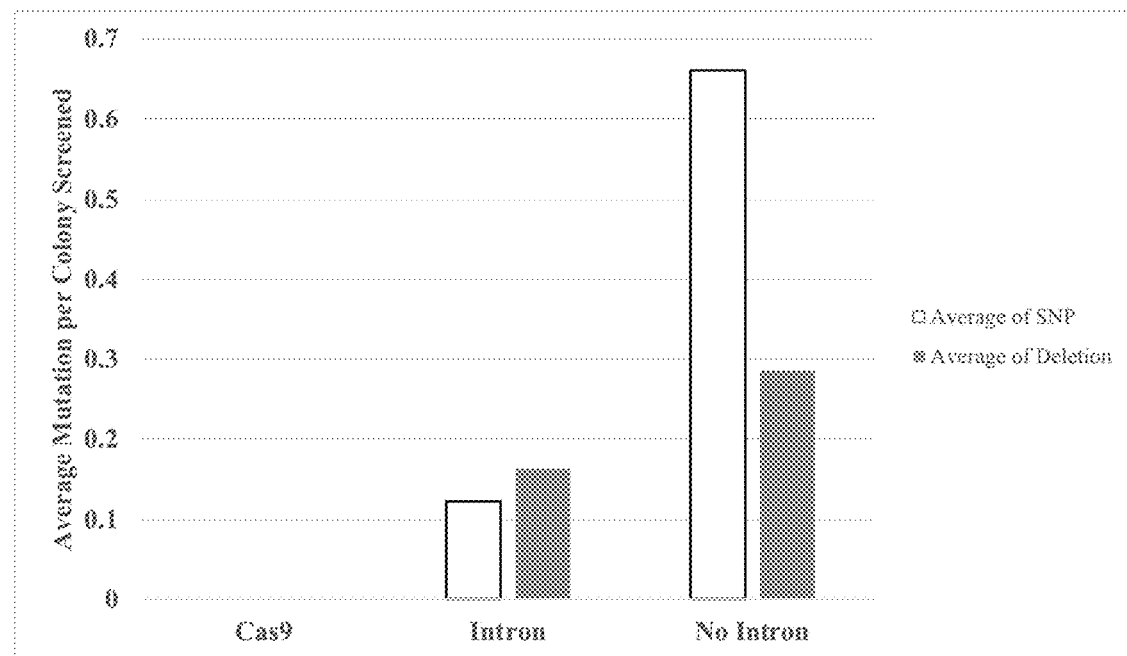
FIG. 1. Average mutation per colony screened. The number of SNPs or deletions was averaged across the total amount of colonies screened in each group.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "enhance," "enhancing," "improve" and "improving" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the reference organism. A "homologous" nucleic acid sequence is a nucleotide sequence naturally associated with a host cell into which it is introduced.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

A "portion" or "fragment" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. As an example, a repeat sequence of guide nucleic acid of this invention may comprise a portion of a wild type CRISPR-Cas repeat sequence (e.g., a wild type Cas9 repeat, wild type Cas12a repeat, and the like).

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, the nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The polynucleotide and/or recombinant nucleic acid constructs of this invention can be codon optimized for expression. In some embodiments, the polynucleotides, nucleic acid constructs, expression cassettes, and/or vectors of the invention (comprising/encoding a base editor, e.g., CRISPR-Cas nuclease, deaminase domain, linkers) are codon optimized for expression in a plant (e.g., in a particular plant species). In some embodiments, the codon optimized nucleic acid constructs, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the nucleic acid constructs, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a CRISPR-Cas nuclease polypeptide or domain (e.g., Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 polypeptide or domain) and a polypeptide of interest (e.g., a nucleic acid-editing domain, a deaminase domain, an adenosine deaminase, a cytosine deaminase). A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or a peptide. In some embodiments, the linker is a peptide.

In some embodiments, a peptide linker useful with this invention may be about 4 to about 100 or more amino acids in length, for example, about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. In some embodiments, a peptide linker may be a GS linker.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227). In some embodiments, a promoter region may comprise at least one intron (e.g., SEQ ID NO:61, SEQ ID NO:62 or SEQ ID NO:63).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA$_2$-δ promoter from *Arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)); the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-metathionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron.

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof. As a non-limiting example, a nucleic acid construct of the present invention may encode a base editor comprising an optimized CRISPR-Cas nuclease (e.g., SEQ ID NOs:1-11 or 23-25) and a deaminase, wherein the nucleic acid construct further comprises a promoter comprising/associated with an intron. As a further non-limiting example, a nucleic acid construct of the present invention may encode a base editor comprising an optimized CRISPR-Cas nuclease (e.g., SEQ ID NOs:1-11 or 23-25) and a deaminase, wherein the nuclease and/or the deaminase comprises one or more introns and optionally, the nucleic acid construct further comprises a promoter comprising/associated with an intron.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a nucleic acid construct of the invention (e.g., encoding a base editor comprising a CRISPR-Cas nuclease and a deaminase domain), wherein the nucleic acid construct is operably associated with at least a control sequence (e.g., a promoter). Thus, some embodiments of the invention provide expression cassettes designed to express, for example, a nucleic acid construct of the invention (e.g., a nucleic acid construct of the invention encoding a base editor comprising a CRISPR-Cas nuclease and a deaminase domain, wherein the nucleic acid construct is optimized for expression in a plant).

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to a gene encoding a CRISPR-Cas nuclease or a gene encoding a deaminase encoded by a nucleic acid construct of the invention, may be native to a host cell, or may be native to another source (e.g., foreign or heterologous to the promoter, to a gene encoding the CRISPR-Cas nuclease or a gene encoding the deaminase encoded by a nucleic acid construct of the invention, to a host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or Agrobacterium binary vectors in double or single stranded linear or circular form which may or may not be self transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid construct of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). Thus, for example, a target nucleic acid may be contacted with a nucleic acid construct of the invention encoding a base editor comprising a codon optimized CRISPR-Cas nuclease, and a guide nucleic acid, under conditions whereby the CRISPR-Cas nuclease is expressed, whereby the CRISPR-Cas nuclease forms a complex with the guide nucleic acid, and the complex hybridizes to the target nucleic acid, thereby modifying the target nucleic acid. In some embodiments, a target nucleic acid may be contacted with a nucleic acid construct of the invention encoding a base editor comprising a codon optimized CRISPR-Cas nuclease linked to a deaminase domain, and a guide nucleic acid, under conditions wherein the CRISPR-Cas nuclease and deaminase domain are expressed as a fusion protein, whereby the fusion protein forms a complex with the guide nucleic acid, and the complex hybridizes to the target nucleic acid, thereby modifying (editing) the target nucleic acid. As described herein, the target nucleic acid may be contacted with the nucleic acid constructs of the invention prior to, concurrently with, or after contact with the guide nucleic acid.

As used herein, "modifying" or "modification" in reference to a target nucleic acid includes editing (e.g., mutating), covalent modification, exchanging/substituting nucleic acids/nucleotide bases, deleting, cleaving, nicking, and/or transcriptional control of a target nucleic acid.

"Introducing," "introduce," "introduced" (and grammatical variations thereof) in the context of a polynucleotide of interest means presenting a nucleotide sequence of interest (e.g., polynucleotide, a nucleic acid construct, and/or a guide nucleic acid) to a host organism or cell of said organism (e.g., host cell; e.g., a plant cell) in such a manner that the nucleotide sequence gains access to the interior of a cell. Thus, for example, a nucleic acid construct of the invention encoding a base editor optimized for expression in a plant as described herein and guide nucleic acid may be introduced into a cell of an organism, thereby transforming the cell with the base editor and guide nucleic acid.

The term "transformation" as used herein refers to the introduction of a heterologous nucleic acid into a cell. Transformation of a cell may be stable or transient. Thus, in some embodiments, a host cell or host organism may be stably transformed with a polynucleotide/nucleic acid molecule of the invention. In some embodiments, a host cell or host organism may be transiently transformed with a nucleic acid construct of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., encoding a CRISPR-Cas nuclease codon optimized for plant expression (e.g., SEQ ID NOs:1-11, 23-25) and/or encoding a base editor comprising a codon optimized CRISPR-Cas nuclease and a deaminase domain (e.g., a fusion protein comprising the CRISPR-Cas nuclease linked to the deaminase domain) (e.g., SEQ ID NOs:12-22) may be transiently introduced into a cell with a guide nucleic acid and as such, no DNA maintained in the cell.

A nucleic acid construct of the invention can be introduced into a cell by any method known to those of skill in the art. In some embodiments of the invention, transformation of a cell comprises nuclear transformation. In other embodiments, transformation of a cell comprises plastid transformation (e.g., chloroplast transformation). In still further embodiments, the recombinant nucleic acid construct of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)).

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, and/or in separate transformation events, or, alternatively, where relevant, a nucleotide sequence can be incorporated into a plant, for example, as part of a breeding protocol.

Studies utilizing base editing in plants are limited. Zong et al. examined cytosine base editing (CBE) activity in rice, wheat, and maize (*Nature Biotechnol.* 35:438-440 (2017)) but found that while high base editing activity could be found in rice, the amount of activity in wheat and maize was quite low. Additionally, the only base editing architectures that have been utilized in plants are based on the base editing 1 or base editing 3 variants. In contrast, the present invention uses base editing 4 architecture, which comprises an additional UGI domain and longer linker sequence between the APOBEC1 domain and nuclease. See, e.g., Rees et al. *Nat. Rev. Genet.* 19:770-788 (2018).

In some embodiments, the present invention provides nucleic acid constructs encoding CRISPR-Cas nucleases codon optimized for expression in a plant, for example, SEQ ID NOs:1-11 and 23-25. In some embodiments, the nucleic acid constructs of the invention comprise base editors comprising a CRISPR-Cas nuclease and a deaminase domain, wherein the CRISPR-Cas nuclease, and optionally, the deaminase sequence, is/are codon optimized for expression in a plant. In some embodiments, a base editor of the invention can comprise, for example, a nucleotide sequence of any one of SEQ ID NOs:12 to 22.

In some embodiments, a nucleic acid construct encoding a CRISPR-Cas nuclease or base editor of the invention may be operably linked to at least one regulatory sequence, optionally, wherein the at least one regulatory sequence may be codon optimized for expression in a plant. In some embodiments, the at least one regulatory sequence may be, for example, a promoter, an operon, a terminator, or an enhancer. In some embodiments, the at least one regulatory sequence may be a promoter. In some embodiments, the regulatory sequence may be an intron. In some embodiments, the at least one regulatory sequence may be, for example, a promoter operably associated with an intron or a promoter region comprising an intron. In some embodiments, the at least one regulatory sequence may be, for example a ubiquitin promoter and its associated intron (e.g., *Medicago truncatula* and/or *Zea mays* and their associated introns). In some embodiments, the at least one regulatory sequence may be a terminator nucleotide sequence and/or an enhancer nucleotide sequence.

In some embodiments, the present invention provides a nucleic acid construct encoding a CRISPR-Cas nuclease (e.g., a Type I, Type II, Type III, Type IV, Type V, or Type VI CRISPR-Cas nuclease as described herein) operably associated with a promoter region, wherein the promoter region comprises an intron, optionally wherein the promoter region may be a ubiquitin promoter and intron (e.g., a *Medicago* or a maize ubiquitin promoter and intron, e.g., SEQ ID NOs:61-63). In some embodiments, the CRISPR-Cas nuclease operably associated with a promoter region comprising an intron may be codon optimized for expression in a plant.

In some embodiments, a nucleic acid construct of the invention encoding a CRISPR-Cas nuclease may further encode one or more polypeptides of interest, optionally wherein the one or more polypeptides of interest may be codon optimized for expression in a plant.

A polypeptide of interest useful with this invention can include, but is not limited to, a polypeptide or protein domain having deaminase activity, nickase activity, recombinase activity, transposase activity, methylase activity, glycosylase (DNA glycosylase) activity, glycosylase inhibitor activity (e.g., uracil-DNA glycosylase inhibitor (UGI)), demethylase activity, transcription activation activity, transcription repression activity, transcription release factor activity, histone modification activity, nuclease activity, single-strand RNA cleavage activity, double-strand RNA cleavage activity, restriction endonuclease activity (e.g., Fok1), nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity. In some embodiments, the polypeptide of interest is a deaminase (e.g., an adenine deaminase, a cytosine deaminase). In some embodiments, the polypeptide of interest is a Fok1 nuclease, or a uracil-DNA glycosylase inhibitor. When encoded in the polynucleotide of interest, the encoded polypeptide or protein domain may be codon optimized for expression in a plant.

In some embodiments, a nucleic acid construct of the invention encoding a base editor comprising a CRISPR-Cas nuclease and a deaminase domain (e.g., encoding a fusion protein comprising a CRISPR-Cas nuclease and a deaminase domain) may further encode a polypeptide of interest, optionally wherein the polypeptide of interest may be codon optimized for expression in a plant.

A CRISPR-Cas nuclease useful with this invention may be any CRISPR-Cas nuclease functional with a deaminase polypeptide or deaminase domain (e.g., functional with a cytosine deaminase domain and/or an adenine deaminase domain). A CRISPR-Cas nuclease can include, but is not limited to, Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3'', Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5.

In some embodiments, a CRISPR-Cas nuclease useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas nuclease having a mutation in its nuclease active site, and therefore, no longer comprising nuclease activity, is commonly referred to as "dead," e.g., dCas. In some embodiments, a CRISPR-Cas nuclease domain or polypeptide having a mutation in its nuclease active site may have impaired activity or reduced activity as compared to the same CRISPR-Cas nuclease without the mutation.

A CRISPR Cas9 polypeptide or CRISPR Cas9 domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes*, *S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. Exemplary Cas9 nucleases of the present invention include the amino acid sequence of any one of SEQ ID NOs:1-11, 67 or 68 (e.g., SEQ ID NOs:1, 2, 3, 4, 5, 6, 7, 8, 9, 10, 11 and/or 67 or 68) or a polynucleotide encoding the same.

Cas12a is a Type V Clustered Regularly Interspaced Short Palindromic Repeats (CRISPR)-Cas nuclease. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a polypeptide or CRISPR Cas12a domain useful with this invention may be any known or later identified Cas12a nuclease (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity.

In some embodiments, a Cas12a polypeptide/domain that may be optimized according to the present invention can include, but is not limited to, the amino acid sequence of any one of SEQ ID NOs:26-42 (e.g., SEQ ID NOs: 26, 27, 28, 29, 30, 31, 32, 33, 34, 35, 36, 37, 38, 39, 40, 41, or 42), or a polynucleotide encoding the same. In some embodiments, example optimized Cas12a polypeptides of the invention comprise the amino acid sequence of any one of SEQ ID NOs:23-25 (e.g., SEQ ID NOs:23, 24, or 25), or a polynucleotide encoding the same.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally-occurring cytosine deaminase, including but not limited to a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), an hAID and evolved versions of the same. In some embodiments, the cytosine deaminase may be an APOBEC1 deaminase having the amino acid sequence of SEQ ID NO:50, SEQ ID NO:55 or SEQ ID NO:57. In some embodiments, the cytosine deaminase may be an APOBEC3A deaminase having the amino acid sequence of SEQ ID NO:51. In some embodiments, the cytosine deaminase may be an CDA1 deaminase, optionally a CDA1 having the amino acid sequence of SEQ ID NO:52 or SEQ ID NO:54. In some embodiments, the cytosine deaminase may be a FERNY deaminase, optionally a FERNY having the amino acid sequence of SEQ ID NO:53 or SEQ ID NO:56. In some embodiments, the cytosine deaminase may be an hAID deaminase, optionally a hAID deaminase having the amino acid sequence of SEQ ID NO:58 or SEQ ID NO:59. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NOs:50-59 (e.g., at least 80%, at least 85%, at least 90%, at least 92%, at least 95%, at least 96%, at least 97%, at least 98%, at least 99%, or at least 99.5% identical to the amino acid sequence of SEQ ID NOs:50-59). In some embodiments, a polynucleotide encoding a cytosine deaminase may be codon optimized for expression in an organism and the codon optimized polypeptide may be about 70% to 99.5% identical to the reference polynucleotide.

In some embodiments, a base editor of this invention comprising a CRISPR-Cas nuclease and a cytosine deaminase may further comprise a polypeptide of interest. In some embodiments, the polypeptide of interest may be a uracil glycosylase inhibitor (UGI) (e.g., uracil-DNA glycosylase inhibitor) polypeptide/domain. In some embodiments, a nucleic acid construct encoding an optimized CRISPR-Cas nuclease of this invention and a cytosine deaminase domain (e.g., encoding a fusion protein comprising a CRISPR-Cas nuclease and a cytosine deaminase domain) may further encode a uracil-DNA glycosylase inhibitor (UGI), optionally wherein the UGI is codon optimized for expression in a plant. In some embodiments, the invention provides a fusion protein comprising a CRISPR-Cas nuclease, a cytosine deaminase domain, and a UGI and/or one or more polynucleotides encoding the same, optionally wherein the one or more polynucleotides may be codon optimized for expression in a plant.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO: 60 or a polypeptide having about 70% to about 99.5% identity to the amino acid sequence of SEQ ID NO:60 (e.g., at least 80%, at least 85%, at least 90%, at least 92%, at least 95%, at least 96%, at least 97%, at least 98%, at least 99%, or at least 99.5% identical to the amino acid sequence of SEQ ID NO:60). For example, in some embodiments, a UGI domain may comprise a fragment of the amino acid sequence of SEQ ID NO:60 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:60. In some embodiments, a UGI domain may be a variant of a known UGI (e.g., SEQ ID NO:60) having about 70% to about 99.5% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% identity, and any range or value therein) to the known UGI. In some embodiments, a polynucleotide encoding a UGI may be codon optimized for expression in a plant and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally-occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:43. In some embodiments, a mutated/evolved *E. coli* TadA* comprises the amino acid sequence of SEQ ID NOs:44-49 (e.g., SEQ ID NOs: 44, 45, 46, 47, 48 or 49). In some embodiments, a polynucleotide encoding a TadA/TadA* may be codon optimized for expression in a plant.

The nucleic acid constructs of the invention encoding a base editor comprising a CRISPR-Cas nuclease domain and a deaminase domain may be used in combination with a guide RNA (gRNA, CRISPR array, CRISPR RNA, crRNA), designed to function with the encoded CRISPR-Cas nuclease domain, to modify a target nucleic acid. A guide nucleic acid useful with this invention comprises a spacer sequence and a repeat sequence. The guide nucleic acid is capable of forming a complex with the CRISPR-Cas nuclease domain encoded and expressed by the nucleic acid construct of the invention and the spacer sequence is capable of hybridizing to a target nucleic acid, thereby guiding the nucleic acid construct (e.g., the CRISPR-Cas nuclease, the CRISPR-Cas nuclease and the deaminase domain (e.g., a base editor of the invention)) to the target nucleic acid, wherein the target nucleic acid may be modified (e.g., cleaved or edited) or modulated (e.g., modulating transcription) by the encoded deaminase domain and/or polypeptide of interest.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas nuclease encoded by the nucleic acid constructs of the invention that encode a base editor. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35(Web Server issue):W52-7). In some embodiments, a repeat sequence or portion thereof is linked at its 3' end to the 5' end of a spacer sequence, thereby forming a repeat-spacer sequence (e.g., guide RNA, crRNA).

In some embodiments, a repeat sequence comprises, consists essentially of, or consists of at least 10 nucleotides depending on the particular repeat and whether the guide RNA comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein; e.g., about). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprises a pseudoknot-like structure at its 5' end (e.g., "handle").

A "spacer sequence" as used herein is a nucleotide sequence that is complementary to a target nucleic acid (e.g., target DNA) (e.g., protospacer). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 23 nucleotides in length.

In some embodiments, the 5' region of a spacer sequence of a guide RNA may be identical to a target DNA, while the 3' region of the spacer may be substantially complementary to the target DNA (e.g., Type V CRISPR-Cas), or the 3' region of a spacer sequence of a guide RNA may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of an organism's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide RNA of this invention. A region useful for a CRISPR-Cas system, known as the protospacer adjacent motif (PAM), is located adjacent to the spacer (or target) sequence. These PAM DNA sequences are typically described by referencing their sequence and location with respect to the non-target strand of the CRISPR complex. PAM sequences can be either 3' (e.g., Type V CRISPR-Cas system) or 5' (e.g., Type II CRISPR-Cas system) to the end of the protospacer sequence. A target region (also referred to as the protospacer) may be selected from any region of at least 15 consecutive nucleotides (e.g., 15, 16, 17, 18, 19, 20, 21, 22, 23, 24, 25, 26, 27, 28, 29, 30 or more than 30 nucleotides, and the like) located adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide RNAs, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention. In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct that is codon optimized for expression in plants and comprising a CRISPR-Cas nuclease and a deaminase domain (e.g., a fusion protein)) may be comprised on the same or on a separate expression cassette or vector from that comprising the guide nucleic acid. When the nucleic acid construct encoding a base editor is comprised on a separate expression cassette or vector from that comprising the guide nucleic acid, a target nucleic acid may be contacted with (e.g., provided with) the expression cassette or vector encoding the base editor prior to, concurrently with, or after the expression cassette comprising the guide nucleic acid is provided (e.g., contacted with the target nucleic acid).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors encoding the

```
5'-NNNNNNNNNNNNNNNNNNNN-3'   RNA Spacer (SEQ ID NO: 64)
   ||||||||||||||||||||
3'-AAANNNNNNNNNNNNNNNNNNNN-5'  Target strand (SEQ ID NO: 65)
   ||||
5'-TTTNNNNNNNNNNNNNNNNNNNN-3'  Non-target strand (SEQ ID NO: 66)
``` same CRISPR-Cas nuclease and/or deaminase domain but which have not been codon optimized for expression in a plant.

In some embodiments, the invention provides cells comprising one or more polynucleotides, guide nucleic acids, nucleic acid constructs, expression cassettes or vectors of the invention.

The nucleic acid constructs of the invention (e.g., a construct that is codon optimized for expression in plants and comprising a codon optimized CRISPR-Cas nuclease and/or a codon optimized CRISPR-Cas nuclease and a deaminase domain (e.g., a fusion protein)) and expression cassettes/vectors comprising the same may be used for modifying target nucleic acids and/or their expression.

In some embodiments, a nucleic acid construct of the invention may encode a codon optimized CRISPR-Cas nuclease linked to a deaminase domain (a base editor) for use in base editing a target nucleic acid in a plant, wherein the codon optimized CRISPR-Cas nuclease can be any Cas nuclease (e.g., a codon optimized Cas12a nuclease (e.g., SEQ ID NOs:23-25) or a codon optimized Cas9 nuclease (e.g., SEQ ID NOs:1-11) and the deaminase domain is a cytosine or an adenosine deaminase domain, wherein the codon optimization is for expression in a plant. In some embodiments, the nucleic acid constructs comprise promoters, introns and other regulatory sequences as described herein.

When used in combination with guide nucleic acids, the nucleic acid constructs of the invention of the invention may be used to modify a target nucleic acid. A target nucleic acid may be contacted with a nucleic acid construct of the invention prior to, concurrently with or after contacting the target nucleic acid with the guide nucleic acid. In some embodiments, the nucleic acid constructs of the invention and a guide nucleic acid may be comprised in the same expression cassette or vector and therefore, a target nucleic acid may be contacted concurrently with the nucleic acid constructs of the invention and guide nucleic acid. In some embodiments, the nucleic acid constructs of the invention and a guide nucleic acid may be in different expression cassettes or vectors and thus, a target nucleic acid may be contacted with the nucleic acid constructs of the invention prior to, concurrently with, or after contact with a guide nucleic acid.

In some embodiments, a method of modifying a target nucleic acid is provided, the method comprising contacting a cell or a cell free system comprising the target nucleic acid with (a) a nucleic acid construct encoding a codon optimized CRISPR-Cas nuclease of the invention, and/or an expression cassette or vector comprising the same, and (b) a guide nucleic acid (e.g., CRISPR RNA, CRISPR DNA, crRNA, crDNA), under conditions whereby the nucleic acid construct is expressed and produces the codon optimized CRISPR-Cas nuclease, which forms a complex with the guide nucleic acid, and wherein the complex hybridizes to the target nucleic acid, thereby modifying the target nucleic acid in the cell or cell free system. In some embodiments, the codon optimized CRISPR-Cas nuclease comprises the nucleotide sequence of any one of SEQ ID NOs:1 to 11 and/or SEQ ID NOs:23-25 or any combination thereof.

In some embodiments, a method of modifying a target nucleic acid is provided, the method comprising contacting a cell or a cell free system comprising the target nucleic acid with (a) a nucleic acid construct encoding a base editor of the invention comprising a codon optimized CRISPR-Cas nuclease and deaminase domain, and/or an expression cassette or vector comprising the same, and (b) a guide nucleic acid (e.g., CRISPR RNA, CRISPR DNA, crRNA, crDNA), under conditions whereby the nucleic acid construct is expressed to produce the base editor (e.g., the CRISPR-Cas nuclease and deaminase domain), which forms a complex with the guide nucleic acid (e.g., the codon optimized CRISPR-Cas nuclease complexes with the guide nucleic acid), and wherein the complex hybridizes to the target nucleic acid, thereby modifying the target nucleic acid in the cell or cell free system. In some embodiments, the base editor of the invention comprising a CRISPR-Cas nuclease and a deaminase domain comprises the nucleotide sequence of any one of SEQ ID NOs:12-22 or 69-71, or any combination thereof.

In some embodiments, a method of modifying a target nucleic acid in a plant is provided, the method comprising contacting a cell of the plant comprising the target nucleic acid with (a) a nucleic acid construct encoding a codon optimized CRISPR-Cas nuclease of the invention, and/or an expression cassette or vector comprising the same, and (b) a guide nucleic acid (e.g., CRISPR RNA, CRISPR DNA, crRNA, crDNA), under conditions whereby the nucleic acid construct is expressed to produce the CRISPR-Cas nuclease, which forms a complex with the guide nucleic acid, and the complex hybridizes to the target nucleic acid, thereby modifying the target nucleic acid in the plant. In some embodiments, the codon optimized CRISPR-Cas nuclease comprises the nucleotide sequence of any one of SEQ ID NOs:1 to 11 and/or SEQ ID NOs:23-25, or any combination thereof. In some embodiments, a plant cell modified by the methods of this invention may be regenerated into a plant and/or a plant part.

In some embodiments, a method of modifying a target nucleic acid in a plant is provided, the method comprising contacting a cell of the plant comprising the target nucleic acid with (a) a nucleic acid construct encoding a base editor of the invention comprising a CRISPR-Cas nuclease and a deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid, thereby modifying the target nucleic acid in the plant. In some embodiments, the base editor of the invention comprising a CRISPR-Cas nuclease and a deaminase domain comprises the nucleotide sequence of any one of SEQ ID NOs:12-22 or 69-71, or any combination thereof. In some embodiments, a plant cell modified by the methods of this invention may be regenerated into a plant and/or a plant part.

In some embodiments, a method of editing a target nucleic acid is provided, the method comprising contacting a cell or a cell free system comprising the target nucleic acid with: (a) a nucleic acid construct of the invention encoding a base editor comprising a codon optimized CRISPR-Cas nuclease and adenosine deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid, and the adenine deaminase domain converts an adenosine (A) to a guanine (G) in the target nucleic acid, thereby editing the target nucleic acid to produce a (point) mutation in the target nucleic acid.

In some embodiments, a method of editing a target nucleic acid in a plant is provided, the method comprising contacting a cell of the plant comprising the target nucleic acid with: (a) a nucleic acid construct of the invention encoding a base editor comprising a codon optimized CRISPR-Cas nuclease and adenosine deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid, and the adenine deaminase domain converts an adenosine (A) to a guanine (G) in the target nucleic acid, thereby editing the target nucleic acid to produce a mutation (e.g., point mutation) in the target nucleic acid in the plant. In some embodiments, a plant cell modified by the methods of this invention may be regenerated into a plant and/or a plant part.

In some embodiments, a method of editing a target nucleic acid is provided, the method comprising contacting a cell or a cell free system comprising the target nucleic acid with: (a) a nucleic acid construct of the invention encoding a base editor comprising a codon optimized CRISPR-Cas nuclease and cytosine deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid and the cytosine deaminase domain converts a cytosine (C) to a thiamine (T) in the target nucleic acid, thereby editing the target nucleic acid to produce a (point) mutation.

In some embodiments, a method of editing a target nucleic acid is provided, the method comprising contacting a cell or a cell free system comprising the target nucleic acid with: (a) a nucleic acid construct of the invention encoding a base editor comprising the nucleotide sequence of any one of SEQ ID NOs:12-22 or 69-71, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid and the cytosine deaminase domain converts a cytosine (C) to a thiamine (T) in the target nucleic acid, thereby editing the target nucleic acid to produce a (point) mutation.

In some embodiments, a method of editing a target nucleic acid in a plant is provided, the method comprising contacting a cell of the plant comprising the target nucleic acid with: (a) a nucleic acid construct of the invention encoding a base editor comprising a codon optimized CRISPR-Cas nuclease and cytosine deaminase domain, and/or an expression cassette or vector comprising the same, and (b) a guide nucleic acid, under conditions whereby the nucleic acid construct is expressed to produce the base editor, which forms a complex with the guide nucleic acid, and wherein the complex hybridizes to the target nucleic acid and the cytosine deaminase domain converts a cytosine (C) to a thiamine (T) in the target nucleic acid, thereby editing the target nucleic acid to produce a (point) mutation in the target nucleic acid in the plant. In some embodiments, a plant cell modified by the methods of this invention may be regenerated into a plant and/or plant part.

In some embodiments, a method of editing a target nucleic acid in a plant is provided, the method comprising contacting a cell of the plant comprising the target nucleic acid with: (a) a nucleic acid construct of the invention encoding a base editor comprising the nucleotide sequence of any one of SEQ ID NOs:12-22 or 69-71, and/or an expression cassette or vector comprising the same, and (b) a guide nucleic acid, under conditions whereby the nucleic acid construct is expressed to produce the base editor, which forms a complex with the guide nucleic acid, and wherein the complex hybridizes to the target nucleic acid and the cytosine deaminase domain converts a cytosine (C) to a thiamine (T) in the target nucleic acid, thereby editing the target nucleic acid to produce a (point) mutation in the target nucleic acid in the plant. In some embodiments, a plant cell modified by the methods of this invention may be regenerated into a plant and/or plant part.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a codon optimized CRISPR-Cas nuclease and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention encoding a base editor comprising a codon optimized CRISPR-Cas nuclease and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt transcription factor binding; and/or generation of point mutations in genomic DNA to disrupt splice junctions.

A target nucleic acid of any plant or plant part may be modified (e.g., mutated, e.g., base edited, cleaved, nicked, etc.) using the nucleic acid constructs of the invention (e.g., SEQ ID NOs:1-25 or 69-71). Any plant (or groupings of plants, for example, into a genus or higher order classification) may be modified using the nucleic acid constructs of this invention including an angiosperm, a gymnosperm, a monocot, a dicot, a C3, C4, CAM plant, a bryophyte, a fern and/or fern ally, a microalgae, and/or a macroalgae. A plant and/or plant part useful with this invention may be a plant and/or plant part of any plant species/variety/cultivar. The term "plant part," as used herein, includes but is not limited to, embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell can be in the form of an isolated single cell or can be a cultured cell or can be a part of a higher-organized unit such as, for example, a plant tissue or a plant organ.

Non-limiting examples of plants useful with the present invention include turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, sunflower, raspberry, blackberry, black raspberry and/or cherry.

The present invention further comprises a kit or kits to carry out the methods of this invention. A kit of this invention can comprise reagents, buffers, and apparatus for mixing, measuring, sorting, labeling, etc., as well as instructions and the like as would be appropriate for modifying a target nucleic acid.

In some embodiments, the invention provides a kit comprising one or more nucleic acid constructs of the invention (e.g., SEQ ID NOs:1-25 or 69-71), and/or expression cassettes and/or vectors comprising the same, with optional instructions for the use thereof. In some embodiments, a kit may further comprise a CRISPR-Cas guide nucleic acid (corresponding to the CRISPR-Cas nuclease encoded by the polynucleotide of the invention) and/or expression cassette and/or vector comprising the same. In some embodiments, the guide nucleic acid may be provided on the same expression cassette and/or vector as a nucleic acid construct of the invention. In some embodiments, the guide nucleic acid may be provided on a separate expression cassette or vector from that comprising the nucleic acid construct of the invention.

Accordingly, in some embodiments, kits are provided comprising a nucleic acid construct comprising (a) a polynucleotide encoding a base editor as provided herein and (b) a promoter that drives expression of the polynucleotide of (a). In some embodiments, the kit may further comprise a nucleic acid construct encoding a guide nucleic acid, wherein the construct comprises a cloning site for cloning of a nucleic acid sequence identical or complementary to a target nucleic acid sequence into backbone of the guide nucleic acid.

In some embodiments, the nucleic acid construct of the invention encoding the base editor may be an mRNA that may encode one or more introns within the encoded base editor. In some embodiments, the nucleic acid construct of the invention encoding a base editor, and/or an expression cassette and/or vector comprising the same, may further encode one or more selectable markers useful for identifying transformants (e.g., a nucleic acid encoding an antibiotic resistance gene, herbicide resistance gene, and the like).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

Polynucleotides encoding a base editor that comprises a CRISPR-Cas nuclease and either a cytosine deaminase or an adenine deaminase were generated (e.g., SEQ ID NOs:12 to 22). The polynucleotides that were generated are codon optimized for expression in soybean or corn.

In maize, six different optimized polynucleotides encoding base editors that include a CRISPR-Cas9 nuclease and a cytosine deaminase domain are provided, and in soybean, five different optimized polynucleotides encoding base editors are provided. The optimizations were placed behind a plant-specific promoter and transformed into plants via *Agrobacterium* mediated transformation protocols.

TABLE 1

Listing of the optimized base editors

| Coding sequence optimized version | Plant Type | SEQ ID NO: | Cas 9 SEQ ID NO |
|---|---|---|---|
| Mon_GS_V1 | Monocot | 12 | 1 |
| Mon_GS_V2 | Monocot | 13 | 2 |
| Mon-GS_V3 | Monocot | 14 | 3 |
| Mon_BY_V1 | Monocot | 15 | 4 |
| Mon_BY_V2 | Monocot | 16 | 5 |
| Mon_BY_V3 | Monocot | 17 | 6 |
| Di_GS_V1 | Dicot | 18 | 7 |
| Di_GS_V2 | Dicot | 19 | 8 |
| Di_GS_V3 | Dicot | 20 | 9 |
| Di_BY_V1 | Dicot | 21 | 10 |
| Di_BY_V2 | Dicot | 22 | 11 |

To examine the amount of base editing achievable with different optimizations, target regions were chosen that contained cytosine residues within a known targeting region (13-17 bp upstream of the PAM sequence). Specifically, the target nucleic acids that were chosen for maize are in the genes CenH3 and glossy2 (g12). In soybean, the target nucleic acid that was chosen is in the Mir1509 gene.

TABLE 2

Guide nucleic acids

| Guide # | Target | Protospacer |
|---|---|---|
| PWg090001 | gl2 | CAGATCACAAACTTCAAATG |
| PWg090002 | ZmCENH3 | AGCCCTCCTTGCGCTGCAAG |
| PWg090005 | MIR1509 | GAAATCACGGTTGAGTGTGA |

The constructs comprising the codon optimized polynucleotides and the guides comprising the spacers targeting the target nucleic acids were introduced into soybean and maize plants using *Agrobacterium* transformation methods as known in the art.

Following transformation and regeneration of the corn and soybean plantlets, leaf tissues were sampled from each plant and editing efficiency was measured via amplicon sequencing followed by next generation sequencing. Bioinformatic analysis of the sequencing results examined the genetic region targeted by the nuclease to determine if the targeted cytosine residues had been converted to thymine residues. Plasmid sequencing was performed using the PlexWell service from seqWell.

When the codon optimizations were introduced to plants through *Agrobacterium* transformation, the amount of base editing that resulted differed between the different targets and optimizations. Notably, at the CenH3 target, which was previously reported to have a 10% editing efficiency, showed an overall editing efficiency of over 25%. Editing efficiency is measured as the number of plants showing at least 10% of reads with a single edit divided by the total number of plants exposed to the editing reagent (Table 3). At the g12 target in corn, overall editing efficiency was over 60% with four of six optimizations obtaining over 80% editing efficiency.

TABLE 3

Editing efficiency of the plant optimized base editors in maize and soybean. The optimization column includes entries for 'Cas9', which is a baseline, unoptimized version of the Cas9 protein.

| Crop | Target | Construct | Optimization | n. Total | Edit. BE | Edit. Efficiency |
|---|---|---|---|---|---|---|
| Corn | gl2 | pWISE27 | GS-V1 | 94 | 79 | 84% |
| Corn | gl2 | pWISE30 | GS-V2 | 63 | 47 | 75% |
| Corn | gl2 | pWISE33 | GS-V3 | 75 | 45 | 60% |
| Corn | gl2 | pWISE36 | Cas9 | 67 | 0 | 0% |
| Corn | gl2 | pWISE179 | BY-V1 | 21 | 17 | 81% |
| Corn | gl2 | pWISE180 | BY-V2 | 91 | 77 | 85% |
| Corn | gl2 | pWISE181 | BY-V3 | 41 | 34 | 83% |
| Corn | ZmCenH3 | pWISE28 | GS-V1 | 118 | 46 | 39% |
| Corn | ZmCenH3 | pWISE34 | GS-V3 | 46 | 12 | 26% |
| Corn | ZmCenH3 | pWISE189 | BY-V1 | 24 | 12 | 50% |
| Corn | ZmCenH3 | pWISE190 | BY-V2 | 90 | 33 | 37% |
| Corn | ZmCenH3 | pWISE191 | BY-V3 | 6 | 4 | 67% |
| Corn | ZmCENH3 | pWISE28 | GS-V1 | 118 | 46 | 39% |
| Corn | ZmCENH3 | pWISE31 | GS-V2 | 49 | 23 | 57% |
| Corn | ZmCENH3 | pWISE37 | Cas9 | 5 | 1 | 20% |
| Soy | mir1509 | pWISE39 | GS-V1 | 156 | 0 | 0% |
| Soy | mir1509 | pWISE41 | GS-V2 | 19 | 0 | 0% |
| Soy | mir1509 | pWISE45 | Cas9 | 232 | 0 | 0% |
| Soy | mir1509 | pWISE182 | BY-V1 | 12 | 10 | 83% |
| Soy | mir1509 | pWISE183 | BY-V2 | 13 | 6 | 46% |

Example 2

In Example 1, different promoters were used to drive the base editing cassettes. As indicated in Table 3, in soy, the ubiquitin2 promoter, containing the native intron from the ubiquitin2 gene, from *Medicago truncatula* was used to drive cassette expression. In the case of GS-V1, GS-V2 and unoptimized Cas9, no edits were obtained. For BY-V1 and BY-V2, edits were obtained, however, the number of edits was unsatisfactory.

A third set of constructs were tested which comprised a tandem viral promoter driving the base editing cassette. The viral promoter has known leaky expression in prokaryotic systems. Complete plasmid sequencing of the vectors recovered after *Agrobacterium* and *E. coli* propagations consistently revealed C->T base changes. Indels could also be observed in some of the vectors with this leaky prokaryotic expression. These changes were found only in the viral promoter constructs lacking introns in the coding sequence of the cytosine base editor. It is interpreted that leaky expression in the prokaryotic system is leading to off-site editing of the plasmids and very likely the prokaryotic genome. This mutational activity is likely leading to construct instability in the prokaryotic systems.

Thus, a fourth set of constructs were tested utilizing the same MtUbq2 promoter but with an addition of an intron. The data from these tests are shown in Table 4.

TABLE 4

Editing efficiency in soy when a promoter region comprising an intron is used

| Crop | Target | Construct | Optimization | n. Total | Edit. BE | Edit. Efficiency |
|---|---|---|---|---|---|---|
| Soy | mir1509 | pWISE652 | GS-V1 + Intron | 30 | 2 | 7% |
| Soy | mir1509 | pWISE653 | GS-V2 + Intron | 30 | 10 | 33% |
| Soy | mir1509 | pWISE655 | BY-V1 + Intron | 50 | 26 | 52% |

In the case of GS-V1, while the editing efficiency remained low at 7%, the same construct without an intron did not make any edits. For GS-V2, an editing efficiency of 33% was achieved. For BY-V1, while the editing efficiency decreased from 83% to 52%, there was a 250% increase in the number of edits made, indicating a much better editing system.

Example 3

As a further means of improving editing efficiency and to prevent leaky expression in the prokaryotic system, constructs can be made utilizing an additional intron in either the APOBEC/deaminase domain or the UGI domain.

The nucleic acid constructs of the invention provide precision modification of plants through base editing. Prior to this work, the ability to confer specific base changes was limited by the low efficiency of the editing reagent. As a result, large quantities of starting material were required to generate plants with a desired mutation/genotype. However, the nucleic acid constructs provided by the present invention, now provide base editing at consistently higher levels than previously achievable.

Example 4

When assembling constructs containing a cytosine deaminase domain, Apobec1 and Apobec3a (A3A), instability was observed in the resulting clones in the form of mutant sequences. The most prominent change observed were C>T changes in the plasmid sequence. Also observed were large deletions in the plasmid, and in particular, deletions that disrupted the deaminase itself. The prevalence of mutations in the deaminase suggests a selection for such mutations and therefore likelihood that the deaminase may be cytotoxic in the bacteria.

Introns for Improving Stability

The stability of the base editor constructs designed for use with Cas9 was improved by utilizing a promoter, the *Medicago* ubiquitin 2 promoter (MtUbq2, SEQ ID NO:63), which contains an intron at the 3' end following the promoter and 5' UTR.

The *Medicago* ubiquitin intron, which cannot be excised by prokaryotes, prevents the downstream deaminase from being expressed, and therefore, reduces or prevents construct instability. Constructs that utilized the MtUbq2 promoter to drive expression of a cytosine base editor (APOBE1) (see, e.g., SEQ ID NOs:12-22), as well as those that utilize a constitutive tandem viral promoter, were transformed into *E. coli* and then sequenced by next generation sequencing. The resulting sequence was aligned to the reference sequence and the number of SNPs or deletions was tabulated for each construct. A total of 10 colonies for a standard Cas9 construct, 49 colonies having the base editor driven by MtUbq2 containing an intron, and 56 colonies having the base editor without an intron were screened. As seen in Table 5 and FIG. 1, the number of mutations observed is lower when an intron is present proceeding the editor.

TABLE 5

Sum of SNP and Deletions in base editor constructs when compared to nuclease vector control.

| Editor | Sum of SNP | Sum of Deletion | Colonies Counted |
|---|---|---|---|
| Cas9 Nuclease | 0 | 0 | 10 |
| Cytosine Base Editor with Intron | 6 | 8 | 49 |
| Cytosine Base Editor without Intron | 37 | 16 | 56 |

Cas12a Cytosine Base Editor Comprising an Intron in an A3A Deaminase (APOBEC3A)

The ability to assemble plasmids that match the originally intended sequence (i.e., a base editor construct of the invention, for example, but not limited to, SEQ ID NOs:12-22, that have not been edited by the cytosine deaminase in the construct) and that contain base editors is greatly impaired by instability caused by the deaminase domain. To assist with the assembly of a cytosine base editor for testing in a human cell system, a human chimeric intron (GTAAGTAT-CAAGGTTACAAGACAGGTTTAAGGAGAC-CAATAGAAACTGG GCTTGTCGAGACAGAGAA-GACTCTTGCGTTTCTGATAGGCACCTATTGGTCTTAC TGACATCCACTTTGCCTTTCTCTCCACAG) (SEQ ID NO:75) comprising the 5'-donor site from the first intron of the human β-globin gene and the branch and 3'-acceptor site from the intron that is between the leader and the body of an immunoglobulin gene heavy chain variable region (see, e.g., Younis et al. *Mol. Cell. Biol.* 30:1718-1728 (2010)) was placed into the active site of the human A3A deaminase. Specifically, the intron was placed 152 bases after the start of the intron coding sequence, which causes a premature stop codon and prevents further translation of the editor unless the intron sequence is removed.

When the assembly of the full base editor construct containing the A3A deaminase was performed, the ability to recover the desired clones was assessed. In this case, the assembly places the editor into a full transformation backbone, so that all of the components are put together at once. A fragment that contained A3A and a fragment that contained A3A with an intron were used. It was determined that when the intron was included it was much more likely to contain the originally designed sequence. Specifically, in this experiment, the deaminase was assembled with or without the intron as described and fused to a dCas12a enzyme (i.e., no nuclease activity) to create a Cas12a cytosine base editor via golden gate assembly. Following assembly, reactions were transformed into *E. coli* cells and the resulting clones sequenced by next generation sequencing. Of 6 constructs tested, when the intron was not present, only one (⅙) clone was detected through screening that had a 100% match with the intended sequence, whereas, when the intron was present, all of the clones (6/) had a 100% match with the intended sequence. The overall success rate was 20% when an intron was included in contrast to only 2% without an intron (Table 6).

TABLE 6

Summary of cloning results for the assembly of a cytosine deaminase vector

|  | Number of Colonies Screened | Correct Colonies (100% match to the expected sequence) | Success rate |
| --- | --- | --- | --- |
| A3A + intron | 90 | 18 | 20% |
| A3A | 176 | 3 | 2% |

Exemplary mutations identified among the potential clones of cytosine base editor assembly reactions are shown in Table 7.

TABLE 7

Example mutations found by sequencing potential clones of cytosine base editor assembly reactions

| Colony Name | UGI Region | A3A Region |
| --- | --- | --- |
| 1720_1-5 | correct | T missing in A3A |
| 1720_2-8 | correct | C missing in A3A |
| 1720_3-4 | no UGI | Linker missing |
| 1720_3-8 | Correct | A missing in A3A |
| 1720_6-8 | correct | C to G point mutation |
| 1720_7-8 | correct | No A3A |
| 1716_2-4 | correct | G missing in A3A |
| 1716_3-4 | correct | wrong UGI, missing linker, G missing in A3A |
| 1716_10-1 | correct | extra A in A3A |
| 1716_10-2 | correct | 2 sites incorrect |
| 1716_10-3 | correct | C missing in A3A |
| 1716_11-8 | correct | C missing in A3A |

Base Editing Using a Base Editor Construct Comprising an Intron

Figure 2:
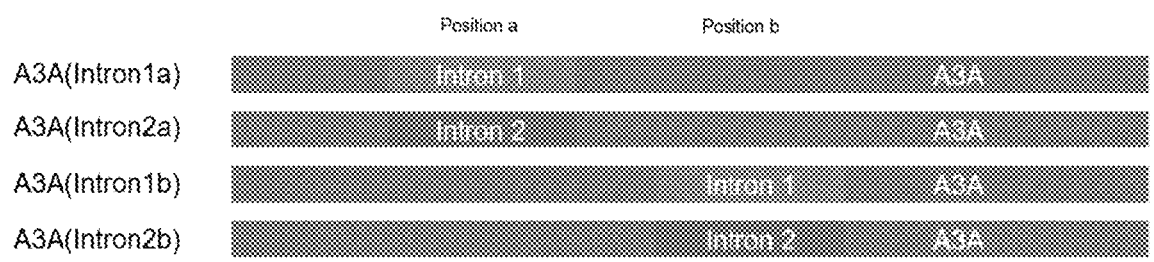
FIG. 2. Graphical representation of the architecture of the intron placement in the Apobec3A domain. Intron 1—Beta-globin/immunoglobin chimeric intron; Intron 2—SV40 intron FIG. 3. Comparison of base editing activity at the RNF2 locus in human cells. Apobec1 and evoCDA1 deaminase constructs do not contain an intron and the A3A constructs contain either the β-globulin/immunoglobulin chimeric intron (intron 1), or the SV40 intron (Intron 2). Y axis is % sequence reads with C>T conversions. C3, C6 and C12 are the positions of each of the cytosines that are edited in at the RNF2 locus.

Two different introns, the human chimeric intron discussed previously and the SV40 intron (Xu et al., *J Cell Mol Med.* 22(4):2231-2239 (2018) (GTAAGTTTAGTCTTTTTGTCT TTTATTTCAGGTCCCGGATCCGGTGGTGGTGCAAATCAAAGAACTGCTCCTCAGT GGATGTTGCCTTTACTTCTAGGC) (SEQ ID NO:76), were introduced into the A3A deaminase and fused to a deactivated Cas9 protein. The introns were placed in two different regions of the deaminase domain (FIG. 2). Specifically, the intron was placed within the motif (A/C)AG [Intron]G(G/T), in order to maintain the canonical intron splicing sequence context. It is expected that other sites with this motif would also allow for efficient intron splicing.

Each base editor construct was compared against a base editor construct with the apobec1- or evoCDA1-deaminase at four loci in the human 293T cells, the RNF2 locus, the FANCF1 locus, AAVS1b locus and the AAVS1c locus. The results are shown in FIGS. 3-6.

Figure 3:
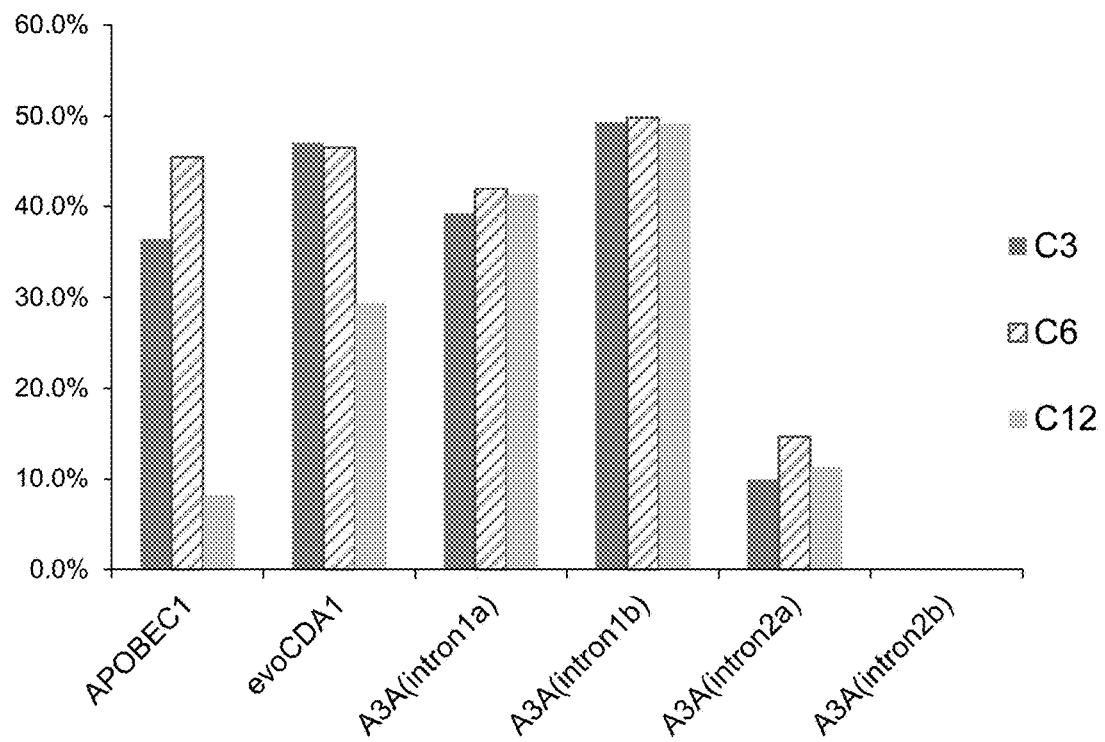
Figure 4:
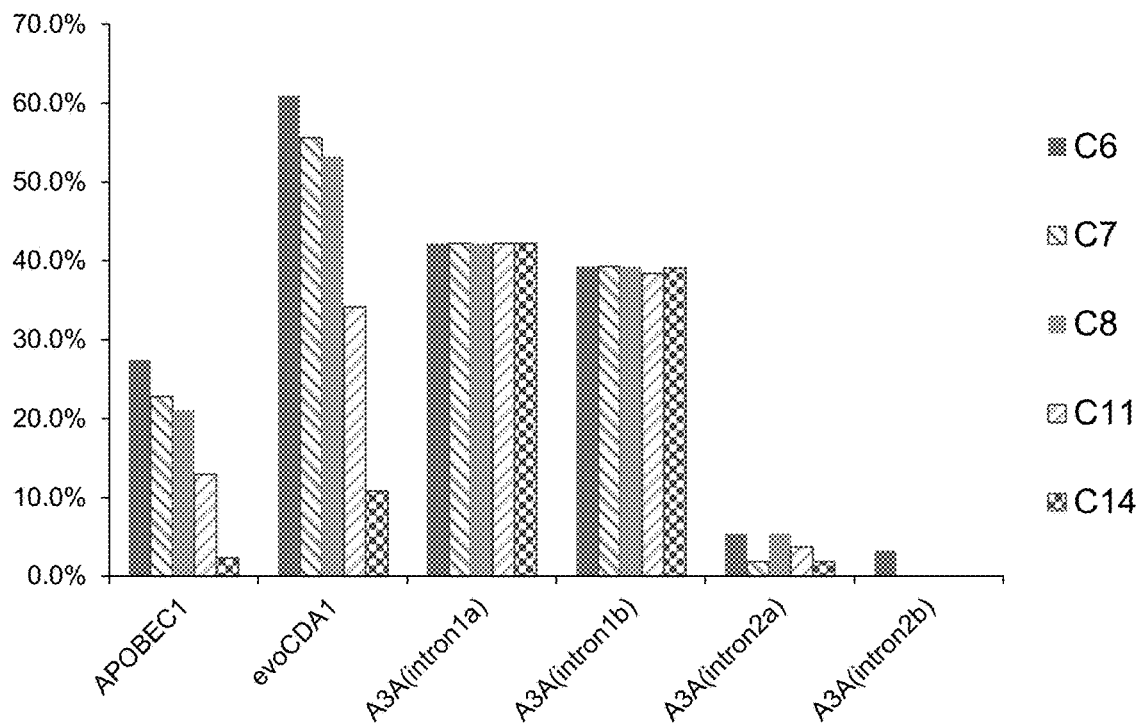
FIG. 4. Comparison of base editing activity with and without introns at the FANCF1 locus in human cells. Apobec1 and evoCDA1 deaminase constructs do not contain an intron, A3A constructs contain either the β-globulin/immunoglobulin chimeric intron (intron 1), or the SV40 intron (Intron 2). Y axis is % sequence reads with C>T conversions. C6, C7, C8, C11, and C14 are the cytosine positions at the FANCF1 locus.
Figure 5:
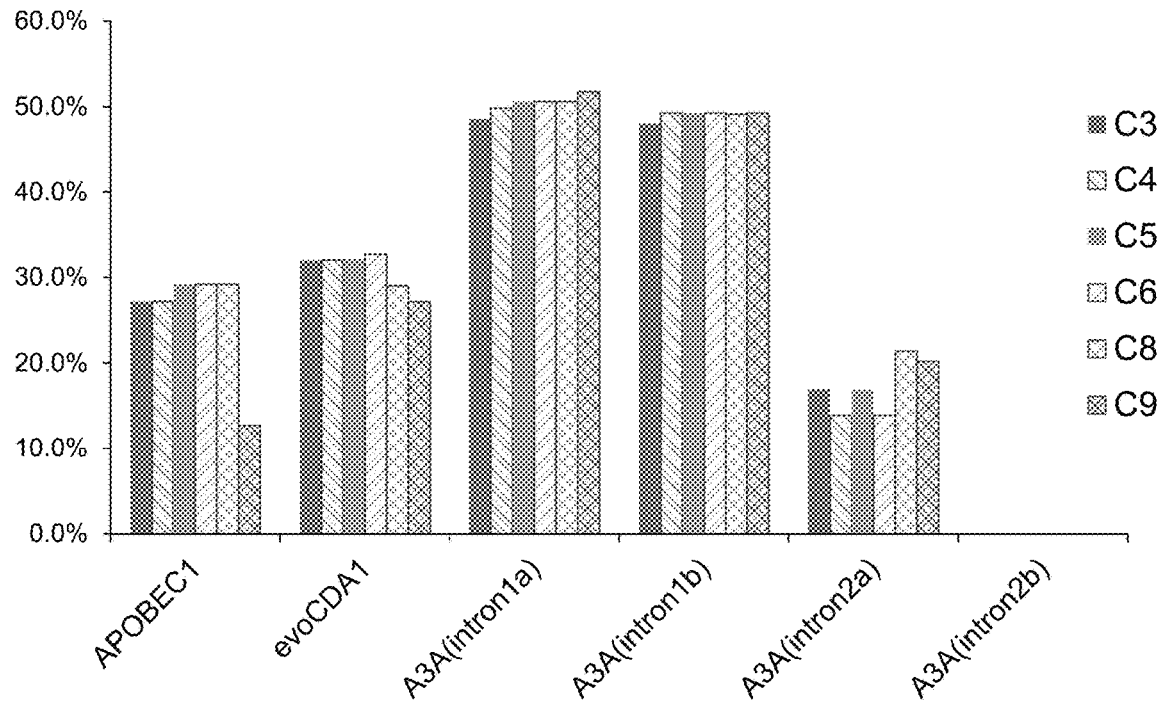
FIG. 5. Comparison of base editing activity with and without introns at the AAVS1b locus in human cells. Apobec1 and evoCDA1 deaminase constructs do not contain an intron and the A3A constructs contain either the β-globulin/immunoglobulin chimeric intron (intron 1), or the SV40 intron (Intron 2). Y axis is % sequence reads with C>T conversions. C3, C4, C5, C6, C8 and C9 are the positions of each of the cytosines that are edited in the AAVS1b locus.
Figure 6:
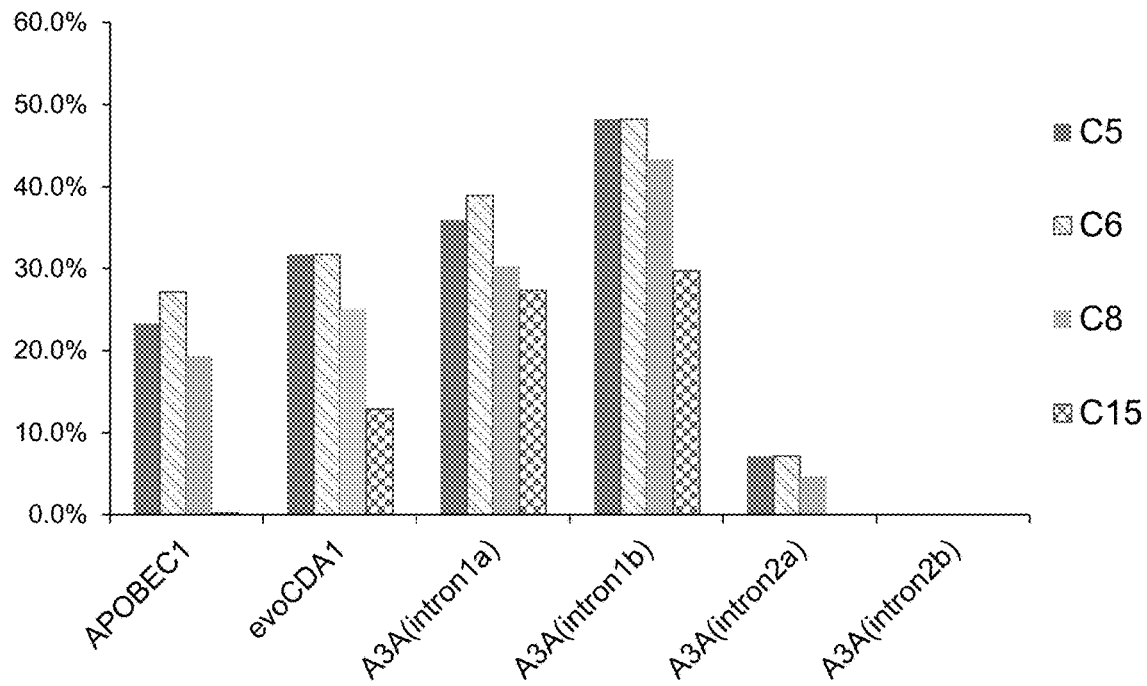
FIG. 6 Comparison of base editing activity at the AAVS1c locus in human cells. Apobec1 and evoCDA1 deaminase constructs do not contain an intron and the A3A constructs contain either the β-globulin/immunoglobulin chimeric intron (intron 1), or the SV40 intron (Intron 2). Y axis is % sequence reads with C>T conversions. C5, C6 C8 and C15 are the positions of each of the cytosines that are edited in the AAVS1c locus.

In FIG. 3, the base editing activity is shown using constructs with and without the introns. The editing is at the RNF2 locus in the human cells. The Apobec1 and evoCDA1 deaminase constructs do not contain an intron and the A3A constructs contain either the β-globulin/immunoglobulin chimeric intron (intron 1), or the SV40 intron (Intron 2). FIG. 4 shows a comparison of base editing activity at the FANCF1 locus in human cells for Apobec1 and evoCDA1 deaminase constructs that do not contain an intron, and A3A constructs that contain either the β-globulin/immunoglobulin chimeric intron (intron 1), or the SV40 intron (Intron 2). FIG. 8 compares base editing activity at the AAVS1b locus in human cells for Apobec1 and evoCDA1 deaminase constructs that do not contain an intron, and A3A constructs that contain either the β-globulin/immunoglobulin chimeric intron (intron 1), or the SV40 intron (Intron 2). In FIG. 9 base editing activity at the AAVS1c locus in human cells is compared for Apobec1 and evoCDA1 deaminase constructs that do not contain an intron, and A3A constructs that contain either the β-globulin/immunoglobulin chimeric intron (intron 1), or the SV40 intron (Intron 2). As shown in each of FIGS. 3-6, the chimeric intron resulted in base editing rates similar to editing rates without an intron, demonstrating that the presence of the intron is not preventing deaminase activity but with the advantage that constructs comprising intron as described herein can be produced without generating mutations in the vector sequence.

Example 5

Adenine base editors were constructed by placing the TadA deaminase and the variant TadA* directly 5' of a nickase variant of Cas9. The TadA and TadA* are separated by a protein linker, and there is an additional linker between the deaminase proteins and the start of nCas9. Similar to the cytosine base editors, the monocot vectors utilize the *Zea mays* Ubiquitin 1 promoter, and the dicot vectors utilize the *Medicago truncatula* Ubiquitin 2 promoter. These editor sequences were then codon optimized via proprietary algorithms for either corn and soy and the predicted sequences synthesized via solid state synthesis.

Nucleic acid constructs encoding an adenosine base editor that comprises a CRISPR-Cas nuclease and an adenine deaminase were generated (e.g., SEQ ID NOs:69-71). The nucleic acid constructs that were generated were codon optimized for expression in soybean (dicot, Di) or corn (monocot, Mon).

The constructs for optimized adenosine base editors as described herein are provided in Table 8.

TABLE 8

Optimized base editors

| Coding sequence optimized version | Plant Type |
| --- | --- |
| Mon_BY_V1_ABE (SEQ ID NO: 69) | Monocot |
| Di_BY_V1_ABE (SEQ ID NO: 70) | Dicot |
| Di_BY_V2_ABE (SEQ ID NO: 71) | Dicot |

TABLE 9

Editing efficiency of the base editors in corn and soy

| Target | Codon Optimization | Edited Plants | Total Samples | Editing Efficiency* |
|---|---|---|---|---|
| Corn Target 2 (Locus1) | Mon_BY_V1_ABE | 6 | 101 | 5.9% |
| Corn Target 2 (Locus2) | Mon_BY_V1_ABE | 18 | 101 | 17.8% |
| Soy Target 2 | Di_BY_V2_ABE | 1 | 46 | 2% |

*Editing over 10% of reads.

Editing in dicots with the V1_ABE was below the 10% cutoff used for higher-activity tools, however, activity was detected. Using a lower threshold of activity of 1%, the editing efficiency is shown in Table 10.

TABLE 10

Editing efficiency of the tested base editors in soy

| Target | Codon Optimization | Edited Plants | Total Samples | Editing Efficiency* |
|---|---|---|---|---|
| Soy Target 1 | Di_BY_V1_ABE | 11 | 235 | 4.6% |
| Soy Target 2 | Di_BY_V1_ABE | 31 | 235 | 13.2% |
| Soy Target 1 | Di_BY_V2_ABE | 0 | 46 | 0% |

*Editing over 1% of reads.

The foregoing is illustrative of the present invention, and is not to be construed as limiting thereof. The invention is defined by the following claims, with equivalents of the claims to be included therein.

That which is claimed is:

1. A nucleic acid construct encoding a CRISPR-Cas nuclease operably associated with a promoter region, wherein the promoter region comprises an intron, optionally wherein the promoter region comprises a ubiquitin promoter and intron, wherein the nucleic acid construct encoding the CRISPR-Cas nuclease comprises the nucleotide sequence of any one of SEQ ID NOs: 2, 4 or 6.

2. The nucleic acid construct of claim 1, further encoding a deaminase domain.

3. The nucleic acid construct of claim 2, wherein the deaminase domain is codon optimized for expression in a plant.

4. The nucleic acid construct of claim 2, wherein the CRISPR-Cas nuclease and the deaminase domain are expressed as a fusion protein and the CRISPR-Cas nuclease is linked to the deaminase domain via a linker.

5. The nucleic acid construct of claim 2, wherein the deaminase domain is a cytosine deaminase domain or an adenosine deaminase domain.

6. The nucleic acid construct of claim 5, wherein the nucleic acid construct further encodes a uracil-DNA glycosylase inhibitor (UGI), optionally wherein the UGI is codon optimized for expression in a plant.

7. An expression cassette or vector comprising the nucleic acid construct of claim 1.

8. The expression cassette or vector of claim 7, further comprising a guide nucleic acid.

9. A cell comprising the nucleic acid construct of claim 1 and/or an expression cassette or vector comprising the nucleic acid construct.

10. The cell of claim 9, wherein the cell is a plant cell.

11. The cell of claim 10, wherein the cell is from maize, soybean, wheat, canola, rice, tomato, pepper, sunflower, raspberry, blackberry, black raspberry or cherry.

12. A method of modifying a target nucleic acid, comprising contacting a cell or a cell free system comprising the target nucleic acid with:
    (a) the nucleic acid construct of claim 2, or an expression cassette and/or vector comprising the same, and
    (b) a guide nucleic acid, under conditions whereby the CRISPR-Cas nuclease encoded by the nucleic acid construct is expressed and forms a complex with the guide nucleic acid, the complex hybridizing to the target nucleic acid, thereby modifying the target nucleic acid.

13. The method of claim 12, wherein the deaminase domain is an adenine deaminase domain and the adenine deaminase domain converts an adenosine (A) to a guanine (G) in the target nucleic acid, thereby editing the target nucleic acid to produce a mutation in the target nucleic acid.

14. The method of claim 13, wherein the point mutation is an A-to-G conversion in the sense strand of the target nucleic acid or a T-to-C conversion in the antisense strand of the target nucleic acid.

15. The method of claim 12, wherein the deaminase domain is a cytosine deaminase domain and the cytosine deaminase domain converts a cytosine (C) to a thiamine (T) in the target nucleic acid, thereby editing the target nucleic acid to produce a mutation.

16. A kit comprising the nucleic acid construct of claim 1, and/or an expression cassette or vector comprising the nucleic acid construct, optionally with instructions for the use thereof.

17. A nucleic acid construct encoding a CRISPR-Cas nuclease, wherein the nucleic acid construct comprises the nucleotide sequence of any one of SEQ ID NOs: 2, 4 or 6.

18. The nucleic acid construct of claim 17, further encoding a deaminase domain.

19. An expression cassette or vector comprising the nucleic acid construct of claim 17.

20. A cell comprising the nucleic acid construct of claim 17 and/or an expression cassette or vector comprising the nucleic acid construct of claim 17.

* * * * *

UNITED STATES PATENT AND TRADEMARK OFFICE
CERTIFICATE OF CORRECTION

| | | |
|---|---|---|
| PATENT NO. | : 11,591,607 B2 | |
| APPLICATION NO. | : 17/078576 | |
| DATED | : February 28, 2023 | |
| INVENTOR(S) | : Graham | |

It is certified that error appears in the above-identified patent and that said Letters Patent is hereby corrected as shown below:

On the Title Page

Item (12): Please delete "Graham et al." and insert --Graham--

Item (72) Inventors: Please delete "Aaron Hummel, Hillsborough, NC (US)"

Item (72) Inventors: Please delete "Yongjoo Kim, Durham, NC (US)"

Item (72) Inventors: Please delete "Joseph Matthew Watts, Cary, NC (US)"

In the Specification

Column 3, Line 55: Please correct "SEQ ID NOs: 72-73 provide exemplary" to read --SEQ ID NOs: 72-73 provide exemplary CRISPR spacers.--

Column 23, Line 63: Please correct "15, 6, 17," to read --15, 16, 17,--

Signed and Sealed this
Thirteenth Day of June, 2023

Katherine Kelly Vidal
*Director of the United States Patent and Trademark Office*